US009890133B2

(12) United States Patent
Jung et al.

(10) Patent No.: US 9,890,133 B2
(45) Date of Patent: *Feb. 13, 2018

(54) INDANONE DERIVATIVES, PHARMACEUTICALLY ACCEPTABLE SALTS OR OPTICAL ISOMERS THEREOF, PREPARATION METHOD FOR SAME, AND PHARMACEUTICAL COMPOSITIONS CONTAINING SAME AS ACTIVE INGREDIENT FOR PREVENTING OR TREATING VIRAL DISEASES

(71) Applicants: KOREA RESEARCH INSTITUTE OF CHEMICAL TECHNOLOGY, Daejeon-si (KR); KATHOLIEKE UNIVERSITEIT LEUVEN K.U. LEUVEN R & D, Belgium (BE)

(72) Inventors: Young Sik Jung, Daejeon (KR); Chong Kgo Lee, Daejeon (KR); Hae Soo Kim, Daejeon (KR); Hee Chun Jeong, Daejeon (KR); Pil Ho Kim, Daejeon (KR); Soo Bong Han, Daejeon (KR); Jin Soo Shin, Chungcheongnam-do (KR); Johan Neyts, Belgium (BE); Hendrik Jan Thibaut, Belgium (BE)

(73) Assignees: KATHOLIEKE UNIVERSITEIT LEUVEN K.U. LEUVEN R&D, Belgium (BE); KOREA RESEARCH INSTITUTE OF CHEMICAL TECHNOLOGY, Daejeon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/189,771

(22) Filed: Jun. 22, 2016

(65) Prior Publication Data
US 2016/0297789 A1 Oct. 13, 2016

Related U.S. Application Data

(63) Continuation of application No. 14/126,485, filed as application No. PCT/KR2012/004806 on Jun. 18, 2012, now Pat. No. 9,464,067.

(30) Foreign Application Priority Data

Jun. 16, 2011 (KR) .................. 10-2011-0058705
Jun. 18, 2012 (KR) .................. 10-2012-0065022

(51) Int. Cl.
| | | |
|---|---|---|
| C07D 307/93 | (2006.01) |
| C07D 405/12 | (2006.01) |
| C07D 409/12 | (2006.01) |
| C07D 471/04 | (2006.01) |
| C07D 487/04 | (2006.01) |
| C07D 209/94 | (2006.01) |
| C07D 405/04 | (2006.01) |
| C07D 407/12 | (2006.01) |
| C07D 417/12 | (2006.01) |
| C07C 233/32 | (2006.01) |
| C07D 413/12 | (2006.01) |

(Continued)

(52) U.S. Cl.
CPC .......... *C07D 307/93* (2013.01); *C07C 233/32* (2013.01); *C07D 209/94* (2013.01); *C07D 405/04* (2013.01); *C07D 405/12* (2013.01); *C07D 407/12* (2013.01); *C07D 409/12* (2013.01); *C07D 413/12* (2013.01); *C07D 417/12* (2013.01); *C07D 471/04* (2013.01); *C07D 487/04* (2013.01); *C07D 491/048* (2013.01); *C07F 9/65517* (2013.01)

(58) Field of Classification Search
CPC .................................................. C07D 307/93
USPC ........................................................ 549/457
See application file for complete search history.

(56) References Cited

U.S. PATENT DOCUMENTS

| | | | |
|---|---|---|---|
| 3,892,807 | A | 7/1975 | Sahm |
| 3,984,552 | A | 10/1976 | Cragoe, Jr. et al. |
| 2010/0261706 | A1 | 10/2010 | Jagtap et al. |

FOREIGN PATENT DOCUMENTS

| | | |
|---|---|---|
| EP | 409410 A1 | 1/1991 |
| EP | 0481708 A1 | 4/1992 |

(Continued)

OTHER PUBLICATIONS

Kuprava et al., Soobshcheniya Akademii Nauk Gruzinskoi SSR (1964), vol. 36(3), pp. 573-577.*

(Continued)

*Primary Examiner* — Taofiq A Solola
(74) *Attorney, Agent, or Firm* — Brinks Gilson & Lione

(57) ABSTRACT

Disclosed are novel indanone derivatives, pharmaceutically acceptable salts thereof or enantiomers, a preparation method thereof, and a pharmaceutical composition for the prevention or treatment of viral diseases, comprising the same as an active ingredient. The indanone derivatives have excellent inhibitory activity against picornaviruses including coxsackie-, entero-, echo-, Polio-, and rhinoviruses, as well as exhibiting low cytotoxicity, so that they can be useful as an active ingredient of a pharmaceutical composition for the prevention or treatment of viral diseases including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis or otitis media.

18 Claims, No Drawings

(51) Int. Cl.
C07D 491/048 (2006.01)
C07F 9/655 (2006.01)

(56) References Cited

FOREIGN PATENT DOCUMENTS

| | | |
|---|---|---|
| GB | 1 425 295 | 2/1976 |
| SU | 725559 | 3/1980 |
| UA | 79834 | 7/2007 |
| WO | WO 2003/082265 A2 | 10/2003 |
| WO | WO 2004/041201 A2 | 5/2004 |
| WO | WO 2004/041812 A2 | 5/2004 |
| WO | WO 2004/087153 A2 | 10/2004 |
| WO | WO 2010/003023 A2 | 1/2010 |

OTHER PUBLICATIONS

King, Med. Chem: Principle and Practice (1994), pp. 206-208.*
Aleman, J. et al., "Organocatalytic Highly Enantio selective 'α -Arylation of β-Ketoesters", Angewandte Chemie International Edition, 2007, vol. 46, pp. 5515-5519.
Almog, Joseph et al., "The reaction between phloroglucinol and vic polycarbonyl compounds: extension and mechanistic elucidation of Kim's synthesis for bipolarofacial bowl-shaped compounds", Tetrahedron 65, (2009), pp. 7954-7962.
Black, D.S.C., et al., "Reactions of Ninhydrin with Activated Anilines: Formation of Indole Derivatives", Tetrahedron, (1994), vol. 50, No. 37, pp. 10983-10994.
Bullington, J.L. et al., "Synthesis of Spiro[2H-indole]-3,3'-diones and Spiro[benzofuran-2,1'-isobenzofuran]-3,3'-diones via Trans-annular Reactions of Eight Membered Ring Intermediates", Journal of Heterocyclic Chemistry, vol. 35 (Mar.-Apr. 1998), pp. 397-403.
Bullington, James L., et al., "Synthesis of tetrahydroineno[1,2-b] indol-10-ones and Their rearrangement to [2] Benzopyrano[4,3-b]indol-5-ones", Journal of Organic Chemistry, vol. 58, No. 18, (1993), pp. 4833-4836.
Das, S. et al., "A Facile Synthesis of Benzofuroisocoumarins from C-2 Arylated 1,3-Indanediones", Synlett, 2006, vol. 2, pp. 207-210.
Das, Suven et al., "A simple synthesis of 4-substituted 2,3-benzoxazinones from C-2 arylated 1,3-indanediones", Tetrahedron Letters, vol. 52, No. 25, (Apr. 27, 2011) pp. 3243-3246.
Diana, Guy D. "Inhibitors of Picornavirus Replication", Current Medicinal Chemistry-Anti-Infective Agents, vol. 2. No. 1. (Mar. 2003), pp. 1-12.
Extended European Search Report for EP 12800577.4, dated Mar. 24, 2015.
Groarke, James M. et al. "Attenuated Virulence of Pleconaril-Resistant Coxsackievirus B3 Variants", The Journal of Infectious Diseases, (Jun. 1999), vol. 179(6); pp. 1538-1541.
Hark, Richard R. et al. "Synthetic studies of novel ninhydrin analogs", Can. J. Chem., vol. 79, (2001); pp. 1632-1654.
Hashimoto, Suzumi et al., "Dynamic behavior of cyclic hemiacetals of 2-Hydroxy-2-(2-hydroxyphenyl)-1,3-indandione derivatives", Chemistry Letters, vol. 37, No. 7, (2008), pp. 696-697.
Heffner, Robert J., Joullie, Madeleine, "A Synthesis of Two Novel Benzo[f]Ninhydrin Analogs: 6-Methoxybenzo[f]Ninhydrin and Thieno[f]Ninhydrin", Synthetic Communications, 21(8&9), (1991), pp. 1055-1069.
Heffner, Robert J., Joullie, Madeleine, "Synthetic Routes to Ninhydrines, Preparation of Ninhydrin, 5-Methoxyninhydrin, and 5-(Methylthio)Ninhydrin.", Synthetic Communications, 21(21); (1991); pp. 2231-2256.
Heinz, Beverly A. et al., "The Antiviral Compound Enviroxime Targets the 3A Coding Region of Rhinovirus and Poliovirus", Journal of Virology, vol. 6, No. 7, (Jul. 1995), pp. 4189-4197.
International Search Report and Written Opinion of the International Searching Authority for PCT/KR2012/004806, dated Dec. 6, 2012.
Kundu, Sandip Kumar et al., "Theoretical studies of the acid-catalyzed condensation of ninhydrin with aromatic compounds", Indian Journal of Chemistry, Section B: Organic Chemistry, vol. 43B, No. 10, (2004), pp. 2212-2216.
Kundu, Sandip Kumar et al., "6-(α-Hydroxy-α-aryl/naphthyl)methyl-3,4-dihydro-2,5-benzodiazocin-1(2H)-ones and diphenylmethanes from C-2 arylated 1,3-indanediones", Journal of Chemical Research, vol. 11, (2004), pp. 781-783.
Ledford, Rebecca M. et al., "VP1 Sequencing of All Human Rhinovirus Serotypes: Insights into Genus Phylogeny and Susceptibility to Antiviral Capsid-Binding Compounds", Journal of Virology, vol. 78, No. 7, (Apr. 2004), pp. 3663-3674.
Leuchs, Hermann, Wulkow, Gerhard, and Gerland, Heinz, "Indolenines V. Addition of Acid Halides to Indolenines", Bericte der Deutschen Chemischen Gesellschaft, (1932), vol. 151, pp. 1586-1592, via Caplus.
Leuchs, H. et al. "New reactions of indolenines and inolinols", Justus Liebigs Annalen der Chemie, (1928), vol. 461, pp. 27-46, via Caplus.
McKinlay, Mark A. et al., "Treatment of the Picornavirus Common Cold by Inhibitors of Viral Uncoating and Attachment", Annual Review of Microbiology, (Oct. 1992), vol. 46. pp. 635-654.
Miller, F. Dewolfe et al., "Controlled Trial of Enviroxime Against Natural Rhinovirus Infections in a Community", Antimicrobial Agents and Chemotherapy, (Jan. 1985), vol. 27. No. 1, pp. 102-106.
Mudiganti, N.V.S., et al., "Ytterbium triflate-catalyzed conjugate addition of β-ketoesters to activated 1,4-naphthoquinones", Tetrahedron Letters, vol. 65, (2009), pp. 1716-1723.
Na, J. E. et al., "Serendipitous one-pot synthesis of brand-new, bowl-shaped molecular architecture from phloroglucinol and ninhydrin", Tetrahedron Letters, vol. 46, No. 26, (Jun. 27, 2005), pp. 4505-4508.
Na, Jeong Eun et al., "Selective methylation of the Ninhydrin-phenol adducts with I2 in MeOH", Bulletin of the Korean Chemical Society, vol. 25, No. 4, (2004), pp. 569-572.
Na, Jeong Eun et al., "Synthesis of benzo[b]indeno [2,1-d]furanone skeleton from ninhydrin and cyclohexane-1, 3-dione derivatives", Bulletin of the Korean Chemical Society, vol. 24, No. 12, (2003), pp. 1725-1726.
Patick, A.K. et al., "In Vitro Antiviral Activity of AG7088, a Potent Inhibitor of Human Rhinovirus 3C Protease", Antimicrobial Agents and Chemotherapy, (Oct. 1999), vol. 43. No. 10. pp. 2444-2450.
Pevear, Daniel C. et al., "Activity of Pleconaril against Enteroviruses", Antimicrobial Agents and Chemotherapy, (Sep. 1999), vol. 43, No. 9, pp. 2109-2115.
Poupelin, J.P. et al., "Dervies de 1 hydroy-2 indanedione-1, 3.II. Produits de condensation de la ninhydrine avec les polyphenols et leurs derives 0-methyles//2-hydroxy-1,3-indanedione derivatives. II. (Condensation of ninhydrin with polyphenols and their 3-methylated derivatives)", European Journal of Medicinal Chemistry, Editions Scientifique, vol. 15, No. 3, (Jan. 1, 1980), pp. 253-262 (including English abstract).
Poupelin, Jean Pierre et al., "Synthese Et Proprietes Pharmalogiques De Derives De l'Hydroxy-2 Indanedione-1,3; I. Produits De Condensation De La Ninhydrine Avec Les Phenols C-Alkyles", Eur. J. Med. Chem.—Chimica Therapeutique, March-April, vol. 14, No. 2, (Jan. 1, 1979), pp. 171-179 (including English abstract).
Prabhakar, et al., "Identification and evaluation of antioxidant, analgesic/anti-inflammatory activity of the most active ninhydrin-phenol adducts synthesized", Bioorganic & Medicinal Chemistry, vol. 14, No. 21, (Nov. 1, 2006), pp. 7113-7120.
Registry 908828-65-9 (Sep. 27, 2006); 907954-66-9 (Sep. 20, 2006); 408315-53-7 (Apr. 26, 2002).
Roth, H.J., et al., "Reaktionen mit Dimethoxyanilinen und reaktiven Aromaten", Archiv der Pharmazie, (1976), vol. 82, pp. 81-91.
Sastry Mudiganti, N. V. et al., "Ytterbium triflate-catalyzed conjugate addition of beta-ketoesters to activated 1, 4-naphthoquinones", Tetrahedron, (Feb. 21, 2009), vol. 65, No. 8, pp. 1716-1723.
Song, H.N. et al., "Formation of Benzo[b]Indeno [2,1-d]Furanone Ring System During Alkylation of 2-(2-Hydroxyaryl)-2-Hydroxy-1,3-Indanedione Derivatives", Synthetic Communications, (1999), vol. 29, No. 16, pp. 2759-2767.
Song, Hyun Nam et al., "A Study on the Friedel-Crafts Type Reaction of Ninhydrin with Arenes", Synthetic Communications, 28(10), pp. 1865-1870, (1998).

(56) References Cited

OTHER PUBLICATIONS

Song, Hyun Nam et al., "Difference in Reactivity during Alkylation of 2-(2-Hydroxyaryl)-1,3-indanedione and N-(2-Hydroxyphenyl)phthalimide", *Bull. Korean Chem. Soc.*, (1999); vol. 20, No. 6, pp. 631-632.

Song, Hyun Nam et al., "Friedel-Crafts Type Reactions of Some Activated Cyclic Ketones with Phenol Derivatives", *Synthetic Communications*, 29(19), pp. 3303-3311, (1999).

Song, Hyun Nam et al., "The Reaction of Ninhydrin with Polymethylbenzenes in the Presence of Acid Catalyst: Formation of 2-aryl-1,3-indanedione and indenoindanone Derivatives", *Bull. Korean Chem. Soc.*, vol. 20, No. 10, pp. 1229-1231, (Oct. 20, 1999).

Song, Hyun Nam et al., "The Reaction of Ninhydrink with Trimethylbenzenes Under Friedel-Crafts Reaction Conditions", *Synthetic Communications*, 30(6), pp. 1057-1066, (2000).

Stadlbauer, W. et al. DN, "Thermal Cyclization of 3-Azido-2-phenyl-indan-1-one to 5H-Indeno[1,2-b]indol-10-one", *Journal of Heterocyclic Chemistry*, (2002) 39(1), pp. 131-135 (Abstract).

Thibaut et al., "A novel class of highly potent small molecule inhibitors of entero/rhinovirus replication with an excellent safety and pharmacokinetic profile are highly effective against enterovirus infections in mice.", Poster presented at *26th International Conference on Antiviral Research*, San Francisco, CA, (May 11-15, 2013).

Thibaut et al., "A novel class of highly potent small molecule inhibitors of entero/rhinovirus replication that target the non-structural protein 2C", Poster presented at 26th International Conference on Antiviral Research, San Francisco, CA (May 11-15, 2013).

Yin-Murphy, Marguerite and Almond, Jeffrey W., "Chapter 53Picornaviruses", *Medical Microbiology*, 4th Ed., Galveston (TX): Univ. of Texas Medical Branch at Galveston, (1996), pp. 1-18.

Sun, Fang-Gang, et al., "N-Heterocyclic carbine-catalyzed [4+1] annulation of phthalaldehyde and imines," Organic & Biomolecular Chemistry, vol. 9, No. 10, May 21, 2011, pp. 3573-3635.

Arens, A., et al., "Amino derivatives of 2-piperonyl-1,3-idandione," Zhurnal Obshchei Khimii, 1964, vol. 34, No. 2, pp. 442-445.

Jasinskas, L., et al., "Synthesis of secondary amines of 4-methyl-2-phenylindandione," Lietuvos TSR Auksju Mokyklu Mokslo Darbai, Chem. Ir Chem. Technol., 1965, vol. 7, pp. 77-80.

Vasilev, G., et al., "Synthesis, chemical structure, and biological activity of certain N-substituted 2-ureido-or thioureido-2-phenyl-1,3-indandiones," Doklady Bolgarskoi Akademii Nauk, 1986, vol. 39, No. 2, pp. 93-96.

Grinsteins, V., et al., "Synthesis and study of thioureas. Infrared spectra of 2-aryl-2-thiocarbamido-1,3-indandiones," Latvijas PSR Zinatnu Akademijas Vestis, Kimijas Serija, 1972, vol. 4, pp. 441-444.

Bite, Dz., et al., "Substituted thiourea β-dicarbonyl compounds. IX. Spectroscopic study of 2-substituted N-[1, 3-indandion-2-yl] thiourea and 2-(2-iminothiazolidin-3-yl]-2-substituted 1, 3-indandiounes," Latvijas PSR Zinatnu Akademijas Vestis Kimijas Serija, 1969, vol. 1, pp. 109-112.

Arens, A., et al., "Isomerization of 2-amino-2-substituted 1,3-indandiones," Latvijas PSR Zinatnu Akademijas Vestis, Kimijas Serija, 1980, vol. 6, pp. 667-691.

Rotbergs, J., et al., "Condensation of dicarboxylic acid anhydrides with compounds containing active methylene groups. XXVII. 2-Aryl-1,3-indandiones containing methyl groups," Latvijas PSR Zinatnu Akademijas Vestis, Kimijas Serija, 1974, vol. 1, pp. 75-78.

Zalukaev, L.P., et al., "Synthesis of new α-nitro-α-arylmethylenephthal ides," Izvestiya Vysshikh Uchebnykh Zavedenii, Khimiya I Khimicheskaya Tekhnologiya, 1970, vol. 13, No. 10, pp. 1453-1456.

Arens, Augusts, et al., "Reduction of aminodicarboxylic compounds. III. 2-Alkylamino-2-phenyl-3-indanon-1-ol and 2-alkylamino-2-phenyl-1,3-indandiol," Journal of Organic Chemistry of the USSR, 1969, vol. 5, No. 9, pp. 2094-2097.

Zalukaev, L.P., et al., "Synthesis of α-nitromethylpyridine and its derivatives," Khimiya Geterotsiklicheskikh Soedinenii, 1967, vol. 3, pp. 515-517.

Briede, V., et al., "4,5-Dimethoxy-2-β-naphthyl-1,3-indandione," Latvijas PSR Zinatnu Akademijas Vestis, Kimijas Serija, 1967, vol. 3, pp. 329-333.

Arens, A., et al., "2-Amino derivatives of 4,5-and 5,6-dimethoxy-2-phenylindan-1,3-diones," Latvijas PSR Zinatnu Akademijas Vestis, Kimijas, 1966, vol. 3, pp. 342-346.

Eckstein, Zygmunt, et al., "Infrared absorption spectra of 2-nitroindandione derivatives," Bulletin de l'Academie Polonaise des Sciences, Serie des Sciences Chimiques, 1960, vol. 8, No. 10, pp. 579-586.

Zalukajevs, L., et al., "Nitration of phthalones," Zhurnal Obshchei Khimii, 1957, vol. 27, pp. 3278-3282.

Vegnere, V., et al., "Adsorptive capacity of 2-amino-substituted indans on a mercury electrode," Latvijas PSR Zinatnu Akademijas Vestis, Kimijas Serija, 1973, vol. 4, pp. 446-451.

Arens, Augusts, et al., "2-Amino-2-halophenyl-1,3-indandiones," Latvijas PSR Zinatnu Akademijas Vestis, Kimijas Serija, 1969, vol. 4, pp. 446-451.

Gudriniece, E., et al., "2-Azido-2-substituted indan-1,3-dione," Doklady Akademii Nauk SSSR, 1966, vol. 171, No. 4, pp. 869-871.

* cited by examiner

INDANONE DERIVATIVES, PHARMACEUTICALLY ACCEPTABLE SALTS OR OPTICAL ISOMERS THEREOF, PREPARATION METHOD FOR SAME, AND PHARMACEUTICAL COMPOSITIONS CONTAINING SAME AS ACTIVE INGREDIENT FOR PREVENTING OR TREATING VIRAL DISEASES

CROSS REFERENCE TO RELATED APPLICATIONS

This patent application is a continuation application of non-provisional application Ser. No. 14/126,485, filed Dec. 16, 2013, and titled "INDANONE DERIVATIVE, PHARMACEUTICALLY ACCEPTABLE SALT THEREOF OR ENANTIOMER THEREOF, PREPARATION METHOD THEREOF, AND PHARMACEUTICAL COMPOSITION FOR PREVENTION OR TREATMENT OF VIRAL DISEASE COMPRISING THE SAME", the content of which is hereby incorporated by reference in its entirety.

TECHNICAL FIELD

The present invention relates to indanone derivatives, pharmaceutically acceptable salts thereof or enantiomers thereof, preparation methods thereof, and pharmaceutical compositions for the prevention and treatment of viral diseases, comprising the same.

BACKGROUND ART

Picornaviruses are non-enveloped, positive single-stranded RNA viruses with an RNA genome 7.2-8.5 Kb long. These viruses are very small and globular in shape with a size of about 22~30 nm, and were first identified a long time ago. Among the viruses belonging to the family Picomaviridae are enteroviruses including rhinovirus, poliovirus, coxsackievirus A, coxsackievirus B, and echovirus, and hepatitis A virus.

The diseases that picornaviruses cause are varied, ranging from respiratory diseases to digestive diseases, to circulatory diseases and to dermal diseases, examples of which include poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, and foot-and-mouth disease. However, there are no therapeutics for curing these diseases. Most of the drugs under development are uncoating inhibitors. Viruses belonging to the family Picornaviridae cause various diseases including the aforementioned respiratory diseases, which evoke hygienic, social and economic issues. Picornaviruses are the main causative agents of waterborne diseases. Being very stable and difficult to disinfect, the RNA viruses incessantly cause related diseases.

Human rhinoviruses (hRV) have been recently associated with the majority of asthma exacerbations, and are known to exist even in bronchial tissues of many stable asthma patients. Comparison of respective bronchial mucosa biopsy specimens taken from asthma and non-asthma patients showed significantly higher frequencies of detection of human rhinoviruses in the lower respiratory tract of asthma patients, compared to non-asthma patients. It has also been reported that there is correlation between the presence of human rhinovirus and the clinical severity of asthma. In addition, rhinoviruses cause chronic obstructive pulmonary disease, pneumonia, sinusitis, and otitis media as well as asthma.

Rhinoviruses are the main causative of the common cold while enterovirus-induced diseases include meningitis, respectory tract infection, etc. Extensive effort to provide vaccination against poliovirus has significantly reduced the onset of poliomyelitis worldwide, but there are still reports of cases of the disease in Niger, Nigeria, Egypt, India, Pakistan, and Afghanistan. Hepatitis A is now possible to control to some degree thanks to vaccines for hepatitis A viruses. However, no vaccines for coxsackieviruses, echoviruses, or rhinoviruses have been developed, thus far.

Particularly, coxsackievirus B is a main cause of myocarditis, which may develop, in serious cases, into idiopathic dilated cardiomyopathy, which requires heart transplantation Enviroxime derivatives are considered the most promising candidate with a broad anti-enterovirus- and anti-rhinovirus activity. Enviroxime interferes with the synthesis of plus-strand RNA by binding to the virus protein 3A that is required for the formation of RNA intermediates in the virus reproduction (Heinz B A and Vance L M: J Virol, 1995, 69(7), 4189-97). In clinical studies, however, the compound was observed to have insignificant or few therapeutic effects, with the concomitant detection of bad pharmacokinetics and unwanted side effects (Miller F D et al.: Antimicrob Agents Chemother, 1985, 27(1), 102-6).

The protease inhibitor AG 7088 has been developed on the basis of the knowledge about the fine structure and function of the viral protease 2C. In the cell culture in the nanomolar concentration range, AG 7088 has an effect against 48 rhinovirus types and coxsackievirus A21, B3, enterovirus 70 and echovirus 11 (Pattick A K et al.: Antimicrobila Agents Chemother, 1999, 43(10), 2444-50).

Thanks to the clarification of the molecular structure of the viral capsids, the preconditions for a purposeful design of capsid blockers, the "WIN substances", have been obtained (Diana G D: Curr Med Chem 2003, 2, 1-12). They inhibit the adsorption and/or the uncoating of rhinoviruses and enteroviruses. Some of the WIN substances have a highly specific effect only against individual genera or virus types of the picornaviruses. Other derivatives inhibit the replication both of rhinoviruses and enteroviruses. Arildone, disoxaril and pirodavir belong, for example, to the WIN substances. These compounds showed very good antiviral effects in the cell culture. However, a poor solubility (arildone), low bioavailability (arildone and disoxaril, a rapid metabolization and excretion (disoxaril and WIN 54954) as well as side effects, such as skin rash (WIN 54954), made a clinical application impossible.

Pleconaril, a kind of WIN substance, has a very good oral bioavailability and after its binding to the hydrophobe pocket in the viruscapsid, it inhibits the penetration of rhino-, echo- and coxsackieviruses (Pevear D C et al.: Antimicrob Agents Chemother 1999, 43(9), 2109-15; McKinlay M A et al.: Annu Rev Microbiol 1992, 46, 635-54). Therefore, pleconaril is potentially effective against a broad spectrum of virus diseases, ranging from the common cold to the viral meningitis or myocarditis. Resistances were observed for rhinoviruses, enterovirus 71 and coxsackievirus B3 (Ledford R M et al.: J Virol 2004, 78(7), 3663-74; Groarke J M et al.: J Infect Dis 1999, 179(6), 1538-41). However, the proven therapeutic effect was not sufficient for the registration of pleconaril (Picovir, Viropharma, USA) as an agent for the treatment of rhinovirus infections in the USA. In March 2002, a corresponding application was refused by the Food and Drug Administration (FDA) because therapy success was too low and side effects were observed.

BTA-798 was found to have higher antiviral activity than pleconaril, as evaluated in vitro and in vivo with rhinoviruses, and is now being under a clinical test (Ryan, J. et al. Antiviral Res [18th Intl Conf Antiviral Res (April 11-14, Barcelona) 2005]2005, 65(3): Abst LB-11).

However, no antiviral drugs that have gained approval for use in the treatment of entero- or rhinoviruses have been developed, so far.

Leading to the present invention, intensive and thorough research into effective virustatics against picornaviruses including coxsackie-, entero-, echo-, polio-, and rhinoviruses, culminated in the finding that novel indanone derivatives exhibit highly inhibitory activity against picornaviruses including coxsackie-, entero-, echo-, polio-, and rhinoviruses.

DISCLOSURE

Technical Problem

It is therefore an object of the present invention to provide a novel indanone derivative, a pharmaceutically acceptable salt thereof, or an enantiomer thereof.

It is another object of the present invention to provide a method for the preparation of the indanone derivative, pharmaceutically acceptable salt, or enantiomer.

It is a further object of the present invention to provide a pharmaceutical composition for the prevention or treatment of a viral disease, comprising the indanone derivative, pharmaceutically acceptable salt, or enantiomer as an active ingredient.

Technical Solution

In accordance with an aspect thereof, the present invention provides an indanone derivative represented by the following Chemical Formula 1, a pharmaceutically acceptable salt thereof, or an enantiomer thereof:

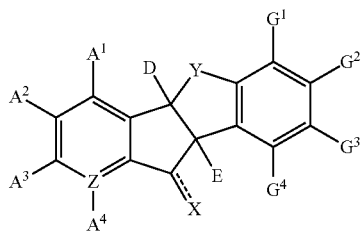

[Chemical Formula 1]

(wherein,
$A^1$, $A^2$, $A^3$, $A^4$, D, E, Z, $G^1$, $G^2$, $G^3$, $G^4$, X, and Y are respectively as defined in the following description of the specification.)

In accordance with another aspect thereof, the present invention provides a method for the preparation of the indanone derivative, pharmaceutically acceptable salt or enantiomer.

In accordance with a further aspect thereof, the present invention provides a pharmaceutical composition for the prevention or treatment of a viral disease, comprising the indanone derivative, pharmaceutically acceptable salt or enantiomer as an active ingredient.

Advantageous Effects

Having excellent inhibitory activity against picornaviruses including coxsackie-, entero-, echo-, Polio-, and rhinoviruses, as well as exhibiting low cytotoxicity, the indanone derivative of Chemical Formula 1 can be useful as an active ingredient of a pharmaceutical composition for the prevention or treatment of viral diseases including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis or otitis media.

BEST MODE

Below, a detailed description will be given of the present invention.

According to one aspect thereof, the present invention addresses an indanone derivative represented by the following Chemical Formula 1, a pharmaceutically acceptable salt thereof, or an enantiomer thereof:

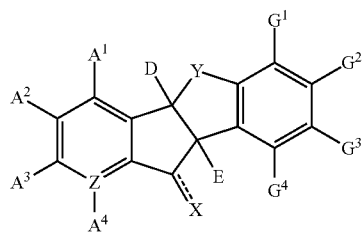

[Chemical Formula 1]

wherein,
$A^1$, $A^2$, $A^3$, and $A^4$ are, independently or optionally, selected from the group consisting of —H, halogen, —OH, —CN, —N$_3$, alkoxy of $C_1$~$C_{10}$, linear or branched alkyl of $C_1$~$C_{10}$, 5-~7-membered heterocycloalkyl unsubstituted or substituted with —OH or methoxyphenylalkyl, aryl of $C_6$~$C_{12}$, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$, —NR$^1$(SO$_2$)R$^2$, and —NR$^1$(C=S)—NR$^2$R$^3$, with a proviso that at least two of A$^1$, A$^2$, A$^3$ and A$^4$ may form a ring together if they are adjacent to each other;

D is —OH, halogen, linear or branched alkyl of $C_1$~$C_{10}$, alkoxy of $C_1$~$C_{10}$ unsubstituted or substituted with phenyl, —O(CH$_2$)$_n$OH, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(O)R$^2$, —NR$^1$(C=O)R$^2$, —NR$^1$(C=S)R$^2$, —NR$^1$(C=O)OR$^2$, —NR$^1$(C=O)—NR$^1$R$^2$, or —NR$^1$(C=S)—NR$^1$R$^2$;

E is halogen, —OH, —CN, —N=C=O, —N$_3$, alkoxy of $C_1$~$C_{10}$, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^1$R$^2$, —NR$^1$(C=O)NR$^2$OR$^3$, —NR$^1$(SO$_2$)R$^2$, —NR$^1$(C=S)—NR$^1$R$^2$, —NR$^1$(P=O)(OR$^2$)$_2$, or

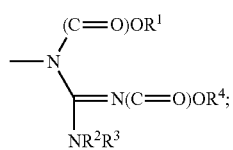

$G^1$, $G^2$, $G^3$, and $G^4$ are independently or optionally selected from the group consisting of —H, halogen, —OH, CN, alkoxy of $C_1$~$C_{10}$, linear or branched alkyl of $C_1$~$C_{20}$, aryl of $C_6$~$C_{12}$, —O(C=O)R$^1$, —(C=O)R$^1$, —(C=O)OR$^1$, —(CH$_2$)$_n$—(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$, and —NR$^1$(C=S)—NR$^2$R$^3$, with a proviso that at least two of $G^1$, $G^2$, $G^3$, and $G^4$ may form a ring together if they are adjacent to each other;

X is hydrogen, oxygen, sulfur, hydroxy, linear or branched alkyl of $C_1$~$C_{10}$, linear or branched alkylene of $C_1$~$C_{10}$, =N—NR$^1$R$^2$, —NR$^1$—OR$^2$, or =N—OR$^1$;

Y is —O—, —CH$_2$—, —NH—, or —(NR$^5$)—;

R$^5$ is —(C=O)H, —(C=O)OH, —(C=O)R$^1$, —(C=S)R$^1$, or —(C=O)OR$^1$;

Z is C or N;

R$^1$, R$^2$, R$^3$, and R$^4$ are independently hydrogen, linear or branched alkyl of $C_1$~$C_{10}$, linear or branched alkylene of $C_1$~$C_{10}$ unsubstituted or substituted with phenyl, cycloalkyl of $C_3$~$C_7$, heterocycloalkyl of $C_3$~$C_7$, aryl of $C_6$~$C_{12}$, or 5-~14-membered heteroaryl;

wherein the heterocycloalkyl may be substituted with at least one oxygen atom via a double bond, the aryl is mono- or bicyclic and may have at least one substituent selected from the group consisting of halogen, —CN, phenyl, linear or branched alkyl of $C_1$~$C_6$, R$^5$, and alkoxy of $C_1$~$C_6$, the heteroaryl is mono-, bi- or tricyclic, and may have at least one substituent selected from the group consisting of halogen, —OH, —NO$_2$, —NH$_2$, —CN, =O or —O$^-$, linear or branched alkyl of $C_1$~$C_1$, linear or branched alkoxy of $C_1$~$C_{10}$, and phenyl, the linear or branched alkyl may be unsubstituted or substituted with at least one substituent selected from the group consisting of phenyl, halogen, 5-~7-membered heteroaryl, and —NHBoc, the phenyl may be substituted with at least one selected from the group consisting of halogen, phenyl, or phenyl-substituted alkoxy of $C_1$~$C_6$, the heterocycloalkyl or heteroaryl contains at least one heteroatom selected from the group consisting of N, O, and S, the halogen is F, Cl, Br, or I, n is an integer of 1~10, and '---' represents a single or double bond.

In a preferred embodiment,

A$^1$, A$^2$, A$^3$, and A$^4$ are, independently or optionally, selected from the group consisting of —H, alkoxy of $C_1$~$C_5$, linear or branched alkyl of $C_1$~$C_5$, 5-~7-membered heterocycloalkyl unsubstituted or substituted with —OH or methoxyphenylalkyl, aryl of $C_6$~$C_{12}$, —NO$_2$, and —NR$^1$R$^2$;

D is —OH, halogen, linear or branched alkyl of $C_1$~$C_5$, or alkoxy of $C_1$~$C_5$ unsubstituted or substituted with phenyl;

E is halogen, —OH, or alkoxy of $C_1$~$C_5$;

E is halogen, —OH, alkoxy of $C_1$~$C_5$, —NR$^1$(C=O)R$^2$, —NR$^1$(C=O)OR$^2$, or —NR$^1$(C=O)—NR$^1$R$^2$;

$G^1$, $G^2$, $G^3$, and $G^4$ are, independently or optionally, selected from the group consisting of —H, alkoxy of $C_1$~$C_5$, and linear or branched alkyl of $C_1$~$C_{16}$;

X is oxygen, hydroxyl, or linear or branched alkyl of $C_1$~$C_5$;

Y is —O— or —CH$_2$—;

Z is C or N;

R$^1$, R$^2$, R$^3$, and R$^4$ are independently hydrogen, linear or branched alkyl of $C_1$~$C_7$, heterocycloalkyl of $C_3$~$C_7$, aryl of $C_6$~$C_{12}$, or 5-~14-membered heteroaryl;

wherein the heterocycloalkyl may be substituted with at least one oxygen atom via a double bond, the aryl is mono- or bicyclic and may have at least one substituent selected from the group consisting of halogen, phenyl, linear or branched alkyl of $C_1$~$C_3$, and alkoxy of $C_1$~$C_3$, the heteroaryl is mono-, bi- or tricyclic, and may have at least one substituent selected from the group consisting of halogen, —OH, —NO$_2$, —NH$_2$, —CN, =O or —O$^-$, linear or branched alkyl of $C_1$~$C_{10}$, linear or branched alkoxy of $C_1$~$C_{10}$, and phenyl, the linear or branched alkyl may be unsubstituted or substituted with at least one substituent selected from the group consisting of phenyl, halogen, and 5-~7-membered heteroaryl, the phenyl may be substituted with at least one selected from the group consisting of halogen, and phenyl, the hetetrocycloalkyl or heteroaryl contains at least one heteroatom selected from the group consisting of N, O, and S, the halogen is F, or Cl, and '---' represents a single or double bond.

In a more preferred embodiment,

A$^1$, A$^2$, A$^3$, and A$^4$ are, independently or optionally, selected from the group consisting of —H and —NR$^1$R$^2$;

D is —OH;

E is —OH or —NR$^1$(C=O)R$^2$;

$G^1$, $G^2$, $G^3$, and $G^4$ are, independently or optionally, linear or branched alkyl of $C_1$~$C_{15}$;

X is oxygen;

Y is —O—;

Z is C;

R$^1$, R$^2$, R$^3$, and R$^4$ are, independently, hydrogen or 5-~14-membered heteroaryl;

wherein, the 5-~14-membered heteroaryl is monocyclic, bicyclic, or tricyclic, and may be substituted with a substituent selected from the group consisting of halogen, —OH, —NO$_2$, —NH$_2$, —CN, =O or —O$^-$, linear or branched alkyl of $C_1$~$C_{10}$, linear or branched alkoxy of $C_1$~$C_{10}$, and phenyl, the phenyl may be substituted with at least one selected form the group consisting of halogen and phenyl, the heteroaryl contains a heteroatom selected from the group consisting of N, O, and S, and the halogen is F or Cl, and '---' represents a single or double bond.

In a further more preferred embodiment,

A$^1$, A$^2$, and A$^3$ are —H, and A$^4$ is —NH$_2$;

D is —OH;

E is —NR$^1$(C=O)R$^2$;

$G^1$, $G^3$ and $G^4$ are —H, and $G^2$ is isopropyl;

X is oxygen;

Y is —O—;

Z is C;

R$^1$ is hydrogen and R$^2$ is 5-~14-membered heteroaryl;

wherein the heteroaryl is furane, benzofurane, pyridine, pyrazolopyridine, pyrimidine, pyrazolopyrimidine, pyrazine, thiopene, quinoline, isoquinoline, triazole, thiazole, indole, pyrazole, indazole, tetrazole, benzotriazole, chromene, pyrane, pyrrole, benzopyrazole, isoxazole, xanthene, cinnoline, imidazole, benzoimidazole, acridine, imidazopyridine, imidazopyrimidine, quinoxaline, pyridazine, tetrazolopyridine, triazolopyridine, triazolopyrimidine or indolizine, and may be substituted with at least one substituent selected from the group consisting of halogen, —OH, —NO$_2$, —NH$_2$, —CN, =O or —O$^-$, linear or branched alkyl of C$_1$~C$_{10}$, linear or branched alkoxy of C$_1$~C$_{10}$, and phenyl, and the halogen is F or Cl, and '$\text{---}$' represents a double bond.

Concrete examples of the compound represented by Chemical Formula 1 include:

1) 4b,9b-dihydroxy-7-methyl-4bH-benzo[d]indeno[1,2-b]furan-10(9bH)-one;
2) 7-methyl-10-oxo-9b,10-dihydro-4bH-benzo[d]indeno[1,2-b]furane-4b,9b-diyl diacetate;
3) ethyl 2-(4b,9b-dihydroxy-6-methoxy-10-oxo-9b,10-dihydro-4bH-benzo[d]indeno[1,2-b]furane-8-yl)acetate;
4) 4b,9b-dihydroxy-7,8-dimethyl-4bH-benzo[d]indeno[1,2-b]furan-10(9bH)-one;
5) 2-hydroxy-2-(2-hydroxyphenyl)-1H-indene-1,3(2H)-dione;
6) 2-(5-fluoro-2-hydroxyphenyl)-2-hydroxy-1H-indene-1,3(2H)-dione;
7) 4b,9b-dihydroxy-7-methoxy-4bH-benzo[d]indeno[1,2-b]furan-10(9bH)-one;
8) 6,7-dichloro-4b,9b-dihydroxy-4bH-benzo[d]indeno[1,2-b]furan-10(9bH)-one;
9) 7-ethyl-4b,9b-dihydroxy-4bH-benzo[d]indeno[1,2-b]furan-10(9bH)-one;
10) 4b,9b-dihydroxy-7-isopropyl-4bH-benzo[d]indeno[1,2-b]furan-10(9bH)-one;
11) 7-isopropyl-10-oxo-9b,10-dihydro-4bH-benzo[d]indeno[1,2-b]furane-4b,9b-diyl diacetate;
12) 4b,9b-dihydroxy-8-methoxy-4bH-benzo[d]indeno[1,2-b]furan-10(9bH)-one;
13) 4b,9b-dihydroxy-6-phenyl-4bH-benzo[d]indeno[1,2-b]furan-10(9bH)-one;
14) 4b,9b-dihydroxy-8-nitro-4bH-benzo[d]indeno[1,2-b]furan-10(9bH)-one;
15) 4b,11b-dihydroxy-4bH-indeno[1,2-b]naphtho[2,3-d]furan-12(11bH)-one;
16) 6b,11b-dihydroxy-6bH-indeno[1,2-b]naphtho[2,1-d]furan-7(11bH)-one;
17) 4b,9b-dihydroxy-8-propyl-4bH-benzo[d]indeno[1,2-b]furan-10(9bH)-one;
18) 8-ethyl-4b,9b-dihydroxy-4bH-benzo[d]indeno[1,2-b]furan-10(9bH)-one;
19) 8-sec-butyl-4b,9b-dihydroxy-4bH-benzo[d]indeno[1,2-b]furan-10(9bH)-one;
20) 8-tert-butyl-4b,9b-dihydroxy-4bH-benzo[d]indeno[1,2-b]furan-10(9bH)-one;
21) 6-tert-butyl-4b,9b-dihydroxy-4bH-benzo[d]indeno[1,2-b]furan-10(9bH)-one;
22) 4b,9b-dihydroxy-7,8,9-trimethyl-4bH-benzo[d]indeno[1,2-b]furan-10(9bH)-one;
23) 4b,9b-dihydroxy-8-tert-pentyl-4bH-benzo[d]indeno[1,2-b]furan-10(9bH)-one;
24) 6,8-di-tert-butyl-4b,9b-dihydroxy-4bH-benzo[d]indeno[1,2-b]furan-10(9bH)-one;
25) 6,8-di-tert-butyl-10-oxo-9b,10-dihydro-4bH-benzo[d]indeno[1,2-b]furane-4b,9b-diyl diacetate;
26) 4b,9b-dihydroxy-8-nonyl-4bH-benzo[d]indeno[1,2-b]furan-10(9bH)-one;
27) 4b,9b-dihydroxy-8-pentadecyl-4bH-benzo[d]indeno[1,2-b]furan-10(9bH)-one;
28) 6,8-bis-(1,1-dimethyl-propyl)-4b,9b-dihydroxy-4b,9b-dihydro-5-oxa-indeno[2,1-a]inden-10-one;
29) isopropyl 4b,9b-dihydroxy-7-isopropyl-10-oxo-9b,10-dihydro-4bH-benzo[d]indeno[1,2-b]furan-1-ylcarbamate;
30) 2,6'-dihydroxy-2',3'-dihydro-1'H-[2,5']biindenyl-1,3-dione;
31) 6b,11b-dihydroxy-1,2,3,4,6b,11b-hexahydro-12-oxa-benzo[4,5]pentaleno[2,1-a]naphthalen-7-one;
32) 4b,9b-dihydroxy-7-isopropyl-2-methoxy-4b,9b-dihydro-5-oxa-indeno[2,1-a]inden-10-one;
33) 7-isopropyl-10-oxo-9b,10-dihydro-4bH-benzo[d]indeno[1,2-b]furan-4b,9b-diyl bis(2,2-dimethylpropanoate);
34) (2E,2'E)-7-isopropyl-10-oxo-9b,10-dihydro-4bH-benzo[d]indeno[1,2-b]furan-4b,9b-diyl bis(3-phenylacrylate);
35) 9b-hydroxy-7-isopropyl-10-oxo-9b,10-dihydro-4bH-benzo[d]indeno[1,2-b]furan-4b-yl acrylate;
36) 9b-hydroxy-7-isopropyl-10-oxo-9b,10-dihydro-4bH-benzo[d]indeno-b]furan-4b-yl furane-2-carboxylate-furane-2-carboxylic acid;
37) diethyl 7-isopropyl-10-oxo-9b,10-dihydro-4bH-benzo[d]indeno[1,2-b]furane-4b,9b-diyl dicarbonate;
38) ethyl 9b-hydroxy-7-isopropyl-10-oxo-9b,10-dihydro-4bH-benzo[d]indeno[1,2-b]furan-4b-yl carbonate;
39) methyl 4b,9b-dihydroxy-10-oxo-9b,10-dihydro-4bH-benzo[d]indeno[1,2-b]furan-8-carboxylate;
40) 9b-hydroxy-7-isopropyl-10-oxo-9b,10-dihydro-4bH-benzo[d]indeno[1,2-b]furan-4b-yl diethylcarbamate;
41) 4b-hydroxy-7-isopropyl-10-oxo-9b,10-dihydro-4bH-benzo[d]indeno[1,2-b]furan-9b-yl diethylcarbamate;
42) 2,3-difluoro-4b,9b-dihydroxy-7-isopropyl-4bH-benzo[d]indeno[1,2-b]furan-10(9bH)-one;
43) 1,4b,9b-trihydroxy-7-isopropyl-4bH-benzo[d]indeno[1,2-b]furan-10(9bH)-one;
44) 4b,9b-dihydroxy-7-isopropyl-1H-cyclopenta[b]naphthaleno[1,2-b]furan-10(9bH)-one;
45) 9b-hydroxy-7-isopropyl-4b-methoxy-1-nitro-4bH-benzo[d]indeno[1,2-b]furan-10(9bH)-one;
46) 1-amino-4b,9b-dihydroxy-7-isopropyl-4bH-benzo[d]indeno[1,2-b]furan-10(9bH)-one;
47) 1-amino-7-isopropyl-10-oxo-9b,10-dihydro-4bH-benzo[d]indeno[1,2-b]furane-4b,9b-diyl diacetate;
48) N-(4b,9b-dihydroxy-7-isopropyl-10-oxo-9b,10-dihydro-4bH-benzo[d]indeno[1,2-b]furan-1-yl)acetamide;
49) methyl 4b,9b-dihydroxy-7-isopropyl-10-oxo-9b,10-dihydro-4bH-benzo[d]indeno[1,2-b]furan-1-ylcarbamate;
50) 1-amino-7-ethyl-4b,9b-dihydroxy-4b,9b-dihydro-5-oxa-indeno[2,1-a]inden-10-one;
51) 7-ethyl-4b,9b-dihydroxy-1-nitro-4b,9b-dihydro-5-oxa-indeno[2,1-a]inden-10-one;
52) 7-ethyl-2,4b,9b-trihydroxy-4b,9b-dihydro-5-oxa-indeno[2,1-a]inden-10-one;
53) acetic acid 4b-acetoxy-1-amino-7-isopropyl-10-oxo-4b,10-dihydro-5-oxa-indeno[2,1-a]inden-9b-yl ester;
54) acetic acid 4b-acetoxy-7-isopropyl-1-methanesulfonylamino-10-oxo-4b,10-dihydro-5-oxa-indeno[2,1-a]inden-9b-yl ester;
55) 1-(4b,9b-dihydroxy-7-isopropyl-10-oxo-9b,10-dihydro-4bH-benzo[d]indeno[1,2-b]furan-1-yl)-3-isopropylurea;
56) N-(9b-amino-4b-hydroxy-7-isopropyl-10-oxo-9b,10-dihydro-4bH-benzo[d]indeno[1,2-b]furan-1-yl)acetamide;
57) N,N'-(4b-hydroxy-7-isopropyl-10-oxo-9b,10-dihydro-4bH-benzo[d]indeno[1,2-b]furan-1,9b-diyldiacetamide;
58) N-(7-amino-2-hydroxy-2-(4-isopropyl-2-hydroxyphenyl)-1,3-dioxo-2,3-dihydro-1H-inden-4-yl)acetamide;

59) N-(2-amino-4b,9b-dihydroxy-7-isopropyl-10-oxo-9b,10-dihydro-4bH-benzo[d]indeno[1,2-b]furan-1-yl)acetamide;
60) 1-amino-4b,9b-dihydroxy-7-isopropyl-2-nitro-4bH-indeno[1,2-b]benzofuran-10(9bH)-one;
61) 1,4-diamino-4b,9b-dihydroxy-7-isopropyl-4bH-benzo[d]indeno[1,2-b]furan-10(9bH)-one;
62) 1,2-diamino-4b,9b-dihydroxy-7-isopropyl-4bH-indeno[1,2-b]benzofuran-10(9bH)-one;
63) 2-(2-hydroxy-4-isopropylphenyl)-1,3-dioxo-2,3-dihydro-1H-inden-2-yl dimethylcarbamate;
64) 4b,9b-dihydroxy-6,8-diisopropyl-4b,9b-dihydro-5-oxa-indeno[2,1-a]inden-10-one;
65) 9b-amino-4b-hydroxy-7-isopropyl-4b,9b-dihydro-5-oxa-indeno[2,1-a]inden-10-one;
66) N-(4b-hydroxy-7-isopropyl-10-oxo-4b,10-dihydro-5-oxa-indeno[2,1-a]inden-9b-yl)-acetamide;
67) 9b-hexylamino-4b-hydroxy-7-isopropyl-4b,9b-dihydro-5-oxa-indeno[2,1-a]inden-10-one;
68) 9b-amino-4b-hydroxy-6,8-diisopropyl-4b,9b-dihydro-5-oxa-indeno[2,1-a]inden-10-one;
69) 4b-hydroxy-9b-isocyanato-7-isopropyl-4b,9b-dihydro-5-oxa-indeno[2,1-a]-inden-10-one;
70) (9b-hydroxy-7-isopropyl-10-oxo-9b,10-dihydro-5-oxa-indeno[2,1-a]inden-4b-yl)-carbamic acid methyl ester;
71) pentanoic acid (9b-hydroxy-7-isopropyl-10-oxo-9b,10-dihydro-5-oxa-indeno[2,1-a]inden-4b-yl-amide;
72) N-(9b-hydroxy-7-isopropyl-10-oxo-9b,10-dihydro-5-oxa-indeno[2,1-a]inden-4b-yl)-isobutylamide;
73) N-(1-amino-9b-hydroxy-7-isopropyl-10-oxo-9b,10-dihydro-5-oxa-indeno[2,1-a]inden-4b-yl)-acetamide;
74) N-(9b-hydroxy-6,8-diisopropyl-10-oxo-9b,10-dihydro-5-oxa-indeno[2,1-a]inden-4b-yl)-acetamide;
75) N-(9b-hydroxy-7-isopropyl-10-oxo-9b,10-dihydro-5-oxa-indeno[2,1-a]inden-4b-yl)-N-methyl-acetamide;
76) 1-(4b-hydroxy-7-isopropyl-1-nitro-10-oxo-4b,10-dihydro-5-oxa-indeno[2,1-a]inden-9b-yl-3-isopropyl-urea;
77) N-(1-amino-4b-hydroxy-7-isopropyl-10-oxo-4b,10-dihydro-5-oxa-indeno[2,1-a]inden-9b-yl-isobutylamide;
78) pentanoic acid (1-amino-4b-hydroxy-7-isopropyl-10-oxo-4b,10-dihydro-5-oxa-indeno[2,1-a]inden-9b-yl-amide;
79) 9b-hydroxy-4b-(2-hydroxyethoxy)-7-isopropyl-4bH-benzo[d]indeno[1,2-b]furan-10(9bH)-one;
80) 4b,9b-dihydroxy-7-isopropyl-1-nitro-4bH-benzo[d]indeno[1,2-b]furan-10(9bH)-one;
81) 4b,9b-dihydroxy-7-isopropyl-2,3-dimethoxy-4bH-benzo[d]indeno[1,2-b]furan-10(9bH)-one;
82) 4b,9b-dihydroxy-7-isopropyl-2,3-dimethyl-4bH-benzo[d]indeno[1,2-b]furan-10(9bH)-one;
83) a mixture of 6:4 (4bS,9bS)-2-bromo-4b,9b-dihydroxy-7-isopropyl-4bH-benzo[d]indeno[1,2-b]furan-10(9bH)-one and (4bS,9bS)-3-bromo-4b,9b-dihydroxy-7-isopropyl-4bH-benzo[d]indeno[1,2-b]furan-10(9bH)-one;
84) methyl (4bS,9bS)-4b-hydroxy-7-isopropyl-10-oxo-9b,10-dihydro-4bH-benzo[d]indeno[1,2-b]furan-9b-ylcarbamate;
85) isopropyl (4bS,9bS)-4b-hydroxy-7-isopropyl-10-oxo-9b,10-dihydro-4bH-benzo[d]indeno[1,2-b]furan-9b-ylcarbamate;
86) ethyl(4bS,9bS)-4b-hydroxy-7-isopropyl-10-oxo-9b,10-dihydro-4bH-benzo[d]indeno[1,2-b]furan-9b-ylcarbamate;
87) N,N'-((4bS,9bS)-4b-hydroxy-7-isopropyl-10-oxo-9b,10-dihydro-4bH-benzo[d]indeno[1,2-b]furane-1,9b-diyl) diacetamide;
88) 4b,9b-dihydroxy-7-isopropyl-4bH-indeno[1,2-b]benzofuran-10(9bH)-one O-methyl oxime;
89) butyric acid 9b-butyrylamino-7-isopropyl-10-oxo-9b,10-dihydro-5-oxa-indeno[2,1-a]inden-4b-yl ester;
90) octanoic acid [2-(2-hydroxy-4-isopropyl-phenyl)-1,3-dioxo-indan-2-yl]-amide;
91) hexanoic acid 9b-hexanoylamino-7-isopropyl-10-oxo-9b,10-dihydro-5-oxa-indeno[2,1-a]inden-4b-yl ester;
92) heptanoic acid 9b-heptanoylamino-7-isopropyl-10-oxo-9b,10-dihydro-5-oxa-indeno[2,1-a]inden-4b-yl ester;
93) N-((4bS,9bS)-1-amino-4b-hydroxy-7-isopropyl-10-oxo-9b,10-dihydro-4bH-indeno[1,2-b]benzofuran-9b-yl)octanamide;
94) (4bR,9bS)-1-amino-7-isopropyl-10-oxo-9b-propionamido-9b,10-dihydro-4bH-indeno[1,2-b]benzofuran-4b-yl propionate;
95) (4bR,9bS)-1-amino-9b-butyramido-7-isopropyl-10-oxo-9b,10-dihydro-4bH-indeno[1,2-b]benzofuran-4b-yl butyrate;
96) 1-amino-7-isopropyl-10-oxo-9b-pentanamido-9b,10-dihydro-4bH-benzo[d]indeno[1,2-b]furan-4b-yl pentanoate;
97) 1-amino-9b-hexanamido-7-isopropyl-10-oxo-9b,10-dihydro-4bH-benzo[d]indeno[1,2-b]furan-4b-yl hexanoate;
98) (4bS,9bS)-4b-hydroxy-7-isopropyl-9b-methoxy-4bH-indeno[1,2-b]benzofuran-10(9bH)-one;
99) 1-amino-9b-heptanamido-7-isopropyl-10-oxo-9b,10-dihydro-4bH-benzo[d]indeno[1,2-b]furan-4b-yl heptanoate;
100) 1-((4bS,9bS)-7-isopropyl-4b-methoxy-10-oxo-9b,10-dihydro-4bH-indeno[1,2-b]benzofuran-9b-yl)urea;
101) 1-((4bS,9bS)-4b-hydroxy-7-isopropyl-10-oxo-9b,10-dihydro-4bH-indeno[1,2-b]benzofuran-9b-yl-3-methylurea;
102) 1-ethyl-3-((4bS,9bS)-4b-hydroxy-7-isopropyl-10-oxo-9b,10-dihydro-4bH-indeno[1,2-b]benzofuran-9b-yl)urea;
103) 1-((4bS,9bS)-4b-hydroxy-7-isopropyl-10-oxo-9b,10-dihydro-4bH-indeno[1,2-b]benzofuran-9b-yl-3-methoxyurea;
104) 5-acetyl-4b,9b-dihydroxy-7,8-dimethyl-4b,5-dihydroindeno[1,2-b]indol-10(9bH)-one;
105) 4b,9b-dihydroxy-7,8-dimethyl-5-propionyl-4b,5-dihydroindeno[1,2-b]indol-10(9bH)-one;
106) 4b,9b-dihydroxy-7,8-dimethyl-4b,5-dihydroindeno[1,2-b]indol-10(9bH)-one;
107) 5-acetyl-7,8-dimethyl-10-oxo-4b,5,9b,10-tetrahydroindeno[1,2-b]indole-4b,9b-diyl diacetate;
108) 5-acetyl-9b-amino-4b-hydroxy-5,9b-dihydro-4bH-indeno[1,2-b]indol-10-one;
109) N-(9b-amino-4b-hydroxy-7-isopropyl-4-nitro-10-oxo-9b,10-dihydro-4bH-5-oxa-indeno[2,1-a]inden-1-yl)-acetamide;
110) acetic acid 1,9b-bis-acetylamino-7-isopropyl-4-nitro-10-oxo-9b,10-dihydro-5-oxa-indeno[2,1-a]inden-4b-yl ester;
111) 9b-acetamido-7-isopropyl-10-oxo-9b,10-dihydro-4bH-indeno[1,2-b]benzofuran-4b-yl methyl carbonate;
112) 9b-acetamido-7-isopropyl-10-oxo-9b,10-dihydro-4bH-indeno[1,2-b]benzofuran-4b-yl pentanoate;
113) 9b-acetamido-1-amino-7-isopropyl-10-oxo-9b,10-dihydro-4bH-indeno[1,2-b]benzofuran-4b-yl methyl carbonate;
114) N-(1-amino-4b-hydroxy-7-isopropyl-10-oxo-9b,10-dihydro-4bH-benzo[d]indeno[1,2-b]furan-9b-yl)pivalamide;

115) 9b-acetamido-1-amino-7-isopropyl-10-oxo-9b,10-dihydro-4bH-benzo[d]indeno[1,2-b]furan-4b-yl butyl carbonate;
116) 9b-acetamido-7-isopropyl-10-oxo-9b,10-dihydro-4bH-benzo[d]indeno[1,2-b]furan-4b-yl ethyl carbonate;
117) 9b-acetamido-7-isopropyl-10-oxo-9b,10-dihydro-4bH-benzo[d]indeno[1,2-b]furan-4b-yl pivalate;
118) 9b-acetamido-7-isopropyl-10-oxo-9b,10-dihydro-4bH-benzo[d]indeno[1,2-b]furan-4b-yl methylcarbamate;
119) N,N'-(7-isopropyl-10-oxo-9b,10-dihydro-4bH-indeno[1,2-b]benzofurane-4b,9b-diyl)diacetamide;
120) 4b-(benzyloxy)-9b-hydroxy-7-isopropyl-4bH-indeno[1,2-b]benzofuran-10(9bH)-one;
121) carbonic acid 9b-acetylamino-7-isopropyl-10-oxo-9b,10-dihydro-5-oxa-indeno[2,1-a]inden-4b-yl ester phenyl ester;
122) phenyl-thiocarbamic acid O-(9b-azido-7-isopropyl-10-oxo-9b,10-dihydro-5-oxa-indeno[2,1-a]inden-4b-yl ester;
123) 9b-acetamido-1-amino-7-isopropyl-10-oxo-9b,10-dihydro-4bH-benzo[d]indeno[1,2-b]furan-4b-yl ethyl carbonate;
124) N,N'-(7-isopropyl-10-oxo-9b,10-dihydro-4bH-indeno[1,2-b]benzofurane-4b,9b-diyldipropionamide;
125) N,N'-(7-isopropyl-10-oxo-9b,10-dihydro-4bH-indeno[1,2-b]benzofurane-4b,9b-diylbis(2-methylpropanamide);
126) 4b,9b-dihydroxy-7-isopropyl-4bH-benzofuro[2',3':3,4]cyclopenta[1,2-b]pyridin-10(9bH)-one;
127) 10-hydroxy-7-isopropyl-9b,10-dihydro-4bH-indeno[1,2-b]benzofurane-4b,9b-diyl diacetate;
128) 9b-hydroxy-7-isopropyl-4b-(methoxyamino)-4bH-indeno[1,2-b]benzofuran-10(9bH)-one O-methyl oxime;
129) 7-isopropyl-4b-methoxy-10-methylene-9b,10-dihydro-4bH-indeno[1,2-b]benzofuran-9b-ol;
130) 9b-hydroxy-7-isopropyl-4b-methoxy-4bH-indeno[1,2-b]benzofuran-10(9bH)-one O-methyl oxime;
131) a mixture of 1-bromo and 4-bromo-4b,9b-dihydroxy-7-isopropyl-4bH-indeno[1,2-b]benzofuran-10(9bH)-one;
132) 1-(benzylamino)-4b,9b-dihydroxy-7-isopropyl-4bH-indeno[1,2-b]benzofuran-10(9bH)-one;
133) 1-(ethylamino)-4b,9b-dihydroxy-7-isopropyl-4bH-indeno[1,2-b]benzofuran-10(9bH)-one;
134) 9b-hydroxy-7-isopropyl-4b-methyl-4bH-indeno[1,2-b]benzofuran-10(9bH)-one;
135) 4b,9b-dihydroxy-5-isobutyryl-7,8-dimethyl-4b,5-dihydroindeno[1,2-b]indol-10(9bH)-one;
136) 7-isopropyl-10-methyl-9b,10-dihydro-4bH-indeno[1,2-b]benzofuran-4b,9b-diol;
137) N-(1-bromo-4b-hydroxy-7-isopropyl-10-oxo-9b,10-dihydro-4bH-indeno[1,2-b]benzofuran-9b-yl)acetamide;
138) 4b,9b-dihydroxy-5-isobutyryl-7,8-dimethoxy-5,9b-dihydro-4bH-indeno[1,2-b]indol-10-one;
139) 4b,9b-dihydroxy-7-isopropyl-2-piperidinyl-4bH-benzo[d]indeno[1,2-b]furan-10(9bH)-one;
140) 4b,9b-dihydroxy-7-isopropyl-2-morpholinyl-4bH-benzo[d]indeno[1,2-b]furan-10(9bH)-one;
141) 4b,9b-dihydroxy-7-isopropyl-1-piperidinyl-4bH-benzo[d]indeno-[1,2-b]furan-10(9bH)-one;
142) 4b,9b-dihydroxy-7-isopropyl-1-morpholinyl-4bH-benzo[d]indeno[1,2-b]furan-10(9bH)-one;
143) N-(1-amino-4b-hydroxy-7-isopropyl-10-oxo-9b,10-dihydro-4bH-indeno[1,2-b]benzofuran-9b-yl)propionamide;
144) N-(1-amino-4b-hydroxy-7-isopropyl-10-oxo-9b,10-dihydro-4bH-indeno[1,2-b]benzofuran-9b-yl)butyramide;
145) 4b,9b-dihydroxy-5-isobutyryl-7-isopropyl-5,9b-dihydro-4bH-indeno[1,2-b]indol-10-one;
146) 4b,9b-dihydroxy-7-isopropyl-2-(hydroxypiperidinyl)-4bH-benzo[d]indeno[1,2-b]furan-10(9bH)-one;
147) 4b,9b-dihydroxy-1-(4-hydroxypiperidin-1-yl)-7-isopropyl-4bH-benzo[d]indeno[1,2-b]furan-10(9bH)-one;
148) 4b,9b-dihydroxy-7-isopropyl-2-(4-(4-methoxybenzyl)piperazin-1-yl)-4bH-benzo[d]indeno[1,2-b]furan-10 (9bH)-one;
149) 4b,9b-dihydroxy-7-isopropyl-1-(4-(4-methoxybenzyl)piperazin-1-yl)-4bH-benzo[d]indeno[1,2-b]furan-10 (9bH)-one;
150) 2-(dimethylamino)-4b,9b-dihydroxy-7-isopropyl-4bH-benzo[d]indeno[1,2-b]-furan-10(9bH)-one;
151) 1-(dimethylamino)-4b,9b-dihydroxy-7-isopropyl-4bH-benzo[d]indeno[1,2-b]-furan-10(9bH)-one;
152) 10-hydrazono-7-isopropyl-9b,10-dihydro-4bH-benzo[d]indeno[1,2-b]furan-4b,9b-diol;
153) N-(1-amino-4b-hydroxy-7-isopropyl-10-oxo-9b,10-dihydro-4bH-indeno[1,2-b]benzofuran-9b-yl)benzamide;
154) N-(1-amino-4b-hydroxy-7-isopropyl-10-oxo-9b,10-dihydro-4bH-indeno[1,2-b]benzofuran-9b-yl)-3-methoxybenzamide;
155) N-(1-amino-4b-hydroxy-7-isopropyl-10-oxo-9b,10-dihydro-4bH-indeno[1,2-b]benzofuran-9b-yl)-4-chlorobenzamide;
156) N-(1-amino-4b-hydroxy-7-isopropyl-10-oxo-9b,10-dihydro-4bH-indeno[1,2-b]benzofuran-9b-yl)-4-nitrobenzamide;
157) 1-amino-4b,9b-dihydroxy-6,8-diisopropyl-4 bH-benzo[d]indeno[1,2-b]furan-10(9bH)-one;
158) N-(1-amino-4b-hydroxy-7-isopropyl-10-oxo-9b,10-dihydro-4bH-indeno[1,2-b]benzofuran-9b-yl)cyclopropanecarboxamide;
159) 1-(4b-hydroxy-6,8-diisopropyl-1-amino-10-oxo-9b,10-dihydro-4bH-benzo[d]-indeno[1,2-b]furan-9b-yl)-3-(4-methoxyphenyl)thiourea;
160) 1-(4b-hydroxy-6,8-diisopropyl-1-amino-10-oxo-9b,10-dihydro-4bH-benzo[d]-indeno[1,2-b]furan-9b-yl)-3-(phenyl)thiourea;
161) N-(4b-hydroxy-7-isopropyl-10-oxo-9b,10-dihydro-4bH-indeno[1,2-b]benzofuran-9b-yl)thiophene-2-carboxamide;
162) 1-(1-amino-4b-hydroxy-7-isopropyl-10-oxo-9b,10-dihydro-4bH-indeno[1,2-b]benzofuran-9b-yl)-3-(4-methoxyphenyl)urea;
163) 1-(1-amino-4b-hydroxy-7-isopropyl-10-oxo-9b,10-dihydro-4bH-indeno[1,2-b]benzofuran-9b-yl)-3-butylurea;
164) 1-(1-amino-4b-hydroxy-7-isopropyl-10-oxo-9b,10-dihydro-4bH-indeno[1,2-b]benzofuran-9b-yl)-3-(4-fluorophenyl)urea;
165) 1-(1-amino-4b-hydroxy-7-isopropyl-10-oxo-9b,10-dihydro-4bH-indeno[1,2-b]benzofuran-9b-yl)-3-(tert-butyl)urea;
166) N-(1-amino-4b-hydroxy-7-isopropyl-10-oxo-9b,10-dihydro-4bH-indeno[1,2-b]benzofuran-9b-yl)formamide;
167) N-(1-formamido-4b-hydroxy-7-isopropyl-10-oxo-9b,10-dihydro-4bH-benzo[d]-indeno[1,2-b]furan-9b-yl)acetamide;
168) N-(1-amino-4b-hydroxy-7-isopropyl-10-oxo-9b,10-dihydro-4bH-benzo[d]indeno[1,2-b]furan-9b-yl)methanesulfonamide;
169) diethyl (1-amino-4b-hydroxy-7-isopropyl-10-oxo-9b,10-dihydro-4bH-indeno[1,2-b]furan-9b-yl)phosphoamidate;
170) N-(1-amino-4b-hydroxy-7-isopropyl-10-oxo-9b,10-dihydro-4bH-indeno[1,2-b]benzofuran-9b-yl)-4-cyanobenzamide;

171) N-(1-amino-4b-hydroxy-7-isopropyl-10-oxo-9b,10-dihydro-4bH-indeno[1,2-b]benzofuran-9b-yl)-2-naphthamide;
172) N-(1-amino-4b-hydroxy-7-isopropyl-10-oxo-9b,10-dihydro-4bH-indeno[1,2-b]benzofuran-9b-yl)-[1,1'-biphenyl]-4-carboxamide;
173) 1-(1-amino-4b-hydroxy-7-isopropyl-10-oxo-9b,10-dihydro-4bH-benzo[d]indeno[1,2-b]furan-9b-yl)-3-ethylurea;
174) N-(1-amino-4b-hydroxy-7-isopropyl-10-oxo-9b,10-dihydro-4bH-benzo[d]indeno[1,2-b]furan-9b-yl)tetrahydrofurane-2-carboxamide;
175) N-(1-amino-4b-hydroxy-7-isopropyl-10-oxo-9b,10-dihydro-4bH-indeno[1,2-b]benzofuran-9b-yl)-2,2,2-trifluoroacetamide;
176) N-(1-amino-4b-hydroxy-7-isopropyl-10-oxo-9b,10-dihydro-4bH-benzo[d]indeno[1,2-b]furan-9b-yl)-1,1,1-trifluoromethanesulfonamide;
177) N-(4b-hydroxy-7-isopropyl-10-oxo-9b,10-dihydro-4bH-indeno[1,2-b]benzofuran-9b-yl)formamide;
178) 1,1,1-trifluoro-N-(4b-hydroxy-10-oxo-9b,10-dihydro-4bH-benzo[d]indeno[1,2-b]furan-9b-yl)methanesulfonamide;
179) N-(1-amino-4b-hydroxy-7-isopropyl-10-oxo-9b,10-dihydro-4bH-indeno[1,2-b]benzofuran-9b-yl)-2-phenylacetamide;
180) (E)-N-(1-amino-4b-hydroxy-7-isopropyl-10-oxo-9b,10-dihydro-4bH-indeno[1,2-b]benzofuran-9b-yl)-3-(3,4-dichlorophenyl)acrylamide;
181) N-(1-amino-4b-hydroxy-7-isopropyl-10-oxo-9b,10-dihydro-4bH-indeno[1,2-b]benzofuran-9b-yl)-4-(benzyloxy)benzamide;
182) 2-([1,1-biphenyl]-4-yl)-N-(1-amino-4b-hydroxy-7-isopropyl-10-oxo-9b,10-dihydro-4bH-indeno[1,2-b]benzofuran-9b-yl)acetamide;
183) N-(1-amino-4b-hydroxy-7-isopropyl-10-oxo-9b,10-dihydro-4bH-indeno[1,2-b]benzofuran-9b-yl)-2-methoxybenzamide;
184) tert-butyl(2R)-1-(4b-hydroxy-7-isopropyl-10-oxo-9b,10-dihydro-4bH-benzo[d]indeno[1,2-b]furan-9b-ylamino)-1-oxopropan-2-ylcarbamate;
185) tert-butyl(2R)-1-(4b-hydroxy-7-isopropyl-10-oxo-9b,10-dihydro-4bH-benzo[d]indeno[1,2-b]furan-9b-ylamino)-1-oxo-3-phenylpropan-2-ylcarbamate;
186) N-(1-amino-4b-hydroxy-7-isopropyl-10-oxo-9b,10-dihydro-4bH-benzo[d]indeno[1,2-b]furan-9b-yl)-2-methylbenzamide;
187) N-(1-amino-4b-hydroxy-7-isopropyl-10-oxo-9b,10-dihydro-4bH-benzo[d]indeno[1,2-b]furan-9b-yl)-3-methylbenzamide;
188) N-(1-amino-4b-hydroxy-7-isopropyl-10-oxo-9b,10-dihydro-4bH-benzo[d]indeno[1,2-b]furan-9b-yl)-4-methylbenzamide;
189) methyl-4-(1-amino-4b-hydroxy-7-isopropyl-10-oxo-9b,10-dihydro-4bH-benzo[d]indeno[1,2-b]furan-9b-ylcarbamoyl)benzoate;
190) N-(1-amino-4b-hydroxy-7-isopropyl-10-oxo-9b,10-dihydro-4bH-indeno[1,2-b]benzofuran-9b-yl)-3-chlorobenzamide;
191) N-(1-amino-4b-hydroxy-7-isopropyl-10-oxo-9b,10-dihydro-4bH-indeno[1,2-b]benzofuran-9b-yl)-3,5-dimethylbenzamide;
192) N-(1-amino-4b-hydroxy-7-isopropyl-10-oxo-9b,10-dihydro-4bH-indeno[1,2-b]benzofuran-9b-yl)-2,4,6-trichlorobenzamide;
193) N-(1-amino-4b-hydroxy-7-isopropyl-10-oxo-9b,10-dihydro-4bH-benzo[d]indeno[1,2-b]furan-9b-yl)-2-fluoroacetamide;
194) N-(1-amino-4b-hydroxy-7-isopropyl-10-oxo-9b,10-dihydro-4bH-benzo[d]indeno[1,2-b]furan-9b-yl)-2-chloroacetamide;
195) N-(1-amino-4b-hydroxy-7-isopropyl-10-oxo-9b,10-dihydro-4bH-benzo[d]indeno[1,2-b]furan-9b-yl)-2,2-dichloroacetamide;
196) 1-amino-9b-(4-butyl-1H-1,2,3-triazol-1-yl)-4b-hydroxy-7-iso propy-4bH-indeno[1,2-b]benzofuran-10(9bH)-one;
197) N-(1-amino-4b-hydroxy-7-isopropyl-10-oxo-9b,10-dihydro-4bH-indeno[1,2-b]benzofuran-9b-yl)picolinamide;
198) N-(1-amino-4b-hydroxy-7-isopropyl-10-oxo-9b,10-dihydro-4bH-indeno[1,2-b]benzofuran-9b-yl)nicotinamide;
199) N-(1-amino-4b-hydroxy-7-isopropyl-10-oxo-9b,10-dihydro-4bH-indeno[1,2-b]benzofuran-9b-yl)isonicotinamide;
200) N-(1-amino-4b-hydroxy-7-isopropyl-10-oxo-9b,10-dihydro-4bH-indeno[1,2-b]benzofuran-9b-yl)pirazine-2-carboxamide;
201) N-(1-amino-4b-hydroxy-7-isopropyl-10-oxo-9b,10-dihydro-4bH-indeno[1,2-b]benzofuran-9b-yl)furane-2-carboxamide;
202) N-(1-amino-4b-hydroxy-7-isopropyl-10-oxo-9b,10-dihydro-4bH-indeno[1,2-b]benzofuran-9b-yl)quinoline-8-carboxamide;
203) N-(1-amino-4b-hydroxy-7-isopropyl-10-oxo-9b,10-dihydro-4bH-indeno[1,2-b]benzofuran-9b-yl)quinoline-6-carboxamide;
204) N-(1-amino-4b-hydroxy-7-isopropyl-10-oxo-9b,10-dihydro-4bH-benzo[d]indeno[1,2-b]furan-9b-yl) benzofurane-2-carboxamide;
205) N-(1-amino-4b-hydroxy-7-isopropyl-10-oxo-9b,10-dihydro-4bH-benzo[d]indeno[1,2-b]furan-9b-yl)-3-methylbenzofurane-2-carboxamide;
206) N-(1-amino-4b-hydroxy-7-isopropyl-10-oxo-9b,10-dihydro-4bH-indeno[1,2-b]benzofuran-9b-yl)-4-methylthiazole-5-carboxamide;
207) (4R)—N-(1-amino-4b-hydroxy-7-isopropyl-10-oxo-9b,10-dihydro-4bH-indeno[1,2-b]benzofuran-9b-yl)-2-oxothiazolidine-4-carboxamide;
208) N-(4b-hydroxy-7-isopropyl-10-oxo-9b,10-dihydro-4bH-indeno[1,2-b]benzofuran-9b-yl)-1H-indole-2-carboxamide;
209) N-(4b-hydroxy-7-isopropyl-10-oxo-9b,10-dihydro-4bH-indeno[1,2-b]benzofuran-9b-yl)-1H-indole-3-carboxamide;
210) N-(4b-hydroxy-7-isopropyl-10-oxo-9b,10-dihydro-4bH-indeno[1,2-b]benzofuran-9b-yl)formamide;
211) N-(4b-hydroxy-7-isopropyl-10-oxo-9b,10-dihydro-4bH-indeno[1,2-b]benzofuran-9b-yl)-1-phenyl-5-(trifluoromethyl)-1H-pyrazole-4-carboxamide;
212) N-(1-amino-4b-hydroxy-7-isopropyl-10-oxo-9b,10-dihydro-4bH-benzo[d]indeno[1,2-b]furan-9b-yl)-1H-indazole-3-carboxamide;
213) N-(1-amino-4b-hydroxy-7-isopropyl-10-oxo-9b,10-dihydro-4bH-benzo[d]indeno[1,2-b]furan-9b-yl)-2-(1H-tetrazol-1-yl)acetamide;
214) N-(1-amino-4b-hydroxy-7-isopropyl-10-oxo-9b,10-dihydro-4bH-indeno[1,2-b]benzofuran-9b-yl)quinoline-3-carboxamide;
215) N-(1-amino-4b-hydroxy-7-isopropyl-10-oxo-9b,10-dihydro-4bH-indeno[1,2-b]benzofuran-9b-yl)quinoline-4-carboxamide;

216) N-(1-amino-4b-hydroxy-7-isopropyl-10-oxo-9b,10-dihydro-4bH-indeno[1,2-b]benzofuran-9b-yl)-5-methylthiophene-2-carboxamide;
217) N-(1-amino-4b-hydroxy-7-isopropyl-10-oxo-9b,10-dihydro-4bH-indeno[1,2-b]benzofuran-9b-yl)-2-methoxythiophene-3-carboxamide;
218) N-(4b-hydroxy-7-isopropyl-10-oxo-9b,10-dihydro-4bH-indeno[1,2-b]benzofuran-9b-yl)picolinamide;
219) N-(4b-hydroxy-7-isopropyl-10-oxo-9b,10-dihydro-4bH-indeno[1,2-b]benzofuran-9b-yl)pyrimidine-4-carboxamide;
220) N-(4b-hydroxy-7-isopropyl-10-oxo-9b,10-dihydro-4bH-benzo[d]indeno[1,2-b]furan-9b-yl)-2-(1H-tetrazol-5-yl)acetamide;
221) N-(4b-hydroxy-7-isopropyl-10-oxo-9b,10-dihydro-4bH-benzo[d]indeno[1,2-b]furan-9b-yl)-1H-benzo[d][1,2,3]triazole-5-carboxamide;
222) N-(4b-hydroxy-7-isopropyl-10-oxo-9b,10-dihydro-4bH-benzo[d]indeno[1,2-b]furan-9b-yl)-1H-1,2,4-triazole-3-carboxamide;
223) N-(4b-hydroxy-7-isopropyl-10-oxo-9b,10-dihydro-4bH-benzo[d]indeno[1,2-b]furan-9b-yl)-5-nitrothiophene-2-carboxamide;
224) N-(4b-hydroxy-7-isopropyl-10-oxo-9b,10-dihydro-4bH-benzo[d]indeno[1,2-b]furan-9b-yl)-2,6-dioxo-1,2,3,6-tetrahydropyrimidine-4-carboxamide;
225) N-(4b-hydroxy-7-isopropyl-10-oxo-9b,10-dihydro-4bH-benzo[d]indeno[1,2-b]furan-9b-yl)-2-oxo-2H-chromene-3-carboxamide;
226) N-(4b-hydroxy-7-isopropyl-10-oxo-9b,10-dihydro-4bH-benzo[d]indeno[1,2-b]furan-9b-yl)-2-oxo-2H-pyrane-5-carboxamide;
227) N-(4b-hydroxy-7-isopropyl-10-oxo-9b,10-dihydro-4bH-benzo[d]indeno[1,2-b]furan-9b-yl)-1H-benzo[d]imidazole-2-carboxamide;
228) N-(1-amino-4b-hydroxy-7-isopropyl-10-oxo-9b,10-dihydro-4bH-indeno[1,2-b]benzofuran-9b-yl)-3-(2-chloro-6-fluorophenyl)-5-methylisooxazole-4-carboxamide;
229) N-(4b-hydroxy-7-isopropyl-10-oxo-9b,10-dihydro-4bH-indeno[1,2-b]benzofuran-9b-yl)-3-phenyl-1H-pyrazole-5-carboxamide;
230) N-(4b-hydroxy-7-isopropyl-10-oxo-9b,10-dihydro-4bH-indeno[1,2-b]benzofuran-9b-yl)nicotinamide;
231) N-(1-amino4b-hydroxy-7-isopropyl-10-oxo-9b,10-dihydro-4bH-indeno[1,2-b]benzofuran-9b-yl)-2-oxo-2-(thiophen-2-yl)acetamide;
232) 5-amino-N-(1-amino-4b-hydroxy-7-isopropyl-10-oxo-9b,10-dihydro-4bH-indeno[1,2-b]benzofuran-9b-yl)furane-2-carboxamide;
233) N-(1-amino-4b-hydroxy-7-isopropyl-10-oxo-9b,10-dihydro-4bH-indeno[1,2-b]benzofuran-9b-yl)-1H-pyrrole-2-carboxamide;
234) N-(1-amino-4b-hydroxy-7-isopropyl-10-oxo-9b,10-dihydro-4bH-indeno[1,2-b]benzofuran-9b-yl)-2-methoxyisonicotinamide;
235) N-(1-amino-4b-hydroxy-7-isopropyl-10-oxo-9b,10-dihydro-4bH-benzo[d]indeno[1,2-b]furan-9b-yl)benzo[b]thiophene-2-carboxamide;
236) 3-(2,6-dichlorophenyl)-N-(4b-hydroxy-7-isopropyl-10-oxo-9b,10-dihydro-4bH-benzo[d]indeno[1,2-b]furan-9b-yl)-5-methylisooxazole-4-carboxamide;
237) N-(1-amino-4b-hydroxy-7-isopropyl-10-oxo-9b,10-dihydro-4bH-benzo[d]indeno[1,2-b]furan-9b-yl)-9H-xanthene-9-carboxamide;
238) N-(1-amino-4b-hydroxy-7-isopropyl-10-oxo-9b,10-dihydro-4bH-benzo[d]indeno[1,2-b]furan-9b-yl)cinnoline-4-carboxamide;
239) N-(4b-hydroxy-7-isopropyl-10-oxo-9b,10-dihydro-4bH-benzo[d]indeno[1,2-b]furan-9b-yl)cinnoline-4-carboxamide;
240) N-(4b-hydroxy-7-isopropyl-10-oxo-9b,10-dihydro-4bH-benzo[d]indeno[1,2-b]furan-9b-yl)-1H-benzo[d]imidazole-5-carboxamide;
241) N-(1-amino-4b-hydroxy-7-isopropyl-10-oxo-9b,10-dihydro-4bH-benzo[d]indeno[1,2-b]furan-9b-yl)acridine-9-carboxamide;
242) N-(1-amino-4b-hydroxy-7-isopropyl-10-oxo-9b,10-dihydro-4bH-benzo[d]indeno[1,2-b]furan-9b-yl)-4-nitro-1H-pyrazole-3-carboxamide;
243) N-(1-amino-4b-hydroxy-7-isopropyl-10-oxo-9b,10-dihydro-4bH-benzo[d]indeno[1,2-b]furan-9b-yl)-4-methylpicolinamide;
244) N-(1-amino-4b-hydroxy-7-isopropyl-10-oxo-9b,10-dihydro-4bH-benzo[d]indeno[1,2-b]furan-9b-yl)-4-(trifluoromethyl)picolinamide;
245) N-(1-amino-4b-hydroxy-7-isopropyl-10-oxo-9b,10-dihydro-4bH-benzo[d]indeno[1,2-b]furan-9b-yl)-5-cyanopicolinamide;
246) N-(1-amino-4b-hydroxy-7-isopropyl-10-oxo-9b,10-dihydro-4bH-benzo[d]indeno[1,2-b]furan-9b-yl)-3-chloropicolinamide;
247) N-(1-amino-4b-hydroxy-7-isopropyl-10-oxo-9b,10-dihydro-4bH-benzo[d]indeno[1,2-b]furan-9b-yl)-4-methoxyquinoline-2-carboxamide;
248) N-(1-amino-4b-hydroxy-7-isopropyl-10-oxo-9b,10-dihydro-4bH-indeno[1,2-b]benzofuran-9b-yl)isoquinoline-3-carboxamide;
249) N-(1-amino-4b-hydroxy-7-isopropyl-10-oxo-9b,10-dihydro-4bH-indeno[1,2-b]benzofuran-9b-yl)-2-methylisonicotinamide;
250) N-(1-amino-4b-hydroxy-7-isopropyl-10-oxo-9b,10-dihydro-4bH-indeno[1,2-b]benzofuran-9b-yl)-3-fluoroisonicotinamide;
251) N-(1-amino-4b-hydroxy-7-isopropyl-10-oxo-9b,10-dihydro-4bH-indeno[1,2-b]benzofuran-9b-yl)-3-chloroisonicotinamide;
252) N-(1-amino-4b-hydroxy-7-isopropyl-10-oxo-9b,10-dihydro-4bH-indeno[1,2-b]benzofuran-9b-yl)-1-methyl-1H-imidazole-2-carboxamide;
253) 2-((1-amino-4b-hydroxy-7-isopropyl-10-oxo-9b,10-dihydro-4bH-indeno[1,2-b]benzofuran-9b-yl)carbamoyl)pyridine 1-oxide;
254) N-(1-amino-4b-hydroxy-7-isopropyl-10-oxo-9b,10-dihydro-4bH-indeno[1,2-b]benzofuran-9b-yl)-4-chloronicotinamide;
255) N-(1-amino-4b-hydroxy-7-isopropyl-10-oxo-9b,10-dihydro-4bH-indeno[1,2-b]benzofuran-9b-yl)-5-fluoronicotinamide;
256) N-(1-amino-4b-hydroxy-7-isopropyl-10-oxo-9b,10-dihydro-4bH-indeno[1,2-b]benzofuran-9b-yl)-5-hydroxynicotinamide;
257) N-(1-amino-4b-hydroxy-7-isopropyl-10-oxo-9b,10-dihydro-4bH-indeno[1,2-b]benzofuran-9b-yl)-3-hydroxypicolinamide;
258) N-(1-amino-4b-hydroxy-7-isopropyl-10-oxo-9b,10-dihydro-4bH-indeno[1,2-b]benzofuran-9b-yl)-4-methylnicotinamide;
259) N-(1-amino-4b-hydroxy-7-isopropyl-10-oxo-9b,10-dihydro-4bH-indeno[1,2-b]benzofuran-9b-yl)-5-methylnicotinamide;
260) N-(1-amino-4b-hydroxy-7,8-dimethyl-10-oxo-9b,10-dihydro-4bH-indeno[1,2-b]benzofuran-9b-yl)nicotinamide;

261) N-(1-amino-4b-hydroxy-7-isopropyl-10-oxo-9b,10-dihydro-4bH-indeno[1,2-b]benzofuran-9b-yl)-5-methoxynicotinamide;
262) N-(1-amino-4b-hydroxy-7,8-dimethyl-10-oxo-9b,10-dihydro-4bH-indeno[1,2-b]benzofuran-9b-yl)quinoline-6-carboxamide;
263) N-(1-amino-4b-hydroxy-7-isopropyl-10-oxo-9b,10-dihydro-4bH-benzo[d]indeno[1,2-b]furan-9b-yl)quinoline-2-carboxamide;
264) N-(1-amino-4b-hydroxy-7-isopropyl-10-oxo-9b,10-dihydro-4bH-benzo[d]indeno[1,2-b]furan-9b-yl)-3-bromobenzo[b]thiophene-2-carboxamide;
265) N-(1-amino-4b-hydroxy-7-isopropyl-10-oxo-9b,10-dihydro-4bH-benzo[d]indeno[1,2-b]furan-9b-yl)-1H-indole-2-carboxamide;
266) N-(1-amino-4b-hydroxy-7-isopropyl-10-oxo-9b,10-dihydro-4bH-benzo[d]indeno[1,2-b]furan-9b-yl)isoquinoline-1-carboxamide;
267) N-(1-amino-4b-hydroxy-7-isopropyl-10-oxo-9b,10-dihydro-4bH-indeno[1,2-b]benzofuran-9b-yl)-6-fluoro-4-methoxyquinoline-3-carboxamide;
268) N-(1-amino-4b-hydroxy-7-isopropyl-10-oxo-9b,10-dihydro-4bH-indeno[1,2-b]benzofuran-9b-yl)-1-methyl-1H-indole-2-carboxamide;
269) N-(1-amino-4b-hydroxy-7-isopropyl-10-oxo-9b,10-dihydro-4bH-indeno[1,2-b]benzofuran-9b-yl)-3-chloro-6-fluorobenzo[b]thiophene-2-carboxamide;
270) N-(1-amino-4b-hydroxy-7-isopropyl-10-oxo-9b,10-dihydro-4bH-indeno[1,2-b]benzofuran-9b-yl)-3-chloro-6-methylbenzo[b]thiophene-2-carboxamide;
271) N-(1-amino-4b-hydroxy-7-isopropyl-10-oxo-9b,10-dihydro-4bH-indeno[1,2-b]benzofuran-9b-yl)-1,3-dimethyl-1H-pyrazolo[3,4-b]pyridine-5-carboxamide;
272) N-(1-amino-4b-hydroxy-7-isopropyl-10-oxo-9b,10-dihydro-4bH-indeno[1,2-b]benzofuran-9b-yl)imidazo[1,2-a]pyridine-6-carboxamide;
273) N-(1-amino-4b-hydroxy-7-isopropyl-10-oxo-9b,10-dihydro-4bH-indeno[1,2-b]benzofuran-9b-yl)pyrazolo[1,5-a]pyrimidine-2-carboxamide;
274) N-(1-amino-4b-hydroxy-7-isopropyl-10-oxo-9b,10-dihydro-4bH-indeno[1,2-b]benzofuran-9b-yl)-3-methyl benzo[b]thiophene-2-carboxamide;
275) N-(1-amino-4b-hydroxy-7-isopropyl-10-oxo-9b,10-dihydro-4bH-indeno[1,2-b]benzofuran-9b-yl)quinoxaline-2-carboxamide;
276) N-(1-amino-4b-hydroxy-7-isopropyl-10-oxo-9b,10-dihydro-4bH-indeno[1,2-b]benzofuran-9b-yl)pyridazine-4-carboxamide;
277) N-(1-amino-4b-hydroxy-7-isopropyl-10-oxo-9b,10-dihydro-4bH-indeno[1,2-b]benzofuran-9b-yl)quinoxaline-6-carboxamide;
278) N-(1-amino-4b-hydroxy-7-isopropyl-10-oxo-9b,10-dihydro-4bH-indeno[1,2-b]benzofuran-9b-yl)tetrazolo[1,5-a]pyridine-6-carboxamide;
279) N-(1-amino-4b-hydroxy-7-isopropyl-10-oxo-9b,10-dihydro-4bH-indeno[1,2-b]benzofuran-9b-yl)tetrazolo[1,5-a]pyridine-8-carboxamide;
280) N-(1-amino-4b-hydroxy-7-isopropyl-10-oxo-9b,10-dihydro-4bH-indeno[1,2-b]benzofuran-9b-yl)-7-methylimidazo[1,2-a]pyridine-2-carboxamide;
281) N-(1-amino-4b-hydroxy-7-isopropyl-10-oxo-9b,10-dihydro-4bH-indeno[1,2-b]benzofuran-9b-yl)-7-methyl-[1,2,4]triazolo[1,5-a]pyrimidine-2-carboxamide;
282) N-(1-amino-4b-hydroxy-7-isopropyl-10-oxo-9b,10-dihydro-4bH-indeno[1,2-b]benzofuran-9b-yl)-5,7-dimethylpyrazolo[1,5-a]pyrimidine-3-carboxamide;
283) N-(1-amino-4b-hydroxy-7-isopropyl-10-oxo-9b,10-dihydro-4bH-indeno[1,2-b]benzofuran-9b-yl)indolizine-2-carboxamide;
284) N-(1-amino-4b-hydroxy-7-isopropyl-10-oxo-9b,10-dihydro-4bH-indeno[1,2-b]benzofuran-9b-yl)-1,6-diisopropyl-1H-pyrazolo[3,4-b]pyridine-4-carboxamide;
285) N-(1-amino-4b-hydroxy-7-isopropyl-10-oxo-9b,10-dihydro-4bH-indeno[1,2-b]benzofuran-9b-yl)imidazo[1,2-a]pyrimidine-2-carboxamide;
286) N-(1-amino-4b-hydroxy-7-isopropyl-10-oxo-9b,10-dihydro-4bH-indeno[1,2-b]benzofuran-9b-yl)-1-oxo-1,2-dihydroisoquinoline-3-carboxamide;
287) N-(1-amino-4b-hydroxy-7-isopropyl-10-oxo-9b,10-dihydro-4bH-benzo[d]indeno[1,2-b]furan-9b-yl)-3-methyl-imidazo[1,5-a]pyridine-1-carboxamide;
288) N-(1-amino-4b-hydroxy-7-isopropyl-10-oxo-9b,10-dihydro-4bH-benzo[d]indeno[1,2-b]furan-9b-yl)-2H-indazole-3-carboxamide;
289) N-(1-amino-4b-hydroxy-7-isopropyl-10-oxo-9b,10-dihydro-4bH-indeno[1,2-b]benzofuran-9b-yl)-7-methylpyrazolo[1,5-a]pyrimidine-6-carboxamide;
290) N-(1-amino-4b-hydroxy-7-isopropyl-10-oxo-9b,10-dihydro-4bH-indeno[1,2-b]benzofuran-9b-yl)-1H-benzo[d]imidazole-2-carboxamide;
291) N-(1-amino-4b-hydroxy-7-isopropyl-10-oxo-9b,10-dihydro-4bH-indeno[1,2-b]benzofuran-9b-yl)-5-fluoro-1H-benzo[d]imidazole-2-carboxamide;
292) N-(1-amino-4b-hydroxy-7-isopropyl-10-oxo-9b,10-dihydro-4bH-indeno[1,2-b]benzofuran-9b-yl)tetrazolo[1,5-a]pyridine-5-carboxamide;
293) N-(1-amino-4b-hydroxy-7-isopropyl-10-oxo-9b,10-dihydro-4bH-indeno[1,2-b]benzofuran-9b-yl)-1-methyl-1H-indazole-3-carboxamide;
294) N-(1-amino-4b-hydroxy-7-isopropyl-10-oxo-9b,10-dihydro-4bH-indeno[1,2-b]benzofuran-9b-yl)-1H-indole-5-carboxamide;
295) N-(1-amino-4b-hydroxy-7-isopropyl-10-oxo-b, O-dihydro-4bH-indeno[1,2-b]benzofuran-9b-yl)-1-methyl-3a,7a-dihydro-1H-indazole-3-carboxamide;
296) N-(1-amino-4b-hydroxy-7-isopropyl-10-oxo-9b,10-dihydro-4bH-indeno[1,2-b]benzofuran-9b-yl)-1-methyl-1H-imidazole-4-carboxamide;
297) N-(1-amino-4b-hydroxy-7-isopropyl-10-oxo-9b,10-dihydro-4bH-indeno[1,2-b]benzofuran-9b-yl)-1H-pyrrole-3-carboxamide;
298) tert-butyl(tert-butoxycarbonylamino)(4b-hydroxy-7-isopropyl-10-oxo-9b,10-dihydro-4bH-benzo[d]indeno[1,2-b]furan-9b-ylamino)methylenecarbamate;
299) N-(1-amino-4b-hydroxy-7-isopropyl-10-oxo-9b,10-dihydro-4bH-indeno[1,2-b]benzofuran-9b-yl)-1H-indazole-5-carboxamide;
300) N-(1-amino-4b-hydroxy-7-isopropyl-10-oxo-9b,10-dihydro-4bH-indeno[1,2-b]benzofuran-9b-yl)-3-methyl-1H-pyrazole-5-carboxamide;
301) 1-amino-9b-(furane-2-carboxamido)-7-methoxy-10-oxo-9b,10-dihydro-4bH-indeno[1,2-b]benzofuran-4b-yl furane-2-carboxylate;
302) N-(4b-hydroxy-7,8-dimethyl-10-oxo-9b,10-dihydro-4bH-indeno[1,2-b]benzofuran-9b-yl)nicotinamide;
303) N-(4b-hydroxy-7,8-dimethyl-10-oxo-9b,10-dihydro-4bH-indeno[1,2-b]benzofuran-9b-yl-1H-pyrrole-2-carboxamide;
304) N-(6-ethyl-4b-hydroxy-10-oxo-9b,10-dihydro-4bH-indeno[1,2-b]benzofuran-9b-yl)-1H-pyrrole-2-carboxamide;
305) N-(6-ethyl-4b-hydroxy-10-oxo-9b,10-dihydro-4bH-indeno[1,2-b]benzofuran-9b-yl)furane-2-carboxamide;

306) N-(8-chloro-4b-hydroxy-10-oxo-9b,10-dihydro-4bH-indeno[1,2-b]benzofuran-9b-yl)quinoline-4-carboxamide; and
307) N-(8-chloro-4b-hydroxy-10-oxo-9b,10-dihydro-4bH-indeno[1,2-b]benzofuran-9b-yl)tetrahydrofurane-2-carboxamide.

Preferred examples of the indanone derivative represented by Chemical Formula 1 are as follows: Compounds 29), 45)~47), 49)~63), 65)~67), 70)~75), 77)~78), and 87)~307).

More preferred examples of the indanone derivative represented by Chemical Formula include: Compounds 196)~207), 212)~217), 228), 231)~235), 237)~238), and 241)~307).

The indanone derivatives, represented by Chemical Formula 1, according to the present invention may be used in the form of pharmaceutical acceptable salts. Useful are acid addition salts formed with pharmaceutically acceptable free acids. As used herein, the term "pharmaceutically acceptable salt" refers to any organic or inorganic salt of the base compounds of Chemical Formula 1, not exhibiting a side effect in which the beneficial activity of the base compounds of Chemical Formula 1 is degraded when it is present at a concentration causing no toxicity and harm in the body. The free acids may be inorganic or organic. Examples of useful inorganic free acids include hydrochloric acid, bromic acid, nitric acid, sulfuric acid, perchloric acid and phosphoric acid. As organic acids, citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D)- or (L)-malic acid, maleic acid, methanesulfonic acid, ethanesulfonic acid, 4-toluenesulfonic acid, salicylic acid, benzoic acid, or malonic acid may be used. The pharmaceutically acceptable salts may include alkali metal salts (sodium salt, potassium salt, etc.) and alkaline earth metal salts (calcium salt, magnesium salt, etc.). Acid addition salts useful in the present invention include, but are not limited to, acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, alamine, potassium, sodium, tromethamine, and zinc salt, with hydrochloride or trifluoroacetate being preferred. Addition salts according to the present invention may be prepared by typical methods. For example, they may be prepared by dissolving the compound of Chemical Formula 1 in an organic solvent, such as methanol, ethanol, acetone, methylene chloride, or acetonitrile, and adding an excess of organic acids or an excess of aqueous inorganic acid solutions so as to precipitate or crystallize salts. These addition salts may be obtained by precipitation or crystallization, or by evaporating the solvent or excess acid and drying or suction-filtering the precipitated salt.

Also, pharmaceutically acceptable metal salts formed with bases may fall within the range of pharmaceutically acceptable salts of the compound of the present invention. Examples of the metal salts useful in the present invention include alkali metal salts and alkaline earth metal salts. By way of example, the compound of the present invention may be dissolved in excess alkali metal hydroxide or alkaline earth metal hydroxide in water, and, after the filtration of the solution to remove non-dissolved compound salts, the filtrate may be dried to afford the pharmaceutically acceptable salts of the compound of the present invention. Suitable for use in pharmaceutics are sodium, potassium or calcium salts. Corresponding silver salts may be obtained by reacting the alkali metal or alkaline earth metal salts with suitable silver salt (e.g., silver nitrate).

Not only the indanone derivatives of compound of Chemical Formula 1 and pharmaceutically acceptable salts thereof, but also solvates, hydrates and isomers prepared therefrom, if having the same effect, are within the scope of the present invention.

Also, the present invention is concerned with a method for the preparation of the indanone derivative according to the present invention. In one embodiment, the method comprises acylating or alkylating the compound of Chemical Formula 1 with a base in a solvent to afford a compound of Chemical Formula 1a (step 1), as illustrated in the following Reaction Scheme 1:

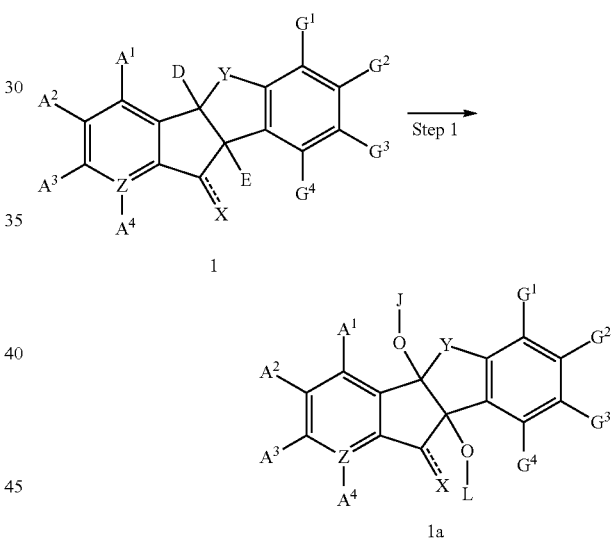

wherein,
the compound of Chemical Formula 1a is a derivative of the compound of Chemical Formula 1, a pharmaceutically acceptable salt thereof, or an enantiomer thereof,
$A^1$, $A^2$, $A^3$, $A^4$, D, E, $G^1$, $G^2$, $G^3$, $G^4$, X, Y, and Z are as defined in Chemical Formula 1, respectively,
J and L are, independently or optionally, the same as $A^1$, $A^2$, $A^3$, $A^4$, D, E, $G^1$, $G^2$, $G^3$, or $G^4$.

As the solvent useful in Reaction Scheme 1, diisopropylether, diethylether, dioxane, tetrahydrofurane (THF), dimethylformamide (DMF), dimethylacetamide (DMA), dimethylsulfoxide (DMSO), methylene chloride (MC), chlorobenzene, toluene, or benzene may be employed.

The base used in this reaction may be pyridine (PPTs), 4-dimethyl aminopyridine, trimethylamine, or ethylamine.

In another embodiment, the method comprises:
reacting the compound of Chemical Formula 1 with thionyl chloride or oxalic chloride in the presence of a base in a solvent and then with ammonia to give a compound of Chemical Formula 2 (step 1); and acylating or alkylating the compound of Chemical Formula 2 in the presence of a base in a solvent to afford a compound of Chemical Formula 1b (step 2), as illustrated in the following Reaction Scheme 2:

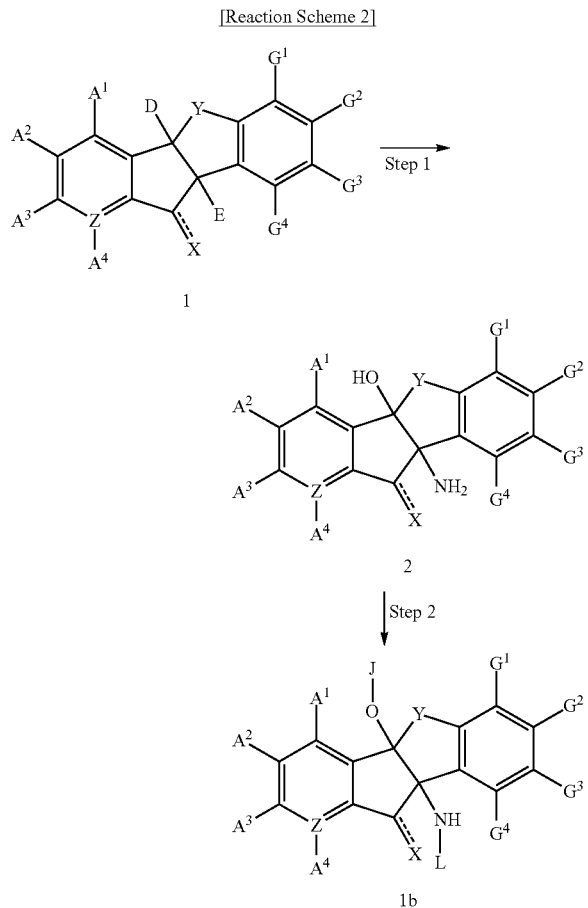

wherein, the compound of Chemical Formula 1b is a derivative of the compound of Chemical Formula 1, a pharmaceutically acceptable salt thereof, or an enantiomer thereof, $A^1$, $A^2$, $A^3$, $A^4$, D, E, $G^1$, $G^2$, $G^3$, $G^4$, X, Y, and Z are as defined in Chemical Formula 1, respectively, J and L are, independently or optionally, the same as $A^1$, $A^2$, $A^3$, $A^4$, D, E, $G^1$, $G^2$, $G^3$, or $G^4$.

The solvents used in steps 1 and 2 in Reaction Scheme 2 of this method may be, independently, selected from the group consisting of diisopropylether, diethylether, dioxane, tetrahydrofurane (THF), dimethylformamide (DMF), dimethylacetamide (DMA), dimethylsulfoxide (DMSO), methylene chloride (MC), chlorobenzene, toluene, and benzene.

As the base for the acylating or alkylating reaction in this method, pyridine (PPTs), trimethylamine, ethylamine, or triphosgene may be used.

Also contemplated in accordance with an aspect of the present invention is a pharmaceutical composition of the prevention or treatment of a viral disease, comprising an indanone derivative represented by Chemical Formula 1, a pharmaceutically acceptable salt thereof, or an enantiomer thereof as an active ingredient.

The viral disease that the pharmaceutical composition of the present invention targets is a disease caused by picornaviruses including coxsackie-, entero-, polio-, and rhinoviruses. Examples of the viral disease include poliomyelitis, paralysis, acute hemorrhagic conjunctivitis, viral meningitis, hand-foot-and-mouth disease, vesicular disease, hepatitis A, myositis, myocarditis, pancreatitis, epidemic myalgia, encephalitis, cold, herpangina, and foot-and-mouth disease.

Having excellent antiviral activity against picornaviruses such as coxsackie-, entero-, echo-, polio- and rhinoviruses as well as exhibiting low cytotoxicity, the indanone derivative of Chemical Formula 1 can be useful as an active ingredient of a pharmaceutical composition for the prevention or treatment of various viral diseases including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis, and otitis media.

Clinically, the compound of the present invention may be administered in the form of various formulations. For this, the compound is usually formulated in combination with a diluent or excipient, such as a filler, a thickening agent, a binder, a wetting agent, a disintegrant, a surfactant, etc.

Solid preparations intended for oral administration of the compound of the present invention may take the form of tablets, pills, powders, granules, capsules, troches, and the like. These solid preparations are formulated in combination with at least one excipient such as starch, calcium carbonate, sucrose, lactose, or gelatine. In addition to a simple excipient, a lubricant such as magnesium stearate, talc, or the like may also be added. Liquid preparations intended for oral administration include suspensions, internal use solutions, emulsion, syrups, and the like. In addition to a simple diluent such as water or liquid paraffin, various excipients, such as wetting agents, sweetening agents, aromatics, preservatives, and the like may be contained in the liquid preparations for the oral administration of the compound of the present invention.

Also, the compound of the present invention may be in a parenteral dosage form such as sterile aqueous solutions, non-aqueous solvents, suspensions, emulsions, lyophilizates, suppositories, and the like. Propylene glycol, polyethylene glycol, vegetable oils such as olive oil, and esters such as ethyl oleate may be suitable for the non-aqueous solvents and suspensions. The basic materials of suppositories include Witepsol, macrogol, Tween 61, cacao butter, laurin butter, and glycerogelatin.

The compound of the present invention is administered in a therapeutically effective amount. The effective dose of the compound of the present invention varies depending on various factors including a patient's age, weight, sex, and health condition, the route of administration, and the severity of disease. Typically, the compound of the present invention may be administered at a daily dose of from 0.001 to 100 mg/kg, and preferably at a daily dose of from 0.01 to 35 mg/kg. For an adult with a weight of 70 kg, the dose of the compound of the present invention may typically range from 0.07 to 7,000 mg/day, and preferably from 0.7 to 2,500 mg/day. The formulations of the compound may be administered in a single dose or may be divided into multiple doses at regular intervals of time according to the instructions of a physician or pharmacist who is responsible for monitoring or observing the administration of the drug.

MODE FOR INVENTION

A better understanding of the present invention may be obtained through the following examples which are set forth to illustrate, but are not to be construed as limiting the present invention.

<Example 1> 4b,9b-Dihydroxy-7-methyl-4bH-benzo[d]indeno[1,2-b]furan-10(9bH)-one

Ninhydrin (6.00 g, 33.6 mmol and m-cresol (3.78 ml, 33.6 mmol were dissolved in acetic acid (30 ml) and heated for 3 hrs under reflux. After cooling, the precipitate thus formed was washed with acetic acid and water in that order to afford the title compound as a white solid. 7.55 g (83%).
mp: 145-147° C.
$^1$H-NMR (300 MHz, CDCl$_3$) δ 2.26 (s, 3H, CH$_3$) 6.63 (s, 1H, ArH) 6.75 (d, J=7.8 Hz, 1H, ArH) 7.34 (d, J=7.8 Hz, 1H, ArH) 7.54 (t, J=7.5 Hz, 1H, ArH) 7.74-7.81 (m, 2H, ArH) 7.97-8.00 (d, J=7.8 Hz, 1H, ArH). MS (EI): 268

<Example 2> 7-Methyl-10-oxo-9b,10-dihydro-4bH-benzo[d]indeno[1,2-b]furane-4b,9b-diyl diacetate 4b,9b-dihydroxy-7-methyl-4bH-benzo[d]indeno[1,2-b]furan-10(9bH)-one (1.00 g, 3.7 mmol) was completely dissolved in anhydrous dichloromethane (50 ml). This solution was added with anhydrous acetic acid (0.7 ml, 7.4 mmol), pyridine (0.3 ml, 3.7 mmol), and 4-dimethyl aminopyridine (0.1 g), and stirred at room temperature for 3 hrs. After the reaction mixture was extracted with dichloromethane, the organic layer was concentrated and purified using column chromatography (ethylacetate:hexane=1:8) to afford the title compound. 0.04 g (3%).
mp: 167-169° C.
$^1$H-NMR (300 MHz, CDCl$_3$) δ 2.15 (s, 3H, OAc) 2.16 (s, 3H, OAc) 2.30 (s, 3H, CH$_3$) 6.69 (s, 1H, ArH) 6.88 (d, J=7.8 Hz, 1H, ArH) 7.47 (d, J=7.7 Hz, 1H, ArH) 7.58 (t, J=7.4 Hz, 1H, ArH) 7.75-7.84 (m, 2H, ArH) 8.14 (d, J=7.7 Hz, 1H, ArH). MS (EI): 352.

<Example 3> Ethyl 2-(4b,9b-dihydroxy-6-methoxy-10-oxo-9b,10-dihydro-4bH-benzo[d]indeno[1,2-b]furane-8-yl)acetate Ninhydrin (2.54 g, 14.2 mmol) and ethyl-2-(4-hydroxy-3-methoxyphenyl)acetate (3.00 g, 14.2 mmol) were dissolved in acetic acid (15 ml) and heated for 21 hrs under reflux, followed by extraction with ethylacetate. The concentrate was purified using column chromatography (ethylacetate:hexane=1:1) to afford the title compound. 1.46 g (29%).
mp: 133-136° C.
$^1$H-NMR (300 MHz, CDCl$_3$) δ 1.20 (t, J=7.2 Hz, 3H, CH$_3$) 3.56 (s, 2H, CH$_2$) 3.82 (s, 3H OCH$_3$) 4.11-4.18 (q, J=7.2 Hz, 14.4H, 2H, OCH$_2$) 6.89 (s, 1H, ArH) 7.12 (s, 1H, ArH) 7.56-8.14 (m, 4H, ArH). MS (EI): 370.

<Example 4> 4b,9b-dihydroxy-7,8-dimethyl-4bH-benzo[d]indeno[1,2-b]furan-10(9bH)-one Ninhydrin (4.37 g, 24.5 mmol) and 3,4-dimethylphenol (3.00 g, 24.5 mmol) were dissolved in acetic acid (15 ml) and heated for 23 hrs under reflux. After cooling, the precipitate thus formed was washed with acetic acid and water in that order to afford the title compound as a white solid. 5.43 g (78%).
mp: 198-200° C.
$^1$H-NMR (300 MHz, CDCl$_3$) δ 2.15 (m, 6H, CH$_3$) 6.55 (s, 1H, ArH) 7.22 (s, 1H, ArH), 7.70-7.88 (m, 4H, ArH). MS (EI): 282.

<Example 5> 2-Hydroxy-2-(2-hydroxyphenyl)-1H-indene-1,3(2H)-dione

Ninhydrin (1.00 g, 5.6 mmol) and phenol (0.53 g, 5.6 mmol) were dissolved in acetic acid (20 ml) and heated for 23 hrs under reflux. The reaction mixture was cooled, washed with acetic acid and water, and then recrystallized in dichloromethane to afford the title compound as a white solid. 0.37 g (26%).
mp: 155-159° C.
$^1$H-NMR (300 MHz, acetone-d$_6$) δ 5.87 (s, 1H, OH) 6.72 (s, 1H, OH) 6.78 (d, J=8.4 Hz, 1H, ArH) 6.95 (t, J=6.6 Hz, 1H, ArH) 7.27 (t, J=6.9 Hz, 1H, ArH) 7.48 (d, J=7.3 Hz, 1H, ArH) 7.64 (t, J=7.5 Hz, 1H, ArH) 7.75 (d, J=7.8 Hz, 1H, ArH) 7.91 (t, J=13.4 Hz, 1H, ArH) 8.01 (d, J=4.8 Hz, 1H, ArH). MS (EI): 254.

<Example 6> 2-(5-Fluoro-2-hydroxyphenyl)-2-hydroxy-1H-indene-1,3(2H)-dione

Ninhydrin (1.00 g, 5.6 mmol) and 4-fluoro-phenol (0.63 g, 5.6 mmol) were dissolved in acetic acid (20 ml) and heated for 23 hrs under reflux. After coiling, the precipitate thus formed was washed with acetic acid and water, and recrystallized in dichloromethane to afford a white solid. This was purified using column chromatography (ethylacetate:hexane=1:4) and washed with dichloromethane to afford the title compound. 0.57 g (37%).
mp: 189-193° C.
$^1$H-NMR (300 MHz, acetone-d$_6$) δ 5.98 (s, 1H, OH) 6.81 (q, J=9.0 Hz, 4.0 Hz, 1H, ArH) 6.88 (s, 1H, OH) 7.06 (dt, J=9.0, 2.7 Hz, 1H, ArH) 7.20 (dd, J=7.8 Hz, 3.0 Hz, 1H, ArH) 7.66 (t, J=6.9 Hz, 1H, ArH) 7.77 (d, J=7.8 Hz, 1H, ArH) 7.92 (t, J=7.8 Hz, 1H, ArH) 8.00-8.03 (m, 1H, ArH). MS (EI): 272.

<Example 7> 4b,9b-Dihydroxy-7-methoxy-4bH-benzo[d]indeno[1,2-b]furan-10(9bH)-one 3-Methoxyphenol (2.09 g, 16.8 mmol) and ninhydrin (3.00 g, 16.8 mmol) were dissolved in acetic acid (20 ml) and heated for 2 hrs under reflux. Then, the reaction mixture was extracted with ethylacetate and the concentrated organic layer was purified using column chromatography (ethylacetate:hexane=1:4), followed by recrystallization with ethylacetate and hexane to afford the title compound. 1.25 g (26%).
mp: 98-100° C.
$^1$H-NMR (300 MHz, CDCl$_3$) δ 3.82 (s, 3H, OCH$_3$) 6.39 (s, 1H, ArH) 6.52 (d, 1H, J=9.0 Hz, ArH) 7.37 (d, 1H, J=9.0 Hz, ArH) 7.57 (t, 1H, J=9.0 Hz, ArH) 7.78-7.81 (m, 2H, ArH) 7.99 (d, J=9.0 Hz, 1H, ArH). MS (EI): 284.

<Example 8> 6,7-Dichloro-4b,9b-dihydroxy-4bH-benzo[d]indeno[1,2-b]furan-10(9bH)-one Ninhydrin (3.00 g, 16.8 mmol) and 2,3-chlorophenol (2.16 g, 16.8 mmol) were dissolved in acetic acid (20 ml) and heated for 28 hrs under reflux. The precipitate thus formed was washed with dichloromethane to afford the title compound as a white solid. 2.35 g (43%).

mp: 142-150° C.

$^1$H-NMR (300 MHz, CDCl$_3$) δ 7.06 (d, J=8.1 Hz, 1H, ArH) 7.33 (d, J=8.1 Hz, 1H, ArH) 7.61 (t, J=7.5 Hz, 1H, ArH) 7.80-7.88 (m, 2H, ArH) 8.07 (d, J=7.8 Hz, 1H, ArH). MS (EI): 323.

<Example 9> 7-Ethyl-4b,9b-dihydroxy-4bH-benzo[d]indeno[1,2-b]furan-10(9bH)-one

Ninhydrin (3.00 g, 16.8 mmol) and m-ethylphenol (2.05 g, 16.8 mmol) were dissolved in acetic acid (20 ml) and heated for 4 hrs under reflux. After cooling, the precipitate thus formed was washed with dichloromethane to afford the title compound as a white solid. 2.80 g (59%).

mp: 168-169° C.

$^1$H-NMR (300 MHz, CDCl$_3$) δ 1.15 (t, J=7.8 Hz, 3H, CH$_3$) 2.53-2.60 (q, J=15.3 Hz, 7.5 Hz, CH$_2$) 3.93 (s, 1H, OH) 4.75 (s, 1H, OH) 6.68 (s, 1H, ArH) 6.80 (d, J=6.0 Hz, 1H, ArH) 7.38 (d, J=7.8 Hz, 1H, ArH) 7.55 (t, J=7.5 Hz, 1H, ArH) 7.79 (t, J=9.0 Hz, 2H, ArH) 8.00 (d, J=7.8 Hz, 1H, ArH). MS(EI): 282.

<Example 10> 4b,9b-Dihydroxy-7-isopropyl-4bH-benzo[d]indeno[1,2-b]furan-10(9bH)-one Ninhydrin (3.00 g, 16.8 mmol) and m-isopropylphenol (2.29 g, 16.8 mmol) were dissolved in acetic acid (20 ml) and heated for 2 hrs under reflux. After cooling, the precipitate thus formed was washed with dichloromethane to afford the title compound as a white solid. 2.82 g (56%).

mp: 195-198° C.

$^1$H-NMR (300 MHz, CDCl$_3$) δ 1.16 (d, J=8.1 Hz, 6H, CH$_3$) 2.77-2.86 (m, 1H, CH) 4.14 (s, 1H, OH) 4.85 (s, 1H, OH) 6.70 (s, 1H, ArH) 6.82 (d, J=7.8 Hz, 1H, ArH) 7.40 (d, J=7.8 Hz, 1H, ArH) 7.54 (t, J=7.8 Hz, 1H, ArH) 7.75-7.82 (m, 2H, ArH) 8.00 (d, J=7.8 Hz, 1H, ArH). MS(EI): 296.

<Example 11> 7-Isopropyl-10-oxo-9b,10-dihydro-4bH-benzo[d]indeno[1,2-b]furane-4b,9b-diyl diacetate 4b,9b-Dihydroxy-7-isopropyl-4bH-benzo[d]indeno[1,2-b]furan-10(9bH)-one (2.00 g, 6.7 mmol) was completely dissolved in anhydrous tetrahydrofurane (20 ml), and mixed with anhydrous acetic acid (1.38 g, 13.5 mmol), pyridine (0.53 g, 6.7 mmol), 4-dimethyl aminopyridine (0.2 g) at room temperature for 12 hrs while stirring. The reaction mixture was concentrated and extracted many times with dichloromethane, and the concentrated organic layer was purified using column chromatography (ethylacetate:hexane=1:4) to afford the title compound. 0.27 g (11%).

mp: 138-140° C.

$^1$H-NMR (300 MHz, CDCl$_3$) δ 1.18 (d, J=6.9 Hz, 6H, CH$_3$) 2.14 (s, 3H, OAc) 2.16 (s, 3H, OAc) 2.83-2.87 (m, 1H, CH) 6.75 (s, 1H, ArH) 6.94 (d, J=7.8 Hz, 1H, ArH) 7.51 (d, J=7.5 Hz, 1H, ArH) 7.59 (t, J=7.5 Hz, 1H, ArH) 7.75-7.85 (m, 2H, ArH) 8.16 (d, J=7.8 Hz, 1H, ArH). MS(EI): 380

<Example 12> 4b,9b-Dihydroxy-8-methoxy-4bH-benzo[d]indeno[1,2-b]furan-10(9bH)-one Ninhydrin (3.00 g, 16.8 mmol) and p-methoxyphenol (2.09 g, 16.8 mmol) were dissolved in acetic acid (20 ml) and heated for 6 hrs under reflux. After cooling, the precipitate thus formed was washed with acetic acid and water in that order to afford the title compound as a yellow solid. 4.00 g (83%).

mp: 186-189° C.

$^1$H-NMR (300 MHz, CDCl$_3$) δ 3.72 (s, 3H, OCH$_3$) 6.59 (d, J=8.8 Hz, 1H, ArH) 6.70 (dd, J=8.8 Hz, 1H, ArH) 6.97 (d, J=2.8 Hz, 1H, ArH) 7.43 (t, J=7.9 Hz, 1H, ArH) 7.64-7.71 (m, 2H, ArH) 7.84-7.87 (d, J=7.7 Hz, 1H, ArH). MS(EI): 284.

<Example 13> 4b,9b-Dihydroxy-6-phenyl-4bH-benzo[d]indeno[1,2-b]furan-10(9bH)-one Ninhydrin (3.00 g, 16.8 mmol) and m-phenylphenol (2.86 g, 16.8 mmol) were added to acetic acid (20 ml) and heated for 20 hrs under reflux. After the removal of the solvent by concentration in a vacuum, the concentrate was extracted many times with dichloromethane. The concentrated organic layer was crystallized with dichlorometan and hexane to afford the title compound as a white solid. 4.10 g (73%).

mp: 182-183° C.

$^1$H-NMR (300 MHz, CDCl$_3$) δ 7.03 (t, J=6.0 Hz, 1H, ArH) 7.30-7.41 (m, 1H, ArH) 7.42-7.48 (m, 4H, ArH) 7.54 (t, J=7.8 Hz, 1H, ArH) 7.63 (d, J=8.4 Hz, 2H, ArH) 7.76-7.81 (m, 2H, ArH) 8.01 (d, J=8.1 Hz, 1H, ArH). MS(EI): 330.

<Example 14> 4b,9b-Dihydroxy-8-nitro-4bH-benzo[d]indeno[1,2-b]furan-10(9bH)-one

Ninhydrin (3.00 g, 16.8 mmol) and 4-nitrophenol (2.34 g, 16.8 mmol) were added to acetic acid (20 ml) and heated for 5 hrs under reflux. The reaction mixture was extracted many times with dichloromethane and the concentrated organic layer was purified using column chromatography (ethylacetate:hexane=1:3) to afford the title compound. White. 0.80 g (16%).

mp: 206-207° C.

$^1$H-NMR (300 MHz, CDCl$_3$) δ 6.94 (d, J=9.0 Hz, 1H, ArH) 7.63 (t, J=7.8 Hz, 1H, ArH) 7.80-7.90 (m, 2H, ArH) 8.03 (d, J=7.8 Hz, 1H, ArH) 8.24 (d, J=9.0 Hz, 1H, ArH) 8.42 (d, J=2.4 Hz, 1H, ArH). MS(EI): 299.

<Example 15> 4b,11b-Dihydroxy-4bH-indeno[1,2-b]naphtho[2,3-d]furan-12(11 bH)-one Ninhydrin (1.00 g, 5.61 mmol) and 2-naphthol (0.81 g, 5.61 mmol) were dissolved in acetic acid (20 ml) and heated for 6 hrs under reflux. After cooling, the precipitate thus formed was washed with acetic acid and water in that order to afford the title compound as a white solid. 1.31 g (77%).

mp: 220-221° C.

$^1$H-NMR (300 MHz, CDCl$_3$) δ 7.06 (d, J=8.7 Hz, 1H, ArH) 7.37 (t, J=7.5 Hz, 1H, ArH) 7.52-7.62 (m, 2H, ArH) 7.76-7.83 (m, 4H, ArH) 8.04 (d, J=7.8 Hz, 1H, ArH) 8.38 (d, J=8.4 Hz, 1H, ArH). MS(EI): 304.

<Example 16> 6b,11b-Dihydroxy-6bH-indeno[1,2-b]naphtho[2,1-d]furan-7(11 bH)-one

Ninhydrin (1.00 g, 5.61 mmol) and 1-naphthol (0.81 g, 5.61 mmol) were added to acetic acid (20 ml) and heated for 7 hrs under reflux. After cooling the reaction mixture, the precipitate thus formed was washed with acetic acid and water in that order to afford the title compound as a white solid. 0.96 g (56%).

mp: 216-218° C.

$^1$H-NMR (300 MHz, CDCl$_3$) δ 7.43-7.57 (m, 5H, ArH) 7.75-7.83 (m, 3H, ArH) 8.03-8.12 (m, 2H, ArH). MS(EI): 304.

<Example 17> 4b,9b-Dihydroxy-8-propyl-4bH-benzo[d]indeno[1,2-b]furan-10(9bH)-one Ninhydrin (1.00 g, 5.61 mmol) and p-propylphenol (0.76 g, 5.61 mmol) were added to acetic acid (20 ml) and heated for 16 hrs under reflux. The reaction mixture was extracted many times with dichloromethane, and the concentrated organic layer was purified using column chromatography (ethylacetate:hexane=1:3 to 1:1) to afford the title compound. 1.10 g (66%).

mp: 126-127° C.

$^1$H-NMR (300 MHz, CDCl$_3$) δ 0.83-0.90 (t, J=7.4 Hz, 3H, CH$_3$) 1.46-1.57 (m, 2H, CH$_2$) 2.45 (t, J=7.8 Hz, 2H, CH$_2$) 6.74 (d, J=8.4 Hz, 1H, ArH) 7.08 (dd, J=1.8, 8.4 Hz, 1H, ArH) 7.31 (s, 1H, ArH) 7.55 (t, J=7.8 Hz, 1H, ArH) 7.77-7.82 (m, 2H, ArH) 8.00 (d, J=7.5 Hz, 1H, ArH). MS(EI): 296.

<Example 18> 8-Ethyl-4b,9b-dihydroxy-4bH-benzo[d]indeno[1,2-b]furan-10(9bH)-one

Ninhydrin (1.00 g, 5.61 mmol) and p-ethylphenol (0.68 g, 5.61 mmol) were dissolved in acetic acid (20 ml) and heated for 15 hrs under reflux. After cooling the reaction mixture for 12 hrs, the precipitate thus formed was washed with acetic acid and water in that order to afford the title compound as a yellowish white solid. 1.10 g (69%).

mp: 157-159° C.

$^1$H-NMR (300 MHz, CDCl$_3$) δ 1.16 (t, J=7.4 Hz, 3H, CH$_3$) 2.50-2.61 (q, J=7.6 Hz, 2H, CH$_2$) 3H, OAc) 6.74 (d, J=8.4 Hz, 1H, ArH) 7.10 (d, J=8.4 Hz, 1H, ArH) 7.33 (s, 1H, ArH) 7.54 (t, J=8.0 Hz, 1H, ArH) 7.76-7.83 (m, 2H, ArH) 8.00 (d, J=7.6 Hz, 1H, ArH). MS(EI): 282.

<Example 19> 8-sec-Butyl-4b,9b-dihydroxy-4bH-benzo[d]indeno[1,2-b]furan-10(9bH)-one Binhydrin (1.00 g, 5.61 mmol) and p-sec-butylphenol (0.84 g, 5.61 mmol) were added to acetic acid (20 ml) and heated for 20 hrs under reflux. The reaction mixture was extracted many times with dichloromethane, and the concentrated organic layer was purified using column chromatography (ethylacetate:hexane=1:4 to 1:2) to afford the title compound. 0.80 g (46%).

mp: 134-136° C.

$^1$H-NMR (300 MHz, CDCl$_3$) δ 0.77 (t, J=7.2 Hz, 3H, CH$_3$) 1.16 (d, J=6.9 Hz, 3H, CH$_3$) 1.31-1.43 (m, 2H, CH$_2$) 2.49-2.56 (m, 1H, CH) 6.75 (d, J=8.1 Hz, 1H, ArH) 7.09 (d, J=8.4 Hz, 1H, ArH) 7.33 (s, 1H, ArH) 7.59 (m, 1H, ArH) 7.79-7.83 (m, 2H, ArH) 8.00 (d, J=7.5 Hz, 1H, ArH). MS(EI): 310.

<Example 20> 8-tert-Butyl-4b,9b-dihydroxy-4bH-benzo[d]indeno[1,2-b]furan-10(9bH)-one Ninhydrin (1.00 g, 5.61 mmol) and p-tert-butylphenol (0.84 g, 5.61 mmol) were added to acetic acid (20 ml) and heated for 16 hrs under reflux. The reaction mixture was extracted many times with dichloromethane, and the concentrated organic layer was purified using column chromatography (ethylacetate:hexane=1:2) to afford the title compound. 0.60 g (34%).

mp: 187-188° C.

$^1$H-NMR (300 MHz, CDCl$_3$) δ 1.22 (s, 9H, CH$_3$) 6.78 (d, J=8.4 Hz, 1H, ArH) 7.27-7.28 (m, 1H, ArH) 7.46 (d, J=2.1 Hz, 1H, ArH) 7.57 (t, J=7.5 Hz, 1H, ArH) 7.79-7.84 (t, J=7.5 Hz, 2H, ArH) 8.00 (d, J=2.1 Hz, 1H, ArH). MS(EI): 310.

<Example 21> 6-tert-Butyl-4b,9b-dihydroxy-4bH-benzo[d]indeno[1,2-b]furan-10(9bH)-one Ninhydrin (0.60 g, 5.6 mmol) and 2-tert-butylphenol (0.84 g, 5.6 mmol) were dissolved in acetic acid (10 ml) and heated for 7 hrs under reflux. After cooling the reaction mixture, the precipitate thus formed was washed with acetic acid and water in that order to afford the title compound as a white solid. 1.09 g (62%).

mp: 148-152° C.

$^1$H-NMR (300 MHz, CDCl$_3$) δ 1.35 (s, 9H, CH$_3$) 6.93 (t, J=7.8 Hz, 1H, ArH) 7.23-7.37 (m, 2H, ArH) 7.57 (t, J=7.4 Hz, 1H, ArH) 7.80 (t, J=7.8 Hz, 2H, ArH) 8.05 (d, J=7.8 Hz, 1H, ArH). MS(EI): 310.

<Example 22> 4b,9b-Dihydroxy-7,8,9-trimethyl-4bH-benzo[d]indeno[1,2-b]furan-10(9bH)-one Ninhydrin (1.00 g, 5.61 mmol) and 3,4,5-trimethylphenol (0.76 g, 5.61 mmol) were dissolved in acetic acid (20 ml) and heated for 16 hrs under reflux. The reaction mixture was extracted many times with dichloromethane and the concentrated organic layer was purified using column chromatography (ethylacetate:hexane=1:4 to 1:2) to afford the title compound. 1.01 g (60%).

mp: 212-214° C.

$^1$H-NMR (300 MHz, CDCl$_3$) δ 2.05 (s, 3H, CH$_3$) 2.19 (s, 3H, CH$_3$) 2.44 (s, 3H, CH$_3$) 6.53 (s, 1H, ArH) 7.53 (t, J=6.9 Hz, 1H, ArH) 7.74-7.80 (m, 2H, ArH) 7.96 (d, J=7.2 Hz, 1H, ArH). MS(EI): 296.

<Example 23> 4b,9b-Dihydroxy-8-tert-pentyl-4bH-benzo[d]indeno[1,2-b]furan-10(9bH)-one Ninhydrin (1.00 g, 5.61 mmol) and 4-tert-pentylphenol (0.92 g, 5.61 mmol) were dissolved in acetic acid (20 ml) and heated for 32 hrs under reflux. The reaction mixture was extracted many times with dichloromethane, and the concentrated organic layer was purified using column chromatography (ethylacetate:hexane=1:4) to afford the title compound. 1.28 g (70%).

mp: 175-176° C.

$^1$H-NMR (300 MHz, CDCl$_3$) δ 0.63 (t, J=7.5 Hz, 3H, CH$_3$) 1.22 (s, 6H, CH$_3$) 1.53-1.60 (q, J=15.0, 7.5 Hz, 2H, CH$_2$) 6.78 (d, J=8.4 Hz, 1H, ArH) 7.28 (m, 1H, ArH 7.46 (d, J=2.1 Hz, 1H, ArH) 7.57 (t, J=7.5 Hz, 1H, ArH) 7.79-7.84 (t, J=7.5 Hz, 2H, ArH) 8.00 (d, J=6.90 Hz, 1H, ArH). MS(EI): 324.

<Example 24> 6,8-di-tert-Butyl-4b,9b-dihydroxy-4bH-benzo[d]indeno[1,2-b]furan-10(9bH)-one Ninhydrin (1.00 g, 5.61 mmol) and 2,4-tert-butyl-phenol (1.16 g, 5.61 mmol) were dissolved in acetic acid (20 ml) and heated for 16 hrs under reflux. The reaction mixture was extracted many times with dichloromethane, and the organic layer was dried, filtered and concentrated in a vacuum. The solid thus formed was washed with hexane to afford the title compound. 0.60 g (34%).

mp: 200-203° C.

$^1$H-NMR (300 MHz, CDCl$_3$) δ 1.25 (s, 9H, CH$_3$) 1.33 (s, 9H, CH$_3$) 7.31 (d, J=2.1 Hz, 1H, ArH) 7.35 (d, J=2.1 Hz, 1H, ArH) 7.55 (t, J=9.0 Hz, 1H, ArH) 7.76-7.81 (m, 2H, ArH) 8.01 (d, J=7.8 Hz, 1H, ArH). MS(EI): 366.

<Example 25> 6,8-di-tert-Butyl-10-oxo-9b,10-dihydro-4bH-benzo[d]indeno[1,2-b]furane-4b,9b-diyl diacetate 6,8-di-tert-Butyl-4b,9b-dihydroxy-4bH-benzo[d]indeno[1,2-b]furan-10(9bH)-one (0.60 g, 0.60 mmol) was completedly dissolved in anhydrous tetrahydrofurane (20 ml), and reacted overnight with anhydrous acetic acid (0.33 g, 3.28 mmol), pyridine (0.13 g, 1.64 mmol), and 4-dimethyl aminopyridine (0.06 g) at room temperature while stirring. The reaction mixture was extracted many times with dichloromethane, and the concentrated organic layer was purified using column chromatography (ethylacetate:hexane=1:3) to afford the title compound. 0.61 g (61%).

mp: 242-247° C.

$^1$H-NMR (300 MHz, CDCl$_3$) δ 1.29 (s, 18H, CH$_3$) 2.13 (s, 3H, OAc) 2.18 (s, 3H, OAc) 7.31 (d, J=2.1 Hz, 1H, ArH) 7.43 (d, J=1.8 Hz, 1H, ArH) 7.57 (t, J=7.5 Hz, 1H, ArH) 7.73-7.84 (m, 2H, ArH) 8.19 (d, J=7.8 Hz, 1H, ArH). MS(EI): 450.

<Example 26> 4b,9b-Dihydroxy-8-nonyl-4bH-benzo[d]indeno[1,2-b]furan-10(9bH)-one

Ninhydrin (1.00 g, 5.61 mmol) and nonylphenol (1.23 g, 5.61 mmol) were dissolved in acetic acid (20 ml) and heated for 20 hrs under reflux. The reaction mixture was extracted many times with dichloromethane, and the concentrated organic layer was purified using column chromatography (ethylacetate:hexane=1:4) to afford the title compound. 1.01 g (47%).

mp: 108-110° C.

$^1$H-NMR (300 MHz, CDCl$_3$) δ 0.50-1.28 (m, 16H, CH$_2$) 2.09 (s, 3H, CH$_3$) 6.76 (d, J=8.4 Hz, 1H, ArH) 7.38-7.44 (m, 1H, ArH) 7.56 (t, J=7.8 Hz, 1H, ArH) 7.81 (t, J=7.5 Hz, 2H, ArH) 8.01 (d, J=7.5 Hz, 1H, ArH). MS(EI): 380.

<Example 27> 4b,9b-Dihydroxy-8-pentadecyl-4bH-benzo[d]indeno[1,2-b]furan-10(9bH)-one Ninhydrin (1.00 g, 5.61 mmol) and 2-pentadecylphenol (1.70 g, 5.61 mmol) were dissolved in acetic acid (20 ml) and heated for 20 hrs under reflux. The reaction mixture was extracted many times with dichloromethane, and the concentrated organic layer was purified using column chromatography (ethylacetate:hexane=1:4) to afford the title compound. 1.01 g (37%).

mp: 105-110° C.

$^1$H-NMR (300 MHz, CDCl$_3$) δ 0.87 (t, J=6.3 Hz, 3H, CH$_3$) 1.24 (s, 24H, CH$_2$) 1.52-1.54 (m, 2H, CH$_2$), 2.53 (t, J=7.6 Hz, 2H, CH$_2$) 6.68 (s, 1H, ArH) 6.81 (d, J=7.6 Hz, 1H, ArH) 7.40 (d, J=7.8 Hz, 1H, ArH) 7.58 (t, J=7.0 Hz, 1H, ArH) 7.83 (t, J=6.80 Hz, 2H, ArH) 8.02 (d, J=8.4 Hz, 1H, ArH). MS(EI): 464.

<Example 28> 6,8-Bis-(1,1-dimethyl-propyl)-4b,9b-dihydroxy-4b,9b-dihydro-5-oxa-indeno[2,1-a]inden-10-one Ninhydrin (1.00 g, 5.6 mmol) and 2,4-di-tert-pentylphenol (1.31 g, 5.6 mmol) were added to acetic acid (20 ml) and heated for 16 hrs under reflux. The reaction mixture was extracted many times with dichloromethane, and the concentrated organic layer was purified using column chromatography (ethylacetate:hexane=1:4) to afford the title compound. 1.28 g (58%).

mp: 195-222° C.

$^1$H-NMR (300 MHz, CD$_3$OD) δ 0.44 (t, J=7.5 Hz, 3H, CH$_3$) 0.62 (t, J=7.5 Hz, 3H, CH$_3$) 1.23 (s, 9H, CH$_3$) 1.56 (s, 3H, CH$_3$) 1.58-1.63 (q, J=15.0 Hz, 7.5 Hz, 2H, CH$_2$) 1.77-1.85 (m, 2H, CH$_2$) 7.11 (s, 1H, ArH) 7.31 (s, 1H, ArH) 7.57 (t, J=7.8 Hz, 1H, ArH) 7.74 (d, J=7.8 Hz, 1H, ArH) 7.81 (t, J=8.4 Hz, 1H, ArH) 7.96 (d, J=7.8 Hz, 1H, ArH). MS(EI): 394.

<Example 29> Isopropyl 4b,9b-dihydroxy-7-isopropyl-10-oxo-9b,10-dihydro-4bH-benzo[d]indeno[1,2-b]furan-1-ylcarbamate To a solution of 4b,9b-dihydroxy-1-isocyanato-7-isopropyl-4bH-benzo[d]indeno[1,2-b]furan-10(9bH)-one (70 mg, 0.2 mmol) in anhydrous tetrahydrofurane was dropwide added 2M ammonia (0.21 ml in isopropyl alcohol). The reaction mixture was heated for 4 hrs under reflux and concentrated in a vacuum, followed by purification using column chromatography (ethylacetate:hexane=1:4) to afford the title compound. 30 mg (38%).

mp: 200-202° C.

$^1$H-NMR (300 MHz, CDCl$_3$) δ 1.16 (dd, J=6.9, 1.8 Hz, 6H, CH$_3$) 1.27-1.34 (m, 6H, CH$_3$) 2.78-2.87 (m, 1H, CH) 3.95 (s, 1H, OH) 4.77 (s, 1H, OH) 4.96-5.05 (m, 1H, CH) 6.71 (s, 1H, ArH) 6.84 (d, J=8.1 Hz, 1H, ArH) 7.42 (d, J=8.1 Hz, 1H, ArH) 7.53 (d, J=7.2 Hz, 1H, ArH) 7.72 (t, J=8.1 Hz, 1H, ArH) 8.27 (d, J=8.4 Hz, 1H, ArH) 9.29 (s, 1H, NH). MS(EI): 397.

<Example 30> 2,6'-Dihydroxy-2',3'-dihydro-1'H-[2,5']biindenyl-1,3-dione

To a solution of ninhydrin (1.00 g, 5.61 mmol) in acetic acid (20 ml) was added 1-(3-hydroxy-phenyl)-ethanone (0.75 g, 5.61 mmol), followed by heating for 3 hrs at 110° C. The reaction mixture was extracted many times with dichloromethane, and the concentrated organic layer was purified using column chromatography (ethylacetate:hexane=1:2) to afford the title compound. White. 1.56 g (94%).

mp: 214-217° C.

$^1$H-NMR (300 MHz, CDCl$_3$) δ 1.90-2.08 (m, 2H, CH$_2$) 2.69-2.82 (m, 4H, CH$_2$) 6.68 (s, 1H, ArH) 7.28 (d, J=12.0 Hz, 1H, ArH) 7.54 (t, J=7.2 Hz, 1H, ArH) 7.75-7.81 (m, 2H, ArH) 7.99 (d, J=7.5 Hz, 1H, ArH). MS(EI): 294.

<Example 31> 6b,11b-Dihydroxy-1,2,3,4,6b,11b-hexahydro-12-oxa-benzo[4,5]pentaleno[2,1-a]naphthalen-7-one To a solution of ninhydrin (1.00 g, 5.61 mmol) in acetic acid (20 ml) was added 5,6,7,8-tetrahydro-naphthalen-1-ol (0.83 g, 5.61 mmol), followed by heating for 3 hrs at 110° C. After cooling, the precipitate thus formed was filtered to afford the title compound as a white solid. 1.48 g (83%).

mp: 252-254° C.

$^1$H-NMR (300 MHz, CDCl$_3$) δ 1.72-1.81 (m, 4H, CH$_2$) 2.58-2.67 (m, 4H, CH$_2$) 6.71 (d, J=7.8 Hz, 1H, ArH) 7.21 (d, J=7.8 Hz, 1H, ArH) 7.56 (t, J=8.4 Hz, 1H, ArH) 7.58-7.83 (m, 2H, ArH) 8.02 (d, J=7.5 Hz, 1H, ArH). MS(EI): 308.

<Example 32> 4b,9b-Dihydroxy-7-isopropyl-2-methoxy-4b,9b-dihydro-5-oxa-indeno[2,1-a]inden-10-one Isopropyl phenol (0.065 g, 0.48 mmol was added to a solution of 5-methoxy-ninhydrin (0.10 g, 0.48 mmol in acetic acid (20 ml) and heated for 15 hrs at 110° C. The reaction mixture was extracted with many times with ethylacetate, and the concentrated organic layer was purified using column chromatography (ethylacetate:hexane=1:4) to afford the title compound. White. 0.12 g (77%).

mp: 98-102° C.

$^1$H-NMR (300 MHz, CDCl$_3$) δ 1.24 (d, J=6.9 Hz, 6H, CH$_3$) 2.78-2.85 (s, 1H, CH) 3.98 (s, 3H, OCH$_3$) 6.71 (s, 1H, ArH) 6.82 (d, J=7.8 Hz, 1H, ArH) 7.04-7.08 (dd, J=8.4 Hz, 3.6 Hz, 1H, ArH) 7.39-7.42 (m, 2H, ArH) 7.70 (d, J=8.4 Hz, 1H, ArH). MS(EI): 326.

<Example 33> 7-Isopropyl-10-oxo-9b,10-dihydro-4bH-benzo[d]indeno[1,2-b]furan-4b,9b-diyl bis(2,2-dimethylpropanoate)

To a solution of 4b,9b-dihydroxy-7-isopropyl-4bH-benzo[d]indeno[1,2-b]furan-10(9bH)-one (1.00 g, 3.3 mmol in anhydrous tetrahydrofurane were added 2,2-dimethyl-propionyl chloride (0.81 g, 6.7 mmol), trimethylamine (0.40 g, 4.0 mmol, and 4-dimethylaminopyridine (0.1 g), followed by heating for 24 hrs under reflux. The reaction mixture was concentrated in a vacuum, and washed many times with dichloromethane. The concentrated organic layer was purified using column chromatography (ethylacetate:hexane=1:6) to afford the title compound. 0.10 g (6%).

mp: 153-157° C.

$^1$H-NMR (300 MHz, CDCl$_3$) δ 1.16-1.26 (m, 24H, CH$_3$) 2.80-2.89 (m, 1H, CH) 6.73 (s, 1H, ArH) 6.93 (d, J=7.8 Hz, 1H, ArH) 7.48 (d, J=7.8 Hz, 1H, ArH) 7.56 (t, J=7.5 Hz, 1H, ArH) 7.75-7.81 (m, 2H, ArH) 8.09 (d, J=7.8 Hz, 1H, ArH). MS(EI): 464.

<Example 34> (2E,2'E)-7-Isopropyl-10-oxo-9b,10-dihydro-4bH-benzo[d]indeno[1,2-b]furan-4b,9b-diyl bis(3-phenylacrylate)

To a solution of 4b,9b-dihydroxy-7-isopropyl-4b,9b-dihydro-5-oxa-indeno[2,1-a]inden-10-one (1.00 g, 3.3 mmol in anhydrous tetrahydrofurane were added, 3-phenyl-acryloyl chloride (1.12 g, 6.7 mmol), trimethylamine (0.40 g, 4.0 mmol), and 4-dimethylaminopyridine (0.1 g), followed by heating for 2 days under reflux. The reaction mixture was concentrated in a vacuum and washed many times with ethylacetate. The concentrated organic layer was purified using column chromatography (ethylacetate:hexane=1:8 to 1:4) to afford the title compound. 0.08 g (9%)

mp: 111-113° C.

$^1$H-NMR (300 MHz, CDCl$_3$) δ 1.20 (dd, J=2.7 Hz, 6.8 Hz, 6H, CH$_3$) 2.88-2.92 (m, 1H, CH) 6.37 (d, J=16.0 Hz, 1H, CH) 6.52 (d, J=16.0 Hz, 1H, CH) 6.81 (s, 1H, ArH) 6.99 (d, J=7.3 Hz, 1H, ArH) 7.17-7.44 (m, 10H, ArH) 7.59-7.91 (m, 6H, CH, ArH) 8.25 (d, J=7.8 z, 1H, ArH). MS(EI): 556.

<Example 35> 9b-Hydroxy-7-isopropyl-10-oxo-9b,10-dihydro-4bH-benzo[d]indeno[1,2-b]furan-4b-yl acrylate To a solution of 4b,9b-dihydroxy-7-isopropyl-4b,9b-dihydro-5-oxa-indeno[2,1-a]inden-10-one (1.00 g, 3.37 mmol in anhydrous tetrahydrofurane were added acryloyl chloride (0.61 g, 6.74 mmol, trimethylamine (0.41 g, 4.0 mmol, and 4-dimethylaminopyridine (0.1 g), followed by heating for 24 hrs under reflux. The reaction mixture was concentrated in a vacuum and washed many times with ethylacetate. The concentrated organic layer was purified using column chromatography (ethylacetate:hexane=1:2 to 1:1) to afford the title compound. 0.02 g (1.7%).

mp: 95-97° C.

$^1$H-NMR (300 MHz, CDCl$_3$) δ 1.18 (d, J=2.1 Hz, 7.2 Hz, 6H, CH$_3$) 2.81-2.87 (m, 1H, CH) 3.91 (s, 1H, OH) 5.95 (d, J=7.5 Hz, 2H, CH$_2$) 6.19-6.28 (m, 1H, OH) 6.50 (d, J=12.0 Hz, 1H, ArH) 6.73 (s, 1H, ArH) 6.88 (d, J=8.1 Hz, 1H, ArH) 7.52 (d, J=7.8 Hz, 1H, ArH) 7.56 (t, J=7.8 Hz, 1H, ArH) 7.80-7.91 (m, 2H, ArH). MS(EI): 350.

<Example 36> 9b-Hydroxy-7-isopropyl-10-oxo-9b,10-dihydro-4bH-benzo[d]indeno[1,2-b]furan-4b-yl furane-2-carboxylatefurane-2-carboxylic acid Furane-2-carbonyl chloride (0.88 g, 6.74 mmol, trimethylamine (0.34 g, 3.37 mmol, 4-dimethylaminopyridine (0.1 g) were added to a solution of 4b,9b-dihydroxy-7-isopropyl-4b,9b-dihydro-5-oxa-indeno[2,1-a]inden-10-one (1.00 g, 3.37 mmol in anhydrous tetrahydrofurane and heated for 24 hrs under reflux. The reaction mixture was concentrated in a vacuum and washed many times with ethylacetate. The concentrated organic layer was purified using column chromatography (ethylacetate:hexane=1:4 to 1:2) to afford the title compound. 0.07 g (5%).

mp: 116-120° C.

$^1$H-NMR (300 MHz, CDCl$_3$) δ 1.20 (d, J=2.1 Hz, 6.9 Hz, 6H, CH$_3$) 2.78-2.88 (m, 1H, CH) 4.77 (s, 1H, OH) 6.46-6.48 (s, 1H, CH) 6.71 (s, 1H, ArH) 6.90 (d, J=7.2 Hz, 1H, ArH) 7.24 (s, 1H, ArH) 7.50-7.56 (m, 3H, CH, ArH) 7.73-7.82 (m, 2H, ArH) 7.93 (d, J=7.8 Hz, 1H, ArH). MS(EI): 390.

<Example 37> Diethyl 7-isopropyl-10-oxo-9b,10-dihydro-4bH-benzo[d]indeno[1,2-b]furane-4b,9b-diyl dicarbonate Ethoxy carbonyl chloride (0.81 g, 6.74 mmol, trimethylamine (0.34 g, 3.37 mmol, and 4-dimethylaminopyridine (0.1 g) were added to a solution of 4b,9b-dihydroxy-7-isopropyl-4b,9b-dihydro-5-oxa-indeno[2,1-a]inden-10-one (1.00 g, 3.37 mmol) in anhydrous tetrahydrofurane, and heated for 24 hrs under reflux. The reaction mixture was concentrated in a vacuum and washed many times with ethylacetate, and the concentrated organic layer was purified using column chromatography (ethylacetate:hexane=1:4 to 1:2) to afford the title compound. 0.03 g (2%).

mp: 150-153° C.

$^1$H-NMR (300 MHz, CDCl$_3$) δ 1.16 (dd, J=6.8, 2.8 Hz, 6H, CH$_3$) 1.20-1.28 (m, 6H, CH$_3$) 2.78-2.85 (m, 1H, CH) 4.14-4.30 (m, 4H, OCH$_2$) 6.77 (s, 1H, ArH) 6.94 (d, J=7.9 Hz, 1H, ArH) 7.53-7.62 (m, 2H, ArH) 7.76-7.87 (m, 2H, ArH) 8.18 (d, J=7.8 Hz, 1H, ArH). MS(EI): 440.

<Example 38> Ethyl 9b-hydroxy-7-isopropyl-10-oxo-9b,10-dihydro-4bH-benzo[d]indeno[1,2-b]furan-4b-yl carbonate Ethoxy carbonyl chloride (0.81 g, 6.74 mmol, trimethylamine (0.34 g, 3.37 mmol, and 4-dimethylaminopyridine (0.1 g) were added to a solution of 4b,9b-dihydroxy-7-isopropyl-4b,9b-dihydro-5-oxa-indeno[2,1-a]inden-10-one (1.00 g, 3.37 mmol) in anhydrous tetrahydrofurane, and heated for 24 hrs under reflux. The reaction mixture was concentrated in a vacuum and washed many times with ethylacetate, and the concentrated organic layer was purified using column chromatography (ethylacetate:hexane=1:4 to 1:2) to afford the title compound. 0.07 g (5%).

mp: 144-147° C.

$^1$H-NMR (300 MHz, CDCl$_3$) δ 1.16 (d, J=6.9 Hz, 6H, CH$_3$) 1.25 (t, J=7.1 Hz, 3H, CH$_3$) 2.78-2.85 (m, 1H, CH) 4.12-4.19 (q, J=14.3, 7.1 Hz, 2H, OCH$_2$) 4.60 (s, 1H, OH) 6.69 (s, 1H, ArH) 6.88 (d, J=7.8 Hz, 1H, ArH) 7.47-7.58 (m, 2H, ArH) 7.75-7.83 (m, 2H, ArH) 7.97 (d, J=7.6 Hz, 1H, ArH). MS(EI): 368.

<Example 39> Methyl 4b,9b-dihydroxy-10-oxo-9b,10-dihydro-4bH-benzo[d]indeno[1,2-b]furan-8-carboxylate Methyl 3-hydroxy-benzoate (0.42 g, 2.8 mmol) was added to a solution of ninhydrin (0.50 g, 2.8 mmol) in glacial acetic acid (10 ml) and heated for 27 hrs under reflux. The reaction mixture was diluted in ethylacetate and washed many times with water, and the concentrated organic layer was purified using column chromatography (ethylacetate:hexane=1:4) to afford the title compound. 0.14 g (16%).

mp: 220-223° C.

$^1$H-NMR (300 MHz, CDCl$_3$) δ 3.87 (s, 3H, OCH$_3$) 4.05 (s, 1H, OH) 4.79 (s, 1H, OH) 6.87 (d, J=8.4 Hz, 1H, ArH) 7.59 (t, J=7.8 Hz, 1H, ArH) 7.80-7.86 (m, 2H, ArH) 7.98-8.02 (m, 1H, ArH) 8.20 (s, 1H, ArH). MS(EI): 312.

<Example 40> 9b-Hydroxy-7-isopropyl-10-oxo-9b,10-dihydro-4bH-benzo[d]indeno[1,2-b]furan-4b-yl diethylcarbamate Triethylamine (0.4 g, 4.0 mmol), diethylcarbamoyl chloride (0.91 g, 6.7 mmol), and 4-dimethylaminopyridine (0.1 g) were added to a solution of 4b,9b-dihydroxy-7-isopropyl-4b,9b-dihydro-5-oxa-indeno[2,1-a]inden-10-one (1.00 g, 3.3 mmol) in anhydrous tetrahydrofurane and heated under reflux. The reaction mixture was concentrated in a vacuum, diluted in dichloromethane and washed many times with water. The concentrated organic layer was purified using column chromatography (ethylacetate:hexane=1:4 to 1:2) to afford the title compound. 0.63 g (47%).

mp: 127-130° C.

$^1$H-NMR (300 MHz, CDCl$_3$) δ 1.08-1.29 (m, 12H, CH$_3$) 2.81-2.86 (m, 1H, CH) 3.22-3.45 (m, 4H, NCH$_2$) 4.73 (s, 1H, OH) 6.70 (s, 1H, ArH) 6.91 (d, J=7.9 Hz, 1H, ArH) 7.53-7.61 (m, 2H, ArH) 7.78-7.91 (m, 3H, ArH). MS(EI): 395.

<Example 41> 4b-Hydroxy-7-isopropyl-10-oxo-9b,10-dihydro-4bH-benzo[d]indeno[1,2-b]furan-9b-yl diethylcarbamate Triethylamine (0.4 g, 4.0 mmol), diethylcarbamoyl chloride (0.91 g, 6.7 mmol), and 4-dimethylaminopyridine (0.1 g) were added to a solution of 4b,9b-dihydroxy-7-isopropyl-4b,9b-dihydro-5-oxa-indeno[2,1-a]inden-10-one (1.00 g, 3.3 mmol) in anhydrous tetrahydrofurane and heated under reflux. The reaction mixture was concentrated in a vacuum, diluted in dichloromethane and washed many times with water. The concentrated organic layer was purified using column chromatography (ethylacetate:hexane=1:4 to 1:2) to afford the title compound. 0.02 g (1.5%).

mp: 101-104° C.

$^1$H-NMR (300 MHz, CDCl$_3$) δ 1.06-1.30 (m, 12H, CH$_3$) 2.79-2.88 (m, 1H, CH) 3.21-3.28 (m, 2H, NCH$_2$) 3.36-3.47 (m, 2H, NCH$_2$) 5.60 (s, 1H, OH) 6.73 (s, 1H, ArH) 6.85 (d, J=7.2 Hz, 1H, ArH) 7.39 (d, J=7.8 Hz, 1H, ArH) 7.54 (t, J=6.3 Hz, 1H, ArH) 7.78-7.88 (m, 2H, ArH) 8.00 (d, J=7.5 Hz, 1H, ArH). MS(EI): 395.

<Example 42> 2,3-Difluoro-4b,9b-dihydroxy-7-isopropyl-4bH-benzo[d]indeno[1,2-b]furan-10(9bH)-one m-Isopropyl phenol (0.21 g, 1.5 mmol) was added to a solution of 5,6-difluoro-2,2-dihydroxy-1H-indene-1,3(2H)-dione (0.33 g, 1.54 mmol) in glacial acetic acid (10 ml) and heated for 2 hrs under reflux. The reaction mixture was diluted in ethylacetate and washed many times with water. The concentrated organic layer was purified using column chromatography (ethylacetate:hexane=1:4 to 1:2) to afford the title compound. 0.32 g (63%).

mp: 134-136° C.

$^1$H-NMR (300 MHz, CDCl$_3$) δ 1.18 (d, J=5.1 Hz, 6H, CH$_3$) 1.19 (s, 3H, CH$_3$) 2.79-2.88 (m, 1H, CH) 3.71 (s, 1H, OH) 4.65 (s, 1H, OH) 6.72 (s, 1H, ArH) 6.87 (d, J=7.8 Hz, 1H, ArH) 7.37 (d, J=8.1 Hz, 1H, ArH) 7.56 (t, J=8.1 Hz, 1H, ArH) 7.77 (t, J=6.7 Hz, 1H, ArH). MS(EI): 332.

<Example 43> 1,4b,9b-Trihydroxy-7-isopropyl-4bH-benzo[d]indeno[1,2-b]furan-10(9bH)-one m-Isopropyl phenol (0.35 g, 2.5 mmol) was added to a solution of 2,2,4-trihydroxy-1H-indene-1,3(2H)-dione (0.50 g, 2.5 mmol) in glacial acetic acid (10 ml) and heated for 4 hrs under reflux. The reaction mixture was diluted in ethylacetate and washed many times with water. The concentrated organic layer was purified using column chromatography (ethylacetate:hexane=1:2) to afford the title compound. 0.33 g (41%).

mp: 205-207° C.

$^1$H-NMR (300 MHz, CDCl$_3$) δ 1.19 (dd, J=1.8 Hz, 6.9 Hz, 6H, CH$_3$) 2.80-2.89 (m, 1H, CH) 3.59 (s, 1H, OH) 4.60 (s, 1H, OH) 6.73 (s, 1H, ArH) 6.88 (dd, J=1.5 Hz, 7.8 Hz, 1H, ArH) 6.95 (d, J=8.1 Hz, 1H, ArH) 7.45 (d, J=7.2 Hz, 2H, ArH) 7.69 (t, J=7.8 Hz, 1H, ArH) 8.40 (s, 1H, OH). MS(EI): 312.

<Example 44> 4b,9b-Dihydroxy-7-isopropyl-1H-cyclopenta[b]naphthaleno[1,2-b]furan-10(9bH)-one m-Isopropyl phenol (0.03 g, 0.2 mmol) was added to a solution of 2,2-dihydroxy-1H-cyclopenta[b]naphthalene-1,3(2H)-dione (50 mg, 0.2 mmol) in glacial acetic acid (5 ml) and heated for 2 hrs under reflux. The reaction mixture was concentrated in a vacuum, and the concentrated organic layer was purified using column chromatography (ethylacetate:hexane=1:4 to 1:3) to afford the title compound. 0.07 g (92%).

mp: 186-189° C.

$^1$H-NMR (300 MHz, CDCl$_3$) δ 1.09 (d, J=6.9 Hz, 6H, CH$_3$) 2.70-2.80 (m, 1H, CH) 6.67 (s, 1H, ArH) 6.76 (d, J=7.8 Hz, 1H, ArH) 7.41 (d, J=7.8 Hz, 1H, ArH) 7.48-7.61 (m, 2H, ArH) 7.92 (m, 2H, ArH) 8.26 (s, 1H, ArH) 8.43 (s, 1H, ArH). MS(EI): 346.

<Example 45> 9b-Hydroxy-7-isopropyl-4b-methoxy-1-nitro-4bH-benzo[d]indeno[1,2-b]furan-10(9bH)-one Iron (0.09 g, 1.6 mmol), conc. HCl (0.05 ml), and water (0.5 ml) were added in that order to a solution of 4b,9b- dihydroxy-7-isopropyl-1-nitro-4bH-benzo[d]indeno[1,2-b]furan-10(9bH)-one (80 mg, 0.2 mmol) in absolute ethanol (5 ml). The reaction mixture was heated for 2 hrs under reflux. After filtration at high temperature to remove iron, the filtrate was concentrated in a vacuum and purified using column chromatography (ethylacetate:hexane=1:1) to afford the title compound. 80 mg (80%).

mp: 181-183° C.

$^1$H-NMR (300 MHz, CDCl$_3$) δ 1.19 (dd, J=2.7 Hz, 6.9 Hz, 6H, CH$_3$) 2.80-2.89 (m, 1H, CH) 3.73 (s, 3H, OCH$_3$) 5.56 (s, 1H, OH) 6.59 (d, J=8.1 Hz, 1H, ArH) 6.73 (s, 1H, ArH) 6.86 (dd, J=1.5 Hz, 7.8 Hz, 1H, ArH) 7.08 (d, J=7.2 Hz, 1H, ArH) 7.46 (m, 2H, ArH). MS(EI): 326.

<Example 46> 1-Amino-4b,9b-dihydroxy-7-isopropyl-4bH-benzo[d]indeno[1,2-b]furan-10(9bH)-one Iron (0.48 g, 8.5 mmol), conc. HCl (0.1 ml), and water (1 ml) were added in that order to a solution of 4b,9b-dihydroxy-7-isopropyl-1-nitro-4bH-benzo[d]indeno[1,2-b]furan-10(9bH)-one (0.40 g, 1.1 mmol) in absolute ethanol (10 ml). The reaction mixture was heated for 2 hrs under reflux. After removing iron by high-temperature filtration, the remainder was concentrated in a vacuum and purified by column chromatography (ethylacetate:hexane=1:4) to afford the title compound. 0.17 g (47%).

mp: 180-182° C.

$^1$H-NMR (300 MHz, CDCl$_3$) δ 1.19 (dd, J=1.8 Hz, 6.9 Hz, 6H, CH$_3$) 2.79-2.89 (m, 1H, CH) 3.57 (s, 1H, OH) 4.57 (s, 1H, OH) 5.55 (s, 2H, NH$_2$) 6.61 (d, J=8.1 Hz, 1H, ArH) 6.77 (s, 1H, ArH) 6.85 (dd, J=1.5 Hz, 7.8 Hz, 1H, ArH) 7.17 (d, J=7.5 Hz, 1H, ArH) 7.42-7.52 (m, 2H, ArH). MS(EI): 311.

<Example 47> 1-Amino-7-isopropyl-10-oxo-9b,10-dihydro-4bH-benzo[d]indeno[1,2-b]furane-4b,9b-diyl diacetate Iron (0.22 g, 3.8 mmol), conc. HCl (0.05 ml), and water (1 ml) were added in that order to a solution of 7-isopropyl-1-nitro-10-oxo-9b,10-dihydro-4bH-benzo[d]indeno[1,2-b]furane-4b,9b-diyl diacetate (0.23 g, 0.5 mmol) in absolute ethanol (10 ml). The reaction mixture was heated for 2 hrs under reflux. After removing iron by high-temperature filtration, the filtrate was concentrated in a vacuum and purified using column chromatography (ethylacetate:hexane=1:4) to afford the title compound. 0.15 g (71%).

mp: 220-223° C.

$^1$H-NMR (300 MHz, CDCl$_3$) δ 1.18 (dd, J=6.9 Hz, 2.1 Hz, 6H, CH$_3$) 2.15 (s, 6H, OAc) 2.81-2.90 (m, 1H, CH) 5.57 (s, 2H, NH$_2$) 6.64 (d, J=8.1 Hz, 1H, ArH) 6.75 (s, 1H, ArH) 6.92 (dd, J=7.8 Hz, 1.2 Hz, 1H, ArH) 7.29 (d, J=7.8 Hz, 1H, ArH) 7.43-7.51 (m, 2H, ArH). $^{13}$C-NMR (300 MHz, CDCl$_3$) δ 20.22, 21.40, 23.77, 23.82, 34.37, 87.36, 108.54, 110.02, 113.847, 116.11, 117.79, 118.03, 121.31, 124.89, 137.49, 145.40, 147.37, 154.38, 157.54, 167.18, 169.51, 194.17. MS(EI): 395.

<Example 48> N-(4b,9b-Dihydroxy-7-isopropyl-10-oxo-9b,10-dihydro-4bH-benzo[d]indeno[1,2-b]furan-1-yl)acetamide In absolute methanol (2 ml), 1-acetamido-7-isopropyl-10-oxo-9b,10-dihydro-4bH-benzo[d]indeno[1,2-b]furane-4b,9b-diyl diacetate (30 mg, 0.06 mmol) was reacted with potassium carbonate (0.05 g, 0.3 mmol) at room temperature for 1 hr. The reaction mixture was concentrated in a vacuum, diluted in ethylacetate, and washed many times with water. The concentrated organic layer was purified using column chromatography (ethylacetate:hexane=1:4 to 1:2) to afford the title compound. 7 mg (35%).

mp: 152-154° C.

$^1$H-NMR (300 MHz, CDCl$_3$) δ 1.18 (dd, J=1.9 Hz, 6.7 Hz, 6H, CH$_3$) 2.16 (s, 3H, NHAc) 2.72-2.81 (m, 1H, CH) 3.76 (s, 1H, OH) 4.60 (s, 1H, OH) 6.65 (s, 1H, ArH) 6.79 (d, J=8.1 Hz, 1H, ArH) 7.35 (d, J=7.8 Hz, 1H, ArH) 7.53 (d, J=7.5 Hz, 1H, ArH) 7.66 (t, J=8.1 Hz, 1H, ArH) 8.44 (d, J=8.1 Hz, 1H, ArH) 9.88 (s, 1H, NH). MS(EI): 353.

<Example 49> Methyl 4b,9b-dihydroxy-7-isopropyl-10-oxo-9b,10-dihydro-4bH-benzo[d]indeno[1,2-b]furan-1-ylcarbamate A solution of 4b,9b-dihydroxy-1-isocyanato-7-isopropyl-4bH-benzo[d]indeno[1,2-b]furan-10(9bH)-one (50 mg, 0.14 mmol) in absolute methanol (5 ml) was heated for 40 min under reflux, concentrated in a vacuum, and purified using column chromatography (ethylacetate:hexane=1:4) to afford the title compound. 12 mg (22%).

mp: 96-99° C.

$^1$H-NMR (300 MHz, CDCl$_3$) δ 1.16 (dd, J=6.9, 1.8 Hz, 6H, CH$_3$) 2.77-2.87 (m, 1H, CH) 3.80 (s, 3H, OCH$_3$) 6.70 (s, 1H, ArH) 6.84 (d, J=8.1 Hz, 1H, ArH) 7.41 (d, J=7.8 Hz, 1H, ArH) 7.54 (d, J=7.8 Hz, 1H, ArH) 7.71 (t, J=8.1 Hz, 1H, ArH) 8.23 (d, J=8.4 Hz, 1H, ArH) 9.37 (s, 1H, NH). MS(EI): 369.

<Example 50> 1-Amino-7-ethyl-4b,9b-dihydroxy-4b,9b-dihydro-5-oxa-indeno[2,1-a]inden-10-one Iron (0.31 g, 5.57 mmol) and conc. HCl (0.05 ml) were added to a solution of 7-ethyl-4b,9b-dihydroxy-1-nitro-4b,9b-dihydro-5-oxa-indeno[2,1-a]inden-10-one (0.25 g, 0.76 mmol) in ethanol (5 ml) and water (0.5 ml). After 2 hrs of reaction, the reaction mixture was washed with methanol, and the filtrate was concentrated and purified using column chromatography (ethylacetate:hexane=1:2) to afford the title compound. 0.05 g (22%).

mp: 200-203° C.

$^1$H-NMR (300 MHz, CDCl$_3$) δ 1.16 (t, J=7.5 Hz, 3H, CH$_3$) 2.57 (q, J=7.5 Hz, 2H, CH$_2$) 5.47 (s, 2H, NH$_2$) 6.61 (d, J=8.1 Hz, 1H, ArH) 6.66 (s, 1H, ArH) 6.80 (d, J=7.8 Hz, 1H, ArH) 7.14 (d, J=7.5 Hz, 1H, ArH) 7.29-7.39 (m, 2H, ArH). MS(EI): 297.

<Example 51> 7-Ethyl-4b,9b-dihydroxy-1-nitro-4b,9b-dihydro-5-oxa-indeno[2,1-a]inden-10-one Triethylamine (0.09 g, 0.96 mmol) and chloroformic acid methyl ester (0.09 g, 0.96 mmol) were added to a solution of 1-amino-4b,9b-dihydroxy-7-isopropyl-4b,9b-dihydro-5-oxa-indeno[2,1-a]inden-10-one (0.10 g, 0.32 mmol) in anhydrous tetrahydrofurane (15 ml), and heated for 14 hrs under reflux. The organic layer was concentrated and purified using column chromatography (ethylacetate:hexane=1:4 to 1:2) to afford the title compound. 80 mg (58%).

mp: 110-120° C.

$^1$H-NMR (300 MHz, CDCl$_3$) δ 1.19 (d, J=6.9 Hz, 6H, CH$_3$) 2.84-2.89 (m, 1H, CH) 3.71 (s, 3H, OCH$_3$) 3.76 (s, 3H, OCH$_3$) 5.67 (s, 2H, NH$_2$) 6.88-6.93 (m, 2H, ArH) 7.19 (d, J=8.4 Hz, 1H, ArH) 7.25 (d, J=7.5 Hz, 1H, ArH) 7.56 (t, J=7.8 Hz, 1H, ArH) 7.66 (d, J=8.4 Hz, 1H, ArH)

MS(EI): 427. .

<Example 52> 7-Ethyl-2,4b,9b-trihydroxy-4b,9b-dihydro-5-oxa-indeno[2,1-a]inden-10-one m-Ethyl phenol (0.60 g, 4.97 mmol) was added to a solution of 2,2,5-trihydroxy-2H-indene-1,3-dione (0.99 g, 4.97 mmol) in acetic acid (10 ml) and heated for 10 hrs under reflux. The filtrate was concentrated and subjected to column chromatography (ethylacetate:hexane=1:4) to afford the title compound. 1.02 g (69%).

mp: 208-213° C.
$^1$H-NMR (300 MHz, CDCl$_3$) δ 1.17 (t, J=7.5 Hz, 3H, CH$_3$) 2.57 (q, J=15.0 Hz, 7.5 Hz, 2H, CH$_2$) 6.64 (s, 3H, ArH) 6.79 (d, J=7.8 Hz, 1H, ArH) 6.97 (dd, J=8.5 Hz, 1.9 Hz 1H, ArH) 7.28 (s, 1H, ArH) 7.42 (d, J=7.8 Hz, 1H, ArH) 7.65 (d, J=8.5 Hz, 1H, ArH). MS(EI): 298.29.

<Example 53> Acetic acid 4b-acetoxy-1-amino-7-isopropyl-10-oxo-4b,10-dihydro-5-oxa-indeno[2,1-a]inden-9b-yl ester Triethylamine (0.11 g, 1.16 mmol) was added to a solution of 4b,9b-dihydroxy-7-isopropyl-1-nitro-4b,9b-dihydro-5-oxa-indeno[2,1-a]inden-10-one (0.20 g, 0.58 mmol) in anhydrous chloroform (10 ml) at room temperature. To this reaction mixture, a dilution of 10% acetyl chloride (1 ml) in chloroform was slowly added at 0° C. and incubated at the same temperature for 1 hr. The reaction mixture was diluted in dichloromethane and washed many times with water. The concentrated organic layer was purified using column chromatography (ethylacetate:hexane=1:4 to 1:2) to afford the title compound. 30 mg (12%).

mp: 201-203° C.
$^1$H-NMR (300 MHz, CDCl$_3$) δ 1.21 (dd, J=8.4 Hz, 2.0 Hz, 6H, CH$_3$) 2.16 (s, 6H, OAc) 2.85-2.90 (m, 1H, CH) 6.75 (s, 1H, ArH) 6.96 (d, J=7.9 Hz, 1H, ArH) 7.49 (d, J=7.9 Hz, 1H, ArH) 7.88-7.91 (m, 2H, ArH) 8.39 (dd, J=6.7 Hz, 2.0 Hz, 1H, ArH). MS(EI): 425.

<Example 54> acetic acid 4b-acetoxy-7-isopropyl-1-methanesulfonylamino-10-oxo-4b,10-dihydro-5-oxa-indeno[2,1-a]inden-9b-yl ester Triethylamine (0.05 g, 0.50 mmol) was added to a solution of acetic acid 4b-acetoxy-1-amino-7-isopropyl-10-oxo-4b,10-dihydro-5-oxa-indeno[2,1-a]inden-9b-yl ester (0.10 g, 0.25 mmol) in anhydrous chloroform (10 ml) at room temperature. To this solution, 0° C. 에서 methanesulfonyl chloride (0.05 g, 0.50 mmol) was slowly added at 0° C. and reacted at room temperature for 12 hrs. The reaction mixture was diluted in dichloromethane and washed many times with water. The organic layer was dried and filtered, followed by purification through column chromatography (ethylacetate:hexane=1:2 to 1:1) to afford the title compound. 10 mg (8%).

mp: 96-100° C.
$^1$H-NMR (300 MHz, CDCl$_3$) δ 1.19 (d, J=6.9 Hz, 6H, CH$_3$) 2.07 (s, 3H, OAc) 2.20 (s, 3H, OAc) 2.83-2.88 (m, 1H, CH) 3.16 (s, 3H, CH$_3$) 6.83 (s, 1H, ArH) 7.14 (d, J=8.1 Hz, 1H, ArH) 7.59 (q, J=8.1 Hz, 1H, ArH) 7.67 (d, J=7.5 Hz, 1H, ArH) 7.86 (t, J=7.5 Hz, 1H, ArH) 7.98 (d, J=8.1 Hz, 1H, ArH) 9.23 (s, 1H, NH). MS(EI): 473.

<Example 55> 1-(4b,9b-Dihydroxy-7-isopropyl-10-oxo-9b,10-dihydro-4bH-benzo[d]indeno[1,2-b]furan-1-yl-3-isopropylurea Isopropylamine (0.012 ml was dropwise added to a solution of 4b,9b-dihydroxy-1-isocyanato-7-isopropyl-4bH-benzo[d]indeno[1,2-b]furan-10(9bH)-one (40 mg, 0.11 mmol) in anhydrous tetrahydrofurane.

The reaction mixture was heated for 12 hrs under reflux, concentrated in a vacuum, and purified using column chromatography (ethylacetate:hexane=1:4) to afford the title compound. 10 mg (21%).

mp: 81-85° C.
$^1$H-NMR (300 MHz, CDCl$_3$) δ 0.98 (t, J=7.4 Hz, 6H, CH$_3$) 1.15-1.32 (m, 6H, CH$_3$) 2.81-2.85 (m, 1H, CH) 3.78 (s, 1H, OH) 4.14 (t, J=6.6 Hz, 2H, NH, CH) 4.67 (s, 1H, OH) 6.72 (s, 1H, ArH) 6.86 (d, J=7.8 Hz, 1H, ArH) 7.42 (d, J=7.8 Hz, 1H, ArH) 7.53 (d, J=7.8 Hz, 1H, ArH) 7.71 (t, J=8.0 Hz, 1H, ArH) 8.27 (d, J=8.3 Hz, 1H, ArH) 9.36 (s, 1H, NH). MS(EI): 396.

<Example 56> N-(9b-Amino-4b-hydroxy-7-isopropyl-10-oxo-9b,10-dihydro-4bH-benzo[d]indeno[1,2-b]furan-1-ylacetamide To a solution of N-(4b-chloro-9b-hydroxy-7-isopropyl-10-oxo-9b,10-dihydro-4bH-benzo[d]indeno[1,2-b]furan-1-ylacetamide (0.53 g, 1.4 mmol in anhydrous tetrahydrofurane (10 ml) was added 2M ammonia (1.42 ml in isopropylalcohol) at 5° C., and the reaction mixture was stirred at room temperature for 2 hrs. After concentration in a vacuum, the reaction mixture was diluted in dichloromethane, and washed with an aqueous sodium bicarbonate solution. The concentrated organic layer was purified using column chromatography (ethylacetate:hexane=1:4) to afford the title compound. 40 mg (8%).

mp: 152-156° C.
$^1$H-NMR (300 MHz, CDCl$_3$) δ 1.17 (dd, J=1.8, 6.9 Hz, 6H, CH$_3$) 2.23 (s, 3H, CH$_3$) 2.78-2.87 (m, 1H, CH) 6.70 (s, 1H, ArH) 6.84 (d, J=7.8 Hz, 1H, ArH) 7.34 (d, J=7.8 Hz, 1H, ArH) 7.63 (d, J=7.2 Hz, 1H, ArH) 7.75 (t, J=8.1 Hz, 1H, ArH) 8.54 (d, J=8.1 Hz, 1H, ArH) 9.99 (s, 1H, NH). MS(EI): 352.

<Example 57> N,N'-(4b-Hydroxy-7-isopropyl-10-oxo-9b,10-dihydro-4bH-benzo[d]indeno[1,2-b]furane-1,9b-diyl)diacetamide N-(9b-amino-4b-hydroxy-7-isopropyl-10-oxo-9b,10-dihydro-4bH-benzo[d]indeno[1,2-b]furan-1-yl)acetamide (400 mg, 0.11 mmol) was dissolved in anhydrous acetic acid (3 ml) was reacted with anhydrous acetic acid (0.01 g, 0.11 mmol) for 2 hrs at 80° C. The reaction mixture was concentrated in a vacuum and purified using column chromatography (ethylacetate:hexane=1:4) to afford the title compound. 12 mg (27%).

mp: 189-191° C.
$^1$H-NMR (300 MHz, CDCl$_3$) δ 1.16 (dd, J=2.1, 6.9 Hz, 6H, CH$_3$) 2.03 (s, 3H, CH$_3$) 2.20 (s, 3H, CH$_3$) 2.77-2.86 (m, 1H, CH) 5.40 (s, 1H, OH) 6.52 (s, 1H, NH) 6.70 (s, 1H, ArH) 6.84 (dd, J=1.2, 8.1 Hz, 1H, ArH) 7.29 (d, J=8.1 Hz, 1H, ArH) 7.57 (d, J=7.5 Hz, 1H, ArH) 7.72 (t, J=8.1 Hz, 1H, ArH) 8.54 (d, J=8.1 Hz, 1H, ArH) 10.00 (s, 1H, NH). MS(EI): 394.

<Example 58> N-(7-Amino-2-hydroxy-2-(4-isopropyl-2-hydroxyphenyl)-1,3-dioxo-2,3-dihydro-1H-inden-4-yl)acetamide Water (1.5 ml), iron (0.71 g), and conc. HCl (0.05 ml) were added in that order to a solution of 1-amino-4b,9b-dihydroxy-7-isopropyl-4-nitro-4bH-benzo[d]indeno[1,2-b]furan-10(9bH)-one (0.70 g, 1.75 mmol) in ethanol (15 ml)

and heated for 2 hrs under reflux. The reaction mixture was washed with methanol, concentrated in a vacuum, and purified using column chromatography (ethylacetate:hexane=1:1) to afford the title compound. 0.33 g (51%).

mp: 278-280° C.

$^1$H-NMR (300 MHz, acetone-$d_6$) δ 1.18 (dd, J=6.3 Hz, 6H, $CH_3$) 2.17 (s, 3H, $CH_3$) 2.78-2.86 (m, 1H, CH) 6.38 (m, 2H, NH, ArH) 6.65 (s, 2H, ArH) 6.83 (d, J=8.1 Hz, 2H, ArH). MS(EI): 368.

<Example 59> N-(2-Amino-4b,9b-dihydroxy-7-isopropyl-10-oxo-9b,10-dihydro-4bH-benzo[d]indeno[1,2-b]furan-1-yl)acetamide Water (0.3 ml), iron (0.10 g), and conc. HCl (0.05 ml) were added in that order to a solution of N-(4b,9b-dihydroxy-7-isopropyl-2-nitro-10-oxo-9b,10-dihydro-4bH-benzo[d]indeno[1,2-b]furan-1-yl)acetamide (0.10 g, 0.25 mmol) in ethanol (3 ml) and heated for 90 min under reflux. The reaction mixture was washed with methanol, concentrated in a vacuum and purified using column chromatography (ethylacetate:hexane=2:1) to afford the title compound. 22 mg (24%).

mp: 177-181° C.

$^1$H-NMR (300 MHz, acetone-$d_6$) δ 1.16 (d, J=3.0, 6.9 Hz, 6H, $CH_3$) 2.30 (s, 3H, $CH_3$) 2.77-2.86 (m, 1H, CH) 5.93 (s, 2H, $NH_2$) 6.62 (s, 1H, ArH) 6.79 (d, J=7.8 Hz, 1H, ArH) 6.99 (s, 1H, ArH) 7.29-7.40 (m, 2H, ArH) 8.86 (s, 1H, NH).

<Example 60> 1-Amino-4b,9b-dihydroxy-7-isopropyl-2-nitro-4bH-indeno[1,2-b]benzofuran-10(9bH)-one N-(2,2-Dihydroxy-7-nitro-1,3-dioxo-2,3-dihydro-1H-inden-4-yl)acetamide (0.10 mg, 0.25 mmol) was dissolved in 6 M HCl (1.4 ml) and methanol (1 ml) and heated for 90 min at 90° C. This solution was added with sodium carbonate and 2 N NaOH, and extracted with methylene chloride. The organic layer was concentrated to afford the title compound. 87 mg (97%).

mp: 12-116° C.

$^1$H-NMR (300 MHz, $CDCl_3$) δ 1.19 (d, J=6.9 Hz, 6H, $CH_3$) 2.83-2.88 (m, 1H, CH) 4.60 (s, 1H, OH) 6.75 (s, 1H, ArH) 6.90 (d, J=6.9 Hz, 1H, ArH) 7.19 (d, J=8.4 Hz, 1H, ArH) 7.43 (d, J=8.1 Hz, 1H, ArH) 7.96 (s, 2H, $NH_2$) 8.56 (d, J=9.0 Hz, 1H, ArH). MS(EI): 356.

<Example 61> 1,4-diamino-4b,9b-dihydroxy-7-isopropyl-4bH-benzo[d]indeno[1,2-b]furan-10(9bH)-one Water (1.5 ml), iron (0.68 g), and conc. HCl (0.05 ml) were added in that order to a solution of 1-amino-4b,9b-dihydroxy-7-isopropyl-4-nitro-4bH-benzo[d]indeno[1,2-b]furan-10(9bH)-one (0.60 g, 1.68 mmol) in ethanol (15 ml) and heated for 2 hrs under reflux. The reaction mixture was washed with methanol, concentrated in a vacuum, and purified using column chromatography (ethylacetate:hexane=1:2) to afford the title compound. 0.22 g (36%).

mp: 223-231° C.

$^1$H-NMR (300 MHz, $CD_3OD$) δ 1.19 (d, J=6.9 Hz, 6H, $CH_3$) 2.78-2.82 (m, 1H, CH) 6.56 (s, 1H, ArH) 6.77 (d, J=8.1 Hz, 1H, ArH) 6.99 (s, 2H, ArH) 7.43 (d, J=8.1 Hz, 1H, ArH). MS(EI): 326.

<Example 62> 1,2-Diamino-4b,9b-dihydroxy-7-isopropyl-4bH-indeno[1,2-b]benzofuran-10(9bH)-one Water (0.3 ml), iron (0.08 g), and conc. HCl (0.03 ml) were added in that order to a solution of 1-amino-4b,9b-dihydroxy-7-isopropyl-2-nitro-4bH-benzo[d]indeno[1,2-b]furan-10(9bH)-one (75 mg, 0.21 mmol) in ethanol (3 ml) and heated for 90 min under reflux. The reaction mixture was washed with methanol, concentrated in a vacuum, and purified using column chromatography (ethylacetate:hexane=1:1) to afford the title compound. 12 mg (17%).

mp: 163-166° C.

$^1$H-NMR (300 MHz, acetone-$d_6$) δ 1.03 (d, J=6.9 Hz, 6H, $CH_3$) 2.61-2.70 (m, 1H, CH) 5.46 (s, 1H, ArH) 6.01 (s, 1H, ArH) 6.51-6.58 (m, 2H, ArH) 6.98 (d, J=9.0 Hz, 1H, ArH). MS(EI): 326.

<Example 63> 2-(2-Hydroxy-4-isopropylphenyl)-1,3-dioxo-2,3-dihydro-1H-inden-2-yl dimethylcarbamate Dimethyl carbamoyl chloride (0.72 g, 6.7 mmol) and trimethylamine (0.41 g, 4.0 mmol) were added to a solution of 4-dimethylaminopyridine (0.1 g) 4b,9b-dihydroxy-7-isopropyl-4b,9b-dihydro-5-oxa-indeno[2,1-a]inden-10-one (1.00 g, 3.3 mmol) in anhydrous tetrahydrofurane (10 ml) and heated for 24 hrs under reflux. The reaction product was concentrated, and extracted with ethylacetate. The concentrated organic layer was purified using column chromatography (ethylacetate:hexane=1:4 to 1:2) to afford the title compound. 0.19 g (15%).

mp: 114-118° C.

$^1$H-NMR (300 MHz, $CDCl_3$) δ 1.19 (d, J=6.8 Hz, 6H, $CH_3$) 2.78-2.91 (m, 4H, CH, $NCH_3$) 3.06 (s, 3H, $NCH_3$) 5.57 (s, 1H, OH) 6.72 (s, 1H, ArH) 6.88 (d, J=7.8 Hz, 1H, ArH) 7.51 (d, J=8.1 Hz, 1H, ArH) 7.56-7.78 (m, 3H, ArH) 7.99 (d, J=7.8 Hz, 1H, ArH). MS(EI): 367.

<Example 64> 4b,9b-Dihydroxy-6,8-diisopropyl-4b,9b-dihydro-5-oxa-indeno[2,1-a]inden-10-one To a solution of ninhydrin (0.30 g, 1.68 mmol) in acetic acid (10 ml) was added 2,4-diisopropylphenol (0.27 g, 1.51 mmol) which was then heated for 12 hrs under reflux. After vacuum concentration, recrystallization in methylene chloride afforded the title compound (0.40 g, 70%).

mp: 205-206° C., $^1$H-NMR (300 MHz, $CDCl_3$) δ 1.14-1.24 (m, 12H), 2.81 (q, J=7.2 Hz, 1H), 3.07 (q, J=7.2 Hz, 1H), 3.65 (s, 1H), 4.55 (s, 1H), 7.00 (d, J=1.7 Hz, 1H), 7.17 (s, 1H), 7.54 (d, J=8.4 Hz, 1H), 7.76-7.81 (m, 2H), 8.00 (d, J=7.6 Hz, 1H).

<Example 65> 9b-Amino-4b-hydroxy-7-isopropyl-4b,9b-dihydro-5-oxa-indeno[2,1-a]inden-10-one Oxalyl chloride (0.69 ml, 8.15 mmol) and two drops of dimethylformamide were added to a solution of 4b,9b-dihydroxy-7-isopropyl-4b,9b-dihydro-5-oxa-indeno[2,1-a]inden-10-one (2.00 g, 6.79 mmol) in methylene chloride (20 ml) and stirred at room temperature for 3 hrs. Concentration in a vacuum gave 9b-chloro-4b-hydroxy-7-isopropyl-4b,9b-dihydro-5-oxa-indeno-[2,1-a]inden-10-one (2.33 g, 109%).

9b-Chloro-4b-hydroxy-7-isopropyl-4b,9b-dihydro-5-oxa-indeno-[2,1-a]inden-10-one (1.00 g, 3.18 mmol) was dissolved in tetrahydrofurane (10 ml), cooled to 5° C., and mixed with 2.0 M ammonia in isopropyl alcohol (3.18 ml, 6.36 mmol) at room temperature for 4 hrs with stirring. After concentration in a vacuum, purification through column chromatography (ethyl acetate:hexane=1:4) afforded the title compound (0.75 g, 80%).

mp: 151-152° C., $^1$H-NMR (300 MHz, CDCl$_3$) δ 1.16 (dd, J=1.9 Hz, 7.0 Hz, 6H), 2.81 (q, J=7.2 Hz, 1H), 6.68 (s, 1H), 6.81 (d, J=7.8 Hz, 1H), 7.33 (d, J=7.8 Hz, 1H), 7.51 (t, J=8.3 Hz, 1H), 7.73-7.80 (m, 2H), 8.01 (d, J=7.8 Hz, 1H).

<Example 66> N-(4b-Hydroxy-7-isopropyl-10-oxo-4b,10-dihydro-5-oxa-indeno[2,1-a]inden-9b-yl)-acetamide Anhydrous acetic acid (0.08 ml, 0.88 mmol) was added to a solution of 9b-amino-4b-hydroxy-7-isopropyl-4b,9b-dihydro-5-oxa-indeno[2,1-a]inden-10-one (0.26 g, 0.88 mmol) in acetic acid (5 ml) and heated for 2 hrs under reflux. Concentration in a vacuum and recrystallization in methylene chloride afforded the title compound (0.25 g, 84%).

mp: 183-184° C., $^1$H-NMR (300 MHz, CDCl$_3$) δ 1.15 (d, J=3.0 Hz, 3H), 1.17 (d, J=3.0 Hz, 3H), 2.06 (s, 3H), 2.81 (q, J=7.1 Hz, 1H), 5.73 (s, 1H), 6.70 (d, J=1.1 Hz, 1H), 6.81 (dd, J=1.4 Hz, 7.9 Hz, 1H), 7.25 (d, J=7.2 Hz, 1H), 7.54 (t, J=8.2 Hz, 1H), 7.76-7.82 (m, 2H), 7.99 (d, J=7.7 Hz, 1H).

<Example 67> 9b-Hexylamino-4b-hydroxy-7-isopropyl-4b,9b-dihydro-5-oxa-indeno[2,1-a]inden-10-one To a solution of 4b,9b-dihydroxy-7-isopropyl-4b,9b-dihydro-5-oxa-indeno[2,1-a]inden-10-one (1.00 g, 3.39 mmol) in methylene chloride (10 ml) were added oxalyl chloride (0.35 ml, 4.08 mmol) and two drops of dimethylformamide, followed by stirring at room temperature for 3 hrs. concentration in a vacuum gave 9b-chloro-4b-hydroxy-7-isopropyl-4b,9b-dihydro-5-oxa-indeno-[2,1-a]inden-10-one (1.33 g, 109%).

9b-chloro-4b-hydroxy-7-isopropyl-4b,9b-dihydro-5-oxa-indeno[2,1-a]inden-10-one (1.00 g, 3.18 mmol) was dissolved in tetrahydrofurane (10 ml), cooled to 5° C., and reacted with hexylamine (0.84 ml, 6.36 mmol) at room temperature for 3 hrs while stirring. Concentration in a vacuum and purification through column chromatography (ethyl acetate:hexane=1:4) afforded the title compound (0.58 g, 48%).

$^1$H-NMR (300 MHz, CDCl$_3$) δ 0.84 (t, J=7.8 Hz, 3H), 1.15 (d, J=2.5 Hz, 3H), 1.17 (d, J=2.7 Hz, 3H), 1.20-1.33 (m, 6H), 1.42-1.52 (m, 2H), 2.45 (t, J=8.3 Hz, 2H), 2.81 (q, J=7.7 Hz, 1H), 6.69 (s, 1H), 6.81 (dd, J=1.0 Hz, 7.9 Hz, 1H), 7.30 (d, J=7.6 Hz, 1H), 7.49 (t, J=8.6 Hz, 1H), 7.73-7.78 (m, 2H), 8.00 (d, J=7.6 Hz, 1H).

<Example 68> 9b-Amino-4b-hydroxy-6,8-diisopropyl-4b,9b-dihydro-5-oxa-indeno[2,1-a]inden-10-one To a solution 4b,9b-dihydroxy-6,8-diisopropyl-4b,9b-dihydro-5-oxa-indeno[2,1-a]inden-10-one (0.30 g, 0.88 mmol) in methylene chloride (10 ml) were oxalyl chloride (0.35 ml, 4.08 mmol) and two drops of dimethylformamide, followed by reaction at room temperature for 3 hrs while stirring. Concentration in a vacuum gave 9b-chloro-4b-hydroxy-6,8-diisopropyl-4b,9b-dihydro-5-oxa-indeno[2,1-a]inden-10-one (0.35 g, 111%).

9b-chloro-4b-hydroxy-6,8-diisopropyl-4b,9b-dihydro-5-oxa-indeno[2,1-a]inden-10-one (0.35 g, 0.98 mmol) was dissolved in tetrahydrofurane (10 ml), cooled to 5° C., and reacted with, 2.0 M ammonia in isopropyl alcohol (0.98 ml, 1.96 mmol) at room temperature for 4 hrs. Concentration in a vacuum and purification through column chromatography (ethyl acetate:hexane=1:2) afforded the title compound (0.10 g, 30%).

mp: 199-200° C.

$^1$H-NMR (300 MHz, CDCl$_3$) δ 1.15-1.23 (m, 12H), 2.80 (q, J=7.3 Hz, 1H), 3.06 (q, J=7.3 Hz, 1H), 4.43 (s, 2H), 7.00 (d, J=1.4 Hz, 1H), 7.21 (d, J=1.6 Hz, 1H), 7.51 (t, J=9.0 Hz, 1H), 7.73-7.80 (m, 2H), 8.00 (d, J=6.8 Hz, 1H).

<Example 69> 4b-Hydroxy-9b-isocyanato-7-isopropyl-4b,9b-dihydro-5-oxa-indeno[2,1-a]-inden-10-one To a solution of 9b-amino-4b-hydroxy-7-isopropyl-4b,9b-dihydro-5-oxa-indeno[2,1-a]inden-10-one (0.50 g, 1.69 mmol) in toluene (10 ml) were added triethylamine (0.26 ml, 1.86 mmol) and triphosgene (0.55 g, 1.86 mmol), followed by heating for 3 hrs under reflux. After vacuum concentration, the concentrate was purified using column chromatography (ethyl acetate:hexane=1:2) to afford the title compound (0.40 g, 73%).

mp: 150-152° C.

$^1$H-NMR (300 MHz, CDCl$_3$) δ 1.16 (d, J=3.1 Hz, 3H), 1.18 (d, J=3.1 Hz, 3H), 2.85 (q, J=7.4 Hz, 1H), 6.82 (s, 1H), 6.90 (dd, J=1.0 Hz, 7.9 Hz, 1H), 7.51 (d, J=8.0 Hz, 1H), 7.65 (t, J=8.6 Hz, 1H), 7.77 (s, 1H), 7.85-7.89 (m, 2H), 8.01 (d, J=8.0 Hz, 1H).

<Example 70> (9b-hydroxy-7-isopropyl-10-oxo-9b,10-dihydro-5-oxa-indeno[2,1-a]inden-4b-yl)-carbamic acid methyl ester To a solution of 9b-amino-4b-hydroxy-7-isopropyl-4b,9b-dihydro-5-oxa-indeno[2,1-a]inden-10-one (0.30 g, 1.01 mmol) in tetrahydrofurane (10 ml) were added triethylamine (0.17 ml, 1.21 mmol) and methyl chloroformate (0.07 ml, 1.01 mmol), followed by reaction at room temperature for 3 hrs while stirring.

After vacuum concentration, the concentrate was extracted with water and methylene chloride, and purified using column chromatography (ethyl acetate:hexane=1:2) to afford the title compound (30 mg, 8%).

mp: 150-152° C.

$^1$H-NMR (300 MHz, CDCl$_3$) δ 1.15 (d, J=3.0 Hz, 3H), 1.17 (d, J=3.1 Hz, 3H), 2.82 (q, J=7.8 Hz, 1H), 3.66 (s, 3H), 5.54 (s, 1H), 5.94 (s, 1H), 6.70 (s, 1H), 6.83 (d, J=7.5 Hz, 1H), 7.28 (d, J=7.9 Hz, 1H), 7.55 (t, J=8.7 Hz, 1H), 7.78-7.84 (m, 2H), 8.01 (d, J=7.9 Hz, 1H).

<Example 71> Pentanoic acid (9b-hydroxy-7-isopropyl-10-oxo-9b,10-dihydro-5-oxa-indeno[2,1-a]inden-4b-yl)-amide To a solution of 9b-amino-4b-hydroxy-7-isopropyl-4b,9b-dihydro-5-oxa-indeno[2,1-a]inden-10-one (0.30 g, 1.01 mmol) in tetrahydrofurane (10 ml) were added triethylamine (0.17 ml, 1.21 mmol) and valeroyl chloride (0.12 ml, 1.01 mmol), followed by reaction at room temperature for 1 hr while stirring.

After vacuum concentration, the concentrate was extracted with water and methylene chloride, and purified by column chromatography (ethyl acetate:hexane=1:4) to afford the title compound (0.21 g, 55%).

mp: 110-112° C.

$^1$H-NMR (300 MHz, CDCl$_3$) δ 0.89 (t, J=8.0 Hz, 3H), 1.15 (d, J=3.3 Hz, 3H), 1.17 (d, J=3.1 Hz, 3H), 1.28-1.38 (m, 2H), 1.54-1.64 (m, 2H), 2.30 (t, J=9.1 Hz, 2H), 2.82 (q, J=7.8 Hz, 1H), 5.73 (s, 1H), 6.63 (s, 1H), 6.71 (d, J=1.3 Hz, 1H), 6.81 (dd, J=1.1 Hz, 7.9 Hz, 1H), 7.24 (d, J=7.5 Hz, 1H), 7.55 (t, J=8.0 Hz, 1H), 7.77-7.84 (m, 2H), 8.01 (d, J=7.7 Hz, 1H).

<Example 72> N-(9b-Hydroxy-7-isopropyl-10-oxo-9b,10-dihydro-5-oxa-indeno[2,1-a]inden-4b-yl)-isobutylamide To a solution of 9b-amino-4b-hydroxy-7-isopropyl-4b,9b-dihydro-5-oxa-indeno[2,1-a]inden-10-one (0.30 g, 1.01 mmol) in tetrahydrofurane (10 ml) were added triethylamine (0.17 ml, 1.21 mmol) and isobutyryl chloride (0.10 ml, 1.01 mmol), followed by reaction at room temperature for 1 hr while stirring.

After vacuum concentration, the concentrate was extracted with water and methylene chloride, and purified by column chromatography (ethyl acetate:hexane=1:2) to afford the title compound (0.21 g, 54%).

mp: 109-111° C.

$^1$H-NMR (300 MHz, CDCl$_3$) δ 1.17 (d, J=6.7 Hz, 12H), 2.51 (q, J=7.2 Hz, 1H), 2.82 (q, J=7.7 Hz, 1H), 5.73 (s, 1H), 6.63 (s, 1H), 6.71 (s, 1H), 6.81 (d, J=7.7 Hz, 1H), 7.24 (d, J=8.3 Hz, 1H), 7.55 (t, J=8.1 Hz, 1H), 7.76-7.86 (m, 2H), 8.00 (d, J=7.6 Hz, 1H).

<Example 73> N-(1-Amino-9b-hydroxy-7-isopropyl-10-oxo-9b,10-dihydro-5-oxa-indeno[2,1-a]inden-4b-yl)-acetamide To a solution of N-(9b-hydroxy-7-isopropyl-1-nitro-10-oxo-9b,10-dihydro-5-oxa-indeno[2,1-a]inden-4b-yl)-acetamide (0.30 g, 0.78 mmol) in ethanol/water (9 ml/0.9 ml) were added iron (0.30 g, 5.46 mmol) and one drop of conc. HCl, followed by heating for 1 hr under reflux. After neutralization with sodium bicarbonate, the reaction mixture was concentrated in a vacuum and purified by column chromatography (ethyl acetate:hexane=1:1) to afford the title compound (0.20 g, 72%).

mp: 278-280° C.

$^1$H-NMR (300 MHz, CD$_3$OD) δ 1.15 (d, J=7.0 Hz, 6H), 2.00 (s, 3H), 2.80 (q, J=7.0 Hz, 1H), 6.61-6.68 (m, 2H), 6.83 (d, J=7.5 Hz, 1H), 6.97 (d, J=7.2 Hz, 1H), 7.35 (d, J=7.8 Hz, 1H), 7.41 (t, J=9.6 Hz, 1H).

<Example 74> N-(9b-Hydroxy-6,8-diisopropyl-10-oxo-9b,10-dihydro-5-oxa-indeno[2,1-a]inden-4b-yl)-acetamide Anhydrous acetic acid (0.02 ml, 0.20 mmol) was added to a solution of 9b-amino-4b-hydroxy-6,8-diisopropyl-4b,9b-dihydro-5-oxa-indeno[2,1-a]inden-10-one (70 mg, 0.20 mmol) in acetic acid (5 ml), and heated for 2 hrs under reflux. After neutralization with sodium bicarbonate, the reaction mixture was concentrated in a vacuum and purified by column chromatography (ethyl acetate:hexane=1:1) to afford the title compound (50 mg, 66%).

mp: 217-219° C.

$^1$H-NMR (300 MHz, CDCl$_3$) δ 1.15 (d, J=7.0 Hz, 3H), 1.19 (d, J=3.6 Hz, 3H), 1.21 (d, J=2.4 Hz, 3H), 1.23 (d, J=5.7 Hz, 3H), 2.20 (s, 3H), 2.85 (q, J=6.7 Hz, 1H), 3.06 (q, J=7.6 Hz, 1H), 7.05 (d, J=1.7 Hz, 1H), 7.25 (d, J=1.7 Hz, 1H), 7.56 (t, J=8.3 Hz, 1H), 7.74-7.82 (m, 2H), 7.96 (d, J=7.6 Hz, 1H).

<Example 75> N-(9b-hydroxy-7-isopropyl-10-oxo-9b,10-dihydro-5-oxa-indeno[2,1-a]inden-4b-yl)-N-methyl-acetamide Anhydrous acetic acid (0.03 ml, 0.32 mmol) was added to a solution of 4b-hydroxy-7-isopropyl-9b-methylamino-4b,9b-dihydro-5-oxa-indeno[2,1-a]inden-10-one (0.10 g, 0.32 mmol) in acetic acid (5 ml), and heated for 2 hrs under reflux. After neutralization with sodium bicarbonate, the reaction mixture was concentrated in a vacuum and purified by column chromatography (ethyl acetate:hexane=1:1) to afford the title compound (70 mg, 62%).

mp: 216-217° C.

$^1$H-NMR (300 MHz, CD$_3$OD) δ 1.17 (d, J=6.7 Hz, 6H), 2.13 (s, 3H), 2.75-2.90 (m, 3H), 6.69 (s, 1H), 6.84 (d, J=7.6 Hz, 1H), 7.34 (d, J=8.0 Hz, 1H), 7.44 (t, J=8.4 Hz, 1H), 7.64 (t, J=8.3 Hz, 1H), 7.71 (d, J=7.6 Hz, 1H), 7.80 (d, J=7.6 Hz, 1H).

<Example 76> 1-(4b-Hydroxy-7-isopropyl-1-nitro-10-oxo-4b,10-dihydro-5-oxa-indeno[2,1-a]inden-9b-yl)-3-isopropyl-urea Triphosgene (0.28 g, 0.97 mmol) was added to a solution of 9b-amino-4b-hydroxy-7-isopropyl-1-nitro-4b,9b-dihydro-5-oxa-indeno[2,1-a]inden-10-one (0.30 g, 0.88 mmol) in tetrahydrofurane (10 ml) and stirred at room temperature for 2 hrs. Concentration in a vacuum and purification through column chromatography (ethyl acetate:hexane=1:2) gave 4b-hydroxy-9b-isocyanato-7-isopropyl-1-nitro-4b,9b-dihydro-5-oxa-indeno[2,1-a]inden-10-one (0.20 g, 62%).

4b-hydroxy-9b-isocyanato-7-isopropyl-1-nitro-4b,9b-dihydro-5-oxa-indeno[2,1-a]inden-10-one (0.20 g, 0.54 mmol) was dissolved in tetrahydrofurane (10 ml), added with triethylamine (0.18 ml, 1.30 mmol) and isopropyl amine (0.05 ml, 0.65 mmol), and heated for 48 hrs under reflux.

After vacuum concentration, the concentrate was extracted with water and methylene chloride, and purified by column chromatography (ethyl acetate:hexane=1:1) to afford the title compound (40 mg, 17%).

mp: 228-229° C.

$^1$H-NMR (300 MHz, (CD$_3$)$_2$CO-d$_6$) δ 1.00 (d, J=6.8 Hz, 3H) 1.14 (d, J=4.5 Hz, 3H), 1.17 (d, J=4.5 Hz, 3H), 1.50 (d, J=6.6 Hz, 3H), 2.78-2.88 (m, 1H), 3.87 (q, J=7.2 Hz, 1H), 5.84 (s, 1H), 6.34 (s, 1H), 6.61 (s, 1H), 6.66 (s, 1H), 6.84 (d, J=7.9 Hz, 1H), 7.46 (d, J=7.9 Hz, 1H), 7.77 (t, J=8.5 Hz, 1H), 8.08 (d, J=7.2 Hz, 1H), 8.19 (d, J=7.9 Hz, 1H).

<Example 77> N-(1-Amino-4b-hydroxy-7-isopropyl-10-oxo-4b,10-dihydro-5-oxa-indeno[2,1-a]inden-9b-yl)-isobutylamide Iron (0.09 g, 1.70 mmol) and one drop of conc. HCl were added to a solution of N-(4b-hydroxy-7-isopropyl-1-nitro-10-oxo-4b,10-dihydro-5-oxa-indeno[2,1-a]inden-9b-yl)-isobutylamide (100 mg, 0.24 mmol) in ethanol/water (3 ml/0.3 ml) and heated for 1 hr under reflux. After neutralization with sodium bicarbonate, the reaction mixture was concentrated in a vacuum and purified by column chromatography (ethyl acetate:hexane=1:1) to afford the title compound (60 mg, 66%).

mp: 141-143° C.

$^1$H-NMR (300 MHz, CDCl$_3$) δ 1.17 (d, J=6.7 Hz, 12H), 2.51 (q, J=7.2 Hz, 1H), 2.83 (q, J=7.7 Hz, 1H), 5.60 (s, 2H), 6.67-6.72 (m, 1H), 6.78-6.82 (m, 1H), 6.86-6.91 (m, 1H), 7.16 (t, J=7.7 Hz, 1H), 7.22 (d, J=6.7 Hz, 1H), 7.46 (t, J=8.8 Hz, 1H).

<Example 78> Pentanoic acid (1-amino-4b-hydroxy-7-isopropyl-10-oxo-4b,10-dihydro-5-oxa-indeno[2,1-a]inden-9b-yl)-amide To a solution of pentanoic acid (4b-hydroxy-7-isopropyl-1-nitro-10-oxo-4b,10-dihydro-5-oxa-indeno[2,1-a]inden-9b-yl)-amide (100 mg, 0.23 mmol) in ethanol/water (3 ml:0.3 ml) was added iron (0.09 g, 1.64 mmol). After addition of one drop of conc. HCl, the solution was refluxed for 1 hr. After neutralization with sodium bicarbonate, the reaction mixture was concentrated in a vacuum and purified by column chromatography (ethyl acetate:hexane=1:1) to afford the title compound (70 mg, 77%).

mp: 165-168° C.

$^1$H-NMR (300 MHz, CD$_3$OD) δ 0.93 (t, J=8.1 Hz, 3H), 1.17 (d, J=1.0 Hz, 3H), 1.20 (d, J=1.0 Hz, 3H), 1.35-1.44 (m, 2H), 1.52-1.63 (m, 2H), 2.28 (t, J=8.6 Hz, 2H), 2.84 (q, J=7.1 Hz, 1H), 6.65-6.72 (m, 2H), 6.86 (dd, J=1.1 Hz, 7.9 Hz, 1H), 6.99 (d, J=7.4 Hz, 1H), 7.37 (d, J=7.7 Hz, 1H), 7.43 (t, J=8.6 Hz, 1H).

<Example 79> 9b-Hydroxy-4b-(2-hydroxyethoxy)-7-isopropyl-4bH-benzo[d]indeno[1,2-b]furan-10 (9bH)-one Iodine (1.71 g, 6.74 mmol) was added to a solution of 4b,9b-dihydroxy-7-isopropyl-4bH-benzo[d]indeno[1,2-b] furan-10(9bH)-one (1 g, 3.37 mmol) in ethylene glycol (20 ml) and stirred at room temperature for 3 hrs. After water (100 ml) was poured thereto, the solution was extracted with ethyl acetate, and the reaction mixture was purified by silica gel column chromatography (40% ethyl acetate in hexane) to afford the title compound. 0.40 g (39%).

mp: 100-105° C.

$^1$H-NMR (300 MHz, CDCl$_3$) δ 1.12-1.25 (m, 6H, CH$_3$) 2.51 (s, 1H, OH, D$_2$O exchan gable) 2.82-2.86 (septet, 1H, CH), 3.83 (t, 2H, CH$_2$) 4.04-4.15 (m, 3H, CH$_2$ and OH, D$_2$O exchan gable) 6.72 (s, 1H, ArH) 6.87 (d, J=7.8 Hz, 1H, ArH) 7.42 (d, J=7.8 Hz, 1H, ArH) 7.57 (t, J=7.5 Hz, 1H, ArH) 7.92 (t, J=7.5 Hz, 2H, ArH) 7.94 (d, J=7.8 Hz, 2H, ArH). MS(EI): 340.

<Example 80> 4b,9b-Dihydroxy-7-isopropyl-1-nitro-4bH-benzo[d]indeno[1,2-b]furan-10(9bH)-one A solution of 4-nitro-2,3-dihydro-1H-inden-1-one (1.50 g, 8.4 mmol) in 1,4-dioxane (15 ml) and glacial acetic acid (3.5 ml) was added with cesium dioxide (1.87 g, 16.9 mmol), and refluxed at 110° C. for 2 hrs. After filtration, the filtrate was concentrated, mixed with water, and extracted with ethyl acetate. The reaction mixture was concentration to give 2,2-dihydroxy-4-nitro-2H-indene-1,3-dione (600 mg).

In glacial acetic acid (5 ml), 2,2-dihydroxy-4-nitro-2H-indene-1,3-dione (0.50 g, 2.24 mmol) and 3-isopropyl phenol (0.37 ml, 2.7 mmol) were refluxed for 2 hrs. The reaction mixture was concentrated and purified by silica gel column chromatography (20% ethyl acetate in hexane) to afford the title compound as a white solid. 0.30 g (39%).

mp: 186-188° C.

$^1$H-NMR (300 MHz, CDCl$_3$) δ 1.15-1.18 (m, 6H, CH$_3$) 2.81-2.86 (septet, 1H, CH) 3.53 (s, 1H, OH) 6.24 (s, 1H, OH) 6.71 (s, 1H, ArH) 6.92 (d, J=7.9 Hz, 1H, ArH) 7.48 (d, J=7.9 Hz, 1H, ArH) 7.79 (t, J=8.6 Hz, 1H, ArH) 8.19 (d, J=7.7 Hz, 1H, ArH) 8.50 (d, J=7.1 Hz, 1H, ArH). MS(EI): 341.

<Example 81> 4b,9b-Dihydroxy-7-isopropyl-2,3-dimethoxy-4bH-benzo[d]indeno[1,2-b]furan-10 (9bH)-one To a solution of 5,6-dimethoxy-2,3-dihydro-1H-inden-1-one (1.00 g, 5.2 mmol) in 1,4 dioxane (20 ml) and glacial acetic acid (2 ml) was added cesium dioxide (1.16 g, 10.4 mmol), followed by reaction at 110° C. for 2 hrs while stirring. The reaction mixture was concentrated, diluted in water, and extracted with ethyl acetate to give 0.80 g of 2,2-dihydroxy-5,6-dimethoxy-2H-indene-1,3-dione.

In glacial acetic acid (6 ml), 2,2-dihydroxy-5,6-dimethoxy-2H-indene-1,3-dione (0.55 g, 2.30 mmol) and 3-isopropyl phenol (1.10 ml, 2.76 mmol) were refluxed for 2 hrs. The concentrated reaction mixture was purified by silica gel column chromatography (30% ethyl acetate in hexane) to afford the title compound, white 0.22 g (57%).

mp: 127-129° C.

$^1$H-NMR (300 MHz, CDCl$_3$) δ 1.18 (d, J=6.9 Hz, 6H, CH$_3$) 2.81-2.86 (septet, 1H, CH) 3.71 (s, 1H, OH) 3.9 (s, 3H, CH$_3$) 4.1 (s, 3H, CH$_3$) 4.6 (s, 1H, OH) 6.72 (s, 1H, ArH) 6.86 (d, J=7.8 Hz, 1H, ArH) 7.14 (s, 1H, ArH) 7.37-7.43 (m, 2H, ArH). MS(EI): 356.

<Example 82> 4b,9b-dihydroxy-7-isopropyl-2,3-dimethyl-4bH-benzo[d]indeno[1,2-b]furan-10(9bH)-one To a solution of 5,6-dimethyl-2,3-dihydro-1H-inden-1-one (0.50 g, 3.12 mmol) in 1,4-dioxane (10 ml) and glacial acetic acid (1 ml) was added cesium dioxide (0.69 g, 6.24 mmol), followed by reaction at 110° C. for 2 hrs while stirring. The reaction mixture was filtered through a cellite layer, and the resulting organic solution was concentrated and purified by silica gel column chromatography (40% ethyl acetate in hexane) to give 2,2-dihydroxy-5,6-dimethyl-2H-indene-1,3-dione. 0.40 g (63%).

2,2-dihydroxy-5,6-dimethyl-2H-indene-1,3-dione (0.35 g, 1.7 mmol) and 3-isopropyl phenol (0.28 ml, 2.03 mmol) were dissolved in glacial acetic acid (4 ml) and refluxed for 4 hrs. The concentrated reaction mixture was purified by silica gel column chromatography (30% ethyl acetate in hexane) to afford the title compound. White 0.39 g (71%).

mp: 138-140° C.

$^1$H-NMR (300 MHz, CDCl$_3$) δ 1.16 (d, J=6.9 Hz, 6H, CH$_3$) 2.30 (s, 3H, CH$_3$) 2.40 (s, 3H, CH$_3$) 2.77-2.86 (septet, 1H, CH) 3.99 (s, 1H, OH) 4.73 (s, 1H, OH) 6.70 (s, 1H, ArH) 6.81 (d, J=7.9 Hz, 1H, ArH) 7.39 (d, J=7.9 Hz, 1H, ArH) 7.53 (s, 1H, ArH) 7.8 (s, 1H, ArH). MS(EI): 324.

<Example 83> Mixture of 6:4 (4bS,9bS)-2-bromo-4b,9b-dihydroxy-7-isopropyl-4bH-benzo[d]indeno [1,2-b]furan-10(9bH)-one and (4bS,9bS)-3-bromo-4b,9b-dihydroxy-7-isopropyl-4bH-benzo[d]indeno [1,2-b]furan-10(9bH)-one To a solution of 5-bromo-2,3-dihydro-1H-inden-1-one (0.81 g, 3.83 mmol) in 1,4-dioxane (15 ml) and glacial acetic acid (1.5 ml) was added cesium dioxide (0.94 g, 8.44 mmol), followed by reaction at 110° C. for 2.5 hrs while stirring. The reaction mixture was filtered through a cellite pad, and the filtrate was concentrated and purified by silica gel column chromatography (ethyl acetate:hexane=1:1) to give 5-bromo-2,2-dihydroxy-2H-indene-1,3-dione 0.80 g.

5-bromo-2,2-dihydroxy-2H-indene-1,3-dione (0.70 g, 2.7 mmol) and 3-isopropyl phenol (0.45 ml, 3.3 mmol) were dissolved in glacial acetic acid (8 ml) and refluxed for 4 hrs. The concentrated reaction mixture was purified by silica gel column chromatography (ethyl acetate:hexane=1:2) to afford the title compounds as a 6:4 mixture. White 760 mg (75%).

mp: 160-162° C.
$^1$H-NMR (300 MHz, CDCl$_3$) δ 1.12 (m, 6H, CH$_3$) 2.72-2.81 (septet, 1H, CH) 5.12 (s, 1H, OH) 5.60 (s, 1H, OH) 6.63 (d, J=5.7 Hz, 1H, ArH) 6.75 (d, J=7.8 Hz, 1H, ArH) 7.32 (d, J=7.8 Hz, 1H, ArH) 7.49-7.59 (m, 1.3H, ArH) 7.76-7.81 (m, 1H, ArH) 8.11 (s, 0.6H, ArH). MS(EI): 341.

<Example 84> Methyl (4bS,9bS)-4b-hydroxy-7-isopropyl-10-oxo-9b,10-dihydro-4bH-benzo[d]indeno[1,2-b]furan-9b-ylcarbamate A solution of 2,3-dihydro-2-(4-isopropyl-2-methoxyphenyl)-1,3-dioxo-1H-inden-2-ylcarbamate (120 mg, 0.32 mmol) in dichloromethane (5 ml) was added at –78° C. over 5 min to a solution of boron tribromide (1.0 M, 0.71 ml, 0.71 mmol) in dichloromethane (3 ml), and stirred at –10° C. for 3 hrs. The reaction mixture was poured with water, extracted with dichloromethane, and purified by silica gel column chromatography (30% ethyl acetate in hexane) to afford the title compound. 90 mg (78%).

mp: 161-163° C.
$^1$H-NMR (300 MHz, CDCl$_3$) δ 1.15-1.18 (m, 6H, CH$_3$) 2.82 (septet, J=6.9 Hz, 1H, CH) 3.64 (s, 3H, OCH$_3$) 5.49 (s, 1H, OH) 5.93 (s, 1H, NH) 6.70 (s, 1H, ArH) 6.82-6.85 (m, 1H, ArH) 7.25-7.29 (m, 1H, ArH) 7.53-7.59 (m, 1H, ArH) 7.79-7.84 (m, 2H, ArH) 8.00-8.03 (m, 1H, ArH). MS(EI): 353.

<Example 85> Isopropyl (4bS,9bS)-4b-hydroxy-7-isopropyl-10-oxo-9b,10-dihydro-4bH-benzo[d]indeno[1,2-b]furan-9b-ylcarbamate Boron tribromide (1.0 M in dichloromethane, 0.55 ml, 0.55 mmol) was dissolved in dichloromethane (3 ml) and cooled to –78° C. To this solution, isopropyl 2-(4-isopropyl-2-methoxyphenyl)-1,3-dioxo-2,3-dihydro-1H-inden-2-ylcarbamate (100 mg, 0.25 mmol) in dichloromethane (5 ml) was dropwise added over 5 min, and stirred at 0° C. for 4 hrs. The reaction mixture was poured with water, extracted with dichloromethane, and purified by silica gel column chromatography (30% ethyl acetate in hexane) to afford the title compound. 45 mg (47%).

mp: 114-116° C.
$^1$H-NMR (300 MHz, CDCl$_3$) δ 1.15-1.18 (m, 12H, CH$_3$) 2.82 (septet, J=6.9 Hz, 1H, CH) 4.83 (septet, J=6.3 Hz, 1H, CH) 5.83 (s, 1H, NH) 6.69 (d, J=1.5 Hz, 1H, ArH) 6.83 (dd, J=1.5 Hz, J=7.8 Hz, 1H, ArH) 7.29 (d, J=7.8 Hz, 1H, ArH) 7.52-7.58 (m, 1H, ArH) 7.78-7.84 (m, 2H, ArH) 8.01 (d, J=7.5 Hz, 1H, ArH). MS(EI): 395.

<Example 86> ethyl(4bS,9bS)-4b-hydroxy-7-isopropyl-10-oxo-9b,10-dihydro-4bH-benzo[d]indeno[1,2-b]furan-9b-ylcarbamate Boron tribromide (1.0 M in dichloromethane, 4.3 ml, 4.3 mmol) was dissolved in dichloromethane (15 ml), and cooled to –78° C. To this solution, ethyl 2-(4-isopropyl-2-methoxyphenyl)-1,3-dioxo-2,3-dihydro-1H-inden-2-ylcarbamate (750 mg, 1.96 mmol) in dichloromethane (20 ml) was dropwise added over 10 min, and stirred at 0° C. for 4 hrs. The reaction mixture was poured with water, extracted with dichloromethane, and purified by silica gel column chromatography (30% ethyl acetate in hexane) to afford the title compound. 500 mg (70%).

mp: 115-118° C.
$^1$H-NMR (300 MHz, CDCl$_3$) δ 1.14-1.17 (m, 9H, CH$_3$) 2.81 (septet, J=6.9 Hz, 1H, CH) 4.03-4.09 (m, 2H, OCH$_2$) 5.67 (br, 1H, OH) 5.92 (br, 1H, NH) 6.68 (s, 1H, ArH) 6.83 (dd, J=1.5 Hz, J=8.1 Hz, 1H, ArH) 7.29 (d, J=8.1 Hz, 1H, ArH) 7.51-7.56 (m, 1H, ArH) 7.76-7.81 (m, 2H, ArH) 8.00 (d, J=7.5 Hz, 1H, ArH). MS(EI): 367.

<Example 87> N,N'-((4bS,9bS)-4b-Hydroxy-7-isopropyl-10-oxo-9b,10-dihydro-4bH-benzo[d]indeno[1,2-b]furane-1,9b-diyl)diacetamide Boron tribromide (1.0 M in dichloromethane, 1.32 ml, 1.32 mmol) was dissolved in dichloromethane (5 ml) and cooled to –78° C. To this solution, N,N'-(2-(4-isopropyl-2-methoxyphenyl)-1,3-dioxo-2,3-dihydro-1H-inden-2,4-diyl)diacetamide (200 mg, 0.49 mmol) in dichloromethane (10 ml) was dropwise added over 10 min, and stirred at room temperature for 12 hrs. The reaction mixture was poured with water, extracted with dichloromethane, and purified by silica gel column chromatography (ethyl acetate:hexane=2:1) to afford the title compound. 130 mg (67%).

mp: 205-207° C.
$^1$H-NMR (300 MHz, CDCl$_3$) δ 1.15 (d, J=6.9 Hz, 6H, CH$_3$) 1.98 (s, 3H, NAc) 2.19 (s, 3H, NAc) 2.8 (septet, J=6.9 Hz, 1H, CH) 5.61 (s, 1H, OH) 6.61 (s, 1H, NH) 6.68 (d, J=1.2 Hz, 1H, ArH) 6.82 (dd, J=1.2 Hz, J=7.8 Hz, 1H, ArH) 7.28 (d, J=7.8 Hz, 1H, ArH) 7.55 (dd, J=0.6 Hz, J=7.8 Hz, 1H, ArH) 7.66-7.72 (m, 1H, ArH) 8.50 (d, J=8.4 Hz, 1H, ArH) 10.03 (s, 1H, NH). MS(EI): 394.

Step 2:
4b,5,9b,10-tetrahydroindeno[2,1-a]inden-4b-ol

Chrome chloride (2.50 g, 16.00 mmol) and nickel chloride (130 mg, 1 mmol) were dissolved in dimethylformamide (25 ml), and stirred at room temperature for 10 min. The resulting solution was reacted with a solution of 1-(2-bromobenzyl)-1H-inden-2(3H)-one (2.50 g, 0.83 mmol) in dimethylformamide (25 ml) at 120-125° C. for 18 hrs. The reaction mixture was poured with water, extracted with diethyl ether, and purified by silica gel column chromatography (ethylacetate:hexane=1:10) to afford the title compound. 0.30 g (16%).

$^1$H-NMR (300 MHz, CDCl$_3$) δ 2.05 (s, 1H, OH) 3.05 (dd, J=1.5 Hz, J=16.2 Hz, 1H) 3.56 (d, J=2.4 Hz, 2H) 3.59-3.67 (m, 1H, CH) 3.87 (d, J=7.8 Hz, 1H) 7.11-7.26 (m, 7H, ArH) 7.51-7.53 (m, 1H, ArH)

Step 3: 5,10-dihydroindeno[2,1-a]indene 4b,5,9b,10-tetrahydroindeno[2,1-a]inden-4b-ol (0.10 g, 0.82 mmol) was dissolved in benzene (5 ml) and added a little amount of paratoluene sulfonyl acid at room temperature. The reaction mixture was refluxed 85° C. for 12 hrs to completely evaporate benzene, and the residue was separated using silica gel column chromatography (2% ethyl acetate in hexane) to afford the title compound as a solid. 45 mg (50%).

¹H-NMR (300 MHz, CDCl₃) δ 3.63 (s, 4H, CH₂) 7.16-7.34 (m, 4H, ArH) 7.42-7.53 (m, 4H, ArH).

Step 4: (4b,9b)-4b,5,9b,10-tetrahydroindeno[2,1-a]indene-4b,9b-diol

Osmium tetroxide (0.02 ml, 0.002 mmol, 2.5% in t-butanol), potassium ferricyanide (193 mg, 0.6 mmol), potassium carbonate (81 mg, 0.6 mmol), and quinolidine (2.2 mg, 0.02 mmol) were mixed in a mixture of t-butanol and water (1:1, 3 ml) to which a solution of methane sulfonamide (19 mg, 0.2 mmol) and 5,10-dihydroindeno[2,1-a]indene (40 mg, 0.2 mmol) in 1 ml of a mixture of t-butanol and water (1:1) was then added.

The resulting mixture was stirred for 4.5 hrs at room temperature and then added with sodium sulfite (0.2 g) and stirred for an additional 15 min. The reaction mixture was poured with water, extracted with diethyl ether, concentrated, and purified by silica gel column chromatography (ethyl acetate:hexane=1:2) to afford the title compound. White 25 mg (54%).

mp: 157-159° C.

¹H-NMR (300 MHz, CDCl₃) δ 2.89 (s, 2H, OH) 3.40 (q, J=16.8 Hz, J=8.4 Hz, 4H, CH₂) 7.13-7.28 (m, 6H, ArH) 7.50-7.53 (m, 2H, ArH). MS(EI): 238.

<Example 88> 4b,9b-Dihydroxy-7-isopropyl-4bH-indeno[1,2-b]benzofuran-10(9bH)-one O-methyl oxime To a solution of 4b,9b-dihydroxy-7-isopropyl-4bH-indeno[1,2-b]benzofuran-10(9bH)-one (1.00 g, 3.37 mmoels) in anhydrous pyridine (1 ml) was added O-methyl hydroxylamine hydrochloride (564 mg, 6.75 mmoles), followed by reaction at room temperature for 3 hrs while stirring. After removal of the solvent pyridine, extraction with DCM and water was conducted, and the concentrated organic layer was separated and purified by silica gel column chromatography (30% ethylacetate mixed with 30% hexane) to afford the title compound. 70 mg (30%).

¹H-NMR (300 MHz, DMSO) δ 1.17 (d, J=6.9 Hz, 6H, CH₃) 2.79 (septet, J=6.9 Hz, 1H, CH) 3.9 (s, 3H, N—OCH₃), 6.44 (s, 1H, ArH/OH), 6.64 (s, 1H, ArH) 6.75 (d, J=7.8 Hz, 1H, ArH) 7.54 (d, J=7.8 Hz, 1H, ArH) 7.71-7.76 (m, 1H, ArH) 7.84-7.88 (m, 2H, ArH) 8.40 (d, J=8.1 Hz, 1H, ArH) 9.25 (s, 1H, OH/NH).

<Example 89> Butyric acid 9b-butyrylamino-7-isopropyl-10-oxo-9b,10-dihydro-5-oxa-indeno[2,1-a]inden-4b-yl ester To a solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml) were added triethylamine (0.20 g, 2.01 mmol) and butyryl chloride (0.18 g, 1.69 mmol) at room temperature, followed by reaction for 3 hrs at room temperature while stirring. The reaction product was concentrated, and extracted with ethylacetate, after which the concentrated organic layer was purified using column chromatography (ethylacetate:hexane=1:4 to 1:2) to afford the title compound. 50 mg (17%).

¹H-NMR (300 MHz, CDCl₃) δ 0.90-1.00 (m, 6H, CH₃) 1.18 (dd, J=2.7, 6.9 Hz, 6H, CH₃) 1.50-1.72 (m, 4H, CH₂) 2.02-2.30 (m, 2H, CH₂) 2.33-2.54 (m, 2H, CH₂) 2.79-2.88 (m, 1H, CH) 6.00 (s, 1H, NH) 6.67 (s, 1H, ArH) 6.90 (d, J=8.1 Hz, 1H, ArH) 7.44 (d, J=7.8 Hz, 1H, ArH) 7.56 (t, J=7.5 Hz, 1H, ArH) 7.76 (t, J=7.5 Hz, 1H, ArH) 7.85 (d, J=7.8 Hz, 1H, ArH) 7.93 (d, J=7.8 Hz, 1H, ArH).

<Example 90> Octanoic acid [2-(2-hydroxy-4-isopropyl-phenyl)-1,3-dioxo-indan-2-yl]-amide To a solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml) were added triethylamine (0.20 g, 2.01 mmol) and octanoyl chloride (0.27 g, 1.67 mmol), followed by reacting at room temperature for 28 hrs while stirring. The reaction product was concentrated, and extracted with ethylacetate, after which the concentrated organic layer was purified using column chromatography (ethylacetate:hexane=1:6→1:4) to afford the title compound as a syrup. 0.13 g (45%).

¹H-NMR (300 MHz, CDCl₃) δ 0.84-0.88 (m, 3H, CH₃) 1.17 (dd, J=3.0, 6.9 Hz, 6H, CH₃) 1.26-1.29 (m, 12H, CH₂) 1.58-1.65 (m, 4H, CH₂) 2.31 (t, J=7.2 Hz, 2H, CH₂) 2.77-2.86 (m, 1H, CH) 5.71 (s, 1H, OH) 6.62 (s, 1H, NH) 6.71 (s, 1H, ArH) 6.81 (d, J=7.8 Hz, 1H, ArH) 7.24 (d, J=7.8 Hz, 1H, ArH) 7.55 (t, J=7.8 Hz, 1H, ArH) 7.78-7.84 (m, 2H, ArH) 8.00 (d, J=7.8 Hz, 1H, ArH).

<Example 91> Hexanoic acid 9b-hexanoylamino-7-isopropyl-10-oxo-9b,10-dihydro-5-oxa-indeno[2,1-a]inden-4b-yl ester To a solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml) were added triethylamine (0.20 g, 2.01 mmol), and hexanoyl chloride (0.22 g, 1.69 mmol), followed by reaction for 5 hrs at room temperature while stirring. The reaction product was concentrated, and extracted with ethylacetate, after which the concentrated organic layer was purified using column chromatography (ethylacetate:hexane=1:6 to 1:4) to afford the title compound. 15 mg (4%).

¹H-NMR (300 MHz, CDCl₃) δ 0.79-0.89 (m, 6H, CH₃) 1.17 (dd, J=2.7, 6.9 Hz, 6H, CH₃) 1.22-1.33 (m, 8H, CH₂) 1.40-1.65 (m, 4H, CH₂) 2.04-2.55 (m, 4H, CH₂) 2.82-2.91 (m, 1H, CH) 6.00 (s, 1H, NH) 6.67 (s, 1H, ArH) 6.91 (d, J=8.1 Hz, 1H, ArH) 7.44 (d, J=8.1 Hz, 1H, ArH) 7.56 (t, J=7.5 Hz, 1H, ArH) 7.74-7.89 (m, 2H, ArH) 7.93 (d, J=7.5 Hz, 1H, ArH).

<Example 92> Heptanoic acid 9b-heptanoylamino-7-isopropyl-10-oxo-9b,10-dihydro-5-oxa-indeno[2,1-a]inden-4b-yl ester Triethylamine (0.20 g, 2.01 mmol), and heptanoyl chloride (0.25 g, 1.69 mmol) were added at room temperature to a solution of 9b-amino-4b-hydroxy-7-isopropyl-4b,9b-dihydro-5-oxa-indeno[2,1-a]inden-10-one (0.20 g, 0.67 mmol) in anhydrous methylene chloride (10 ml), and stirred for 3 hrs. The reaction product was concentrated, and extracted with ethylacetate, after which, the concentrated organic layer was purified using column chromatography (ethylacetate:hexane=1:6 to 1:4) to afford the title compound. 0.14 g (40%).

¹H-NMR (300 MHz, CDCl₃) δ 0.84-0.88 (m, 6H, CH₃) 1.17 (dd, J=2.4, 6.9 Hz, 6H, CH₃) 1.25-1.44 (m, 14H, CH₂) 1.59-1.64 (m, 2H, CH₂) 2.06-2.52 (m, 4H, CH₂) 2.79-2.86 (m, 1H, CH) 5.98 (s, 1H, NH) 6.74 (s, 1H, ArH) 6.91 (d, J=7.8 Hz, 1H, ArH) 7.44 (d, J=8.1 Hz, 1H, ArH) 7.56 (t,

J=7.5 Hz, 1H, ArH) 7.76 (t, J=7.5 Hz, 1H, ArH) 7.85 (d, J=7.8 Hz, 1H, ArH) 7.92 (d, J=7.5 Hz, 1H, ArH).

<Example 93> N-((4bS,9bS)-1-Amino-4b-hydroxy-7-isopropyl-10-oxo-9b,10-dihydro-4bH-indeno[1,2-b]benzofuran-9b-yl)octanamide N-(4b-hydroxy-7-isopropyl-1-nitro-10-oxo-9b,10-dihydro-4bH-benzo[d]indeno[1,2-b]furan-9b-yl)octanamide (130 mg, 0.28 mmoles) was dissolved in ethanol:water (9:1, 13 mL), added with iron powder (118 mg, 2.12 mmoles) and conc. HCl (3 drops), and heated for 3 hrs under reflux. After the reaction mixture was filtered, the filtrate was concentrated in a vacuum, and isolated and purified by silica gel column chromatography (30% ethylacetate, 1% triethylamine in hexane) to afford the title compound. 115 mg (96%).
$^1$H-NMR (300 MHz, CDCl$_3$) δ 0.86 (t, J=6.6 Hz, 3H, CH$_3$) 1.17 (d, J=6.9 Hz, 6H, CH$_3$) 1.25 (m, 8H, CH$_2$) 1.59 (t, J=6.9 Hz, 2H, CH$_2$) 2.51 (t, J=6.9 Hz, 2H, CH$_2$) 2.81 (septet, J=6.9 Hz, 1H, CH) 5.66 (br, 2H, NH$_2$) 6.62 (m, 2H, ArH) 6.73-6.79 (m, 2H, ArH) 7.13-7.16 (m, 1H, ArH) 7.39-7.45 (t, J=7.8 Hz, 1H, ArH).

<Example 94> (4bR,9bS)-1-Amino-7-isopropyl-10-oxo-9b-propionamido-9b,10-dihydro-4bH-indeno[1,2-b]benzofuran-4b-yl propionate (4bR,9bS)-7-isopropyl-1-nitro-10-oxo-9b-propionamido-9b,10-dihydro-4bH-benzo[d]indeno[1,2-b]furan-4b-yl propionate (130 mg, 0.29 mmoles) was dissolved in ethanol:water (9:1, 10 mL), added with iron powder (122 mg, 2.18 mmoles), and conc. HCl (3 drops), and heated for 1 hr under reflux. After the reaction mixture was filtered, the filtrate was concentrated in a vacuum, and isolated and purified by silica gel column chromatography (30% ethylacetate, 1% triethylamine in hexane) to afford the title compound. 60 mg (50%).
$^1$H-NMR (300 MHz, CDCl$_3$) δ 1.05-1.20 (m, 12H, CH$_3$) 2.10-2.51 (m, 4H, CH$_2$) 2.85 (septet, J=6.9 Hz, 1H, CH) 4.41 (br, 2H, NH$_2$) 5.99 (br, 1H, NH) 6.73 (s, 1H, ArH) 6.89-6.96 (m, 2H, ArH) 7.22-7.34 (m, 2H, ArH) 7.43 (d, J=7.8 Hz, 1H, ArH).

<Example 95> (4bR,9bS)-1-Amino-9b-butyramido-7-isopropyl-10-oxo-9b,10-dihydro-4bH-indeno[1,2-b]benzofuran-4b-yl butyrate (4bR,9bS)-9b-Butyramido-7-isopropyl-1-nitro-10-oxo-9b,10-dihydro-4bH-benzo[d]indeno[1,2-b]furan-4b-yl butyrate (220 mg, 0.46 mmoles) was dissolved in ethanol:water (9:1, 10 mL), added with iron powder (195 mg, 3.48 mmoles) and conc. HCl (5 drops), and heated for 1 hr under reflux. After the reaction mixture was filtered, the filtrate was concentrated in a vacuum, and isolated and purified by silica gel column chromatography (30% ethylacetate, 1% triethylamine in hexane) to afford the title compound. 100 mg (49%).
$^1$H-NMR (300 MHz, CDCl$_3$) δ 0.90-0.99 (m, 6H, CH$_3$) 1.16-1.19 (m, 6H, CH$_3$) 1.50-1.77 (m, 4H, CHO 2.04-2.50 (m, 4H, CH$_2$) 2.85 (septet, J=6.9 Hz, 1H, CH) 4.40 (br, 2H, NH$_2$) 5.97 (br, 1H, NH) 6.71 (s, 1H, ArH) 6.71-6.97 (m, 2H, ArH) 7.22-7.35 (m, 2H, ArH) 7.41 (d, J=8.1 Hz, 1H, ArH).

<Example 96> 1-Amino-7-isopropyl-10-oxo-9b-pentanamido-9b,10-dihydro-4bH-benzo[d]indeno[1,2-b]furan-4b-yl pentanoate To a solution of 7-isopropyl-1-nitro-10-oxo-9b-pentanamido-9b,10-dihydro-4bH-benzo[d]indeno[1,2-b]furan-4b-yl pentanoate (0.287 g, 0.55 mmol) in ethanol (10 ml) were added 1 ml of water, iron powder (0.22 g, 4.01 mmol), and conc. HCl (0.05 ml), followed by heating for 1.5 hrs under reflux. After the reaction mixture was filtered, the filtrate was concentrated in a vacuum, and isolated and purified by column chromatography (ethylacetate:hexane=1:4 to 1:2) to afford the title compound. 0.12 g (46%).
$^1$H-NMR (300 MHz, CDCl$_3$) δ 0.89 (m, 6H, CH$_3$) 1.17 (dd, J=2.4, 6.9 Hz, 6H, CH$_3$) 1.23-1.48 (m, 4H, CHO 1.50-1.65 (m, 4H, CH$_2$) 2.04-2.37 (m, 2H, CH$_2$) 2.40-2.54 (m, 2H, CH$_2$) 2.80-2.89 (m, 1H, CH) 4.39 (s, 2H, NH$_2$) 5.91 (s, 1H, NH) 6.71 (s, 1H, ArH) 6.88-6.96 (m, 2H, ArH) 7.22-7.34 (m, 2H, ArH) 7.46 (d, J=8.1 Hz, 1H, ArH).

<Example 97> 1-amino-9b-hexanamido-7-isopropyl-10-oxo-9b,10-dihydro-4bH-benzo[d]indeno[1,2-b]furan-4b-yl hexanoate 9b-Hexanamido-7-isopropyl-1-nitro-10-oxo-9b,10-dihydro-4bH-benzo[d]indeno[1,2-b]furan-4b-yl hexanoate (0.17 g, 0.32 mmol) was dissolved in ethanol (15 ml), added with 1.5 ml of water, iron powder (0.13 g, 2.3 mmol), and conc. HCl (0.05 ml), and heated for 1 hr under reflux. After the reaction mixture was filtered, the filtrate was concentrated in a vacuum, and isolated and purified by column chromatography (ethylacetate:hexane=1:6 to 1:4) to afford the title compound. 0.15 g (90%).
$^1$H-NMR (300 MHz, CDCl$_3$) δ 0.77-0.93 (m, 6H, CH$_3$) 1.20 (dd, J=3.6, 6.9 Hz, 6H, CH$_3$) 1.23-1.39 (m, 8H, CH$_2$) 1.50-1.62 (m, 4H, CH$_2$) 2.04-2.51 (m, 4H, CHO 2.80-2.86 (m, 1H, CH) 4.40 (s, 2H, NH$_2$) 5.97 (s, 1H, NH) 6.72 (s, 1H, ArH) 6.88-7.06 (m, 2H, ArH) 7.22-7.34 (m, 2H, ArH) 7.43 (d, J=7.6 Hz, 1H, ArH).

<Example 98> (4bS,9bS)-4b-Hydroxy-7-isopropyl-9b-methoxy-4bH-indeno[1,2-b]benzofuran-10(9bH)-one Anhydrous methanol (0.1 mL) was slowly added at 0° C. over 5 min to a solution of (4bS,9bS)-9b-chloro-4b-hydroxy-7-isopropyl-4bH-benzo[d]indeno[1,2-b]furan-10 (9bH)-one (0.30 g, 0.95 mmoles) in anhydrous THF (10 ml). After reaction for 3 hrs, the reaction mixture was concentrated, and isolated and purified by silica gel column chromatography (30% ethylacetate in 20% hexane) to afford the title compound. 50 mg (17%).
$^1$H-NMR (300 MHz, CDCl$_3$) δ 1.18 (dd, J=2.4 Hz, J=6.9 Hz, 6H, CH$_3$) 2.84 (septet, J=6.9 Hz, 1H, CH) 3.70 (s, 3H, OCH$_3$) 4.51 (s, 1H, OH) 6.72 (s, 1H, ArH) 6.85 (dd, J=1.2 Hz, J=7.8 Hz, 1H, ArH) 7.49 (d, J=7.8 Hz, 1H, ArH) 7.52-7.58 (m, 1H, ArH) 7.77-7.82 (m, 2H, ArH) 7.98 (d, J=7.8 Hz, 1H, ArH).

<Example 99> 1-Amino-9b-heptanamido-7-isopropyl-10-oxo-9b,10-dihydro-4bH-benzo[d]indeno[1,2-b]furan-4b-yl heptanoate 9b-Heptanamido-7-isopropyl-1-nitro-10-oxo-9b,10-dihydro-4bH-benzo[d]indeno[1,2-b]furan-4b-yl heptanoate (0.28 g, 0.50 mmol) was dissolved in ethanol (10 ml), added with 1 ml of water, iron powder (0.20 g, 3.7 mmol), and conc. HCl (0.05 ml), and heated for 1 hr under reflux. After the reaction mixture was filtered, the filtrate was concentrated in a vacuum, and purified by column chromatography (ethylacetate:hexane=1:6 to 1:4) to afford the title compound. 0.15 g (90%).

¹H-NMR (300 MHz, CDCl₃) δ 0.79-0.97 (m, 6H, CH₃) 1.19 (dd, J=3.7, 6.9 Hz, 6H, CH₃) 1.25-1.39 (m, 12H, CH₂) 1.59-1.68 (m, 2H, CH₂) 2.08-2.30 (m, 4H, CH₂) 2.36-2.54 (m, 2H, CH₂) 2.84-2.89 (m, 1H, CH) 4.42 (s, 2H, NH₂) 5.98 (s, 1H, NH) 6.74 (s, 1H, ArH) 6.91-6.98 (m, 2H, ArH) 7.24-7.37 (m, 2H, ArH) 7.43 (d, J=7.8 Hz, 1H, ArH).

<Example 100> 1-((4bS,9bS)-7-Isopropyl-4b-methoxy-10-oxo-9b,10-dihydro-4bH-indeno[1,2-b]benzofuran-9b-yl)urea Conc. HCl (1 mL) was added to a solution of (4bS,9bR)-7-isopropyl-10H-4b,9b-(epiminomethanoimino)indeno[1,2-b]benzofurane-10,12-dione (0.20 g, 0.625 mmoles) in methanol (10 mL) and stirred at room temperature. After reaction for 2.5 hrs, the reaction mixture was concentrated, extracted with ethylacetate and water, and then concentrated in a vacuum to dryness. Purification through silica gel column chromatography (5% MeOH in DCM, 1% TEA) afforded the title compound. (80 mg, 38%).
¹H-NMR (300 MHz, CD₃OD) δ 1.17 (d, J=6.9 Hz, 6H, CH₃) 2.75 (sept, J=6.9 Hz, 1H, CH) 3.68 (s, 3H, CH₃) 6.50 (dd, J=1.2 Hz, J=7.8 Hz, 1H, ArH) 6.68 (s, 1H, ArH) 6.76 (d, J=7.8 Hz, 1H, ArH) 7.35-7.53 (m, 3H, ArH) 7.83 (d, J=7.5 Hz, 1H, ArH).

<Example 101> 1-((4bS,9bS)-4b-Hydroxy-7-isopropyl-10-oxo-9b,10-dihydro-4bH-indeno[1,2-b]benzofuran-9b-yl)-3-methylurea To a solution of (4bS,9bS)-9b-amino-4b-hydroxy-7-isopropyl-4bH-benzo[d]indeno[1,2-b]furan-10(9bH)-one (0.10 g, 0.34 mmoles) in anhydrous THF (2 ml was added methyl isocyanate (32 μL, 0.51 mmoles). After reaction for 1 hr, the reaction mixture was concentrated and purified by silica gel column chromatography (5% MeOH in DCM, 1% TEA) to afford the title compound. 50 mg (42%).
¹H-NMR (300 MHz, CDCl₃) δ 1.20 (d, J=6.9 Hz, 6H, CH₃) 2.78-2.89 (m, 4H, NMe, CH) 6.63 (s, 1H, ArH) 6.86 (dd, J=1.2 Hz, J=7.8 Hz, 1H, ArH) 7.43 (d, J=7.8 Hz, 1H, ArH) 7.56 (br, 2H, ArH) 7.81 (br, 2H, ArH).

<Example 102> 1-Ethyl-3-((4bS,9bS)-4b-hydroxy-7-isopropyl-10-oxo-9b,10-dihydro-4bH-indeno[1,2-b]benzofuran-9b-yl)urea To a solution of (4bS,9bS)-9b-amino-4b-hydroxy-7-isopropyl-4bH-benzo[d]indeno[1,2-b]furan-10(9bH)-one (0.10 g, 0.34 mmoles) in anhydrous THF (5 ml) was added ethyl isocyanate (45 μL, 0.85 mmoles). After reaction for 1 hr, the reaction mixture was concentrated and purified by silica gel column chromatography (5% MeOH in DCM, 1% TEA) to afford the title compound. 60 mg (19%).
¹H-NMR (300 MHz, CDCl₃) δ 1.04 (t, J=7.2 Hz, 3H, CH₃) 1.20 (dd, J=2.4 Hz, J=6.9 Hz, 6H, CH₃) 2.84 (septet, J=6.9 Hz, 1H, CH) 3.36-3.51 (m, 2H, CH₂ 6.62 (d, J=1.2 Hz, 1H, ArH) 6.85 (dd, J=1.2 Hz, J=8.1 Hz, 1H, ArH) 7.46 (d, J=8.1 Hz, 1H, ArH) 7.52-7.62 (m, 2H, ArH) 7.68-7.70 (m, 1H, ArH), 7.77-7.98 (m, 1H, ArH).

<Example 103> 1-((4bS,9bS)-4b-Hydroxy-7-isopropyl-10-oxo-9b,10-dihydro-4bH-indeno[1,2-b]benzofuran-9b-yl)-3-methoxyurea Boron tribromide (1.0 M solution in DCM, 1.72 mL, 1.72 mmoles) was dissolved in anhydrous DCM (10 ml) and cooled to −80° C. To this, a solution of 1-(2-(4-isopropyl-2-methoxyphenyl)-1,3-dioxo-2,3-dihydro-1H-inden-2-yl)-3-methoxyurea (300 mg, 0.78 mmoles) in anhydrous DCM (15 ml) was slowly added. The reaction mixture was maintained for 10 min at −80° C. and stirred for 3 hrs at 0° C. Thereafter, the reaction mixture was extracted with DCM and water, dried, and concentrated in a vacuum. Purification through silica gel column chromatography (5% MeOH in DCM, 1% TEA) afforded the title compound. 110 mg (38%).
¹H-NMR (300 MHz, CDCl₃) δ 1.20 (d, J=6.9 Hz, 6H, CH₃) 2.83 (septet, J=6.9 Hz, 1H, CH) 3.88 (s, 3H, OCH₃) 6.64 (d, J=1.2 Hz, 1H, ArH) 6.85 (dd, J=1.2 Hz, J=7.8 Hz, 1H, ArH) 7.37 (d, J=7.8 Hz, 1H, ArH) 7.55-7.60 (m, 1H, ArH) 7.66-7.71 (m, 1H, ArH), 7.78-7.84 (m, 2H, ArH).

<Example 104> 5-Acetyl-4b,9b-dihydroxy-7,8-dimethyl-4b,5-dihydroindeno[1,2-b]indol-10(9bH)-one N-(3,4-dimethylphenyl)acetamide (300 mg, 1.84 mmol) and ninhydrin (328 mg, 1.84 mmol) were dissolved in dil. sulfuric acid (6 mL) and stirred at room temperature for 5.5 hrs. The reaction was stopped by slowing pouring the solution to 150 g of ice and stirring. The reaction mixture was washed twice with ethylacetate (70 ml), and the organic layer was washed again with water and brine. It was dried over sodium sulfate, concentrated in a vacuum, and purified through column chromatography (ethylacetate:hexane=1:1), followed by recrystallization in ethylacetate/hexane to afford the title compound. 60 mg (10%).
¹H-NMR (300 MHz, DMSO) δ 2.13 (s, 6H, CH₃) 2.74 (s, 3H, NAc) 6.84 (s, 1H, ArH) 7.16 (s, 1H, ArH) 7.49 (br, 1H, ArH) 7.56-7.61 (m, 1H, ArH) 7.63-7.71 (m, 1H, ArH) 7.80-7.89 (m, 2H, ArH) 8.01-8.05 (m, 1H, ArH).

<Example 105> 4b,9b-Dihydroxy-7,8-dimethyl-5-propionyl-4b,5-dihydroindeno[1,2-b]indol-10(9bH)-one Ten drops of conc. HCl were added to a solution of N-(2-(2-hydroxy-1,3-dioxo-2,3-dihydro-1H-inden-2-yl)-4,5-dimethylphenyl)propionamide (0.20 g) in anhydrous THF (10 ml) and stirred. After reaction for 5 hrs, ice water was poured to stop the reaction. Extraction with ethylacetate and water was conducted before concentration in a vacuum. The concentrate was purified by column chromatography (30% ethylacetate mixed with 50% hexane) to afford the title compound. 40 mg (20%).
¹H-NMR (300 MHz, DMSO) δ 1.26 (t, J=7.5 Hz, 3H, CH₃) 2.14 (s, 6H, CH₃) 3.06-3.58 (m, 2H, CH₂) 6.84 (s, 1H, ArH/OH) 7.16 (s, 1H, ArH/OH) 7.48 (s, 1H, ArH/OH) 7.56-7.61 (m, 1H, ArH) 7.70 (d, J=7.8 Hz, 1H, ArH) 7.80-7.86 (m, 2H, ArH) 7.95-8.01 (m, 1H, ArH).

<Example 106> 4b,9b-Dihydroxy-7,8-dimethyl-4b,5-dihydroindeno[1,2-b]indol-10(9bH)-one Conc. HCl (1 ml) was added to a solution of N-(2-(2-hydroxy-1,3-dioxo-2,3-dihydro-1H-inden-2-yl)-4,5-dimethylphenyl)acetamide (0.10 g) in methanol (10 ml) and stirred overnight to concentration. The concentrate was washed with sat. NaHCO₃, extracted with ethylacetate and water, and concentrated in a vacuum to afford the title compound (50 mg, 58%).
¹H-NMR (300 MHz, DMSO) δ 2.33 (s, 3H, CH₃) 2.36 (s, 3H, CH₃) 7.30 (s, 1H, ArH) 7.49 (s, 1H, ArH) 7.55 (t, J=7.8 Hz, 1H, ArH) 7.94 (t, J=7.8 Hz, 1H, ArH) 8.03 (d, J=7.8 Hz, 1H, ArH) 8.25 (d, J=7.8 Hz, 1H, ArH) 11.70 (br, 1H, NH).

\<Example 107> 5-Acetyl-7,8-dimethyl-10-oxo-4b,5,9b,10-tetrahydroindeno[1,2-b]indole-4b,9b-diyl diacetate Acetyl chloride (0.33 mL, 4.64 mmoles), and triethylamine (0.65 mL, 4.64 mmoles) were slowly added at room temperature to a solution of 5-acetyl-4b,9b-dihydroxy-7,8-dimethyl-4b,5-dihydroindeno[1,2-b]indol-10(9bH)-one (300 mg, 0.93 mmol) in anhydrous THF (20 mL). After stirring at room temperature for 24 hrs, the solid thus formed was washed with THF and filtered. After removal of THF, purification through column chromatography (30% ethylacetate mixed with 30% hexane) afford the title compound as a yellowish solid. 150 mg (40%).

$^1$H-NMR (300 MHz, DMSO) δ 2.06 (s, 3H, OAc) 2.10 (s, 3H, OAc) 2.22-2.23 (s, 6H, $CH_3$) 2.47 (s, 3H, NAc) 7.23 (s, 1H, ArH) 7.37 (s, 1H, ArH) 7.64-7.69 (t, 1H, ArH) 7.75 (d, J=7.2 Hz, 1H, ArH) 7.87-7.92 (m, 1H, ArH), 8.33 (d, J=7.8 Hz, 1H, ArH).

\<Example 108> 5-Acetyl-9b-amino-4b-hydroxy-5,9b-dihydro-4bH-indeno[1,2-b]indol-10-one AIBN (0.1 g) and $SO_2Cl_2$ (0.72 g, 5.3 mmol) were added to a solution of N-[2-(1,3-dioxo-indan-2-yl)-phenyl]-acetamide (1.00 g, 3.5 mmol) in $CCl_4$ (20 ml) and heated for 3 hrs under reflux. The solution was concentrated in a vacuum, extracted with $CH_2Cl_2$, dried, filtered, and the concentrated in a vacuum. Purification through column chromatography (ethylacetate:hexane=1:4→1:2) afforded the title compound. 0.60 g (53%).

$^1$H-NMR (300 MHz, $CDCl_3$) δ 2.64 (s, 3H, $CH_3$) 7.19 (t, J=1.5, 8.4 Hz, 1H, ArH) 7.37 (t, J=1.5, 8.4 Hz, 1H, ArH) 7.55 (t, J=7.2 Hz, 1H, ArH) 7.73-7.83 (m, 3H, ArH) 8.20 (d, J=8.1 Hz, 1H, ArH).

\<Example 109> N-(9b-Amino-4b-hydroxy-7-isopropyl-4-nitro-10-oxo-9b,10-dihydro-4bH-5-oxa-indeno[2,1-a]inden-1-yl)-acetamide To a solution of N-(9b-chloro-4b-hydroxy-7-isopropyl-4-nitro-10-oxo-9b,10-dihydro-4bH-5-oxa-indeno[2,1-a]inden-1-yl)-acetamide (3.90 g, 9.3 mmol) in anhydrous THF (40 ml) was added 2M $NH_3$ in IPA (9.36 ml) at 5° C., followed by stirring overnight at room temperature. After removal of the solvent by concentration in a vacuum, the residue was diluted in methylene chloride and washed with an aqueous sodium bicarbonate solution to adjust the pH into 8.0. The organic layer was dried, filtered and concentrated in a vacuum to afford the title compound. 3.98 g (107%).

$^1$H-NMR (300 MHz, $CDCl_3$) δ 1.16 (dd, J=6.9, 2.7 Hz, 6H, $CH_3$) 2.29 (s, 3H, $CH_3$) 2.78-2.87 (sept, 1H, CH) 6.71 (s, 1H, ArH) 6.88 (dd, J=8.1, 2.1 Hz, 1H, ArH) 7.37 (d, J=7.8 Hz, 1H, ArH) 8.48 (d, J=9.3 Hz, 1H, ArH) 8.75 (d, J=9.3 Hz, 1H, ArH) 10.67 (s, 1H, NH).

\<Example 110> Acetic acid 1,9b-bis-acetylamino-7-isopropyl-4-nitro-10-oxo-9b,10-dihydro-5-oxa-indeno[2,1-a]inden-4b-yl ester To a solution of N-(9b-amino-4b-hydroxy-7-isopropyl-4-nitro-10-oxo-9b,10-dihydro-4bH-5-oxa-indeno[2,1-a]inden-1-yl)-acetamide (0.55 g, 1.38 mmol) in anhydrous methylene chloride (20 ml) were added triethylamine (0.21 g, 2.76 mmol) and AcCl (0.20 g, 2.07 mmol) at 0° C., followed by stirring overnight at room temperature. The reaction mixture was concentrated in a vacuum and purified by column chromatography (ethylacetate:hexane=1:4) to afford the title compound. 0.17 g (26%).

$^1$H-NMR (300 MHz, $CDCl_3$) δ 1.19 (dd, J=3.6, 6.9 Hz, 6H, $CH_3$) 2.00 (s, 3H, $CH_3$) 2.17 (s, 3H, $CH_3$) 2.25 (s, 3H, $CH_3$) 2.83-2.92 (m, 1H, CH) 6.15 (s, 1H, NH) 6.71 (s, 1H, ArH) 6.98 (d, J=7.8 Hz, 1H, ArH) 7.43 (d, J=7.8 Hz, 1H, ArH) 8.50 (d, J=9.0 Hz, 1H, ArH) 8.83 (d, J=9.3 Hz, 1H, ArH) 10.72 (s, 1H, NH).

\<Example 111> 9b-Acetamido-7-isopropyl-10-oxo-9b,10-dihydro-4bH-indeno[1,2-b]benzofuran-4b-yl methyl carbonate To N-(4b-Hydroxy-7-isopropyl-10-oxo-9b,10-dihydro-4bH-benzo[d]indeno[1,2-b]furan-9b-yl)acetamide (0.50 g, 1.48 mmol were added 10 ml of THF, $Et_3N$ (0.24 ml, 1.77 mmol, and methyl chloroformate (0.11 ml, 1.48 mmol in that order, after which the solution was stirred at room temperature for 12 hrs.

The reaction mixture was concentrated, extracted with $H_2O$ and $CH_2Cl_2$, and purified by column chromatography (ethylacetate:hexane=1:2) to afford the title compound. 20 mg (3%).

$^1$H-NMR (300 MHz, $CDCl_3$) δ 1.16 (d, J=2.6 Hz, 3H), 1.18 (d, J=2.6 Hz, 3H), 2.17 (s, 3H), 2.84 (q, J=7.8 Hz, 1H), 3.62 (s, 3H), 5.40 (s, 1H), 6.68 (s, 1H), 6.91 (d, J=7.7 Hz, 1H), 7.44 (d, J=8.1 Hz, 1H), 7.58 (t, J=8.5 Hz, 1H), 7.78 (t, J=8.1 Hz, 1H), 7.87 (d, J=7.7 Hz, 1H), 7.98 (d, J=8.1 Hz, 1H).

\<Example 112> 9b-Acetamido-7-isopropyl-10-oxo-9b,10-dihydro-4bH-indeno[1,2-b]benzofuran-4b-yl pentanoate To N-(4b-hydroxy-7-isopropyl-10-oxo-9b,10-dihydro-4bH-benzo[d]indeno[1,2-b]furan-9b-yl)acetamide (0.50 g, 1.48 mmol were added 10 ml of THF, $Et_3N$ (0.24 ml, 1.77 mmol, and valeroyl chloride (0.18 ml, 1.48 mmol in that order, followed by stirring the solution at room temperature for 12 hrs. After concentration, the concentrate was extracted with $H_2O$ and $CH_2Cl_2$ and purified by column chromatography (ethylacetate:hexane=1:2) to afford the title compound. (30 mg, 5%).

$^1$H-NMR (300 MHz, $CDCl_3$) δ 0.91 (t, J=7.4 Hz, 3H), 1.16 (d, J=2.6 Hz, 3H), 1.18 (d, J=2.6 Hz, 3H), 1.33-1.40 (m, 2H), 1.56-1.64 (m, 2H), 1.95 (s, 3H), 2.35-2.55 (m, 2H), 2.84 (q, J=7.6 Hz, 1H), 6.10 (s, 1H), 6.68 (d, J=0.9 Hz, 1H), 6.91 (dd, J=1.3 Hz, 7.8 Hz, 1H), 7.44 (d, J=8.0 Hz, 1H), 7.57 (t, J=8.0 Hz, 1H), 7.77 (t, J=8.2 Hz, 1H) 7.84 (d, J=7.5 Hz, 1H), 7.93 (d, J=7.8 Hz, 1H).

\<Example 113> 9b-acetamido-1-amino-7-isopropyl-10-oxo-9b,10-dihydro-4bH-indeno[1,2-b]benzofuran-4b-yl methyl carbonate To 9b-acetamido-7-isopropyl-1-nitro-10-oxo-9b,10-dihydro-4bH-benzo[d]indeno[1,2-b]furan-4b-yl methyl carbonate (50 mg, 0.11 mmol) were added $EtOH:H_2O$=2 ml:0.2 ml, Fe (40 mg, 0.79 mmol, and one drop of conc. HCl, followed by reflux for 1 hr.

After neutralization with $NaHCO_3$, the reaction mixture was purified by column chromatography (ethylacetate:hexane=1:1) to afford the title compound. (25 mg, 55%).

$^1$H-NMR (300 MHz, $CDCl_3$) δ 1.17 (d, J=2.6 Hz, 3H), 1.19 (d, J=2.6 Hz, 3H), 2.18 (s, 3H), 2.85 (q, J=7.7 Hz, 1H), 3.63 (s, 3H), 4.44 (s, 2H), 6.72 (s, 2H), 6.90 (d, J=7.8 Hz,

1H), 6.97 (d, J=7.7 Hz, 1H), 7.23-7.25 (m, 1H), 7.34 (d, J=7.9 Hz, 1H), 7.41 (d, J=7.9 Hz, 1H).

<Example 114> N-(1-Amino-4b-hydroxy-7-isopropyl-10-oxo-9b,10-dihydro-4bH-benzo[d]indeno[1,2-b]furan-9b-yl)pivalamide Iron powder (0.04 g, 0.85 mmol), conc. HCl (0.05 ml), and water (0.5 ml) were added in that order to a solution of N-(4b-hydroxy-7-isopropyl-1-nitro-10-oxo-9b,10-dihydro-4bH-benzo[d]indeno[1,2-b]furan-9b-yl)pivalamide (50 mg, 0.11 mmol) in absolute ethanol (5 ml). The reaction mixture was heated for 2 hrs under reflux. After the iron powder was filtered off, the filtrate was concentrated in a vacuum and purified by column chromatography (ethylacetate:hexane=1:2) to afford the title compound. (40 mg, 86%).
$^1$H-NMR (300 MHz, CDCl$_3$) δ 1.16-1.19 (m, 15H, CH$_3$) 2.71-2.92 (m, 1H, CH) 6.66 (s, 1H, ArH) 6.81 (d, J=7.2 Hz, 1H, ArH) 6.93-7.01 (m, 2H, ArH) 7.11-7.25 (m, 1H, ArH) 7.38-7.47 (m, 1H, ArH).

<Example 115> 9b-Acetamido-1-amino-7-isopropyl-10-oxo-9b,10-dihydro-4bH-benzo[d]indeno[1,2-b]furan-4b-yl butyl carbonate Iron powder (0.09 g, 1.66 mmol), conc. HCl (0.05 ml), and water (0.5 ml) were added in that order to a solution of 9b-acetamido-7-isopropyl-1-nitro-10-oxo-9b,10-dihydro-4bH-benzo[d]indeno[1,2-b]furan-4b-yl butyl carbonate (0.11 g, 0.22 mmol) in absolute ethanol (5 ml). The reaction mixture was heated for 1.5 hrs under reflux. After the iron powder was filtered off, the filtrate was concentrated in a vacuum, and purified by column chromatography (ethylacetate:hexane=1:2) to afford the title compound (50 mg, 50%).
$^1$H-NMR (300 MHz, CDCl$_3$) δ 0.89 (t, J=7.5 Hz, 3H, CH$_3$) 1.18 (dd, J=2.4 Hz, 6.9 Hz, 3H, CH$_3$) 1.28-1.43 (m, 2H, CH$_2$) 1.56-1.68 (m, 2H, CH$_2$) 1.96 (s, 3H, CH$_3$) 2.81-2.90 (m, 1H, CH) 4.07-4.20 (m, 2H, OCH$_2$) 6.11 (s, 1H, NH) 6.76 (s, 1H, ArH) 6.94 (t, J=7.8 Hz, 2H, ArH) 7.22-7.35 (m, 2H, ArH) 7.46 (d, J=7.8 Hz, 1H, ArH).

<Example 116> 9b-Acetamido-7-isopropyl-10-oxo-9b,10-dihydro-4bH-benzo[d]indeno[1,2-b]furan-4b-yl ethyl carbonate Ethyl chloroformate (0.32 g, 3.11 mmol) and trimethylamine (0.25 g, 2.48 mmol) were added to a solution of 9b-chloro-4b-hydroxy-7-isopropyl-1-nitro-4bH-benzo[d]indeno[1,2-b]furan-10(9bH)-one (0.70 g, 2.07 mmol) in anhydrous THF (15 ml), and stirred for 4 hrs. After THF was removed by concentration in a vacuum, the concentrate was diluted in methylene chloride and washed many times with water. The organic layer was dried, filtered and purified by column chromatography (ethylacetate:hexane=1:4) to afford the title compound. 14 mg (1.6%).
$^1$H-NMR (300 MHz, CDCl$_3$) δ 1.16-1.18 (m, 9H, CH$_3$) 2.17 (s, 3H, CH$_3$) 2.82-2.86 (m, 1H, CH) 4.05-4.13 (m, 2H, OCH$_2$) 5.34 (s, 1H, NH) 6.68 (s, 1H, ArH) 6.91 (d, J=7.5 Hz, 1H, ArH) 7.44 (d, J=6.9 Hz, 1H, ArH) 7.58 (t, J=6.9 Hz, 1H, ArH) 7.79-7.86 (m, 2H, ArH) 7.98 (d, J=7.5 Hz, 1H, ArH).

<Example 117> 9b-Acetamido-7-isopropyl-10-oxo-9b,10-dihydro-4bH-benzo[d]indeno[1,2-b]furan-4b-yl pivalate Pivaroly chloride (0.26 g, 2.22 mmol) and trimethylamine (0.18 g, 1.77 mmol) were added to a solution of 9b-chloro-4b-hydroxy-7-isopropyl-1-nitro-4bH-benzo[d]indeno[1,2-b]furan-10(9bH)-one (0.50 g, 1.48 mmol) in anhydrous THF (15 ml), and heated for 18 hrs under reflux. After removal of THF by vacuum concentration, the residue was diluted in methylene chloride and washed many times with water. The organic layer was dried, filtered and purified by column chromatography (ethylacetate:hexane=1:4) to afford the title compound. 0.13 g (20%).
$^1$H-NMR (300 MHz, CDCl$_3$) δ 1.16-1.19 (m, 15H, CH$_3$) 2.17 (s, 3H, CH$_3$) 2.80-2.89 (m, 1H, CH) 6.11 (s, 1H, NH) 6.68 (s, 1H, ArH) 6.92 (d, J=7.8 Hz, 1H, ArH) 7.45 (d, J=7.8 Hz, 1H, ArH) 7.56 (t, J=7.5 Hz, 1H, ArH) 7.76 (t, J=7.5 Hz, 1H, ArH) 7.86 (d, J=7.8 Hz, 1H, ArH) 7.94 (d, J=7.8 Hz, 1H, ArH).

<Example 118> 9b-Acetamido-7-isopropyl-10-oxo-9b,10-dihydro-4bH-benzo[d]indeno[1,2-b]furan-4b-yl methylcarbamate Methyl isocyanate (0.12 g, 2.22 mmol) and trimethylamine (0.18 g, 1.77 mmol) were added to a solution of 9b-chloro-4b-hydroxy-7-isopropyl-1-nitro-4bH-benzo[d]indeno[1,2-b]furan-10(9bH)-one (0.50 g, 1.48 mmol) in anhydrous THF (15 ml) and heated for 5 hrs under reflux. After removal of THF by vacuum concentration, the residue was diluted in methylene chloride and washed many times with water. The organic layer was dried, filtered and purified by column chromatography (ethylacetate:hexane=1:2) to afford the title compound. 0.10 g (17%).
$^1$H-NMR (300 MHz, CDCl$_3$) δ 1.17 (dd, J=2.4, 6.9 Hz, 6H, CH$_3$) 1.96 (s, 3H, CH$_3$) 2.77-2.88 (m, 4H, CH, CH$_3$) 5.14 (s, 1H, NH) 6.26 (s, 1H, NH) 6.70 (s, 1H, ArH) 6.90 (d, J=7.8 Hz, 1H, ArH) 7.45 (d, J=7.8 Hz, 1H, ArH) 7.56 (t, J=6.9 Hz, 1H, ArH) 7.75 (t, J=6.9 Hz, 1H, ArH) 7.83-7.90 (m, 2H, ArH).

<Example 119> N,N'-(7-Isopropyl-10-oxo-9b,10-dihydro-4bH-indeno[1,2-b]benzofurane-4b,9b-diyl-diacetamide 4b,9b-diazido-7-isopropyl-4bH-benzo[d]indeno[1,2-b]furan-10(9bH)-one (2.50 g, 7.2 mmol was dissolved in 50 ml of EtOH and stirred overnight in the presence of 10% Pd/C (0.38 g) in a hydrogen atmosphere.
The reaction mixture was filtered through a cellite layer and concentrated in a vacuum to give 4b,9b-diamino-7-isopropyl-4bH-benzo[d]indeno[1,2-b]furan-10(9bH)-one (1.60 g, 5.4 mmol. This compound was dissolved in 50 ml of THF, and Et$_3$N (3.02 ml, 21.7 mmol) and acetyl chloride (1.16 ml, 16.3 mmol were added to the solution and stirred overnight at room temperature. After concentration in a vacuum, the residue was purified column chromatography (ethylacetate:hexane=2:1) to afford the title compound. 0.28 g (10%).
$^1$H-NMR (300 MHz, CDCl$_3$) δ 1.14 (d, J=3.1 Hz, 3H), 1.16 (d, J=3.1 Hz, 3H), 1.83 (s, 3H), 1.87 (s, 3H), 2.80 (q, J=7.6 Hz, 1H), 6.62-6.68 (m, 2H), 6.83 (d, J=7.8 Hz, 1H), 7.05 (s, 1H), 7.36 (d, J=7.8 Hz, 1H), 7.54 (t, J=8.7 Hz, 1H), 7.72 (t, J=8.7 Hz, 1H), 7.82 (t, J=9.5 Hz, 1H).

<Example 120> 4b-(Benzyloxy)-9b-hydroxy-7-isopropyl-4bH-indeno[1,2-b]benzofuran-10(9bH)-one p-Toluene sulfuric acid (65 mg, 0.33 mmoles) was added to a solution of 4b,9b-dihydroxy-7-isopropyl-4bH-benzo[d]indeno[1,2-b]furan-10(9bH)-one (0.50 g, 1.68 mmoles) in benzylalcohol (5 mL), and stirred at 60° C. for 3 days. The reaction mixture was concentrated and purified by silica gel column chromatography (30% ethylacetate mixed with 10% hexane) to afford the title compound. 20 mg (3%).

$^1$H-NMR (300 MHz, CDCl$_3$) δ 1.20 (dd, J=3 Hz, J=6.9 Hz, 6H, CH$_3$) 2.86 (sept, J=6.9 Hz, 1H, CH) 3.42 (br, 1H, OH) 5.03 (d, J=11.4 Hz, 1H, CH$_2$) 5.12 (d, J=11.4 Hz, 1H, CH$_2$) 6.76 (s, 1H, ArH) 6.90 (d, J=7.8 Hz, 1H, ArH) 7.29-7.37 (m, 3H, ArH) 7.42-7.47 (m, 3H, ArH) 7.54-7.59 (m, 1H, ArH) 7.77-7.82 (m, 2H, ArH) 7.98 (d, J=7.8 Hz, 1H, ArH).

<Example 121> Carbonic acid 9b-acetylamino-7-isopropyl-10-oxo-9b,10-dihydro-5-oxa-indeno[2,1-a]inden-4b-yl ester phenyl ester Phenyl chloroformate (0.35 g, 2.22 mmol, and trimethylamine (0.18 g, 1.77 mmol were added to a solution of N-(4b-Hydroxy-7-isopropyl-10-oxo-4b,10-dihydro-5-oxa-indeno[2,1-a]inden-9b-yl)-acetamide (0.50 g, 1.48 mmol in anhydrous THF, and heated for 24 hrs under reflux. After removal of THF by vacuum concentration, the residue was diluted in ethylacetate and washed many times with an aqueous sodium bicarbonate solution. The organic layer was dried, filtered and purified by column chromatography (ethylacetate:hexane=1:1) to afford the title compound. 10 mg (1.5%).

$^1$H-NMR (300 MHz, CDCl$_3$) δ 1.17 (dd, J=3.9, 6.9 Hz, 6H, CH$_3$) 2.04 (s, 3H, CH$_3$) 2.78-2.87 (m, 1H, CH) 6.13 (s, 1H, NH) 6.71 (s, 1H, ArH) 6.90 (d, J=7.8 Hz, 1H, ArH) 7.16 (d, J=7.8 Hz, 2H, ArH) 7.36-7.46 (m, 4H, ArH) 7.61 (t, J=7.8 Hz, 1H, ArH) 7.81 (t, J=7.5 Hz, 1H, ArH) 7.88 (d, J=7.5 Hz, 1H, ArH) 8.07 (d, J=9.0 Hz, 1H, ArH).

<Example 122> Phenyl-thiocarbamic acid O-(9b-azido-7-isopropyl-10-oxo-9b,10-dihydro-5-oxa-indeno[2,1-a]inden-4b-yl) ester Phenyl isothiocyanate (0.62 g, 4.66 mmol) and trimethylamine (0.37 g, 3.73 mmol) were added to a solution of 9b-azido-4b-hydroxy-7-isopropyl-4b,9b-dihydro-5-oxa-indeno[2,1-a]inden-10-one (1.00 g, 3.11 mmol) in anhydrous THF, and heated for 24 hrs under reflux. After removal of THF by vacuum concentration, the residue was diluted in ethylacetate and washed many times with an aqueous sodium bicarbonate solution. The organic layer was dried, filtered and purified by column chromatography (ethylacetate:hexane=1:2) to afford the title compound. 0.15 g (10%).

$^1$H-NMR (300 MHz, CDCl$_3$) δ 1.23 (d, J=6.9 Hz, 6H, CH$_3$) 2.86-2.95 (sept, 1H, CH) 6.84 (s, 1H, NH) 6.95-7.05 (m, 3H, ArH) 7.29 (d, J=7.5 Hz, 1H, ArH) 7.36 (d, J=8.1 Hz, 2H, ArH) 7.46-7.61 (m, 3H, ArH) 7.71 (t, J=7.5 Hz, 1H, ArH) 7.91 (d, J=7.8 Hz, 1H, ArH).

<Example 123> 9b-Acetamido-1-amino-7-isopropyl-10-oxo-9b,10-dihydro-4bH-benzo[d]indeno[1,2-b]furan-4b-yl ethyl carbonate Iron powder (0.45 g, 8.0 mmol) and conc. HCl (0.03 ml) were added to a solution of 9b-acetamido-7-isopropyl-1-nitro-10-oxo-9b,10-dihydro-4bH-benzo[d]indeno[1,2-b]furan-4b-yl ethyl carbonate (0.50 g, 1.1 mmol) in ethanol (10 ml) and water (1 ml), and heated for 1 hr under reflux. The reaction mixture was washed with MeOH, filtered, and concentrated in a vacuum. Purification thorough column chromatography (ethylacetate:hexane=1:2) afforded the title compound. 0.32 g (69%).

$^1$H-NMR (300 MHz, CDCl$_3$) δ 1.16-1.19 (m, 9H, CH$_3$) 2.17 (s, 3H, CH$_3$) 2.80-2.89 (m, 1H, CH) 4.05-4.15 (m, 2H, OCH$_2$) 4.44 (s, 3H, NCH$_2$) 5.33 (s, 1H, NH) 6.72 (s, 1H, ArH) 6.90 (d, J=7.8 Hz, 1H, ArH) 6.96 (d, J=7.8 Hz, 1H, ArH) 7.23-7.25 (m, 1H, ArH) 7.32 (t, J=7.8 Hz, 1H, ArH) 7.41 (d, J=7.8 Hz, 1H, ArH).

<Example 124> N,N'-(7-Isopropyl-10-oxo-9b,10-dihydro-4bH-indeno[1,2-b]benzofurane-4b,9b-diyl-dipropionamide To 4b,9b-diamino-7-isopropyl-4bH-benzo[d]indeno[1,2-b]furan-10(9bH)-one (0.50 g, 1.70 mmol was added 10 ml of THF. This solution was stirred overnight, together with Et$_3$N (0.94 ml, 6.79 mmol and propionyl chloride (0.44 ml, 5.09 mmol, at room temperature. After vacuum concentration, purification by column chromatography (ethylacetate:hexane=2:1) afforded the title compound (0.27 g, 39%).

$^1$H-NMR (300 MHz, CDCl$_3$) δ 1.05-1.17 (m, 12H), 2.08-2.39 (m, 4H), 2.82 (q, J=7.6 Hz, 1H), 6.27 (s, 1H), 6.51 (s, 1H), 6.67 (s, 1H), 6.85 (d, J=7.8 Hz, 1H), 7.39 (d, J=8.4 Hz, 1H), 7.56 (t, J=8.4 Hz, 1H), 7.75 (t, J=8.4 Hz, 1H), 7.85 (d, J=7.8 Hz, 2H).

<Example 125> N,N'-(7-isopropyl-10-oxo-9b,10-dihydro-4bH-indeno[1,2-b]benzofurane-4b,9b-diyl-bis(2-methylpropanamide)

To 4b,9b-diamino-7-isopropyl-4bH-benzo[d]indeno[1,2-b]furan-10(9bH)-one (0.50 g, 1.70 mmol) was added 10 ml of THF. This solution was stirred overnight, together with Et$_3$N (0.94 ml, 6.79 mmol and isobutyryl chloride (0.53 ml, 5.09 mmol, at room temperature. After vacuum concentration, purification by column chromatography (ethylacetate:hexane=1:1) afforded the title compound. 0.27 g (39%).

$^1$H-NMR (300 MHz, CDCl$_3$) δ 1.05-1.20 (m, 18H), 2.35-2.46 (m, 2H), 2.80 (q, J=6.9 Hz, 1H), 6.43 (s, 1H), 6.65 (s, 1H), 6.78 (s, 1H), 6.83 (d, J=7.5 Hz, 1H), 7.36 (d, J=8.0 Hz, 1H), 7.52 (t, J=8.0 Hz, 1H), 7.71 (t, J=8.5 Hz, 1H), 7.82 (t, J=8.5 Hz, 2H).

<Example 126> 4b,9b-Dihydroxy-7-isopropyl-4bH-benzofuro[2',3':3,4]cyclopenta[1,2-b]pyridin-10(9bH)-one To 5H-cyclopenta[b]pyridin-7(6H)-one (1.50 g, 11.26 mmol were added 10 ml of dioxane and 1 ml of AcOH. The solution was stirred overnight, together with SeO$_2$ (3.75 g, 33.79 mmol, in a refluxer. Neutralization with a NaHCO$_3$ solution was followed by extraction with ethylacetate. The extract was concentrated in a vacuum to give 6,6-dihydroxy-5H-cyclopenta[b]pyridine-5,7(6H)-dione (1.50 g, 8.37 mmol). This was dissolved in 10 ml of AcOH and stirred overnight, together with isopropylphenol (1.14 g, 8.37 mmol, in a refluxer. Concentration in a vacuum and purification by column chromatography (ethylacetate:hexane=2:1) afforded the title compound (0.70 g, 21%).

$^1$H-NMR (300 MHz, CDCl$_3$) δ 1.17 (d, J=4.1 Hz, 3H), 1.19 (d, J=4.1 Hz, 3H), 2.85 (q, J=7.2 Hz, 1H), 3.77 (s, 1H), 6.74 (s, 1H), 6.94 (d, J=7.5 Hz, 1H), 7.27 (d, J=5.2 Hz, 1H), 7.58 (d, J=7.5 Hz, 1H), 7.65 (s, 1H), 8.07 (d, J=7.9 Hz, 1H).

<Example 127> 10-Hydroxy-7-isopropyl-9b,10-dihydro-4bH-indeno[1,2-b]benzofurane-4b,9b-diyl diacetate A solution of 7-isopropyl-10-oxo-9b,10-dihydro-4bH-indeno[1,2-b]benzofurane-4b,9b-diyl diacetate (0.10 g, 0.26 mmoles) in absolute MeOH (5 mL) was stirred, together with sodium borohydride (20 mg, 0.53 mmoles), at room temperature for 7 hrs. Acetone (5 mL) was added, and the reaction mixture was stirred for 10 min until reaction stopped. Then, the solvent was removed. The reaction mixture was extracted with DCM and water, dried, concentrated in a vacuum, and purified by silica gel column chromatography (30% ethylacetate mixed with 20% hexane) to afford the title compound. 30 mg (30%).

$^1$H-NMR (300 MHz, CDCl$_3$) δ 1.15 (dd, J=3.6 Hz, J=6.9 Hz, 6H, CH$_3$) 2.10 (s, 3H, OAc) 2.16 (s, 3H, OAc) 2.81 (septet, J=6.9 Hz, 1H, CH) 4.38 (d, J=3 Hz, 1H, OH) 5.93 (d, J=3 Hz, 1H, CH) 6.72 (s, 1H, ArH) 6.81 (d, J=8.1 Hz, 1H, ArH) 7.36-7.50 (m, 3H, ArH) 7.57 (d, J=7.8 Hz, 1H, ArH).

<Example 128> 9b-Hydroxy-7-isopropyl-4b-(methoxyamino)-4bH-indeno[1,2-b]benzofuran-10(9bH)-one O-methyl oxime O-methyl hydroxylamine hydrochloride (564 mg, 6.75 mmoles) was added to a solution of 4b,9b-dihydroxy-7-isopropyl-4bH-indeno[1,2-b]benzofuran-10(9bH)-one (1.00 g, 3.37 mmoels) in hydrous pyridine (10 ml) and stirred at room temperature. After 3 hrs, the solvent was removed and the reaction mixture was washed with DCM and 1N HCl. The organic layer was washed again with water and brine, concentrated in a vacuum, and separated by silica gel column chromatography (30% ethylacetate mixed with 10% hexane) to afford the title compound. 100 mg (9%).

$^1$H-NMR (300 MHz, CDCl$_3$) δ 1.20 (d, J=6.9 Hz, 6H, CH$_3$) 2.81 (septet, J=6.9 Hz 1H, CH) 3.98 (s, 3H, N—OCH$_3$), 4.09 (s, 3H, N—OCH$_3$), 4.46 (s, 1H, OH) 6.57 (dd, J=1.8 Hz, J=8.1 Hz, 1H, ArH) 6.82 (d, J=8.1 Hz, 1H, ArH) 6.88 (d, J=1.5 Hz, 1H, ArH) 7.44-7.55 (m, 2H, ArH) 7.87 (dd, J=1.2 Hz, 6.9 Hz, 1H, ArH) 8.20 (dd, J=1.2 Hz, J=6.9 Hz, 1H, ArH) 8.73 (s, 1H, NH).

<Example 129> 7-Isopropyl-4b-methoxy-10-methylene-9b,10-dihydro-4bH-indeno[1,2-b]benzofuran-9b-ol A dilution of 1 M potassium tertiary butoxide (1.25 mL, 1.25 mmol) in THF was slowly added at 0° C. to a solution of methyl triphenylphosphonium bromide (415 mg, 1.16 mmol) in anhydrous THF (5 mL), and stirred at 0° C. for 30 min and then at room temperature for 3 hrs. To this, a solution of 9b-hydroxy-7-isopropyl-4b-methoxy-4bH-benzo[d]indeno[1,2-b]furan-10(9bH)-one (0.30 g, 0.97 mmoles) in anhydrous THF (5 mL) was slowly added at 0° C., and heated for 24 hrs under reflux. The reaction mixture was concentrated in a vacuum, and washed with water (50 mL) and DCM (50 mL×2). The organic layer was washed again with water (30 mL) and brine (30 mL), dried over sodium sulfate, filtered, and concentrated in a vacuum. Purification by column chromatography (30% ethylacetate mixed with 10% hexane) afforded the title compound. 30 mg (10%).

$^1$H-NMR (300 MHz, CDCl$_3$) δ 1.16 (dd, J=3 Hz, J=6.9 Hz, 6H, CH$_3$) 2.81 (sept, J=6.9 Hz, 1H, CH) 2.97 (br, 1H, OH) 3.67 (s, 3H, OMe) 5.71 (d, J=9.9 Hz, 2H, olefinic CH$_2$) 6.69 (s, 1H, ArH) 6.80 (dd, J=1.2 Hz, J=7.8 Hz, 1H, ArH) 7.35-7.40 (m, 3H, ArH) 7.46-7.51 (m, 1H, ArH) 7.66-7.68 (m, 1H, ArH).

<Example 130> 9b-Hydroxy-7-isopropyl-4b-methoxy-4bH-indeno[1,2-b]benzofuran-10(9bH)-one O-methyl oxime O-methyl hydroxylamine hydrochloride (269 mg, 3.20 mmoles) was added to a solution of 9b-hydroxy-7-isopropyl-4b-methoxy-4bH-indeno[1,2-b]benzofuran-10(9bH)-one (0.50 g, 1.61 mmoels) in anhydrous pyridine (10 ml) and stirred overnight at room temperature. After removal of the solvent, the residue was washed with DCM and 1N HCl. The organic layer was washed again with water and brine, concentrated in a vacuum, and purified by silica gel column chromatography (30% ethylacetate mixed with 20% hexane) to afford the title compound. 60 mg (11%).

$^1$H-NMR (300 MHz, CDCl$_3$) δ 1.20 (dd, J=2.4 Hz, J=6.9 Hz, 6H, CH$_3$) 1.40 (s, 3H, CH$_3$), 1.46 (s, 3H, CH$_3$), 2.87 (septet, 1H, CH) 6.76 (d, J=0.9 Hz, 1H, ArH) 6.92 (dd, J=1.2 Hz, J=7.8 Hz, 1H, ArH) 7.55-7.60 (m, 2H, ArH) 7.77-7.82 (m, 2H, ArH) 7.90 (m, 1H, ArH).

<Example 131> Mixture of 1-bromo and 4-bromo-4b,9b-dihydroxy-7-isopropyl-4bH-indeno[1,2-b]benzofuran-10(9bH)-one To a solution of 4-bromo-1-indanone (10.0 g, 47.4 mmol) in AcOH (4.0 mL) and dioxane (40 mL) was added SeO$_2$ (11.5 g, 104 mmol), followed by heating for 4 hrs under reflux. The reaction mixture was filtered and concentrated to give a dark brown oil. m-Isopropylphenol (6.81 g, 50.0 mmol) and AcOH (10 mL) were added to the dark brown oil and stirred overnight. The reaction mixture was purified by column chromatography (eluted with EtOAc/hexane=1/4-1/2) to afford the title compound as a brown solid. 9.28 g (52%).

$^1$H-NMR (300 MHz, CDCl$_3$) δ 1.17 (d, J=6.9 Hz, 6H), 2.84 (heptet, J=6.9 Hz, 1H), 4.07 (s, br, 1H), 4.81 (s, br, 1H), 6.71 (s, 0.34H), 6.79 (d, J=1.2 Hz, 0.66H), 6.85 (dd, J=7.9, 1.2 Hz, 1H), 7.37-7.42 (m, 1.64H), 7.57-7.62 (m, 0.36H), 7.67-7.75 (m, 1H), 7.91-7.97 (m, 1H).

<Example 132> 1-(Benzylamino)-4b,9b-dihydroxy-7-isopropyl-4bH-indeno[1,2-b]benzofuran-10(9bH)-one Benzaldehyde (0.30 g, 2.88 mmol) and NaCNBH$_3$ (0.12 g, 1.92 mmol) were added at 0° C. to a solution of 1-amino-4b,9b-dihydroxy-7-isopropyl-4b,9b-dihydro-5-oxa-indeno[2,1-a]inden-10-one (0.30 g, 0.96 mmol) in absolute MeOH (3 ml), followed by reaction overnight at room temperature. The solvent was removed by vacuum concentration, and purification by column chromatography (ethylacetate:hexane=1:4) afforded the title compound. 80 mg (15%).

$^1$H-NMR (300 MHz, CDCl$_3$) δ 1.18 (d, J=6.9 Hz, 6H, CH$_3$) 2.79-2.88 (m, 1H, CH) 4.50 (d, J=6.0 Hz, 2H, CH$_2$) 6.57 (d, J=8.1 Hz, 1H, ArH) 6.73 (s, 1H, ArH) 6.83 (d, J=7.8 Hz, 1H, ArH) 7.11 (d, J=7.2 Hz, 1H, ArH) 7.31-7.39 (m, 5H, ArH) 7.47-7.53 (m, 2H, ArH).

<Example 133> 1-(Ethylamino)-4b,9b-dihydroxy-7-isopropyl-4bH-indeno[1,2-b]benzofuran-10(9bH)-one Acetaldehyde (0.08 g, 1.92 mmol) and NaCNBH$_3$ (0.08 g, 1.28 mmol) were added at 0° C. to a solution of 1-amino- 4b,9b-dihydroxy-7-isopropyl-4b,9b-dihydro-5-oxa-indeno[2,1-a]inden-10-one (0.20 g, 0.64 mmol) in absolute MeOH (3 ml), and reacted at room temperature for 2 days. After removal of the solvent by vacuum concentration, column chromatography (ethylacetate:hexane=1:2) was performed to afford the title compound. 40 mg (18%).

$^1$H-NMR (300 MHz, CDCl$_3$) δ 1.16 (d, J=6.6 Hz, 6H, CH$_3$) 1.26 (t, J=6.9 Hz, 3H, CH$_3$) 2.77-2.88 (m, 1H, CH) 3.16-3.25 (m, 2H, CH$_2$) 6.57 (d, J=8.1 Hz, 1H, ArH) 6.65 (s, 1H, NH) 6.80 (d, J=7.5 Hz, 1H, ArH) 6.94 (s, 1H, ArH) 7.07 (d, J=7.2 Hz, 1H, ArH) 7.39 (d, J=7.2 Hz, 1H, ArH) 7.54 (t, J=8.1 Hz, 1H, ArH).

<Example 134> 9b-Hydroxy-7-isopropyl-4b-methyl-4bH-indeno[1,2-b]benzofuran-10(9bH)-one 7-Isopropyl-4b-methoxy-10-methylene-9b,10-dihydro-4bH-indeno[1,2-b]benzofuran-9b-ol (50 mg, 0.16 mmoles) was dissolved in THF:conc HCl (1:1, 1 mL) and heated for 30 min under reflux. After removal of the solvent, the residue was washed DCM (50 ml) and water (20 ml). The organic layer was washed again with water and brine, and concentrated in a vacuum. The concentrate was purified by silica gel column chromatography (30% ethylacetate mixed with 15% hexane) to afford the title compound. 20 mg (40%)

$^1$H-NMR (300 MHz, CDCl$_3$) δ 1.16 (dd, J=2.7 Hz, J=6.9 Hz, 6H, CH$_3$) 1.79 (s, 3H, CH$_3$) 2.82 (sept, J=6.9 Hz, 1H, CH) 3.29 (s, 1H, OH) 6.67 (d, J=1 Hz, 1H, ArH) 6.80 (dd, J=1 Hz, J=7.8 Hz, 1H, ArH) 7.35 (d, J=7.8 Hz, 1H, ArH) 7.50 (t, J=7.8 Hz, 1H, ArH) 7.72-7.78 (m, 2H, ArH) 7.83 (d, J=7.8 Hz, 1H, ArH).

<Example 135> 4b,9b-Dihydroxy-5-isobutyryl-7,8-dimethyl-4b,5-dihydroindeno[1,2-b]indol-10(9bH)-one Conc. HCl (5 ml) was added to a solution of N-(2-(2-hydroxy-1,3-dioxo-2,3-dihydro-1H-inden-2-yl)-4,5-dimethylphenyl)isobutyramide (200 mg, 0.57 mmoles) in THF (5 ml) and stirred for 8 hrs. An excess of water (50 ml) was added to terminate the reaction, followed by extraction with ethylacetate and water. The organic layer was washed with brine, concentrated and purified by silica gel column chromatography (30% ethylacetate mixed with 20% hexane) to afford the title compound. 120 mg (6%).

$^1$H-NMR (300 MHz, CDCl$_3$) δ 1.20 (d, J=6.9 Hz, 3H, CH$_3$) 1.25 (d, J=6.9 Hz, 3H, CH$_3$) 2.16 (s, 3H, CH$_3$) 2.17 (s, 3H, CH$_3$) 2.74 (sept, J=6.9 Hz, 1H, CH) 3.91 (s, 1H, OH) 4.90 (s, 1H, OH) 6.48 (s, 1H, ArH) 7.30 (s, 1H, ArH) 7.46-7.54 (m, 1H, ArH) 7.72-7.83 (m, 3H, ArH).

<Example 136> 7-Isopropyl-10-methyl-9b,10-dihydro-4bH-indeno[1,2-b]benzofuran-4b,9b-diol 7-Isopropyl-10-methylene-9b,10-dihydro-4bH-indeno[1,2-b]benzofuran-4b,9b-diol (50 mg, 0.20 mmol) was dissolved in absolute MeOH (5 mL) and stirred for 24 hrs in the presence of Pd/C (10%, 10 mg) in a hydrogen atmosphere. The reaction mixture was washed with DCM, filtered through a cellite filer, and concentrated. Purification by silica gel column chromatography (30% ethylacetate mixed with 20% hexane) afforded the title compound. 30 mg (60%)

$^1$H-NMR (300 MHz, CDCl$_3$) δ 1.13-1.19 (m, 6H+3H, CH$_3$) 2.73-2.83 (sept, J=6.9 Hz, 1H, CH) 3.66-3.74 (m, 1H, CH) 3.82 (s, 1H, OH) 6.34 (d, J=8.1 Hz, 0.8H, ArH) 6.52 (dd, J=1.5 Hz, J=8.1 Hz, 0.8H, ArH) 6.78 (d, J=1.5 Hz, 0.8H, ArH) 7.46-7.51 (m, 1.6H, ArH) 7.70-7.75 (m, 0.8H, ArH) 8.50 (s, 1H, ArH).

<Example 137> N-(1-Bromo-4b-hydroxy-7-isopropyl-10-oxo-9b,10-dihydro-4bH-indeno[1,2-b]benzofuran-9b-yl)acetamide Oxalyl chloride (0.60 mL, 6.88 mmol) and DMF (3 drops) were added to a solution of 1-bromo-4b,9b-dihydroxy-7-isopropyl-4bH-indeno[1,2-b]benzofuran-10(9bH)-one (1.98 g, 5.28 mmol) in DCM (20 mL), and stirred at room temperature for 3 hrs. The reaction was terminated by addition of water, followed by extraction with DCM and water. The organic layer was dried and concentrated in a vacuum to give 1-bromo-9b-chloro-4b-hydroxy-7-isopropyl-4bH-indeno[1,2-b]benzofuran-10(9bH)-one as a solid. 1.81 g.

To a solution of 1-bromo-9b-chloro-4b-hydroxy-7-isopropyl-4bH-indeno[1,2-b]benzofuran-10(9bH)-one (1.81 g) in THF (15 mL) was added 2.0 M NH$_3$ in i-PrOH (8.0 mL, 16 mmol) at 0° C. After 30 min, the temperature was elevated to room temperature, and the solution was stirred for 1 hr. The reaction was terminated by addition of water, followed by extraction with ethylacetate and water. The organic layer was dried and concentrated in a vacuum to obtain 1.57 g of 9b-amino-1-bromo-4b-hydroxy-7-isopropyl-4bH-indeno[1,2-b]benzofuran-10(9bH)-one as a dark brown solid.

This compound (1.55 g) was dissolved in acetic acid (5 ml) and heated for 30 min in the presence of Ac$_2$O (390 mg, 3.82 mmol) under reflux. The reaction mixture was extracted with ethylacetate and water, and the organic layer was concentrated in a vacuum and purified by column chromatography (eluted with EtOAc/hexane=1/1-1/1) to afford the title compound as a yellow solid. 510 mg (23%).

$^1$H-NMR (500 MHz, CDCl$_3$) (major:minor=58:42 regioisomeric mixture) δ 1.16-1.18 (m, 6H), 2.06 (s, 1.7H from major), 2.08 (s, 1.3H from minor), 2.81-2.85 (m, 1H), 6.44 (s, br, 0.58H), 6.70 (d, br, J=1.4 Hz, 0.84H), 6.78 (d, J=1.4 Hz, 0.58H), 6.83-6.86 (m, 1H), 7.25 (d, J=8.1 Hz, 0.42H), 7.29 (d, J=7.9 Hz, 0.58H), 7.40 (t, J=7.7 Hz, 0.58H), 7.61 (t, J=7.7 Hz, 0.42H), 7.69 (dd, J=7.8, 0.9 Hz, 0.42H), 7.75 (dd, J=7.6, 0.8 Hz, 0.58H), 7.91 (dd, J=7.8, 1.0 Hz, 0.58H), 7.95 (dd, J=7.7, 0.9 Hz, 0.48H).

<Example 138> 4b,9b-Dihydroxy-5-isobutyryl-7,8-dimethoxy-5,9b-dihydro-4bH-indeno[1,2-b]indol-10-one Conc. HCl (5 ml) was added to a solution of N-[2-(2-hydroxy-1,3-dioxo-indan-2-yl)-4,5-dimethoxy-phenyl]-isobutyramide (500 mg, 1.30 mmol) in anhydrous THF (5 ml), and stirred at room temperature for 3 hrs. The reaction mixture was washed many times with ethylacetate and water, and the organic layer was dried, filtered, and concentrated in a vacuum, followed by column chromatography (ethylacetate:hexane=1:4) to afford the title compound. 100 mg (20%).

$^1$H-NMR (300 MHz, CDCl$_3$) δ 1.19-1.37 (m, 6H, CH$_3$) 2.70-2.80 (m, 1H, CH), 3.10 (s, 1H, CH) 3.78 (s, 3H, OMe) 3.84 (s, 3H, OMe) 4.87 (s, 1H, OH) 6.25 (s, 1H, ArH), 6.97 (s, 1H, ArH), 7.51 (t, J=7.2 Hz, 1H, ArH) 7.73-7.82 (m, 3H, ArH).

<Example 139> 4b,9b-Dihydroxy-7-isopropyl-2-piperidinyl-4bH-benzo[d]indeno[1,2-b]furan-10(9bH)-one Piperidine (136 mg, 1.60 mmol), and triethylamine (200 mg, 1.98 mmol) were added to a solution of 4b,9b-dihydroxy-7-isopropyl-2-fluoro-4bH-benzo[d]indeno[1,2-b]furan-10(9bH)-one (250 mg, 0.80 mmol) in N,N-dimethylformamide (2 ml) and reacted at 110° C. for 10 min by microwaving. The product was purified by column chromatography to afford the title compound as a yellow solid (50 mg, 8%).

$^1$H-NMR (300 MHz, CD$_3$OD) δ 1.18 (d, J=6.9 Hz, 6H), 1.68 (s, 8H), 2.82 (sep, J=6.9H, 1H), 3.49 (s, 4H), 6.66 (s, 1H), 6.81 (d, J=7.6 Hz, 1H), 7.07 (d, J=9 Hz, 1H), 7.22 (d, J=1.2 Hz, 1H), 7.41 (d, J=7.7 Hz, 1H), 7.55 (d, J=8.6 Hz, 1H).

<Example 140> 4b,9b-Dihydroxy-7-isopropyl-2-morpholinyl-4bH-benzo[d]indeno[1,2-b]furan-10(9bH)-one Morpholine (140 mg, 1.60 mmol), and triethylamine (200 mg, 1.98 mmol) were added to a solution of 4b,9b-dihydroxy-7-isopropyl-2-fluoro-4bH-benzo[d]indeno[1,2-b]furan-10(9bH)-one (250 mg, 0.80 mmol) in N,N-dimethylformamide (2 ml) and reacted at 110° C. for 10 min by microwaving. The product was purified by column chromatography to afford the title compound as a yellow solid (60 mg, 10%).

$^1$H-NMR (500 MHz, CD$_3$OD) δ 1.15 (t, J=5.8 Hz, 6H), 2.80 (sep, J=6.9H, 1H), 3.32 (t, J=1.5 Hz, 4H), 3.76 (t, J=4.5 Hz, 4H), 6.68 (s, 1H), 6.81 (d, J=7.6 Hz, 1H), 7.06 (d, J=8.3 Hz, 1H), 7.24 (s, 1H), 7.41 (d, J=7.8 Hz, 1H), 7.57 (d, J=8.8 Hz, 1H).

<Example 141> 4b,9b-Dihydroxy-7-isopropyl-1-piperidinyl-4bH-benzo[d]indeno-[1,2-b]furan-10(9bH)-one Piperidine (140 mg, 1.60 mmol), and triethylamine (200 mg, 1.98 mmol) were added to a solution of 4b,9b-dihydroxy-7-isopropyl-1-fluoro-4bH-benzo[d]indeno[1,2-b]furan-10(9bH)-one (250 mg, 0.80 mmol) in N,N-dimethylformamide (1 ml) and reacted 110° C. for 10 min by microwaving. The product was purified by column chromatography to afford the title compound as a fluorescent yellow solid (110 mg, 18%).

$^1$H-NMR (500 MHz, CD$_3$OD) δ 1.16 (dd, J=6.9 Hz, 4.9 Hz, 6H), 1.59 (quin, J=5.8 Hz, 2H), 1.74 (m, 4H), 2.81 (sep, J=6.9H, 1H), 3.02 (m, 2H), 3.09 (m, 2H), 6.64 (s, 1H), 6.81 (d, J=7.8 Hz, 1H), 6.93 (d, J=8.2 Hz, 1H), 7.35 (d, J=7.5 Hz, 1H), 7.38 (d, J=7.8 Hz, 1H), 7.61 (t, J=7.8 Hz, 1H).

<Example 142> 4b,9b-Dihydroxy-7-isopropyl-1-morpholinyl-4bH-benzo[d]indeno[1,2-b]furan-10(9bH)-one Morpholine (140 mg, 1.60 mmol), and triethylamine (200 mg, 1.98 mmol) were added to a solution of 4b,9b-dihydroxy-7-isopropyl-1-fluoro-4bH-benzo[d]indeno[1,2-b]furan-10(9bH)-one (250 mg, 0.80 mmol) in N,N-dimethylformamide (1 ml) and reacted 110° C. for 10 min by microwaving. The product was purified by column chromatography to afford the title compound as a fluorescent yellow solid (80 mg, 13%).

$^1$H-NMR (500 MHz, CD$_3$OD) δ 1.14 (t, J=6.25 Hz, 6H), 2.79 (sep, J=6.8H, 1H), 3.00 (m, 2H), 3.11 (m, 2H), 3.83 (s, 4H), 6.67 (s, 1H), 6.81 (d, J=8.0 Hz, 1H), 6.84 (d, J=8.2 Hz, 1H), 7.40 (d, J=7.8 Hz, 1H), 7.44 (d, J=7.5 Hz, 1H), 7.61 (t, J=7.8 Hz, 1H).

<Example 143> N-(1-Amino-4b-hydroxy-7-isopropyl-10-oxo-9b,10-dihydro-4bH-indeno[1,2-b]benzofuran-9b-yl)propionamide Trimethyl acetic anhydride (0.27 g, 1.46 mmol) was added to a solution of 9b-chloro-4b-hydroxy-5,9b-dihydro-4bH-indeno[1,2-b]indol-10-one (0.50 g, 1.46 mmol) in pivalic acid (5 ml), and heated at 100° C. for 30 min. The reaction mixture was diluted in ethylacetate, and washed many times with aq. NaHCO$_3$. The organic layer was dried, filtered, concentrated in a vacuum, and purified by column chromatography (ethylacetate:hexane=1:4) to afford the title compound. 50 mg (14%).

$^1$H-NMR (300 MHz, CDCl$_3$) δ 1.07 (t, J=7.5 Hz, 3H, CH$_3$) 1.16 (d, J=6.9 Hz, 6H, CH$_3$) 2.24-2.32 (m, 2H, CH$_2$) 2.77-2.86 (m, 1H, CH) 6.64-6.65 (m, 2H, ArH) 6.82 (d, J=6.6 Hz, 1H, ArH) 6.98 (d, J=7.2 Hz, 1H, ArH) 7.33 (m, 1H, ArH) 7.38-7.43 (m, 1H, ArH).

<Example 144> N-(1-Amino-4b-hydroxy-7-isopropyl-10-oxo-9b,10-dihydro-4bH-indeno[1,2-b]benzofuran-9b-yl) butyramide H$_2$O (0.5 ml), Fe (0.28 g, 5.14 mmol), and conc. HCl (0.03 mmol) were added to a solution of N-(4b-hydroxy-7-isopropyl-1-nitro-10-oxo-9b,10-dihydro-4bH-indeno[1,2-b]benzofuran-9b-yl)butyramide (0.30 g, 0.70 mmol) in EtOH (5 ml) and heated for 1 hr under reflux. The reaction mixture was washed with ethylacetate, and filtered. Then, the filtrate was concentrated and purified by column chromatography (ethylacetate:hexane=1:4) to afford the title compound. 0.20 g (75%).

$^1$H-NMR (300 MHz, CD$_3$OD) δ 0.95 (t, J=7.5 Hz, 3H, CH$_3$) 1.16 (d, J=6.9 Hz, 6H, CH$_3$) 1.56-1.63 (m, 1H, CH$_2$) 2.23 (t, J=7.5 Hz, 2H, CH$_2$) 2.79-2.83 (m, 1H, CH) 6.64 (s, 2H, ArH) 6.82 (d, J=7.8 Hz, 1H, ArH) 6.98 (d, J=6.6 Hz, 1H, ArH) 7.33 (s, 1H, ArH) 7.40 (t, J=6.6 Hz, 1H, ArH).

<Example 145> 4b,9b-Dihydroxy-5-isobutyryl-7-isopropyl-5,9b-dihydro-4bH-indeno[1,2-b]indol-10-one Conc. HCl (2 ml) was added to a solution of N-[2-(2-hydroxy-1,3-dioxo-indan-2-yl)-5-isopropyl-phenyl]-isobutyramide (80 mg, 0.21 mmol) in anhydrous THF (2 ml) and stirred at room temperature for 3 hrs. The reaction mixture was washed many times with ethylacetate and water, and the organic layer was dried, filtered, and concentrated in a vacuum, followed by purification through column chromatography (ethylacetate:hexane=1:4) to afford the title compound. 33 mg (41%).

$^1$H-NMR (300 MHz, CDCl$_3$) δ 1.15-1.25 (m, 12H, CH$_3$) 2.68-2.84 (m, 2H, CH) 3.08 (s, 1H, OH) 5.02 (s, 1H, OH) 6.51 (s, 1H, ArH) 6.76 (d, J=8.1 Hz, 1H, ArH) 7.44 (d, J=8.1 Hz, 1H, ArH) 7.51 (t, J=7.5 Hz, 1H, ArH) 7.73-7.84 (m, 3H, ArH).

<Example 146> 4b,9b-Dihydroxy-7-isopropyl-2-(hydroxypiperidinyl)-4bH-benzo[d]indeno[1,2-b]furan-10(9bH)-one Hydroxypiperidine (162 mg, 1.60 mmol), and triethylamine (200 mg, 1.98 mmol) were added to a solution of 4b,9b-dihydroxy-7-isopropyl-2-fluoro-4bH-benzo[d]indeno[1,2-b]furan-10(9bH)-one (250 mg, 0.80 mmol) in N,N-dimethylformamide (1 ml) and reacted at 110° C. for 5 min by microwaving. The product was purified by column chromatography to afford the title compound as a yellow solid (65 mg, 10%).

$^1$H-NMR (300 MHz, CD$_3$OD) δ 1.16 (dd, J=6.9 Hz, 1.4 Hz, 6H), 1.57 (m, 2H), 1.95 (m, 2H), 2.80 (sep, J=6.9 Hz, 1H), 3.24 (m, 2H), 3.92 (m, 3H), 6.63 (s, 1H), 6.80 (d, J=7.7 Hz, 1H), 7.12 (d, J=7.7 Hz, 1H), 7.25 (s, 1H), 7.39 (d, J=7.6 Hz, 1H), 7.56 (d, J=8.0 Hz, 1H).

<Example 147> 4b,9b-Dihydroxy-1-(4-hydroxypiperidin-1-yl)-7-isopropyl-4bH-benzo[d]indeno[1,2-b]furan-10(9bH)-one Hydroxypiperidine (162 mg, 1.60 mmol) and triethylamine (200 mg, 1.98 mmol) were added to a solution of 4b,9b-dihydroxy-7-isopropyl-1-fluoro-4bH-benzo[d]indeno[1,2-b]furan-10(9bH)-one (250 mg, 0.80 mmol) in N,N-dimethylformamide (1 ml) and reacted 110° C. for 5 min by microwaving. The product was purified by column chromatography to afford the title compound as a fluorescent yellow solid (60 mg, 10%).

$^1$H-NMR (300 MHz, CD$_3$OD) δ 1.16 (d, J=6.6 Hz, 6H), 1.74 (m, 2H), 1.94 (s, 2H), 2.79 (m, 3H), 3.44 (s, 1H), 3.76 (m, 1H), 6.63 (s, 1H), 6.81 (d, J=7.9 Hz, 1H,) 6.98 (d, J=7.9 Hz, 1H), 7.36 (d, J=7.5 Hz 2H), 7.63 (t, J=7.4 Hz, 1H).

<Example 148> 4b,9b-Dihydroxy-7-isopropyl-2-(4-(4-methoxybenzyl)piperazin-1-yl)-4bH-benzo[d]indeno[1,2-b]furan-10(9bH)-one 1-(4-Methoxybenzyl)piperazine (136 mg, 1.60 mmol) and triethylamine (200 mg, 1.98 mmol) were added to a solution of 4b,9b-dihydroxy-7-isopropyl-2-fluoro-4bH-benzo[d]indeno[1,2-b]furan-10(9bH)-one (250 mg, 0.80 mmol) in N,N-dimethylformamide (1 ml) and reacted 110° C. for 5 min by microwaving. The product was purified by column chromatography to afford the title compound as a yellow solid (70 mg, 9%).

$^1$H-NMR (300 MHz, CD$_3$OD) δ 1.17 (d, 6.8 Hz), 2.60 (s, 4H), 2.80 (sep, J=6.8 Hz, 1H), 3.47 (s, 4H), 3.55 (s, 2H), 3.80 (s, 3H), 6.74 (s, 1H), 6.78 (Br, 1H), 6.87 (d, J=7.8 Hz, 2H), 6.93 (s, 1H), 7.23 (m, 3H), 7.40 (br, 1H), 7.60 (br, 1H).

<Example 149> 4b,9b-Dihydroxy-7-isopropyl-1-(4-(4-methoxybenzyl)piperazin-1-yl)-4bH-benzo[d]indeno[1,2-b]furan-10(9bH)-one 1-(4-methoxybenzyl)piperazine (140 mg, 1.60 mmol) and triethylamine (200 mg, 1.98 mmol) were added to a solution of 4b,9b-dihydroxy-7-isopropyl-1-fluoro-4bH-benzo[d]indeno[1,2-b]furan-10(9bH)-one (250 mg, 0.80 mmol) in N,N-dimethylformamide (1 ml), and reacted 110° C. for 5 min by microwaving. The product was purified by column chromatography to afford the title compound as a fluorescent yellow solid (84 mg, 11%).

$^1$H-NMR (300 MHz, CD$_3$OD) δ1.16 (d, J=6.9 Hz, 6H), 2.65 (m, 4H), 2.81 (sep, J=6.9 Hz, 1H), 3.18 (t, J=4.6 Hz, 4H), 3.53 (d, 2.6 Hz, 2H), 3.80 (s, 3H), 6.70 (s, 1H), 6.79 (d, J=7.8 Hz, 1H), 6.89 (m, 3H), 7.43 (d, J=7.4 Hz, 1H), 7.62 (t, J=7.8 Hz).

<Example 150> 2-(Dimethylamino)-4b,9b-dihydroxy-7-isopropyl-4bH-benzo[d]indeno[1,2-b]furan-10(9bH)-one Dimethylamine hydrochloride (136 mg, 1.60 mmol) and triethylamine (400 mg, 3.96 mmol) were added to a solution of 4b,9b-dihydroxy-7-isopropyl-2-fluoro-4bH-benzo[d]indeno[1,2-b]furan-10(9bH)-one (250 mg, 0.80 mmol) in N,N-dimethylformamide (1 ml) and reacted 110° C. for 5 min by microwaving. The product was purified by column chromatography to afford the title compound as a yellow solid (73 mg, 10%).

$^1$H-NMR (300 MHz, CD$_3$OD) δ 1.16 (d, J=6.9 Hz, 6H), 2.82 (sep, J=6.9 Hz, 1H), 3.14 (s, 6H), 6.71 (s, 1H), 6.80 (t, J=7.5 Hz, 2H), 7.05 (d, J=7.8 Hz, 1H), 7.43 (d, J=7.8 Hz, 1H), 7.62 (d, J=8.8 Hz, 1H).

<Example 151> 1-(Dimethylamino)-4b,9b-dihydroxy-7-isopropyl-4bH-benzo[d]indeno[1,2-b]-furan-10(9bH)-one Dimethylamine hydrochloride (140 mg, 1.60 mmol) and triethylamine (400 mg, 3.96 mmol) were added to a solution of 4b,9b-dihydroxy-7-isopropyl-1-fluoro-4bH-benzo[d]indeno[1,2-b]furan-10(9bH)-one (250 mg, 0.80 mmol) in N, N-dimethylformamide (1 ml) and reacted 110° C. for 10 min by microwaving. The product was purified by column chromatography to afford the title compound as a yellow solid (168 mg, 31%).

$^1$H-NMR (300 MHz, CD$_3$OD) δ1.17 (dd, J=6.9, 2.8 Hz, 6H), 2.82 (sep, J=6.9 Hz, 1H), 2.95 (s, 6H), 6.71 (d, J=1.25 Hz, 1H), 6.80 (m, 2H), 7.30 (t, J=7.9 Hz, 2H), 7.57 (t, J=7.4 Hz, 1H).

<Example 152> 10-Hydrazono-7-isopropyl-9b,10-dihydro-4bH-benzo[d]indeno[1,2-b]furan-4b,9b-diol 4b,9b-dihydroxy-7-isopropyl-4bH-benzo[d]indeno[1,2-b]furan-10(9bH)-one (500 mg, 1.69 mmol) and hydrazine monohydrate (125 mg, 2.50 mmol) were dissolved in toluene (5 ml) in a reactor, and stirred overnight at room temperature. The product was purified by column chromatography to afford the title compound as a white solid (7 mg, 1%).

$^1$H-NMR (300 MHz, DMSO) δ 1.15 (d, J=6.9 Hz, 6H), 2.80 (sep, J=6.8 Hz, 1H), 5.83 (br, 1H), 6.72~6.76 (m, 2H), 7.48 (t, J=7.8 Hz, 1H), 7.64~7.70 (m, 2H), 7.75 (d, J=7.9 Hz, 1H), 7.83 (d, J=7.7 Hz, 1H), 11.24 (s, 1H).

<Example 153> N-(1-Amino-4b-hydroxy-7-isopropyl-10-oxo-9b,10-dihydro-4bH-indeno[1,2-b]benzofuran-9b-yl)benzamide Iron powder (38 mg, 0.68 mmoles) was added to a solution of N-(4b-hydroxy-7-isopropyl-1-nitro-10-oxo-9b,10-dihydro-4bH-indeno[1,2-b]benzofuran-9b-yl)benzamide (0.10 g, 0.23 mmoles) in ethanol:water (10:1, 10 mL) and heated for 3 hrs under reflux. The reaction mixture was filtered, and the filtrate was concentrated in a vacuum and purified by silica gel column chromatography (50% ethylacetate in hexane) to afford the title compound. 80 mg (86%).

$^1$H-NMR (300 MHz, CD$_3$OD) δ 1.18 (d, J=6.9 Hz, 6H, CH$_3$) 2.84 (sept, J=6.9 Hz, 1H, CH) 6.67 (br, 2H, ArH) 6.87-6.89 (m, 1H, ArH) 7.01-7.03 (m, 1H, ArH) 7.40-7.54 (m, 5H, ArH) 7.83-7.86 (m, 2H, ArH).

<Example 154> N-(1-Amino-4b-hydroxy-7-isopropyl-10-oxo-9b,10-dihydro-4bH-indeno[1,2-b]benzofuran-9b-yl)-3-methoxybenzamide N-(4b-hydroxy-7-isopropyl-1-nitro-10-oxo-9b,10-dihydro-4bH-indeno[1,2-b]benzofuran-9b-yl-3-methoxybenzamide (0.10 g, 0.21 mmoles) was dissolved in ethanol:water (10:1, 10 mL) and heated for 3 hrs in the presence of iron powder (36 mg, 0.63 mmoles) under reflux. The reaction mixture was filtered, and the filtrate was concentrated in a vacuum and purified by silica gel column chromatography (50% ethylacetate in hexane) to afford the title compound. 85 mg (90%).

$^1$H-NMR (300 MHz, CD$_3$OD) δ 1.19 (d, J=6.9 Hz, 6H, CH$_3$) 2.84 (sept, J=6.9 Hz, 1H, CH) 3.82 (s, 3H, OCH$_3$) 6.67-6.72 (m, 2H, ArH) 6.89 (d, J=6.3 Hz, 1H, ArH) 7.03-7.09 (m, 2H, ArH) 7.31-7.36 (m, 1H, ArH) 7.43-7.49 (m, 4H, ArH).

<Example 155> N-(1-Amino-4b-hydroxy-7-isopropyl-10-oxo-9b,10-dihydro-4bH-indeno[1,2-b]benzofuran-9b-yl)-4-chlorobenzamide 4-Chloro-N-(4b-hydroxy-7-isopropyl-1-nitro-10-oxo-9b,10-dihydro-4bH-indeno[1,2-b]benzofuran-9b-yl)benzamide (0.08 g, 0.17 mmoles) was dissolved in ethanol:water (10:1, 10 mL) and heated for 3 hrs in the presence of iron powder (28 mg, 0.50 mmoles) under reflux. The reaction mixture was filtered, and the filtrate was concentrated in a vacuum, and purified by silica gel column chromatography (50% ethylacetate in hexane) to afford the title compound. 60 mg (80%).

$^1$H-NMR (300 MHz, CD$_3$OD) δ 1.18 (d, J=6.9 Hz, 6H, CH$_3$) 2.84 (sept, J=6.9 Hz, 1H, CH) 6.66-6.75 (m, 2H, ArH) 6.88 (d, J=7.8 Hz, 1H, ArH) 7.01 (d, J=7.5 Hz, 1H, ArH) 7.41-7.46 (m, 4H, ArH) 8.83 (d, J=8.4 Hz, 2H, ArH).

<Example 156> N-(1-Amino-4b-hydroxy-7-isopropyl-10-oxo-9b,10-dihydro-4bH-indeno[1,2-b]benzofuran-9b-yl)-4-nitrobenzamide N-(4b-hydroxy-7-isopropyl-1-nitro-10-oxo-9b,10-dihydro-4bH-indeno[1,2-b]benzofuran-9b-yl)-4-nitrobenzamide (0.075 g, 0.15 mmoles) was dissolved in ethanol:water (10:1, 10 mL) and heated for 6 hrs in the presence of iron powder (52 mg, 0.92 mmoles) under reflux. The reaction mixture was filtered, and the filtrate was concentrated in a vacuum and purified by silica gel column chromatography (50% ethylacetate in hexane) to afford the title compound. 50 mg (76%).

$^1$H-NMR (300 MHz, CD$_3$OD) δ 1.18 (d, J=6.9 Hz, 6H, CH$_3$) 2.83 (sept, J=6.9 Hz, 1H, CH) 6.60-6.69 (m, 4H, ArH) 6.86-6.88 (m, 1H, ArH) 6.99-7.01 (m, 1H, ArH) 7.40-7.46 (m, 2H, ArH) 7.60-7.63 (m, 2H, ArH).

<Example 157> 1-Amino-4b,9b-dihydroxy-6,8-diisopropyl-4bH-benzo[d]indeno[1,2-b]furan-10(9bH)-one 4b,9b-Dihydroxy-6,8-diisopropyl-1-nitro-4bH-benzo[d]indeno[1,2-b]furan-10(9bH)-one (300 mg, 0.78 mmol) was dissolved in ethanol:water (10 ml:1 ml). To this solution, Fe (319 mg, 5.7 mmol) and one drop of conc. HCl were added, followed by heating for 1 hr under reflux. After neutralization with a NaHCO$_3$ solution, concentration in a vacuum and purification by column chromatography (20% methanol in methylene chloride) afforded the title compound (90 mg, 33%).

$^1$H-NMR (300 MHz, DMSO) δ 1.09~1.17 (m, 12H), 2.81 (sep, J=6.8 Hz, 1H), 2.93 (sep, J=6.8 Hz, 1H), 6.36 (s, 1H), 6.64~6.68 (m, 2H), 6.97 (s, 1H), 7.08 (d, J=1.2 Hz, 1H), 7.43 (t, J=7.7 Hz, 1H), 7.50 (s, 1H).

<Example 158> N-(1-Amino-4b-hydroxy-7-isopropyl-10-oxo-9b,10-dihydro-4bH-indeno[1,2-b]benzofuran-9b-yl)cyclopropanecarboxamide A solution of N-(4b-hydroxy-7-isopropyl-1-nitro-10-oxo-9b,10-dihydro-4bH-indeno[1,2-b]benzofuran-9b-yl)cyclopropanecarboxamide (0.20 g, 0.49 mmoles) in ethanol:water (10:1, 20 mL) was heated for 3 hrs in the presence of iron powder (82 mg, 1.47 mmoles) under reflux. The reaction mixture was filtered, and the filtrate was concentrated in a vacuum and purified by silica gel column chromatography (50% ethylacetate in hexane) to afford the title compound. 150 mg (81%).

$^1$H-NMR (300 MHz, CD$_3$OD) δ 0.74-0.76 (m, 4H, CH$_2$) 1.17 (d, J=6.9 Hz, 6H, CH$_3$) 1.72-1.75 (m, 1H, CH) 2.82 (sept, J=6.9 Hz, 1H, CH) 6.64 (m, 2H, ArH) 6.84-6.86 (m, 1H, ArH) 6.97-6.99 (m, 1H, ArH) 7.42 (m, 2H, ArH).

<Example 159> 1-(4b-Hydroxy-6,8-diisopropyl-1-amino-10-oxo-9b,10-dihydro-4bH-benzo[d]indeno[1,2-b]furan-9b-yl)-3-(4-methoxyphenyl)thiourea 1-(4b-hydroxy-6,8-diisopropyl-1-nitro-10-oxo-9b,10-dihydro-4bH-benzo[d]indeno[1,2-b]furan-9b-yl)-3-(4-methoxyphenyl)thiourea (100 mg, 0.78 mmol) was dissolved in ethanol:water (10 ml:1 ml). To this solution, Fe (319 mg, 5.7 mmol) and one drop of conc. HCl were added, and heated for 1 hr under reflux.

Concentration in a vacuum and purification by column chromatography (20% methanol in methylene chloride) afforded the title compound (60 mg, 64%).

$^1$H-NMR (300 MHz, CD$_3$OD) δ 1.22 (d, J=6.9 Hz, 6H, CH$_3$), 2.84 (sep, J=6.9 Hz, 1H, CH), 3.80 (s, 3H, OCH$_3$), 5.88 (d, J=7.3 Hz, 1H, ArH), 6.64~6.67 (m, 2H, ArH), 6.85~6.89 (m, 3H, ArH), 6.98~7.01 (m, 2H, ArH), 7.16 (t, J=7.8 Hz, 1H, ArH), 7.43 (d, J=8.0 Hz, 1H, ArH).

<Example 160> 1-(4b-Hydroxy-6,8-diisopropyl-1-amino-10-oxo-9b,10-dihydro-4bH-benzo[d]indeno[1,2-b]furan-9b-yl)-3-(phenyl)thiourea 1-(4b-hydroxy-6,8-diisopropyl-1-nitro-10-oxo-9b,10-dihydro-4bH-benzo[d]indeno[1,2-b]furan-9b-yl)-3-(phenyl)thiourea (100 mg, 0.78 mmol) was dissolved in ethanol:water (10 ml:1 ml). To this solution, Fe (319 mg, 5.7 mmol) and one drop of conc. HCl were added and heated for 1 hr under reflux. Concentration in a vacuum and purification by column chromatography (20% methanol in methylene chloride) afforded the title compound (40 mg, 43%).

$^1$H-NMR (300 MHz, acetone-d6) δ 1.21 (dd, J=6.9 Hz, 1.0 Hz, 6H, CH$_3$), 2.84 (sep, J=6.9 Hz, 1H, CH), 5.79 (s, 1H, OH), 5.86 (d, J=7.3 Hz, 1H, ArH), 6.43 (s, 2H, NH$_2$), 6.71 (d, J=8.0 Hz, 1H, ArH), 6.74 (d, J=1.4 Hz, 1H, ArH), 6.85 (dd, J=8.0 Hz, 1.4 Hz, 1H, ArH), 7.12~7.22 (m, 3H, ArH), 7.32~7.35 (m, 3H, ArH), 7.45 (d, J=8.0 Hz, 1H, ArH), 8.73 (s, 1H, NH), 8.78 (s, 1H, NH).

<Example 161> N-(4b-Hydroxy-7-isopropyl-10-oxo-9b,10-dihydro-4bH-indeno[1,2-b]benzofuran-9b-yl)thiophene-2-carboxamide Thiophene carboxylic acid (0.13 g, 1.01 mmol) was dissolved in anhydrous methylene chloride (10 ml) and stirred overnight at 00° C. in the presence of EDCl (0.19 g, 1.01 mmol), and HOBt (0.13 g, 1.01 mmol) (0.30 g, 1.01 mmol). Since the reaction was not completed in spite of such a long period of time, EDCl (0.19 g, 1.01 mmol) and HOBt (0.13 g, 1.01 mmol) were further added. However, the completion of the reaction was not detected. The reaction mixture was diluted in methylene chloride, and washed with water. The organic layer was dried and filtered. Purification by column chromatography (ethylacetate:hexane=1:4) afforded the title compound. 0.12 g (29%).

$^1$H-NMR (300 MHz, CDCl$_3$) δ 1.13-1.15 (m, 6H, CH$_3$) 2.76-2.85 (m, 1H, CH) 6.71 (s, 1H, NH) 6.80 (d, J=7.8 Hz, 1H, ArH) 7.05 (s, 1H, ArH) 7.20 (s, 1H, ArH) 7.33 (d, J=7.8 Hz, 1H, ArH) 7.50-7.55 (m, 2H, ArH) 7.61 (d, J=2.4 Hz, 1H, ArH) 7.76-7.87 (m, 2H, ArH) 8.01 (d, J=7.5 Hz, 1H, ArH).

<Example 162> 1-(1-Amino-4b-hydroxy-7-isopropyl-10-oxo-9b,10-dihydro-4bH-indeno[1,2-b]benzofuran-9b-yl)-3-(4-methoxyphenyl urea 1-(4b-hydroxy-7-isopropyl-1-nitro-10-oxo-9b,10-dihydro-4bH-indeno[1,2-b]benzofuran-9b-yl)-3-(4-methoxyphenylurea (93 mg, 0.19 mmol was added to 5 ml of EtOH:H$_2$O (10:1) to form a pale yellowish turbid solution to which Fe powder (39 mg, 0.70 mmol and two drops of conc. HCl were then added at room temperature, followed by stirring for 1.5 hrs under reflux. A new spot was observed just below the starting material, as monitored by TLC. The reaction mixture was filtered, concentrated, and purified by silica gel column chromatography using EtOAc/Hx (1/2-1/1) to afford the title compound as a pale yellow solid (65 mg, 0.14 mmol, 74%).

$^1$H-NMR (300 MHz, CDCl$_3$+2 drops of CD$_3$OD) δ 1.18 (d, J=6.9 Hz, 6H), 2.38 (s, br, 5H), 2.82 (heptet, J=6.9 Hz, 1H), 3.78 (s, 3H), 6.07 (d, J=7.4 Hz, 1H), 6.58 (d, J=8.2 Hz, 1H), 6.68 (d, J=1.5 Hz, 1H), 6.81-6.87 (m, 1H), 6.84 (d, J=9.0 Hz, 2H), 7.08 (d, J=9.0 Hz, 2H), 7.17 (t, J=7.8 Hz, 1H), 7.34 (d, J=8.0 Hz, 1H).

<Example 163> 1-(1-Amino-4b-hydroxy-7-isopropyl-10-oxo-9b,10-dihydro-4bH-indeno[1,2-b]benzofuran-9b-yl)-3-butylurea 1-Butyl-3-(4b-hydroxy-7-isopropyl-1-nitro-10-oxo-9b,10-dihydro-4bH-indeno[1,2-b]benzofuran-9b-yl)urea (100 mg, 0.228 mmol was added to 5 ml of EtOH:H$_2$O (10:1) to form a pale yellowish turbid solution to which Fe powder (38 mg, 0.680 mmol and two drops of conc. HCl were then added at room temperature, followed by stirring for 2.5 hrs under reflux. A new spot was observed just below the starting material, as monitored by TLC. The reaction mixture was filtered, concentrated, and purified by silica gel column chromatography using EtOAc/Hx (1/2-1/1) to afford the title compound as a pale yellow solid (66 mg, 0.16 mmol, 71%).

$^1$H-NMR (300 MHz, CDCl$_3$+a drop of CD$_3$OD) δ 0.87 (t, J=7.2 Hz, 3H), 1.16 (dd, J=6.9, 0.8 Hz, 6H), 1.27 (sextet, J=7.4 Hz, 2H), 1.36-1.65 (m, 2H), 2.10 (s, br, 3H), 2.79 (heptet, J=6.9 Hz, 1H), 3.16-3.28 (m, 1H), 3.32-3.44 (m, 1H), 6.63 (d, J=8.2 Hz, 1H), 6.69 (d, J=1.5 Hz, 1H), 7.76 (dd, J=8.1, 1.6 Hz, 1H), 6.93 (d, J=7.3 Hz, 1H), 7.15 (d, J=8.0 Hz, 1H), 7.42 (dd, J=8.1, 7.4 Hz, 1H).

<Example 164> 1-(1-Amino-4b-hydroxy-7-isopropyl-10-oxo-9b,10-dihydro-4bH-indeno[1,2-b]benzofuran-9b-yl)-3-(4-fluorophenyl)urea 1-(4-fluorophenyl)-3-(4b-hydroxy-7-isopropyl-1-nitro-10-oxo-9b,10-dihydro-4bH-indeno[1,2-b]benzofuran-9b-ylurea (187 mg, 0.392 mmol was added to 5 ml of EtOH:H$_2$O (10:1) to form a pale yellowish turbid solution to which Fe powder (66 mg, 1.18 mmol and one drop of conc. HCl were then added at room temperature, followed by stirring for 1 hr under reflux. A new spot was observed just below the starting material, as monitored by TLC. The reaction mixture was filtered, concentrated, and purified by silica gel column chromatography using EtOAc/Hx (1/2-1/1) to afford the title compound as a pale yellow solid (107 mg, 0.239 mmol, 61%).

$^1$H-NMR (300 MHz, CD$_3$OD) δ 1.23 (d, J=6.9 Hz, 6H), 2.85 (heptet, J=6.9 Hz, 1H), 5.87 (d, J=7.3 Hz, 1H), 6.64-6.67 (m, 2H), 6.87 (dd, J=8.0, 1.6 Hz, 1H), 7.05-7.20 (m, 5H), 7.48 (d, J=6.5 Hz, 1H).

<Example 165> 1-(1-Amino-4b-hydroxy-7-isopropyl-10-oxo-9b,10-dihydro-4bH-indeno[1,2-b]benzofuran-9b-yl)-3-(tert-butylurea 1-(tert-Butyl-3-(4b-hydroxy-7-isopropyl-1-nitro-10-oxo-9b,10-dihydro-4bH-indeno[1,2-b]benzofuran-9b-ylurea (99 mg, 0.23 mmol was added to 5 ml of EtOH:H$_2$O (10:1) to form a pale yellowish turbid solution to which Fe powder (38 mg, 0.688 mmol and two drops of conc. HCl were then added at room temperature, followed by stirring for 1.5 hrs under reflux. A new spot was observed (PK344) just below the starting material, as monitored by TLC. The reaction mixture was filtered, concentrated, and purified by silica gel column chromatography using EtOAc/Hx (1/2-1/1) to afford the title compound as a yellow solid (84 mg, 0.21 mmol, 91%).

$^1$H-NMR (300 MHz, CD$_3$OD) δ 1.17 (dd, J=6.9, 1.9 Hz, 6H), 1.23 (s, 9H), 2.73-2.88 (m, 1H), 6.58-6.72 (m, 2H), 6.81 (d, br, J=7.3 Hz, 1H), 6.99 (d, br, J=6.9 Hz, 1H), 7.31 (d, br, J=7.2 Hz, 1H), 7.38-7.52 (m, 1H).

<Example 166> N-(1-Amino-4b-hydroxy-7-isopropyl-10-oxo-9b,10-dihydro-4bH-indeno[1,2-b]benzofuran-9b-yl)formamide N-(4b-hydroxy-7-isopropyl-1-nitro-10-oxo-9b,10-dihydro-4bH-indeno[1,2-b]benzofuran-9b-yl)acetamide (123 mg, 0.334 mmol was added to 5 ml of EtOH:H$_2$O (10:1) to form a pale yellowish turbid solution to which Fe powder (46 mg, 0.83 mmol) and one drop of conc. HCl were then added at room temperature, followed by stirring for 2 hrs under reflux. A new spot was observed just below the starting material, as monitored by TLC. The reaction mixture was filtered, concentrated, and purified by silica gel column chromatography using EtOAc/Hx (1/2-1/1) to afford the title compound as a yellow solid (72 mg, 0.21 mmol, 64%).

$^1$H-NMR (300 MHz, CD$_3$OD) δ 1.18 (dd, J=6.9, 1.4 Hz, 6H), 2.83 (heptet, J=6.9 Hz, 1H), 6.66 (s, 1H), 6.68-6.76 (m, 1H), 6.84 (d, J=7.9 Hz, 1H), 7.00 (d, J=7.1 Hz, 1H), 7.33 (d, J=7.9 Hz, 1H), 7.41-7.50 (m, 1H), 8.10 (s, 1H).

<Example 167> N-(1-Formamido-4b-hydroxy-7-isopropyl-10-oxo-9b,10-dihydro-4bH-benzo[d]-indeno[1,2-b]furan-9b-yl)acetamide A mixture of formic acid (5 ml) and acetic anhydride (10 ml) was stirred at 80° C. for 30 min and then cooled to room temperature. To this mixture was added a solution of N-(1-amino-9b-hydroxy-7-isopropyl-10-oxo-9b,10-dihydro-5-oxa-indeno[2,1-a]inden-4b-yl)-acetamide (200 mg, 0.57 mmol) in methylene chloride, followed by stirring at room temperature. After removal of the solvent, the addition of a small amount of methylene chloride formed a white precipitate. This was filtered to afford the title compound (170 mg, 79%).

$^1$H-NMR (300 MHz, CD$_3$OD) δ 1.16 (dd, J=6.9 Hz, 1.6 Hz, 6H, CH$_3$), 1.99 (s, 3H, CH$_3$), 2.82 (sep, J=6.9 Hz, 1H, CH), 6.65 (s, 1H, CH$_3$), 6.88 (dd, J=7.9 Hz, 1.0 Hz, 1H, ArH), 7.38 (d, J=7.9 Hz, 1H, ArH), 7.59 (d, J=7.6 Hz, 1H, ArH), 7.75 (t, J=8.0 Hz, 1H, ArH), 8.46 (s, 1H), 8.50 (d, J=8.1 Hz, 1H, ArH).

<Example 168> N-(1-Amino-4b-hydroxy-7-isopropyl-10-oxo-9b,10-dihydro-4bH-benzo[d]indeno[1,2-b]furan-9b-yl)methanesulfonamide To N-(4b-hydroxy-7-isopropyl-1-nitro-10-oxo-9b,10-dihydro-4bH-benzo[d]indeno[1,2-b]furan-9b-yl)methanesulfonamide (150 mg, 0.36 mmol) were added a mixture of ethanol:water (10 ml:1 ml), Fe (80 mg, 1.43 mmol), and two drops of conc. HCl in that order. After heating for 2 hrs under reflux, the reaction mixture was concentrated in a vacuum and purified by column chromatography (ethylacetate:n-hexane=1:2) to afford the title compound (60 mg, 43%).

$^1$H-NMR (300 MHz, CD$_3$OD) δ 1.34 (d, J=6.9 Hz, 6H, CH$_3$), 3.09 (sep, J==6.9 Hz, 1H, CH), 3.34 (s, 3H, SCH$_3$), 7.11 (d, J=7.7 Hz, 1H, ArH), 7.28~7.35 (m, 2H, ArH), 7.56 (s, 1H, ArH), 7.73 (d, J=7.9 Hz, 1H, ArH), 7.81 (d, J=8.1 Hz, 1H, ArH).

<Example 169> Diethyl (1-amino-4b-hydroxy-7-isopropyl-10-oxo-9b,10-dihydro-4bH-indeno[1,2-b]benzofuran-9b-yl)phosphoamidate Diethyl (4b-hydroxy-7-isopropyl-4-nitro-10-oxo-9b,10-dihydro-4bH-indeno[1,2-b]benzofuran-9b-yl)phosphoamidate (0.050 g, 0.11 mmoles) was dissolved in a mixture of ethanol:water (10:1, 10 mL). To this solution, iron powder (20 mg, 0.36 mmoles) and 2-3 drops of conc. HCl were added before heating for 2.5 hrs under reflux. After completion of the reaction, the reaction mixture was washed with ethylacetate, filtered to remove iron powder, and extracted with ethylacetate and water. The organic layer was washed with brine, dried, and concentration, followed by separation and purification by column chromatography (30% ethylacetate mixed with 50% hexane) to afford the title compound. 6 mg (13%).

$^1$H-NMR (300 MHz, CD$_3$OD) δ 1.13 (t, J=6.9 Hz, 6H, CH$_3$) 1.26 (d, J=6.9 Hz, 6H, CH$_3$) 2.88 (sept, J=6.9 Hz, 1H, CH) 3.65-3.89 (m, 4H, CH$_2$) 6.69 (d, J=7.8 Hz, 1H, ArH) 6.83-6.86 (m, 2H, ArH) 7.03 (d, J=7.8 Hz, 1H, ArH) 7.30 (d, J=8.1 Hz, 1H, ArH) 7.40 (t, J=8.1 Hz, 1H, ArH).

<Example 170> N-(1-Amino-4b-hydroxy-7-isopropyl-10-oxo-9b,10-dihydro-4bH-indeno[1,2-b]benzofuran-9b-yl)-4-cyanobenzamide Iron powder (30 mg, 0.38 mmoles) and 3 drops of conc. HCl were added to a solution of 4-cyano-N-(4b-hydroxy-7-isopropyl-4-nitro-10-oxo-9b,10-dihydro-4bH-indeno[1,2-b]benzofuran-9b-yl)benzamide (0.06 g, 0.13 mmoles) in ethanol:water (10:1, 20 mL), and heated for 3 hrs under reflux. After completion of the reaction, the reaction mixture was washed with ethylacetate, filtered to remove iron powder, and extracted with ethylacetate and water. The organic layer was washed with brine, dried, and concentrated, followed by separation and purification by column chromatography (30% ethylacetate mixed with 30% hexane) to afford the title compound. 50 mg (89%).

$^1$H-NMR (300 MHz, CD$_3$OD) δ 1.17 (d, J=6.9 Hz, 6H, CH$_3$) 2.83 (sept, J=6.9 Hz, 1H, CH) 6.67 (br, 2H, ArH) 6.86-6.88 (m, 1H, ArH) 7.00-7.02 (m, 1H, ArH) 7.43-7.45 (m, 2H, ArH) 7.77-7.80 (m, 2H, ArH) 7.96-7.99 (m, 2H, ArH).

<Example 171> N-(1-Amino-4b-hydroxy-7-isopropyl-10-oxo-9b,10-dihydro-4bH-indeno[1,2-b]benzofuran-9b-yl)-2-naphthamide Iron powder (35 mg, 0.60 mmoles), and 3 drops of conc. HCl were added to a solution of N-(4b-hydroxy-7-isopropyl-4-nitro-10-oxo-9b,10-dihydro-4bH-indeno[1,2-b]benzofuran-9b-yl)-2-naphthamide (0.10 g, 0.20 mmoles) in ethanol:water (10:1, 10 mL) and heated for 3 hrs under reflux. After completion of the reaction, the reaction mixture was washed with ethylacetate, filtered to remove iron powder, and extracted with ethylacetate and water. The organic layer was washed with brine, dried, and concentrated, followed by separation and purification by column chromatography (30% ethylacetate mixed with 40% hexane) to afford the title compound. 85 mg (90%).

$^1$H-NMR (300 MHz, CD$_3$OD) δ 1.20 (d, J=6.9 Hz, 6H, CH$_3$) 2.86 (sept, J=6.9 Hz, 1H, CH) 6.68-6.72 (m, 2H, ArH) 6.90 (d, J=7.5 Hz, 1H, ArH) 7.03 (d, J=7.5 Hz, 1H, ArH) 7.44-7.59 (m, 4H, ArH) 7.89-7.97 (m, 4H, ArH) 8.45 (s, 1H, ArH).

<Example 172> N-(1-Amino-4b-hydroxy-7-isopropyl-10-oxo-9b,10-dihydro-4bH-indeno[1,2-b]benzofuran-9b-yl-[1,1'-biphenyl]-4-carboxamide Iron powder (33 mg, 0.58 mmoles), and 3 drops of conc. HCl were added to a solution of N-(4b-hydroxy-7-isopropyl-4-nitro-10-oxo-9b,10-dihydro-4bH-indeno[1,2-b]benzofuran-9b-yl-[, 1'-biphenyl]-4-carboxamide (0.10 g, 0.19 mmoles) in ethanol:water (10:1, 10 mL), and heated for 3 hrs under reflux. After completion of the reaction, the reaction mixture was washed with ethylacetate, filtered to remove iron powder, and extracted with ethylacetate and water. The organic layer was washed with brine, dried, and concentrated, followed by separation and purification by column chromatography (30% ethylacetate mixed with 30% hexane) to afford the title compound. 85 mg (90%).

$^1$H-NMR (300 MHz, CD$_3$OD) δ 1.19 (d, J=6.9 Hz, 6H, CH$_3$) 2.85 (sept, J=6.9 Hz, 1H, CH) 6.68-6.76 (m, 2H, ArH) 6.89 (d, J=8.1 Hz, 1H, ArH) 7.02 (d, J=7.2 Hz, 1H, ArH) 7.34=7.45 (m, 5H, ArH) 7.53-7.59 (m, 4H, ArH) 7.92-7.94 (m, 2H, ArH).

<Example 173> 1-(1-Amino-4b-hydroxy-7-isopropyl-10-oxo-9b,10-dihydro-4bH-benzo[d]indeno[1,2-b]furan-9b-yl-3-ethylurea Fe (61 mg, 1.09 mmol and 2 drops of con. HCl were added to a solution of 1-(1-nitro-4b-hydroxy-7-isopropyl-10-oxo-9b,10-dihydro-4bH-benzo[d]indeno[1,2-b]furan-9b-yl)-3-ethylurea (150 mg, 0.36 mmol) in a mixture of ethanol:water (10 ml:1 ml, and heated for 3 hrs under reflux. After concentration in a vacuum, purification by column chromatography (ethylacetate:n-hexane=1:1) afforded the title compound as a white solid (50 mg, 36%).

$^1$H-NMR (300 MHz, CD$_3$OD) δ 1.08 (t, J=7.1 Hz, 3H, CH$_3$), 1.19 (d, J=6.9 Hz, 6H, CH$_3$), 2.80 (sep, J=6.9 Hz, 1H, CH), 3.32~3.43 (m, 2H, CH$_2$), 6.60 (d, J=1.3 Hz, 1H, ArH), 6.70 (d, J=8.2 Hz, 1H, ArH), 6.79 (dd, J=8.0 Hz, 1.3 Hz, 1H, ArH), 6.91 (d, J=7.3 Hz, 1H, ArH), 7.36~7.44 (m, 2H, ArH).

<Example 174> N-(1-Amino-4b-hydroxy-7-isopropyl-10-oxo-9b,10-dihydro-4bH-benzo[d]indeno[1,2-b]furan-9b-yl)tetrahydrofurane-2-carboxamide Fe (38 mg, 0.68 mmol) and 2 drops of conc. HCl were added to a solution of 2N-(4b-hydroxy-7-isopropyl-1-nitro-10-oxo-9b,10-dihydro-4bH-benzo[d]indeno[1,2-b]furan-9b-yl)tetrahydrofurane-2-carboxamide (100 mg, 0.23 mmol) in a mixture of ethanol:water (10 ml:1 ml), and heated for 3 hrs under reflux. After concentration in a vacuum, purification by column chromatography (ethylacetate:n-hexane=1:1) afforded the title compound as a white solid (70 mg, 75%).
$^1$H-NMR (300 MHz, CD$_3$OD) δ 1.14 (d, J=6.9 Hz, 6H, CH$_3$), 1.78~2.08 (m, 3H, CH$_2$), 2.11~2.23 (m, 1H, CH$_2$), 2.80 (sep, J=6.9 Hz, 1H, CH), 3.75~3.87 (m, 1H, OCH$_2$), 3.91~4.04 (m, 1H, OCH$_2$), 4.30~4.34 (m, 1H, OCH), 6.63~6.67 (m, 2H, ArH), 6.83 (d, J=7.9 Hz, 1H, ArH), 6.98 (d, J=7.3 Hz, 1H, ArH), 7.32~7.43 (m, 2H, ArH).

<Example 175> N-(1-Amino-4b-hydroxy-7-isopropyl-10-oxo-9b,10-dihydro-4bH-indeno[1,2-b]benzofuran-9b-yl)-2,2,2-trifluoroacetamide Iron powder (0.10 g, 1.8 mmol), conc. HCl (0.03 ml), and water (0.8 ml) were added in that order to a solution of 2,2,2-trifluoro-N-(4b-hydroxy-7-isopropyl-1-nitro-10-oxo-9b,10-dihydro-4bH-indeno[1,2-b]benzofuran-9b-yl)acetamide (0.11 g, 0.25 mmol) in absolute ethanol (8 ml), and heated for 3 hrs under reflux. The reaction mixture was washed with ethylacetate, and filtered to remove iron powder. The filtrate was concentrated in a vacuum, and subjected for 30 min to column chromatography (ethylacetate:hexane=1:4) packed with Et$_3$N-treated silica gel to afford the title compound. 90 mg (90%).
$^1$H-NMR (300 MHz, CD$_3$OD) δ 1.17 (d, J=6.9 Hz, 6H, CH$_3$) 2.80-2.85 (m, 1H, CH) 6.66-6.72 (m, 2H, ArH) 6.86 (d, J=7.8 Hz, 1H, ArH) 6.98 (d, J=7.2 Hz, 1H, ArH) 7.33-7.36 (m, 1H, ArH) 7.45 (t, J=7.8 Hz, 1H, ArH).

<Example 176> N-(1-Amino-4b-hydroxy-7-isopropyl-10-oxo-9b,10-dihydro-4bH-benzo[d]indeno[1,2-b]furan-9b-yl)-1,1,1-trifluoromethanesulfonamide Fe (60 mg, 1.08 mmol) and 2 drops of conc. HCl were added to a solution of 1,1,1-trifluoro-N-(4b-hydroxy-7-isopropyl-1-nitro-10-oxo-9b,10-dihydro-4bH-benzo[d]indeno[1,2-b]furan-9b-yl)methanesulfonamide (170 mg, 0.36 mmol) in ethanol:water (10 ml:1 ml), and heated for 3 hrs under reflux. After concentration in a vacuum, purification by column chromatography (ethylacetate:n-hexane=1:1) afforded the title compound as a white solid (140 mg, 88%).
$^1$H-NMR (300 MHz, CD$_3$OD) δ 1.16 (dd, J=6.9 Hz, 1.6 Hz, 6H, CH$_3$), 2.82 (sep, J=6.9 Hz, 1H, CH), 6.64 (s, 1H, ArH), 6.67 (d, J=8.2 Hz, 1H, ArH), 6.85 (d, J=7.7 Hz, 1H, ArH), 7.00 (d, J=7.4 Hz, 1H, ArH), 7.35 (d, J=8.0 Hz, 1H, ArH), 7.45 (t, J=7.8 Hz, 1H, ArH).

<Example 177> N-(4b-hydroxy-7-isopropyl-10-oxo-9b,10-dihydro-4bH-indeno[1,2-b]benzofuran-9b-yl)formamide A mixture of formic acid (2.5 mL) and acetic anhydride (5.0 mL) was stirred at 80° C. for 30 min, and then cooled to room temperature before a solution of 9b-amino-4b-hydroxy-7-isopropyl-4bH-benzo[d]indeno[1,2-b]furan-10(9bH)-one (400 mg, 1.35 mmol) in DCM was added thereto. The resulting reaction mixture was stirred at room temperature for 1 hr, concentrated, extracted with ethylacetate and water, and concentrated again in a vacuum. The concentrate was purified by silica gel column chromatography (30% ethylacetate mixed with 30% hexane) to afford the title compound. 140 mg (32%).
$^1$H-NMR (300 MHz, CDCl$_3$) δ 1.16 (dd, J=6.9 Hz, J=2.4, 6H, CH$_3$) 2.82 (hept, J=6.9 Hz, 1H, CH) 6.65 (s, 1H, ArH/NH/OH) 6.87 (d, J=7.8 1H, ArH) 7.35 (d, J=7.8, 1H, ArH.) 7.65-7.80 (m, 2H, ArH) 7.81-7.9 (m, 2H, ArH) 8.10 (s, 1H, NH/CHO).

<Example 178> 1,1,1-Trifluoro-N-(4b-hydroxy-10-oxo-9b,10-dihydro-4bH-benzo[d]indeno[1,2-b]furan-9b-yl)methanesulfonamide Methanesulfonic anhydride (229 mg, 0.81 mmol) and triethylamine (123 mg, 1.22 mmol) were added to a solution of 4b-amino-9b-hydroxy-7-isopropyl-4b,9b-dihydro-5-oxa-indeno[2,1-a]-inden-10-one (200 mg, 0.68 mmol) in methylene chloride (10 ml), and stirred at room temperature for 4 hrs. After vacuum concentration, purification by column chromatography (ethylacetate:hexane=1:2) afforded the title compound as a red solid (220 mg, 32%).
$^1$H-NMR (300 MHz, CDCl$_3$) δ 1.16 (d, J=6.9 Hz, 6H, CH$_3$), 2.81 (sep, J=6.9 Hz, 1H, CH), 6.68 (s, 1H, ArH)), 6.81 (d, J=7.6 Hz, 1H, ArH), 7.54 (d, J=7.9 Hz, 1H, ArH), 7.51 (t, J=7.5 Hz, 1H, ArH), 7.75~7.82 (m, 2H, ArH), 8.01 (d, J=7.8 Hz, 1H, ArH).

<Example 179> N-(1-Amino-4b-hydroxy-7-isopropyl-10-oxo-9b,10-dihydro-4bH-indeno[1,2-b]benzofuran-9b-yl)-2-phenylacetamide Iron powder (61 mg, 1.09 mmoles), and 3 drops of conc. HCl were added to a solution of N-(4b-hydroxy-7-isopropyl-1-nitro-10-oxo-9b,10-dihydro-4bH-benzo[d]indeno[1,2-b]furan-9b-yl-2-phenylacetamide (0.10 g, 0.22 mmoles) in ethanol:water (10:1, 10 mL) and heated for 12 hrs under reflux. The reaction mixture was filtered to remove iron powder, and extracted with ethylacetate and water. The organic layer was washed with brine, concentrated in a vacuum, and purified by silica gel column chromatography (50% ethylacetate in hexane) to afford the title compound. 75 mg (81%).
$^1$H-NMR (300 MHz, CD$_3$OD) δ 1.17 (d, J=6.9 Hz, 6H, CH$_3$) 2.82 (sept, J=6.9 Hz, 1H, CH) 3.59 (s, 2H, CH$_2$) 6.64 (br, 2H, ArH) 6.83 (br, 1H, ArH) 6.96-6.98 (br, 1H, ArH) 7.19-7.41 (m, 6H, ArH).

<Example 180> (E)-N-(1-Amino-4b-hydroxy-7-isopropyl-10-oxo-9b,10-dihydro-4bH-indeno[1,2-b]benzofuran-9b-yl)-3-(3,4-dichlorophenylacrylamide Iron powder (42 mg, 0.74 mmoles), and 3 drops of conc. HCl were added to a solution of (E)-3-(3,4-dichlorophenyl)-N-(4b-hydroxy-7-isopropyl-1-nitro-10-oxo-9b,10-dihydro-4bH-benzo[d]indeno[1,2-b]furan-9b-yl)acrylamide (0.08 g, 0.15 mmoles) in ethanol:water (10:1, 10 mL) and heated for 12 hrs under reflux. The reaction mixture was filtered to remove iron powder, and extracted with ethylacetate and water. The organic layer was washed with brine and concentrated in a vacuum. A small amount of methanol was added to the concentrate to form a precipitate which was then filtered to afford the title compound. 30 mg (80%).

¹H-NMR (300 MHz, CD₃OD) δ 1.18 (d, J=6.9 Hz, 6H, CH₃) 2.84 (sept, J=6.9 Hz, 1H, CH) 6.66-6.79 (m, 3H, ArH) 6.86-6.88 (m, 1H, ArH) 6.99-7.01 (m, 1H, ArH) 7.34-7.54 (m, 5H, ArH) 7.74 (s, 1H, ArH).

<Example 181> N-(1-Amino-4b-hydroxy-7-isopropyl-10-oxo-9b,10-dihydro-4bH-indeno[1,2-b]benzofuran-9b-yl)-4-(benzyloxy)benzamide Iron powder (26 mg, 0.47 mmoles) and 2 drops of conc. HCl were added to a solution of 4-benzyl-N-(4b-hydroxy-7-isopropyl-1-nitro-10-oxo-9b,10-dihydro-4bH-benzo[d]indeno[1,2-b]furan-9b-yl)benzamide (0.05 g, 0.094 mmoles) in ethanol:water (10:1, 10 mL), and heated for 6 hrs under reflux. After removal of the iron powder by filtration, the reaction mixture was extracted with ethylacetate and water. The organic layer was washed with brine and concentrated in a vacuum. A small amount of methanol was added to the concentrate to form a precipitate which was then filtered to afford the title compound. 15 mg (32%).

¹H-NMR (300 MHz, CD₃OD) δ 1.18 (d, J=6.9 Hz, 6H, CH₃) 2.83 (sept, J=6.9 Hz, 1H, CH) 5.12 (s, 2H, CH₂) 6.67 (s, 2H, ArH) 6.85 (s, 1H, ArH) 7.00-7.03 (s, 3H, ArH) 7.18-7.43 (m, 7H, ArH) 7.80-7.83 (m, 2H, ArH).

<Example 182> 2-([1,1'-Biphenyl]-4-yl)-N-(1-amino-4b-hydroxy-7-isopropyl-10-oxo-9b,10-dihydro-4bH-indeno[1,2-b]benzofuran-9b-yl)acetamide Iron powder (31.3 mg, 0.56 mmoles), and 3 drops of conc. HCl were added to a solution of N-(4b-hydroxy-7-isopropyl-1-nitro-10-oxo-9b,10-dihydro-4bH-benzo[d]indeno[1,2-b]furan-9b-yl)biphenyl-4-carboxamide (0.1 g, 0.18 mmoles) in ethanol:water (10:1, 10 mL), and heated for 4 hrs under reflux. After removal of the iron powder by filtration, the reaction mixture was extracted with ethylacetate and water. The organic layer was washed with brine and concentrated in a vacuum. A small amount of methanol was added to the concentrate to form a precipitate which was then filtered to afford the title compound. 50 mg (54%).

¹H-NMR (300 MHz, CD₃OD) δ 1.17 (d, J=6.9 Hz, 6H, CH₃) 2.83 (sept, J=6.9 Hz, 1H, CH) 3.64 (s, 2H, CH₂) 6.65 (s, 2H, ArH) 6.83-6.86 (br, 1H, ArH) 6.98 (br, 1H, ArH) 7.27-7.43 (m, 7H, ArH) 7.53-7.60 (m, 4H, ArH).

<Example 183> N-(1-Amino-4b-hydroxy-7-isopropyl-10-oxo-9b,10-dihydro-4bH-indeno[1,2-b]benzofuran-9b-yl)-2-methoxybenzamide Iron powder (0.13 g, 2.46 mmol), conc. HCl (0.03 ml), and water (1 ml) was added in that order to a solution of N-(4b-hydroxy-7-isopropyl-1-nitro-10-oxo-9b,10-dihydro-4bH-indeno[1,2-b]benzofuran-9b-yl)-2-methoxybenzamide (0.16 g, 0.33 mmol) in absolute ethanol (10 ml), and heated for 2 hrs under reflux. The reaction mixture was washed with ethylacetate, and filtered to remove iron powder. The filtrate was purified for 30 by column chromatography (ethylacetate:hexane=1:4) packed with Et₃N-treated silica gel to afford the title compound (80 mg, 54%).

¹H-NMR (300 MHz, CD₃OD) δ 1.22-1.23 (m, 6H, CH₃) 2.81-2.90 (sept, 1H, CH) 4.00 (s, 3H, OCH₃) 6.71 (s, 1H, ArH) 6.86 (s, 1H, ArH) 7.04-7.07 (m, 2H, ArH) 7.12-7.15 (m, 2H, ArH) 7.50-7.55 (m, 3H, ArH) 7.94 (s, 1H, ArH).

<Example 184> tert-Butyl(2R)-1-(4b-hydroxy-7-isopropyl-10-oxo-9b,10-dihydro-4bH-benzo[d]indeno[1,2-b]furan-9b-ylamino)-1-oxopropan-2-ylcarbamate EDCl (233 mg, 1.22 mmol) and HOBt (165 mg, 1.22 mmol) were added to a solution of Boc-L-alanine (231 mg, 1.22 mmol) in methylene chloride (20 ml). 20 min later, 4b-amino-9b-hydroxy-7-isopropyl-4b,9b-dihydro-5-oxa-indeno[2,1-a]-inden-10-one (300 mg, 1.02 mmol) was added to the solution, and stirred overnight at room temperature. After completion of the reaction, the reaction mixture was extracted with methylene chloride and water, and the organic layer was dried over MgSO₄ and concentrated in a vacuum. Purification by column chromatography (ethylacetate:n-hexane=1:2) afforded the title compound (368 mg, 77%).

¹H-NMR (300 MHz, CDCl₃) δ 1.16 (d, J=6.9 Hz, 6H, CH₃), 1.33~1.47 (m, 9H, CH₃), 1.59 (s, 3H, CH₃), 2.81 (sep, J=6.9 Hz, 1H, CH), 4.19 (m, 1H), 4.88 (m, 1H), 5.56 (s, 1H), 6.69 (s, 1H, ArH), 6.79~6.83 (m, 1H, ArH), 7.28 (m, 1H, ArH), 7.54 (t, J=7.4 Hz, 1H, ArH) 7.76~7.81 (m, 2H, ArH), 7.99 (d, J=7.6 Hz, 1H, ArH).

<Example 185> tert-Butyl(2R)-1-(4b-hydroxy-7-isopropyl-10-oxo-9b,10-dihydro-4bH-benzo[d]indeno[1,2-b]furan-9b-ylamino)-1-oxo-3-phenylpropan-2-ylcarbamate EDCl (233 mg, 1.22 mmol) and HOBt (165 mg, 1.22 mmol) were added to a solution of Boc-L-phenylalanine (324 mg, 1.22 mmol) in methylene chloride (20 ml). 20 min later, 4b-amino-9b-hydroxy-7-isopropyl-4b,9b-dihydro-5-oxa-indeno[2,1-a]-inden-10-one (300 mg, 1.02 mmol) was added to the solution, and stirred overnight at room temperature. After completion of the reaction, the reaction mixture was extracted with methylene chloride and water, and the organic layer was dried over MgSO₄ and concentrated in a vacuum. Purification by column chromatography (ethylacetate:n-hexane=1:2) afford the title compound (480 mg, 87%).

¹H-NMR (300 MHz, CDCl₃) δ 1.13 9 m, 6H, CH₃), 1.40 (m, 1H, CH), 2.99'3.12 (m, 2H, CH₂), 4.29~4.42 (m, 1H, CH), 4.90~5.01 (m, 1H, CH), 6.68 (s, 1H, ArH), 6.76~6.84 (m, 1H, ArH), 7.10~7.21 (m, 3H, ArH), 7.27~7.34 (m, 3H, ArH), 7.48~7.55 (m, 1H, ArH), 7.75~7.80 (m, 2H, ArH), 7.96~8.01 (m, 1H, ArH).

<Example 186> N-(1-Amino-4b-hydroxy-7-isopropyl-10-oxo-9b,10-dihydro-4bH-benzo[d]indeno[1,2-b]furan-9b-yl)-2-methylbenzamide Fe (66 mg, 1.18 mmol) and 2 drops of conc. HCl were added to a solution of N-(4b-hydroxy-7-isopropyl-1-nitro-10-oxo-9b,10-dihydro-4bH-benzo[d]indeno[1,2-b]furan-9b-yl)-2-methylbenzamide (180 mg, 0.39 mmol) in ethanol:H₂O (20 ml:2 ml) and heated for 2.5 hrs under reflux. After vacuum concentration, the reaction mixture was purified by column chromatography (ethylacetate:n-hexane=1:3) to afford the title compound as a yellow solid (134 mg, 80%).

¹H-NMR (500 MHz, CD₃OD) δ 1.16 (d, J=6.8 Hz, 6H, CH₃), 2.45 (s, 3H, ArH), 2.82 (sep, J=6.8 Hz, 1H, CH), 6.64 (s, 1H, ArH), 6.68 (d, J=8.3 Hz, 1H, ArH), 6.85 (d, J=7.3 Hz, 1H, ArH), 7.03 (d, J=7.3 Hz, 1H, ArH), 7.18~7.22 (m, 2H, ArH), 7.30 (t, J=7.4 Hz, 1H, ArH), 7.41~7.46 (m, 2H, ArH), 7.51 (d, J=7.3 Hz, 1H, ArH).

<Example 187> N-(1-Amino-4b-hydroxy-7-isopropyl-10-oxo-9b,10-dihydro-4bH-benzo[d]indeno[1,2-b]furan-9b-yl)-3-methylbenzamide Fe (66 mg, 1.18 mmol) and 2 drops of conc. HCl were added to a solution of N-(4b-hydroxy-7-isopropyl-1-nitro-10-oxo-9b,10-dihydro-4bH-benzo[d]indeno[1,2-b]furan-9b-yl)-3-methylbenzamide (1800 mg, 0.39 mmol) in ethanol:$H_2O$ (10 ml:1 ml), and heated for 3 hrs under reflux. After vacuum concentration, the reaction mixture was purified by column chromatography (ethylacetate:n-hexane=1:3) to afford the title compound as a yellow solid (88 mg, 52%).

$^1$H-NMR (500 MHz, $CD_3OD$) δ 1.18 (dd, J=6.9 Hz, 1.4 Hz, 6H, $CH_3$), 2.36 (s, 3H, ArH), 2.84 (sep, J=6.8 Hz, 1H, CH), 6.67~6.70 (m, 2H, ArH), 6.87~6.88 (m, 1H, ArH), 7.02~7.03 (m, 1H, ArH), 7.28~7.35 (m, 2H, ArH), 7.45 (m, 1H, ArH), 7.63 (d, J=7.6 Hz, 1H, ArH), 7.67 (s, 1H, ArH).

<Example 188> N-(1-Amino-4b-hydroxy-7-isopropyl-10-oxo-9b,10-dihydro-4bH-benzo[d]indeno[1,2-b]furan-9b-yl)-4-methylbenzamide Fe (59 mg, 1.05 mmol) and 2 drops of conc. HCl were added to a solution of N-(4b-hydroxy-7-isopropyl-1-nitro-10-oxo-9b,10-dihydro-4bH-benzo[d]indeno[1,2-b]furan-9b-yl)-4-methylbenzamide (160 mg, 0.35 mmol in ethanol:$H_2O$ (20 ml:2 ml) and heated for 4 hrs under reflux. After vacuum concentration, the reaction mixture was purified by column chromatography (ethylacetate:n-hexane=1:3) to afford the title compound as a yellow solid (106 mg, 71%).

$^1$H-NMR (500 MHz, $CD_3OD$) δ 1.16 (d, J=6.8 Hz, 6H, $CH_3$), 2.35 (s, 3H, ArH), 2.81 (sep, J=6.8 Hz, 1H, CH), 6.65~6.69 (m, 2H, ArH), 6.86 (d, J=7.4 Hz, 1H, ArH), 7.00 (d, J=7.4 Hz, 1H, ArH), 7.22 (d, J=7.5 Hz, 1H, ArH), 7.41~7.46 (m, 2H, ArH), 7.74 (d, J=7.5 Hz, 1H, ArH).

<Example 189> Methyl-4-(1-amino-4b-hydroxy-7-isopropyl-10-oxo-9b,10-dihydro-4bH-benzo[d]indeno[1,2-b]furan-9b-ylcarbamoyl)benzoate Fe (93 mg, 1.67 mmol) and 2 drops of conc. HCl were added to a solution of methyl 4-(4b-hydroxy-7-isopropyl-1-nitro-10-oxo-9b,10-dihydro-4bH-benzo[d]indeno[1,2-b]furan-9b-ylcarbamoyl)benzoate (280 mg, 0.56 mmol) in ethanol:$H_2O$ (20 ml:2 ml) and heated for 3 hrs under reflux. After vacuum concentration, the reaction mixture was purified by column chromatography (ethylacetate:n-hexane=1:3) to afford the title compound as a yellow solid (186 mg, 71%).

$^1$H-NMR (500 MHz, $CD_3OD$) δ 1.16 (d, J=6.5 Hz, 6H, $CH_3$), 2.81 (sep, J=6.5 Hz, 1H, CH), 3.89 (s, 3H, $OCH_3$), 6.65~6.68 (m, 2H, ArH), 6.86 (d, J=7.4 Hz, 1H, ArH), 7.02 (d, J=6.9 Hz, 1H, ArH), 7.41~7.46 (m, 2H, ArH), 7.93 (d, J=8.1 Hz, 2H, ArH), 8.04 (d, J=8.0 Hz, 2H, ArH).

<Example 190> N-(1-Amino-4b-hydroxy-7-isopropyl-10-oxo-9b,10-dihydro-4bH-indeno[1,2-b]benzofuran-9b-yl)-3-chlorobenzamide Iron powder (0.17 g, 3.04 mmol), conc. HCl (0.03 ml), and water (1 ml) were added in that order to a solution of 3-chloro-N-(4b-hydroxy-7-isopropyl-1-nitro-10-oxo-9b,10-dihydro-4bH-indeno[1,2-b]benzofuran-9b-yl)benzamide (0.20 g, 0.41 mmol) in absolute ethanol (10 ml), and heated for 2 hrs under reflux. The reaction mixture was washed with ethylacetate and filtered to remove the iron powder. The filtrate was alkalified with $NaHCO_3$, and washed many times with water, and the organic layer was dried, filtered, and subjected for 30 min to column chromatography (ethylacetate:hexane=1:4) packed with $Et_3N$-treated silica gel to afford the title compound. 90 mg (93%).

$^1$H-NMR (300 MHz, $CD_3OD$) δ 1.19 (dd, J=6.9, 2.1 Hz, 6H, $CH_3$) 2.85-2.87 (sept, 1H, CH) 6.68-6.78 (m, 2H, ArH) 6.82-6.86 (m, 1H, ArH) 6.95-7.03 (m, 1H, ArH) 7.38-7.60 (m, 4H, ArH) 7.77-7.79 (m, 1H, ArH) 7.87-7.90 (m, 1H, ArH).

<Example 191> N-(1-Amino-4b-hydroxy-7-isopropyl-10-oxo-9b,10-dihydro-4bH-indeno[1,2-b]benzofuran-9b-yl)-3,5-dimethylbenzamide Iron powder (0.04 g, 0.77 mmol), conc. HCl (0.01 ml), and water (0.5 ml) were added in that order to a solution of N-(4b-hydroxy-7-isopropyl-1-nitro-10-oxo-9b,10-dihydro-4bH-indeno[1,2-b]benzofuran-9b-yl)-3,5-dimethylbenzamide (50 mg, 0.10 mmol) in absolute ethanol (5 ml), and heated for 2 hrs under reflux. The reaction mixture was washed with ethylacetate and filtered to remove the iron powder. The filtrate was alkalified with $NaHCO_3$, and washed many times with water, and the organic layer was dried, filtered, and subjected for 30 min to column chromatography (ethylacetate:hexane=1:4) packed with $Et_3N$-treated silica gel to afford the title compound. 30 mg (68%).

$^1$H-NMR (300 MHz, $CD_3OD$) δ 1.18-1.20 (m, 6H, $CH_3$) 2.33 (s, 6H, $CH_3$) 2.81-2.87 (sept, 1H, CH) 6.67-6.70 (m, 2H, ArH) 6.84-6.86 (m, 1H, ArH) 7.03-7.05 (m, 1H, ArH) 7.18 (s, 1H, ArH) 7.46 (s, 4H, ArH).

<Example 192> N-(1-Amino-4b-hydroxy-7-isopropyl-10-oxo-9b,10-dihydro-4bH-indeno[1,2-b]benzofuran-9b-yl)-2,4,6-trichlorobenzamide Iron powder (37 mg, 0.66 mmoles) and 2 drops of conc. HCl were added to a solution of 2,4,6-trichloro-N-(4b-hydroxy-7-isopropyl-4-nitro-10-oxo-9b,10-dihydro-4bH-indeno[1,2-b]benzofuran-9b-yl)benzamide (0.12 g, 0.22 mmoles) in ethanol:water (10:1, 10 mL), and heated for 3 hrs under reflux. After completion of the reaction, the reaction mixture was washed with ethylacetate, filtered to remove iron powder, and extracted with ethylacetate and water. The organic layer was washed with brine, dried, concentrated, and purified by column chromatography (30% ethylacetate mixed with 20% hexane) to afford the title compound. 85 mg (75%).

$^1$H-NMR (300 MHz, $CD_3OD$) δ 1.17 (d, J=6.9 Hz, 6H, $CH_3$) 2.83 (sept, J=6.9 Hz, 1H, CH) 6.62-6.75 (m, 2H, ArH) 6.83 (m, 1H, ArH) 7.05 (m, 1H, ArH) 7.36-7.54 (m, 3H, ArH) 7.89 (s, 1H, ArH).

<Example 193> N-(1-Amino-4b-hydroxy-7-isopropyl-10-oxo-9b,10-dihydro-4bH-benzo[d]indeno[1,2-b]furan-9b-yl)-2-fluoroacetamide Fe (63 mg, 1.12 mmol) and 3 drops of conc. HCl were added to a solution of 2-fluoro-N-(4b-hydroxy-7-isopropyl-1-nitro-10-oxo-9b,10-dihydro-4bH-benzo[d]indeno[1,2-b]furan-9b-yl)acetamide (150 mg, 0.37 mmol) in ethanol:$H_2O$ (20 ml:2 ml), and heated for 2.5 hrs under reflux. After vacuum concentration, the reaction mixture was purified by column chromatography (EtOAc:hexane=1:1) to afford the title compound as a yellow solid (63 mg, 46%).

$^1$H-NMR (300 MHz, $CD_3OD$) δ 1.15 (d, J=6.3 Hz, 6H, $CH_3$), 2.82 (sep, J=6.3 Hz, 1H, CH), 4.84 (d, J=45 Hz, 2H, CH$_2$F), 6.65~6.68 (m, 2H, ArH), 6.84~6.87 (m, 1H, ArH), 6.97~6.99 (m, 1H, ArH), 7.35~7.45 (m, 2H, ArH).

<Example 194> N-(1-Amino-4b-hydroxy-7-isopropyl-10-oxo-9b,10-dihydro-4bH-benzo[d]indeno[1,2-b]furan-9b-yl)-2-chloroacetamide Fe (45 mg, 0.79 mmol) and 3 drops of conc. HCl were added to a solution of 2-chloro-N-(4b-hydroxy-7-isopropyl-1-nitro-10-oxo-9b,10-dihydro-4bH-benzo[d]indeno[1,2-b]furan-9b-yl)acetamide (110 mg, 0.26 mmol) in ethanol:H$_2$O (10 ml:1 ml), and heated for 3 hrs under reflux. After vacuum concentration, the reaction mixture was purified by column chromatography (EtOAc:hexane=1:1) to afford the title compound as a yellow solid (98 mg, 97%).

$^1$H-NMR (300 MHz, CD$_3$OD) δ 1.15 (d, J=6.9 Hz, 6H, CH$_3$), 2.81 (sep, J=6.9 Hz, 1H, CH), 4.10 (d, J=4.0 Hz, 2H, CH$_2$Cl), 6.64~6.67 (m, 2H, ArH), 6.83~6.87 (m, 1H, ArH), 6.98 (d, J=7.3 Hz, 1H, ArH), 7.35~7.42 (m, 2H, ArH).

<Example 195> N-(1-Amino-4b-hydroxy-7-isopropyl-10-oxo-9b,10-dihydro-4bH-benzo[d]indeno[1,2-b]furan-9b-yl)-2,2-dichloroacetamide Fe (36 mg, 0.65 mmol) and 2 drops of conc. HCl were added to a solution of 2,2-dichloro-N-(4b-hydroxy-7-isopropyl-1-nitro-10-oxo-9b,10-dihydro-4bH-benzo[d]indeno[1,2-b]furan-9b-yl)acetamide (90 mg, 0.22 mmol) in ethanol:H$_2$O (10 ml:1 ml), and heated for 3 hrs under reflux. After vacuum concentration, the reaction mixture was purified by column chromatography (EtOAc:hexane=1:2) to afford the title compound as a yellow solid (62 mg, 74%).

$^1$H-NMR (300 MHz, CD$_3$OD) δ 1.15 (d, J=6.6 Hz, 6H, CH$_3$), 2.81 (sep, J=6.6 Hz, 1H, CH), 6.06 (t, J=5.4 Hz, 1H, CHF$_2$), 6.65~6.68 (m, 2H, ArH), 6.84~6.87 (m, 1H, ArH), 6.97~6.99 (m, 1H, ArH), 7.35~7.45 (m, 2H, ArH).

<Example 196> 1-amino-9b-(4-butyl-1H-1,2,3-triazol-1-yl)-4b-hydroxy-7-isopropyl-4bH-indeno[1,2-b]benzofuran-10(9bH)-one A solution of 9b-(4-butyl-1H-1,2,3-triazol-1-yl)-4b-hydroxy-7-isopropyl-1-nitro-4bH-benzo[d]indeno[1,2-b]furan-10(9bH)-one (0.080 g, 0.18 mmol) in ethanol:water (10:1, 10 mL) was heated for 23 hrs in the present of iron powder (38 mg, 0.68 mmol) under reflux. The reaction mixture was washed with ethylacetate and filtered to remove iron powder, followed by extraction with ethylacetate and water. Separation and purification by silica gel column chromatography (30% ethylacetate mixed with 50% hexane) afforded the title compound. 50 mg (67%).

$^1$H-NMR (300 MHz, CD$_3$OD): δ 0.93 (t, J=7.2 Hz, 3H, CH$_3$) 1.23 (d, J=6.9 Hz, 6H, CH$_3$) 1.33-1.41 (m, 2H, CH$_2$) 1.58-1.68 (m, 2H, CH$_2$) 2.69 (t, J=7.2 Hz, 2H, CH$_2$) 2.90 (sept, J=6.9 Hz, 1H, CH) 6.79 (br, 2H, ArH) 6.98-7.03 (m, 2H, ArH) 7.22-7.41 (m, 2H, ArH) 7.50-7.55 (m, 1H, ArH).

<Example 197> N-(1-Amino-4b-hydroxy-7-isopropyl-10-oxo-9b,10-dihydro-4bH-indeno[1,2-b]benzofuran-9b-yl)picolinamide Iron powder (0.18 g, 3.2 mmol), conc. HCl (0.03 ml), and water (0.8 ml) were added in that order to a solution of N-(4b-hydroxy-7-isopropyl-1-nitro-10-oxo-9b,10-dihydro-4bH-benzo[d]indeno[1,2-b]furan-9b-yl)picolinamide (0.20 g, 0.44 mmol) in absolute ethanol (8 ml), and heated for 4 hrs under reflux. The reaction mixture was washed with ethylacetate, and filtered to remove iron powder. The filtrate was concentrated in a vacuum and purified for 30 min by column chromatography (ethylacetate:hexane=1:2 to methylene chloride:MeOH=20:1) packed with Et$_3$N-treated silica gel to afford the title compound. 80 mg (43%).

$^1$H-NMR (300 MHz, CD$_3$OD) δ 1.20 (d, J=6.9 Hz, 6H, CH$_3$) 2.83-2.87 (m, 1H, CH) 6.70 (s, 2H, ArH) 6.89 (d, J=7.2 Hz, 1H, ArH) 7.02 (d, J=7.2 Hz, 1H, ArH) 7.45-7.48 (m, 2H, ArH) 7.55 (t, J=6.0 Hz, 1H, ArH) 7.90-7.97 (m, 2H, ArH) 8.62 (d, J=3.6 Hz, 1H, ArH).

<Example 198> N-(1-Amino-4b-hydroxy-7-isopropyl-10-oxo-9b,10-dihydro-4bH-indeno[1,2-b]benzofuran-9b-yl)nicotinamide Iron powder (0.18 g, 3.2 mmol), conc. HCl (0.03 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)nicotinamide (0.20 g, 0.44 mmol) in absolute ethanol (10 ml), and heated for 2 hrs under reflux. The reaction mixture was washed with ethylacetate, and filtered to remove iron powder. The filtrate was concentrated in a vacuum and purified for 30 min by column chromatography (ethylacetate:hexane=1:2 to methylene chloride:MeOH=20:1) packed with Et$_3$N-treated silica gel to afford the title compound. 140 mg (75%).

$^1$H-NMR (300 MHz, CD$_3$OD) δ 1.18 (d, J=6.9 Hz, 6H, CH$_3$) 2.79-2.88 (m, 1H, CH) 6.67-6.70 (m, 2H, ArH) 6.88 (d, J=7.8 Hz, 1H, ArH) 7.01 (d, J=7.2 Hz, 1H, ArH) 7.43-7.51 (m, 3H, ArH) 8.25 (d, J=8.1 Hz, 1H, ArH) 8.65 (d, J=3.9 Hz, 1H, ArH) 9.00 (s, 1H, ArH).

<Example 199> N-(1-Amino-4b-hydroxy-7-isopropyl-10-oxo-9b,10-dihydro-4bH-indeno[1,2-b]benzofuran-9b-yl)isonicotinamide Iron powder (0.09 g, 16.3 mmol), conc. HCl (0.03 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)isonicotinamide (0.10 g, 0.22 mmol) in absolute ethanol (10 ml), and heated for 2 hrs under reflux. The reaction mixture was washed with ethylacetate, and filtered to remove iron powder. The filtrate was concentrated in a vacuum and purified for 30 min by column chromatography (ethylacetate:hexane=1:1) packed with Et$_3$N-treated silica gel to afford the title compound. 62 mg (68%).

$^1$H-NMR (300 MHz, CD$_3$OD) δ 1.18 (d, J=6.6 Hz, 6H, CH$_3$) 2.82-2.86 (m, 1H, CH) 6.67-6.71 (s, 2H, ArH) 6.89 (d, J=7.5 Hz, 1H, ArH) 7.01 (d, J=7.2 Hz, 1H, ArH) 7.43-7.48 (m, 2H, ArH) 7.79-7.80 (m, 2H, ArH) 8.64-8.66 (m, 2H, ArH).

<Example 200> N-(1-Amino-4b-hydroxy-7-isopropyl-10-oxo-9b,10-dihydro-4bH-indeno[1,2-b]benzofuran-9b-yl) pyrazine-2-carboxamide Iron powder (0.09 g, 1.63 mmol), conc. HCl (0.03 ml), and water (0.8 ml) were added in that order to a solution of N-(4b-hydroxy-7-isopropyl-1-nitro-10-oxo-9b,10-dihydro-4bH-benzo[d]indeno[1,2-b]furan-9b-yl)pyrazine-2-carboxamide (0.10 g, 0.22 mmol) in absolute ethanol (8 ml), and heated for 3 hrs under reflux.

The reaction mixture was washed with ethylacetate, and filtered to remove iron powder. The filtrate was concentrated in a vacuum and purified for 30 min by column chromatography (ethylacetate:hexane=1:1) packed with Et₃N-treated silica gel to afford the title compound. 90 mg (98%).

¹H-NMR (300 MHz, CD₃OD) δ 1.19 (d, J=6.6 Hz, 6H, CH₃) 2.80-2.89 (m, 1H, CH) 6.69-6.72 (m, 2H, ArH) 6.89 (d, J=8.1 Hz, 1H, ArH) 7.02 (d, J=7.2 Hz, 1H, ArH) 7.43-7.49 (m, 2H, ArH) 8.66 (s, 1H, ArH) 8.78 (s, 1H, ArH) 9.14 (s, 1H, ArH).

<Example 201> N-(1-Amino-4b-hydroxy-7-isopropyl-10-oxo-9b,10-dihydro-4bH-indeno[1,2-b]benzofuran-9b-yl)furane-2-carboxamide Iron powder (0.09 g, 1.68 mmol), conc. HCl (0.03 ml), and water (0.8 ml) were added in that order to a solution of N-(4b-hydroxy-7-isopropyl-1-nitro-10-oxo-9b,10-dihydro-4bH-benzo[d]indeno[1,2-b]furan-9b-yl)furane-2-carboxamide (0.10 g, 0.23 mmol) in absolute ethanol (8 ml), and heated for 2 hrs under reflux. The reaction mixture was washed with ethylacetate, and filtered to remove iron powder. The filtrate was concentrated in a vacuum and purified for 30 min by column chromatography (ethylacetate:hexane=1:2) packed with Et₃N-treated silica gel to afford the title compound. 52 mg (56%).

¹H-NMR (300 MHz, CD₃OD) δ 1.18 (d, J=6.9 Hz, 6H, CH₃) 2.79-2.85 (m, 1H, CH) 6.56 (d, J=1.5 Hz, 1H, ArH) 6.67 (s, 2H, ArH) 6.87 (d, J=6.0 Hz, 1H, ArH) 7.00 (d, J=6.0 Hz, 1H, ArH) 7.12 (d, J=3.3 Hz, 1H, ArH) 7.43-7.51 (m, 2H, ArH) 7.64 (s, 1H, ArH).

<Example 202> N-(1-Amino-4b-hydroxy-7-isopropyl-10-oxo-9b,10-dihydro-4bH-indeno[1,2-b]benzofuran-9b-yl)quinoline-8-carboxamide Fe powder (35 mg, 0.60 mmoles), and 3 drops of conc. HCl were added to a solution of N-(4b-hydroxy-7-isopropyl-4-nitro-0-oxo-9b,10-dihydro-4bH-indeno[1,2-b]benzofuran-9b-ylquinoline-8-carboxamide (0.10 g, 0.20 mmoles) in ethanol:water (10:1, 10 mL), and heated for 3 hrs under reflux. The reaction mixture was washed with ethylacetate, and filtered to remove iron powder. The filtrate was concentrated in a vacuum and purified by column chromatography (30% ethylacetate mixed with 40% hexane) to afford the title compound. 80 mg (85%).

¹H-NMR (300 MHz, CD₃OD): δ 1.23 (dd, J=1.5 Hz, J=6.9 Hz, 6H, CH3) 2.84 (sept, J=6.9 Hz, 1H, CH) 6.69 (s, 2H, ArH) 6.89 (s, 1H, ArH) 7.01 (s, 1H, ArH) 7.45-7.67 (m, 3H, ArH) 7.72 (s, 1H, ArH) 8.14-8.17 (m, 1H, ArH) 8.46-8.58 (m, 2H, ArH) 8.86 (s, 1H, ArH).

<Example 203> N-(1-Amino-4b-hydroxy-7-isopropyl-10-oxo-9b,10-dihydro-4bH-indeno[1,2-b]benzofuran-9b-ylquinoline-6-carboxamide Fe powder (68 mg, 1.21 mmoles), and 3 drops of conc. HCl were added to a solution of N-(4b-hydroxy-7-isopropyl-4-nitro-10-oxo-9b,10-dihydro-4bH-indeno[1,2-b]benzofuran-9b-ylquinoline-6-carboxamide (0.20 g, 0.40 mmoles) in ethanol:water (10:1, 20 mL) and heated for 3 hrs under reflux. The reaction mixture was washed with ethylacetate, and filtered to remove iron powder. The filtrate was concentrated in a vacuum, and recrystallized in 30% ethylacetate mixed with 30% hexane to afford the title compound. 130 mg.

¹H-NMR (300 MHz, CD₃OD): δ 1.19 (d, J=6.9 Hz, 6H, CH₃) 2.85 (sept, J=6.9 Hz, 1H, CH) 6.70 (br, 2H, ArH) 6.88-6.90 (m, 1H, ArH) 7.03-7.06 (m, 1H, ArH) 7.48 (br, 2H, ArH) 7.58-7.62 (m, 1H, ArH) 8.05-8.08 (m, 1H, ArH) 8.10-8.19 (m, 1H, ArH) 8.43-8.51 (m, 2H, ArH) 8.91-8.93 (m, 1H, ArH).

<Example 204> N-(1-Amino-4b-hydroxy-7-isopropyl-10-oxo-9b,10-dihydro-4bH-benzo[d]indeno[1,2-b]furan-9b-yl)benzofurane-2-carboxamide Fe (69 mg, 1.24 mmol and 2 drops of conc. HCl were added to a solution of N-(4b-hydroxy-7-isopropyl-1-nitro-10-oxo-9b,10-dihydro-4bH-benzo[d]indeno[1,2-b]furan-9b-yl)benzofurane-2-carboxamide (200 mg, 0.41 mmol in ethanol:water (10 ml:1 ml) and heated for 3 hrs under reflux. After vacuum concentration, the reaction mixture was purified by column chromatography (ethylacetate:n-hexane=1:1) to afford the title compound as a white solid (118 mg, 63%).

¹H-NMR (300 MHz, CD₃OD) δ 1.12 (d, J=6.7 Hz, 6H, CH₃), 2.77 (sep, J=6.7 Hz, 1H, CH), 6.65~6.67 (m, 2H, ArH), 6.85 (d, J=7.8 Hz, 1H, ArH), 7.03 (d, J=7.3 Hz, 1H, ArH), 7.24 (t, J=7.4 Hz, 1H, ArH), 7.35~7.43 (m, 2H, ArH), 7.46~7.53 (m, 3H, ArH), 7.63 (d, J=7.7 Hz, 1H, ArH).

<Example 205> N-(1-Amino-4b-hydroxy-7-isopropyl-10-oxo-9b,10-dihydro-4bH-benzo[d]indeno[1,2-b]furan-9b-yl-3-methylbenzofurane-2-carboxamide Fe (67 mg, 1.2 mmol, and 2 drops of conc. HCl were added to a solution of N-(4b-hydroxy-7-isopropyl-1-nitro-10-oxo-9b,10-dihydro-4bH-benzo[d]indeno[1,2-b]furan-9b-yl)-3-methylbenzofurane-2-carboxamide (200 mg, 0.40 mmol in an ethanol:water (10 ml:1 ml) solvent, and heated for 23 hrs under reflux. After vacuum concentration, the reaction mixture was purified by column chromatography (ethylacetate:n-hexane=1:1) to afford the title compound as a white solid (162 mg, 86%).

¹H-NMR (300 MHz, CDCl₃) δ 1.20 (d, J=6.9 Hz, 6H, CH₃), 2.49 (s, 3H, CH₃), 2.85 (sep, J=6.9 Hz, 1H, CH), 6.70 (m, 2H, ArH), 6.89 (m, 1H, ArH), 7.03 (m, 1H, ArH), 7.31 (t, J=7.1 Hz, 1H, ArH), 7.42~7.55 (m, 4H, ArH), 7.66 (d, J=7.7 Hz, 1H, ArH).

<Example 206> N-(1-Amino-4b-hydroxy-7-isopropyl-10-oxo-9b,10-dihydro-4bH-indeno[1,2-b]benzofuran-9b-yl)-4-methylthiazole-5-carboxamide N-(4b-hydroxy-7-isopropyl-1-nitro-10-oxo-9b,10-dihydro-4bH-benzo[d]indeno[1,2-b]furan-9b-yl-4-methylthiazole-5-carboxamide (81 mg, 0.17 mmol was added to 5 ml of EtOH:H₂O (10:1) to form a pale yellow turbid solution to which Fe powder (29 mg, 0.51 mmol and one drop of conc. HCl were then added at room temperature, followed by stirring for 2 hrs under reflux. The reaction mixture was filtered, concentrated, and purified by silica gel prep-TLC using EtOAc/Hx (1/1) to afford the title compound as a yellow solid (54 mg, 0.12 mmol, 73%).

¹H-NMR (300 MHz, CDCl₃) appears to be a mixture of 2 isomers) δ 1.17-1.21 (m, 6H), 2.71 (s, 1H), 2.77 (2H), 2.78-2.89 (m, 1H), 5.56 (s, br, 1H), 5.58 (s, 0.6H), 5.75 (s, br, 0.8H), 6.63 (dd, J=8.2, 0.5 Hz, 0.6H), 6.71-6.85 (m, 2H), 6.91-6.96 (m, 2H), 7.19 (dd, J=7.4, 0.5 Hz, 0.6H), 7.28-7.32 (m, 1H), 7.48-7.60 (m, 1H), 8.72 (s, 0.4H), 8.75 (d, J=3.9 Hz, 1H).

<Example 207> (4R)—N-(1-amino-4b-hydroxy-7-isopropyl-10-oxo-9b,10-dihydro-4bH-indeno[1,2-b]benzofuran-9b-yl)-2-oxothiazolidine-4-carboxamide (4R)—N-(4b-hydroxy-7-isopropyl-1-nitro-10-oxo-9b,10-dihydro-4bH-benzo[d]indeno[1,2-b]furan-9b-yl)-2-oxothiazolidine-4-carboxamide (100 mg, 0.213 mmol) was added to 5 ml of EtOH:H₂O (10:1) to form a pale yellow turbid solution to which Fe powder (36 mg, 0.64 mmol) and two drops of conc. HCl were then added at room temperature, followed by stirring for 2 hrs under reflux. The reaction mixture was filtered, concentrated, and purified by silica gel prep-TLC using EtOAc/Hx (1/1) to afford the title compound as a yellow solid (47 mg, 0.11 mmol, 50%).

¹H-NMR (300 MHz, CD₃OD) δ 1.170 (d, J=6.9 Hz, 3H), 1.173 (d, J=6.9 Hz, 3H), 2.83 (heptet, J=6.9 Hz, 1H), 3.49-3.78 (m, 2H), 4.46-4.53 (m, 1H), 6.66 (s, 1H), 6.70 (s, br, 1H), 6.85 (d, br, J=7.3 Hz, 1H), 7.00 (d, J=7.1 Hz, 1H), 7.35 (s, br, 1H), 7.39-7.51 (m, 1H).

<Example 208> N-(4b-hydroxy-7-isopropyl-10-oxo-9b,10-dihydro-4bH-indeno[1,2-b]benzofuran-9b-yl)-1H-indole-2-carboxamide A solution of indole-2-carboxylic acid (130 mg, 0.806 mmol) in anhydrous DCM was stirred, together with oxalyl chloride (0.08 mL, 0.967 mmol) and a catalyst, at room temperature for 1 hr. The reaction mixture was concentrated to obtain indole-2-acyl chloride. 9b-amino-4b-hydroxy-7-isopropyl-4bH-benzo[d]indeno[1,2-b]furan-10(9bH)-one (190 mg, 0.643 mmol), indole-2-acylchloride (130 mg, 0.707 mmol), and triethylamine (0.13 mL, 0.964 mmol) were dissolved in anhydrous DCM (2 ml), and stirred at room temperature for 2 hrs. After extraction with DCM and water, the organic layer was washed with brine, dried over sodium sulfate, and concentrate in a vacuum. Separation and purification by silica gel column chromatography (30% ethylacetate mixed with 20% hexane) afforded the title compound. 50 mg (38%).

¹H-NMR (300 MHz, CDCl₃) δ 1.18 (dd, J=7.2 Hz, 2.4 Hz, 6H, CH₃) 2.85 (hept, J=6.9 Hz, 1H, CH) 6.68 (s, 1H, ArH/NH/OH) 6.92 (d, J=8.1, 1H, ArH) 7.01-7.06 (m, 1H, ArH) 7.19 (d, J=7.8 Hz, 1H, ArH) 7.22 (s, 1H, ArH) 7.38 (d, J=8.1 Hz, 1H, ArH) 7.47 (d, J=8.1 Hz, 1H, ArH) 7.59 (d, J=7.8 Hz, 1H, ArH) 7.74-7.88 (m, 3H, ArH).

<Example 209> N-(4b-Hydroxy-7-isopropyl-10-oxo-9b,10-dihydro-4bH-indeno[1,2-b]benzofuran-9b-yl)-1H-indole-3-carboxamide Triethylamine (0.35 mL, 2.53 mmol) and indole-3-acylchloride (330 mg, 0.186 mmol) were added to a solution of 9b-amino-4b-hydroxy-7-isopropyl-4bH-benzo[d]indeno[1,2-b]furan-10(9bH)-one (500 mg, 1.69 mmol) in anhydrous DCM (5 ml), followed by stirring at room temperature for 3 hrs. The reaction mixture was extracted with DCM and water, and the organic layer was washed with brine, dried over sodium sulfate, and concentrated in a vacuum. Separation and purification by silica gel column chromatography (30% ethylacetate mixed with 30% hexane) afforded the title compound. 60 mg (9%).

¹H-NMR (300 MHz, CDCl₃) δ 1.15 (dd, J=6.8 Hz, J=2.4, Hz 6H, CH₃) 2.78 (hept, J=6.8 Hz, 1H, CH) 6.80 (d, J=8.1 Hz, 1H, ArH) 7.21 (s, 1H, ArH) 7.37-7.58 (m, 2H, ArH) 7.55-7.58 (m, 1H, ArH) 7.75 (d, J=2.7 Hz, 1H, ArH) 7.813-7.850 (m, 2H, ArH) 7.99-8.07 (m, 2H, ArH), 8.95 (s, 1H, NH/ArH).

<Example 210> N-(4b-Hydroxy-7-isopropyl-10-oxo-9b,10-dihydro-4bH-indeno[1,2-b]benzofuran-9b-yl)formamide 9b-Amino-4b-hydroxy-7-isopropyl-4bH-benzo[d]indeno[1,2-b]furan-10(9bH)-one (300 mg, 1.01 mmol) and 5-nitro-3-pyrazolecarboxylic acid (175 mg, 1.11 mmol) were together dissolved in anhydrous DCM (3 ml) to which EDCl.HCl (290 mg, 1.52 mmol and HOBt (205 mg, 1.52 mmol were then added, followed by stirring overnight at room temperature. After extraction with DCM and water, the organic layer was washed with brine, dried over sodium sulfate, and concentrated in a vacuum. Separation and purification by silica gel column chromatography (30% ethylacetate mixed with 40% hexane) afforded the title compound. 150 mg (34%).

¹H-NMR (300 MHz, CDCl₃) δ 1.17 (dd, J=6.9 Hz, J=2.4 Hz, 6H, CH₃) 2.84 (hept, J=6.9 Hz, 1H, CH) 6.91 (d, J=8.1 Hz, 1H, ArH) 6.68 (s, 1H, ArH/NH/OH) 7.42 (d, J=8.1 Hz, 1H, ArH.) 7.60 (s, 2H, ArH.) 7.71-7.9 (m, 2H, ArH) 7.9-7.93 (m, H, ArH) 7.93 (s, Br, 1H, ArH).

<Example 211> N-(4b-hydroxy-7-isopropyl-10-oxo-9b,10-dihydro-4bH-indeno[1,2-b]benzofuran-9b-yl)-1-phenyl-5-(trifluoromethyl-1H-pyrazole-4-carboxamide 9b-Amino-4b-hydroxy-7-isopropyl-4bH-benzo[d]indeno[1,2-b]furan-10(9bH)-one (200 mg, 0.677 mmol) and 1-H-phenyl-5-(trifluoromethyl)-1-H-pyrazole-4-carboxylic acid (190 mg, 0.744 mmol) were dissolved in anhydrous DCM (2 ml) to which EDCl.HCl (190 mg, 1.015 mmol and HOBt (137 mg, 1.015 mmol were then added, followed by stirring overnight at room temperature. After extraction with DCM and water, the organic layer was washed with brine, dried over sodium sulfate, and concentrated in a vacuum. Separation and purification of the dark brown mixture by silica gel column chromatography (30% ethylacetate mixed with 40% hexane) afforded the title compound. 50 mg (14%).

¹H-NMR (300 MHz, CDCl₃) δ 1.17 (dd. J=6.9 Hz, J=2.4 Hz, 6H, CH₃) 2.84 (hept, 1H, CH) 6.68 (s, 1H, ArH/NH/OH) 6.90 (d, J=8.1 Hz, 1H, ArH) 7.42-7.46 (m, 3H, ArH) 7.54-7.62 (m, 4H, ArH) 7.75-7.90 (m, 2H, ArH) 7.90-8.10 (m, 1H, ArH) 8.10 (s, 1H, ArH/NH).

<Example 212> N-(1-Amino-4b-hydroxy-7-isopropyl-10-oxo-9b,10-dihydro-4bH-benzo[d]indeno[1,2-b]furan-9b-yl)-1H-indazole-3-carboxamide N-(4b-hydroxy-7-isopropyl-1-nitro-10-oxo-9b,10-dihydro-4bH-benzo[d]indeno[1,2-b]furan-9b-yl)-1H-indazole-3-carboxamide (190 mg, 0.39 mmol) was dissolved in an ethanol:water (10 ml:1 ml) solvent, and added with Fe (66 mg, 1.17 mmol) and then two drops of conc. HCl. The reaction mixture was heated for 3 hrs under reflux. After vacuum concentration, purification by column chromatography (ethylacetate:n-hexane=1:2) afforded the title compound as a yellow solid (92 mg, 52%).

¹H-NMR (300 MHz, CD₃OD) δ 1.18 (d, J=6.9 Hz, 6H, CH₃), 2.83 (sep, J=6.9 Hz, 1H, CH), 6.67-6.72 (m, 2H, ArH), 6.88 (dd, J=7.9 Hz, 1.0 Hz, 1H, ArH), 7.03 (d, J=7.3 Hz, 1H, ArH), 7.19 (t, J=7.6 Hz, 1H, ArH), 7.38 (t, J=7.5 Hz, 1H, ArH), 7.43-7.57 (m, 3H, ArH), 8.09 (d, J=8.2 Hz, 1H, ArH).

<Example 213> N-(1-Amino-4b-hydroxy-7-isopropyl-10-oxo-9b,10-dihydro-4bH-benzo[d]indeno[1,2-b]furan-9b-yl)-2-(1H-tetrazol-1-yl)acetamide N-(4b-hydroxy-7-isopropyl-1-nitro-10-oxo-9b,10-dihydro-4bH-benzo[d]indeno[1,2-b]furan-9b-yl)-2-(1H-tetrazol-1-yl)acetamide (200 mg, 0.44 mmol) was dissolved in an ethanol:water (10 ml:1 ml) solvent, and added with Fe (74 mg, 1.32 mmol) and then with two drops of con. HCl. The reaction mixture was heated for 3 hrs under reflux. After vacuum concentration, purification by column chromatography (ethylacetate:n-hexane=2:1) afforded the title compound as a yellow solid (104 mg, 56%).

$^1$H-NMR (300 MHz, CD$_3$OD) δ 1.17 (dd, J=6.9 Hz, 1.2 Hz, 6H, CH$_3$), 2.83 (sep, J=6.9 Hz, 1H, CH), 5.36 (m, 2H, CH$_2$), 6.62~6.66 (m, 2H, ArH), 6.87 (dd, J=7.9 Hz, 1.1 Hz, 1H, ArH), 6.96 (d, J=7.3 Hz, 1H, ArH), 7.38~7.43 (m, 2H, ArH), 9.11 (s, 1H, ArH).

<Example 214> N-(1-Amino-4b-hydroxy-7-isopropyl-10-oxo-9b,10-dihydro-4bH-indeno[1,2-b]benzofuran-9b-yl)quinoline-3-carboxamide Iron powder (0.11 g, 1.9 mmol), conc. HCl (0.03 ml), and water (0.8 ml) were added in that order to a solution of N-(4b-hydroxy-7-isopropyl-1-nitro-10-oxo-9b,10-dihydro-4bH-benzo[d]indeno[1,2-b]furan-9b-yl)quinoline-3-carboxamide (0.13 g, 0.27 mmol) in absolute ethanol (8 ml), and heated for 1 hr under reflux. The reaction mixture was washed with ethylacetate, and filtered to remove iron powder. The filtrate was concentrated in a vacuum and purified for 30 min by column chromatography (ethylacetate:hexane=1:4) packed with Et$_3$N-treated silica gel to afford the title compound. 82 mg (65%).

$^1$H-NMR (300 MHz, CD$_3$OD) δ 1.19 (d, J=6.9 Hz, 6H, CH$_3$) 2.80-2.90 (sept, 1H, CH) 6.70-6.74 (m, 2H, ArH) 6.89 (d, J=7.8 Hz, 1H, ArH) 7.04 (d, J=7.2 Hz, 1H, ArH) 7.48 (t, J=7.2 Hz, 2H, ArH) 7.68 (t, J=7.2 Hz, 1H, ArH) 7.87 (t, J=7.8 Hz, 1H, ArH) 8.02-8.08 (m, 2H, ArH) 8.86 (s, 1H, ArH) 9.23 (s, 1H, ArH).

<Example 215> N-(1-Amino-4b-hydroxy-7-isopropyl-10-oxo-9b,10-dihydro-4bH-indeno[1,2-b]benzofuran-9b-yl)quinoline-4-carboxamide Iron powder (0.12 g, 2.20 mmol), conc. HCl (0.03 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)quinoline-4-carboxamide (0.15 g, 0.30 mmol) in absolute ethanol (10 ml) and heated for 1 hr under reflux. The reaction mixture was washed with ethylacetate, and filtered to remove iron powder. The filtrate was concentrated in a vacuum and purified for 30 min by column chromatography (ethylacetate:hexane=1:2) packed with Et$_3$N-treated silica gel to afford the title compound. 0.12 g (92%).

$^1$H-NMR (300 MHz, CD$_3$OD) δ 1.19 (d, J=6.9 Hz, 6H, CH$_3$) 2.77-2.86 (sept, 1H, CH) 6.66 (s, 1H, NH) 6.74-6.87 (m, 2H, ArH) 7.08 (d, J=7.4 Hz, 1H, ArH) 7.40-7.54 (m, 2H, ArH) 7.65-7.72 (m, 2H, ArH) 7.81 (t, J=7.8 Hz, 1H, ArH) 8.06 (d, J=8.7 Hz, 1H, ArH) 8.40 (d, J=8.4 Hz, 1H, ArH) 8.90 (d, J=4.1 Hz, 1H, ArH).

<Example 216> N-(1-Amino-4b-hydroxy-7-isopropyl-10-oxo-9b,10-dihydro-4bH-indeno[1,2-b]benzofuran-9b-yl)-5-methylthiophene-2-carboxamide Iron powder (0.06 g, 1.24 mmol), conc. HCl (0.03 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)-5-methylthiophene-2-carboxamide (0.08 g, 0.17 mmol) in absolute ethanol (10 ml), and heated for 1 hr under reflux. The reaction mixture was washed with ethylacetate, and filtered to remove iron powder. The filtrate was concentrated in a vacuum and purified for 30 min by column chromatography (ethylacetate:hexane=1:4) packed with Et$_3$N-treated silica gel to afford the title compound. 67 mg (90%).

$^1$H-NMR (500 MHz, CD$_3$OD) δ 1.18 (d, J=6.9 Hz, 6H, CH$_3$) 2.53 (s, 3H, Me) 2.75-2.84 (sept, 1H, CH) 6.57 (d, J=8.1 Hz, 1H, ArH) 6.64-6.71 (m, 2H, ArH) 6.76 (s, 1H, ArH) 6.87 (d, J=3.0 Hz, 1H, ArH) 7.24 (d, J=8.1 Hz, 1H, ArH) 7.32 (t, J=8.1 Hz, 1H, ArH) 7.68 (d, J=3.6 Hz, 1H, ArH).

<Example 217> N-(1-Amino-4b-hydroxy-7-isopropyl-10-oxo-9b,10-dihydro-4bH-indeno[1,2-b]benzofuran-9b-yl)-2-methoxythiophene-3-carboxamide Fe powder (0.06 g, 1.24 mmol), conc. HCl (0.03 ml), and (1 ml) were added in that order to a solution of N-(4b-hydroxy-7-isopropyl-1-nitro-10-oxo-9b,10-dihydro-4bH-benzo[d]indeno[1,2-b]furan-9b-yl)-2-methoxythiophene-3-carboxamide (0.28 g, 0.58 mmol), and heated for 1 hrs under reflux. The reaction mixture was washed with ethylacetate, and filtered to remove Fe powder. The filtrate was concentrated in a vacuum and purified for 30 min by column chromatography (ethylacetate:hexane=1:4) packed with Et$_3$N-treated silica gel, followed by recrystallization in methylene chloride to afford the title compound. 77 mg (29%).

$^1$H-NMR (500 MHz, CD$_3$OD) δ 1.18 (d, J=6.9 Hz, 6H, CH$_3$) 2.75-2.84 (sept, 1H, CH) 3.89 (s, 3H, OMe) 6.62-6.69 (m, 3H, ArH) 6.82-6.90 (m, 1H, ArH) 6.96-7.05 (m, 1H, ArH) 7.38-7.47 (m, 2H, ArH) 7.95 (s, 1H, ArH).

<Example 218> N-(4b-Hydroxy-7-isopropyl-10-oxo-9b,10-dihydro-4bH-indeno[1,2-b]benzofuran-9b-yl)picolinamide A solution of picolinic acid (0.26 g, 2.1 mmol) in anhydrous MeCN (30 ml) was stirred together with EDCl (0.45 g, 2.3 mmol) and HOBt (0.25 g, 1.8 mmol) at room temperature for 10 min, and then together with 9b-amino-4b-hydroxy-7-isopropyl-1-nitro-4bH-benzo[d]indeno[1,2-b]furan-10(9bH)-one (0.52 g, 1.76 mmol) at room temperature for 3 hrs. The reaction mixture was diluted in methylene chloride, and washed many times with water, and the organic layer was dried and filtered. Purification by column chromatography (ethylacetate:hexane=1:4) afforded the title compound. 0.53 g (76%).

$^1$H-NMR (300 MHz, CDCl$_3$) δ 1.16 (d, J=6.9 Hz, 6H, CH$_3$) 2.83 (sept, J=6.9 Hz, 1H, CH) 5.69 (s, 1H) 6.75 (s, 1H) 6.83 (d, J=7.8 Hz, 1H, ArH) 7.36 (d, J=7.8 Hz, 1H, ArH) 7.44-7.48 (m, 1H, ArH) 7.55-7.60 (m, 1H, ArH) 7.80-7.86 (m, 3H, ArH) 8.02-8.09 (m, 2H, ArH) 8.60-8.61 (m, 1H, ArH) 9.17 (s, 1H).

<Example 219> N-(4b-Hydroxy-7-isopropyl-10-oxo-9b,10-dihydro-4bH-indeno[1,2-b]benzofuran-9b-yl)pyrimidine-4-carboxamide A solution isonicotinic acid (0.26 g, 2.1 mmol) in anhydrous methylene chloride (20 ml) and dimethylformamide (10 ml) was stirred together with EDCl (0.45 g, 2.3 mmol) and HOBt (0.25 g, 1.8 mmol) for 10 min at room temperature, and then together with 9b-amino-4b-hydroxy-7-isopropyl-1-nitro-4bH-benzo[d]indeno[1,2-b]furan-10(9bH)-one (0.46 g, 1.56 mmol) for 24 hrs at room temperature. The reaction mixture was diluted in methylene chloride, and washed many times with water, and the organic layer was dried and filtered. Purification by column chromatography (ethylacetate:hexane=1:4) afforded the title compound. 0.20 g (32%).

$^1$H-NMR (300 MHz, CD$_3$OD) δ 1.20 (d, J=6.9 Hz, 6H, CH$_3$) 2.81-2.90 (m, 1H, CH) 6.70 (brs, 1H, ArH) 6.91-6.93 (m, 1H, ArH) 7.42-7.47 (m, 1H, ArH) 7.72-7.82 (m, 6H) 8.66-8.68 (m, 2H, ArH).

<Example 220> N-(4b-Hydroxy-7-isopropyl-10-oxo-9b,10-dihydro-4bH-benzo[d]indeno[1,2-b]furan-9b-yl)-2-(1H-tetrazol-5-yl)acetamide A solution of 1H-tetrazole-5-acetic acid (131 mg, 1.02 mmol) in methylene chloride (20 ml) and DMF (5 ml) was stirred together with EDCl (196 mg, 1.02 mmol) and HOBt (138 mg, 1.02 mmol) for 20 min, and then together with 4b-amino-9b-hydroxy-7-isopropyl-4b,9b-dihydro-5-oxa-indeno[2,1-a]-inden-10-one (300 mg, 1.02 mmol) overnight at room temperature. After extraction with methylene chloride and water, the organic layer was dried over MgSO$_4$ and concentrated in a vacuum. Purification by column chromatography (20% methanol in methylene chloride) afforded the title compound as a white solid (136 mg, 33%).

$^1$H-NMR (300 MHz, CD$_3$OD) δ 1.16 (d, J=6.9 Hz, 6H, CH$_3$), 2.83 (sep, J=6.9 Hz, 1H, CH), 3.97 (s, 2H, ArH), 6.66 (s, 1H, ArH), 6.88 (dd, J=8.0 Hz, 1.1 Hz, 1H, ArH), 7.36 (d, J=7.9 Hz, 1H, ArH), 7.68~7.79 (m, 3H, ArH).

<Example 221> N-(4b-Hydroxy-7-isopropyl-10-oxo-9b,10-dihydro-4bH-benzo[d]indeno[1,2-b]furan-9b-yl)-1H-benzo[d][1,2,3]triazole-5-carboxamide A solution of benzotriazole-5-carboxylic acid (166 mg, 1.02 mmol) in methylene chloride (20 ml) and DMF (5 ml) was reacted with EDCl (196 mg, 1.02 mmol) and HOBt (138 mg, 1.02 mmol) for 20 min, and then stirred together with 4b-amino-9b-hydroxy-7-isopropyl-4b,9b-dihydro-5-oxa-indeno[2,1-a]-inden-10-one (300 mg, 1.02 mmol) overnight at room temperature. After extraction with methylene chloride and water, the organic layer was dried over MgSO$_4$ and concentrated in a vacuum. Purification by column chromatography (ethylacetate:n-hexane=2:1) afforded N-(4b-hydroxy-7-isopropyl-10-oxo-9b,10-dihydro-4bH-benzo[d]indeno[1,2-b]furan-9b-yl)-1H-benzo[d][1,2,3]triazole-5-carboxamide as a white solid (210 mg, 47%).

$^1$H-NMR (300 MHz, CD$_3$OD) δ 1.18 (d, J=6.9 Hz, 6H, CH$_3$), 2.85 (sep, J=6.9 Hz, 1H, CH), 6.69 (d, J=1.2 Hz, 1H, ArH), 6.91 (dd, J=7.9 Hz, 1.2 Hz, 1H, ArH), 7.48 (d, J=7.9 Hz, 1H, ArH), 7.62 (m, 1H, ArH), 7.79~7.97 (m, 5H, ArH), 8.49 (s, 1H, ArH).

<Example 222> N-(4b-Hydroxy-7-isopropyl-10-oxo-9b,10-dihydro-4bH-benzo[d]indeno[1,2-b]furan-9b-yl)-1H-1,2,4-triazole-3-carboxamide 1,2,4-triazole-3-carboxylic acid (116 mg, 1.02 mmol) was dissolved in methylene chloride (20 ml) and DMF (5 ml), reacted with EDCl (196 mg, 1.02 mmol) and HOBt (138 mg, 1.02 mmol) for 20 min, and then stirred together with 4b-amino-9b-hydroxy-7-isopropyl-4b,9b-dihydro-5-oxa-indeno[2,1-a]-inden-10-one (300 mg, 1.02 mmol) overnight at room temperature. After extraction with methylene chloride and water, the organic layer was dried over MgSO$_4$ and concentrated in a vacuum. Purification by column chromatography (10% methanol in methylene chloride) afforded the title compound as a white solid. (141 mg, 35%).

$^1$H-NMR (300 MHz, CD$_3$OD) δ 1.17 (d, J=6.9 Hz, 6H, CH$_3$), 2.85 (sep, J=6.9 Hz, 1H, CH), 6.68 (s, 1H, ArH), 6.90 (d, J=8.0 Hz, 1H, ArH), 7.45 (d, J=7.9 Hz, 1H, ArH), 7.60~7.97 (m, 4H, ArH), 8.40 (s, 1H, ArH).

<Example 223> N-(4b-hydroxy-7-isopropyl-10-oxo-9b,10-dihydro-4bH-benzo[d]indeno[1,2-b]furan-9b-yl)-5-nitrothiophene-2-carboxamide 5-Nitrothiophene-2-carboxylic acid (212 mg, 1.22 mmol) was dissolved in methylene chloride (20 ml) and DMF (5 ml), reacted with EDCl (234 mg, 1.22 mmol) and HOBt (165 mg, 1.22 mmol) for 20 min, and then stirred together with 4b-amino-9b-hydroxy-7-isopropyl-4b,9b-dihydro-5-oxa-indeno[2,1-a]-inden-10-one (300 mg, 1.22 mmol) overnight at room temperature. After extraction with methylene chloride and water, the organic layer was dried over MgSO$_4$ and concentrated in a vacuum. Purification by column chromatography (ethylacetate:n-hexane=1:1) afforded N-(4b-hydroxy-7-isopropyl-10-oxo-9b,10-dihydro-4bH-benzo[d]indeno[1,2-b]furan-9b-yl)-5-nitrothiophene-2-carboxamide as a yellow solid (80 mg, 17%).

$^1$H-NMR (300 MHz, CD$_3$OD) δ 1.17 (d, J=6.9 Hz, 6H, CH$_3$), 2.83 (sep, J=6.9 Hz, 1H, CH), 6.67 (s, 1H, ArH), 6.90 (d, J=7.9 Hz, 1H, ArH), 7.43 (d, J=7.9 Hz, 1H, ArH), 7.71~7.73 (m, 2H, ArH), 7.73~7.93 (m, 4H, ArH).

<Example 224> N-(4b-Hydroxy-7-isopropyl-10-oxo-9b,10-dihydro-4bH-benzo[d]indeno[1,2-b]furan-9b-yl)-2,6-dioxo-1,2,3,6-tetrahydropyrimidine-4-carboxamide Orotic acid (190 mg, 1.22 mmol) was dissolved in methylene chloride (20 ml) and DMF (5 ml), reacted with EDCl (233 mg, 1.22 mmol) and HOBt (165 mg, 1.22 mmol) for 20 min, and then stirred together with 4b-amino-9b-hydroxy-7-isopropyl-4b,9b-dihydro-5-oxa-indeno[2,1-a]-inden-10-one (300 mg, 1.02 mmol) overnight at room temperature. After extraction with methylene chloride and water, the organic layer was dried over MgSO$_4$ and concentrated in a vacuum. Purification by column chromatography (10% methanol in methylene chloride) afforded N-(4b-hydroxy-7-isopropyl-10-oxo-9b,10-dihydro-4bH-benzo[d]indeno[1,2-b]furan-9b-yl)-2,6-dioxo-1,2,3,6-tetrahydropyrimidine-4-carboxamide as a white solid (91 mg, 21%).

$^1$H-NMR (300 MHz, CD$_3$OD) δ 1.16 (d, J=6.9 Hz, 6H, CH$_3$), 2.83 (sep, J=6.9 Hz, 1H, CH), 6.30 (s, 1H, ArH), 6.67 (s, 1H, ArH), 6.90 (d, J=8.0 Hz, 1H, ArH), 7.39 (d, J=7.8 Hz, 1H, ArH), 7.60~7.93 (m, 4H, ArH).

<Example 225> N-(4b-hydroxy-7-isopropyl-10-oxo-9b,10-dihydro-4bH-benzo[d]indeno[1,2-b]furan-9b-yl)-2-oxo-2H-chromene-3-carboxamide Coumarin-3-carboxylic acid (232 mg, 1.22 mmol) was dissolved in methylene chloride (20 ml) and DMF (5 ml), reacted with EDCl (234 mg, 1.22 mmol) and HOBt (165 mg, 1.22 mmol) for 20 min, and then stirred together with 4b-amino-9b-hydroxy-7-isopropyl-4b,9b-dihydro-5-oxa-indeno[2,1-a]-inden-10-one (300 mg, 1.02 mmol) overnight at room temperature. After extraction with methylene chloride and water, the organic layer was dried over MgSO$_4$ and concentrated in a vacuum. Purification by column chromatography (ethylacetate:n-hexane=1:2) afforded the title compound as a white solid (377 mg, 79%).

$^1$H-NMR (300 MHz, CD$_3$OD) δ 1.19 (d, J=6.9 Hz, 6H, CH$_3$), 2.86 (sep, J=6.9 Hz, 1H, CH), 6.70 (s, 1H, ArH), 6.92

(d, J=7.9 Hz, 1H, ArH), 7.41~7.45 (m, 3H, ArH), 7.72~7.81 (m, 4H, ArH), 7.88~7.89 (m, 2H, ArH), 8.74 (s, 1H, ArH).

<Example 226> N-(4b-Hydroxy-7-isopropyl-10-oxo-9b,10-dihydro-4bH-benzo[d]indeno[1,2-b]furan-9b-yl)-2-oxo-2H-pyrane-5-carboxamide Coumaric acid (171 mg, 1.22 mmol) was dissolved in methylene chloride (20 ml) and DMF (5 ml), reacted with EDCl (234 mg, 1.22 mmol) and HOBt (165 mg, 1.22 mmol) for 20 min, and then stirred together with 4b-amino-9b-hydroxy-7-isopropyl-4b,9b-dihydro-5-oxa-indeno[2,1-a]-inden-10-one (300 mg, 1.02 mmol) overnight at room temperature. After extraction with methylene chloride and water, the organic layer was dried over $MgSO_4$ and concentrated in a vacuum. Purification by column chromatography (ethylacetate:n-hexane=1:1) afforded the title compound as a yellow solid (60 mg, 14%).

$^1$H-NMR (300 MHz, $CD_3OD$) δ 1.16 (dd, J=6.9 Hz, 2.8 Hz, 6H, $CH_3$), 2.84 (sep, J=6.9 Hz, 1H, CH), 5.61 (d, J=9.3 Hz, 1H, ArH), 6.78 (s, 1H, ArH), 6.93 (dd, J=7.9 Hz, 1.0 Hz, 1H, ArH), 7.44 (d, J=7.9 Hz, 1H, ArH), 7.49 (d, J=9.3 Hz, 1H, ArH), 7.63 (t, J=7.4 Hz, 1H, ArH), 7.81 (d, J=7.7 Hz, 1H, ArH), 7.87~7.92 (m, 2H, ArH), 8.01 (d, J=7.8 Hz, 1H, ArH).

<Example 227> N-(4b-hydroxy-7-isopropyl-10-oxo-9b,10-dihydro-4bH-benzo[d]indeno[1,2-b]furan-9b-yl)-1H-benzo[d]imidazole-2-carboxamide 1H-benzimidazole-2-carboxylic acid (183 mg, 1.02 mmol) was dissolved in methylene chloride (20 ml) and DMF (5 ml), reacted with EDCl (195 mg, 1.02 mmol) and HOBt (138 mg, 1.02 mmol) for 20 min, and stirred together with 4b-amino-9b-hydroxy-7-isopropyl-4b,9b-dihydro-5-oxa-indeno[2,1-a]-inden-10-one (250 mg, 0.85 mmol) overnight at room temperature. After extraction with methylene chloride and water, the organic layer was dried over $MgSO_4$ and concentrated in a vacuum. Purification by column chromatography (ethylacetate:n-hexane=1:1) afforded N-(4b-hydroxy-7-isopropyl-10-oxo-9b,10-dihydro-4bH-benzo[d]indeno[1,2-b]furan-9b-yl)-1H-benzo[d]imidazole-2-carboxamide as a white solid (210 mg, 56%).

$^1$H-NMR (300 MHz, $CD_3OD$) δ 1.19 (d, J=6.9 Hz, 6H, CH3), 2.86 (sep, J=6.9 Hz, 1H, CH), 6.69 (s, 1H, ArH), 6.93 (dd, J=7.9 Hz, 1.2 Hz, 1H, ArH), 7.32~7.35 (m, 2H, ArH), 7.49 (d, J=7.9 Hz, 1H, ArH), 7.63~7.64 (m, 4H, ArH), 7.89~7.91 (m, 2H, ArH).

<Example 228> N-(1-Amino-4b-hydroxy-7-isopropyl-10-oxo-9b,10-dihydro-4bH-indeno[1,2-b]benzofuran-9b-yl)-3-(2-chloro-6-fluorophenyl)-5-methyl-isooxazole-4-carboxamide 5-(2-chloro-6-fluorophenyl)-N-(4b-hydroxy-7-isopropyl-1-nitro-10-oxo-9b,10-dihydro-4bH-benzo[d]indeno[1,2-b]furan-9b-yl)-2-methylcyclopenta-1,4-dienecarboxamide (100 mg, 0.173 mmol) was added to 5 ml of $EtOH:H_2O$ (10:1) to form a pale yellow turbid solution to which Fe powder (41 mg, 0.73 mmol) and three drops of conc. HCl were then added at room temperature, followed by stirring for 2 hrs under reflux. The reaction mixture was filtered, concentrated, and purified by silica gel prep-TLC using EtOAc/Hx (1/1) to afford the title compound as a yellow solid (26.7 mg, 0.487 mmol, 28%).

$^1$H-NMR (300 MHz, $CD_3OD$) δ 1.16 (d, J=6.9 Hz, 3H), 1.17 (d, J=6.8 Hz, 3H), 2.72 (s, 3H), 2.73-2.88 (m, 1H), 6.62 (s, 1H), 6.63-6.82 (m, 2H), 6.93-7.17 (m, 2H), 7.19-7.25 (m, 1H), 7.39-7.52 (m, 3H).

<Example 229> N-(4b-hydroxy-7-isopropyl-10-oxo-9b,10-dihydro-4bH-indeno[1,2-b]benzofuran-9b-yl)-3-phenyl-1H-pyrazole-5-carboxamide 3-Phenyl-1H-pyrazole-5-carboxylic acid (116 mg, 0.616 mmol), HOBt (316 mg, 2.34 mmol), and EDCl.HCl (441 mg, 2.30 mmol) were dissolved together in $CH_2Cl_2$ (10 mL) to which a dilution of 9b-amino-4b-hydroxy-7-isopropyl-4bH-benzo[d]indeno[1,2-b]furan-10(9bH)-one (500 mg, 1.69 mmol) in $CH_2Cl_2$ (5 mL) was then added, followed by stirring at room temperature for 2 hrs. The resulting yellow reaction mixture was mixed with water, and them extracted twice with $CH_2Cl_2$. The organic layer was dehydrated over anhydrous magnesium sulfate and concentrated. The concentrate was purified by silica gel column chromatography using EtOAc/Hx (1/3-1/2) to afford the title compound as a white solid (144.7 mg, 0.311 mmol, 50%).

$^1$H-NMR (300 MHz, $CD_3OD$) δ 1.13-1.23 (m, 6H), 2.77-2.92 (m, 1H), 6.68 (s, 1H), 6.90 (d, J=7.9 Hz, 1H), 6.93-7.09 (m, 2H), 7.31-7.52 (m, 4H), 7.52-8.07 (m, 6H).

<Example 230> N-(4b-Hydroxy-7-isopropyl-10-oxo-9b,10-dihydro-4bH-indeno[1,2-b]benzofuran-9b-yl)nicotinamide At 0° C., EDCl (0.48 g, 2.53 mmol), 9b-amino-4b-hydroxy-7-isopropyl-1-nitro-4bH-benzo[d]indeno[1,2-b]furan-10(9bH)-one (0.50 g, 1.46 mmol), and HOBt (0.34 g, 2.53 mmol) were added in that order to a solution of nicotinic acid (0.31 g, 2.53 mmol) in anhydrous THF (10 ml) and DMF (3 ml), followed by stirring at room temperature for 2 days. During the reaction, solid products were washed with THF and water, filtered, and dried to obtain the title compound. 0.33 g (49%).

$^1$H-NMR (300 MHz, $CDCl_3$) & 1.14 (d, J=6.3 Hz, 6H, $CH_3$) 2.71-2.82 (sept, 1H, CH) 6.67 (s, 1H, NH) 6.80 (d, J=7.5 Hz, 1H, ArH) 7.30 (t, J=6.0 Hz, 1H, ArH) 7.38 (d, J=7.8 Hz, 1H, ArH) 7.53 (t, J=7.2 Hz, 1H, ArH) 7.63 (s, 1H, ArH) 7.73-7.82 (m, 2H, ArH) 7.91 (s, 1H, OH) 7.97 (d, J=7.8 Hz, 1H, ArH) 8.10 (d, J=7.2 Hz, 1H, ArH) 8.56 (d, J=3.9 Hz, 1H, ArH) 8.96 (s, 1H, ArH).

<Example 231> N-(1-Amino4b-hydroxy-7-isopropyl-10-oxo-9b,10-dihydro-4bH-indeno[1,2-b]benzofuran-9b-yl)-2-oxo-2-(thiophen-2-yl)acetamide Fe powder (0.30 g, 5.47 mmol), conc. HCl (0.03 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)thiophene-2-carboxamide (0.36 g, 0.75 mmol) in absolute ethanol (10 ml), and heated for 2 hrs under reflux. The reaction mixture was washed with ethylacetate, and filtered to remove Fe powder. The filtrate was concentrated in a vacuum and purified for 30 min by column chromatography (ethylacetate:hexane=1:4) packed with $Et_3N$-treated silica gel to afford the title compound. 0.28 g (83%).

$^1$H-NMR (500 MHz, $CD_3OD$) δ 1.18 (d, J=6.9 Hz, 6H, $CH_3$) 2.81-2.86 (sept, 1H, CH) 6.61-6.72 (m, 2H, ArH) 6.88 (d, J=7.5 Hz, 1H, ArH) 7.01 (d, J=7.2 Hz, 1H, ArH) 7.20 (t, J=5.1 Hz, 1H, ArH) 7.40 (d, J=7.5 Hz, 1H, ArH) 7.46 (t, J=7.8 Hz, 1H, ArH) 7.96 (d, J=4.5 Hz, 1H, ArH) 8.25 (d, J=2.7 Hz, 1H, ArH).

<Example 232> 5-amino-N-(1-amino-4b-hydroxy-7-isopropyl-10-oxo-9b,10-dihydro-4bH-indeno[1,2-b]benzofuran-9b-yl)furane-2-carboxamide Fe powder (0.32 g, 5.78 mmol), conc. HCl (0.03 ml), and (1 ml) were added in that order to a solution of 5-amino-N-(4b-hydroxy-7-isopropyl-1-nitro-10-oxo-9b,10-dihydro-4bH-benzo[d]indeno[1,2-b]furan-9b-yl)furane-2-carboxamide (0.38 g, 0.79 mmol) in absolute ethanol (10 ml), and heated for 2 hrs under reflux. The reaction mixture was washed with ethylacetate, and filtered to remove Fe powder. The filtrate was concentrated in a vacuum and purified by column chromatography (ethylacetate:hexane=1:4) packed with Et$_3$N-treated silica gel to afford the title compound. 61 mg (48%).
$^1$H-NMR (300 MHz, CD$_3$OD) δ 1.25 (d, J=6.6 Hz, 6H, CH$_3$) 2.84-2.86 (sept, 1H, CH) 6.75 (s, 1H, ArH) 6.88-6.94 (m, 2H, ArH) 7.08-7.11 (m, 1H, ArH) 7.25 (t, J=7.5 Hz, 1H, ArH) 7.34-7.38 (m, 1H, ArH) 7.38-7.50 (m, 2H, ArH).

<Example 233> N-(1-Amino-4b-hydroxy-7-isopropyl-10-oxo-9b,10-dihydro-4bH-indeno[1,2-b]benzofuran-9b-yl)-1H-pyrrole-2-carboxamide Fe powder (0.09 g, 1.6 mmol), conc. HCl (0.03 ml), and water (0.8 ml) were added in that order to a solution of N-(4b-hydroxy-7-isopropyl-1-nitro-10-oxo-9b,10-dihydro-4bH-benzo[d]indeno[1,2-b]furan-9b-yl)-1H-pyrrole-2-carboxamide (0.10 g, 0.23 mmol) in ethanol (8 ml), and heated for 2 hrs under reflux. The reaction mixture was washed with ethylacetate, and filtered to remove Fe powder. The filtrate was concentrated in a vacuum and purified for 30 min by column chromatography (ethylacetate:hexane=1:2) packed with Et$_3$N-treated silica gel to afford the title compound. 90 mg (96%).
$^1$H-NMR (300 MHz, CD$_3$OD) & 1.18 (d, J=6.6 Hz, 6H, CH$_3$) 2.82-2.86 (sept, 1H, CH) 6.16 (d, J=2.7 Hz, 1H, ArH) 6.88 (s, 1H, ArH) 6.70-6.74 (m, 1H, ArH) 6.85-6.90 (m, 3H, ArH) 7.03 (d, J=5.1 Hz, 1H, ArH) 7.30-7.46 (m, 2H, ArH).

<Example 234> N-(1-Amino-4b-hydroxy-7-isopropyl-10-oxo-9b,10-dihydro-4bH-indeno[1,2-b]benzofuran-9b-yl)-2-methoxyisonicotinamide Fe powder (0.12 g, 2.30 mmol), conc. HCl (0.03 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)-2-methoxyisonicotinamide (0.15 g, 0.31 mmol) in absolute ethanol (10 ml), and heated for 2 hrs under reflux. The reaction mixture was washed with ethylacetate, and filtered to remove Fe powder. The filtrate was concentrated in a vacuum and purified for 30 min by column chromatography (ethylacetate:hexane=1:4) packed with Et$_3$N-treated silica gel to afford the title compound. 0.10 g (71%).
$^1$H-NMR (300 MHz, CD$_3$OD) & 1.17 (d, J=6.9 Hz, 6H, CH$_3$) 2.78-2.87 (sept, 1H, CH) 3.91 (s, 3H, OMe) 6.67 (s, 1H, ArH) 6.74 (m, 1H, ArH) 6.85 (d, J=8.1 Hz, 1H, ArH) 7.02 (d, J=7.2 Hz, 1H, ArH) 7.19 (s, 1H, ArH) 7.29 (d, J=5.4 Hz, 1H, ArH) 7.39-7.48 (m, 2H, ArH) 8.20 (d, J=4.8 Hz, 1H, ArH).

<Example 235> N-(1-Amino-4b-hydroxy-7-isopropyl-10-oxo-9b,10-dihydro-4bH-benzo[d]indeno[1,2-b]furan-9b-yl)benzo[b]thiophene-2-carboxamide Fe (50 mg, 0.90 mmol) and 2 drops of con. HCl were sequentially added to a solution of N-(4b-hydroxy-7-isopropyl-1-nitro-10-oxo-9b,10-dihydro-4bH-benzo[d]indeno[1,2-b]furan-9b-yl)benzo[b]thiophene-2-carboxamide (150 mg, 0.30 mmol) in an ethanol:H$_2$O (10 ml:1 ml) solvent, and heated for 3 hrs under reflux. After vacuum concentration, purification by column chromatography (ethylacetate:n-hexane=1:3) afforded the title compound as a yellow solid (76 mg, 54%).
$^1$H-NMR (500 MHz, CD$_3$OD) δ 1.19 (dd, J=6.9 Hz 1.2 Hz, 6H, CH$_3$), 2.85 (sep, J=6.9 Hz, 1H, CH), 6.67~6.70 (m, 2H, ArH), 6.90 (d, J=7.8 Hz, 1H, ArH), 7.01 (d, J=7.3 Hz, 1H, ArH), 7.39~7.48 (m, 4H, ArH), 7.87 (d, J=7.5 Hz, 1H, ArH), 8.10 (s, 1H, ArH).

<Example 236> 3-(2,6-dichlorophenyl)-N-(4b-hydroxy-7-isopropyl-10-oxo-9b,10-dihydro-4bH-benzo[d]indeno[1,2-b]furan-9b-yl)-5-methylisooxazole-4-carboxamide A solution of 4b-amino-9b-hydroxy-7-isopropyl-4b,9b-dihydro-5-oxa-indeno[2,1-a]-inden-10-one (300 mg, 1.02 mmol) in methylene chloride (20 ml) was stirred overnight together with 3-(2,6-dichlorophenyl)-5-methyl-4-isooxazolecarbonyl chloride (355 mg, 1.22 mmol) and triethylamine (0.3 ml, 1.83 mmol) at room temperature. After completion of the reaction, concentration in a vacuum and purification by column chromatography (ethylacetate:n-hexane=1:3) afforded the title compound (109 mg, 19%).
$^1$H-NMR (300 MHz, CDCl$_3$) δ 1.14 (dd, J=6.8 Hz, 6H, CH$_3$), 2.75 (s, 3H, CH$_3$), 2.78 (sep, J=6.8 Hz, 1H, CH), 6.02 (s, 1H), 6.56 (s, 1H), 6680 (s, 1H, ArH), 6.75 (d, J=7.8 Hz, 1H, ArH), 6.88 (d, J=7.8 Hz, 1H, ArH), 7.48 (t, J=7.5 Hz, 1H, ArH), 7.51~7.68 (m, 4H, ArH), 7.76 (t, J=7.5 Hz, 1H, ArH), 7.98 (d, J=7.8 Hz, 1H, ArH).

<Example 237> N-(1-Amino-4b-hydroxy-7-isopropyl-10-oxo-9b,10-dihydro-4bH-benzo[d]indeno[1,2-b]furan-9b-yl)-9H-xanthene-9-carboxamide Fe (37 mg, 0.66 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-9H-xanthene-9-carboxamide (120 mg, 0.22 mmol) in an ethanol:water (10 ml:1 ml) solvent, and heated for 1.5 hrs under reflux. After vacuum concentration, purification by column chromatography (ethylacetate:n-hexane=1:2) afforded the title compound as a yellow solid (65 mg, 57%).
$^1$H-NMR (500 MHz, CD$_3$OD) δ 1.18 (dd, J=6.9 Hz, 2.3 Hz, 6H, CH$_3$), 2.84 (sep, J=6.9 Hz, 1H, CH), 5.09 (s, 1H, CH), 6.59 (s, 1H, ArH), 6.66 (s, 1H, ArH), 6.88~6.94 (m, 2H, ArH), 7.01~7.06 (m, 3H, ArH), 7.15 (m, 1H, ArH), 7.22 (m, 1H, ArH), 7.28 (t, J=7.3 Hz, 1H, ArH), 7.36 (m, 1H, ArH), 7.42~7.45 (m, 2H, ArH), 7.54 (m, 1H, ArH).

<Example 238> N-(1-Amino-4b-hydroxy-7-isopropyl-10-oxo-9b,10-dihydro-4bH-benzo[d]indeno[1,2-b]furan-9b-yl)cinnoline-4-carboxamide Fe (85 mg, 1.51 mmol) and 2 drops of conc. HCl were sequentially added to a solution of N-(4b-hydroxy-7-isopropyl-1-nitro-10-oxo-9b,10-dihydro-4bH-benzo[d]indeno[1, 2-b]furan-9b-yl)cinnoline-4-carboxamide (250 mg, 0.50 mmol) in an ethanol:water (20 ml:2 ml) solvent, and heated for 2 hrs under reflux. After vacuum concentration, purification by column chromatography (ethylacetate:n-hexane=1:1) afforded the title compound as a yellow solid (230 mg, 99%).

$^1$H-NMR (300 MHz, CD$_3$OD) δ 1.16 (d, J=6.9 Hz, 6H, CH$_3$), 2.82 (sep, J=6.9 Hz, 1H, CH), 6.68 (s, 1H, ArH), 6.72 (d, J=8.1 Hz, 1H, ArH), 6.86 (d, J=8.1 Hz, 1H, ArH), 7.07 (d, J=7.1 Hz, 1H, ArH), 7.44~7.51 (m, 2H, ArH), 7.90~8.01 (m, 2H, ArH), 8.44~8.51 (m, 2H, ArH), 9.46 (s, 1H, ArH).

<Example 239> N-(4b-hydroxy-7-isopropyl-10-oxo-9b,10-dihydro-4bH-benzo[d]indeno[1,2-b]furan-9b-yl)cinnoline-4-carboxamide A solution of cinnoline-4-carboxylic acid (183 mg, 1.02 mmol) in methylene chloride (20 ml) was reacted with EDCl (195 mg, 1.02 mmol) and HOBt (138 mg, 1.02 mmol) for 20 min and then stirred, together with 4b-amino-9b-hydroxy-7-isopropyl-4b,9b-dihydro-5-oxa-indeno[2,1-a]-inden-10-one (250 mg, 0.85 mmol), overnight at room temperature. After extraction with methylene chloride and water, the organic layer was dried over MgSO$_4$ and concentrated in a vacuum. Purification by column chromatography (ethylacetate:n-hexane=1:1) afforded the title compound as a white solid (290 mg, 63%).

$^1$H-NMR (300 MHz, CD$_3$OD) δ 1.15 (d, J=6.8 Hz, 6H, CH$_3$), 2.82 (sep, J=6.8 Hz, 1H, CH), 6.69 (s, 1H, ArH), 6.89 (d, J=7.8 Hz, 1H, ArH), 7.45 (d, J=7.9 Hz, 1H, ArH), 7.65 (m, 1H, ArH), 7.85~8.03 (m, 5H, ArH) 8.42 (d, J=8.0 Hz, 1H, ArH), 8.51 (d, J=8.4 Hz, 1H, ArH), 9.45 (s, 1H, ArH).

<Example 240> N-(4b-hydroxy-7-isopropyl-10-oxo-9b,10-dihydro-4bH-benzo[d]indeno[1,2-b]furan-9b-yl)-1H-benzo[d]imidazole-5-carboxamide 5-benzimidazolecarboxylic acid (198 mg, 1.22 mmol) was dissolved in methylene chloride (20 ml) and DMF (3 ml), reacted with, EDCl (233 mg, 1.22 mmol) and HOBt (165 mg, 1.22 mmol) for 20 min, and then stirred, together with 4b-amino-9b-hydroxy-7-isopropyl-4b,9b-dihydro-5-oxa-indeno[2,1-a]-inden-10-one (300 mg, 1.02 mmol), overnight at room temperature. After extraction with methylene chloride and water, the organic layer was dried over MgSO$_4$ and concentrated in a vacuum. Purification by column chromatography (MC in MeOH 10%) afforded the title compound as a white solid (207 mg, 46%).

$^1$H-NMR (300 MHz, CD$_3$OD) δ 1.18 (d, J=6.8 Hz, 6H, CH$_3$), 2.85 (sep, J=6.8 Hz, 1H, CH), 6.68 (s, 1H, ArH), 6.92 (d, J=7.8 Hz, 1H, ArH), 7.49 (d, J=8.1 Hz, 1H, ArH), 7.61~7.64 (m, 2H, ArH), 7.78~7.83 (m, 3H, ArH), 7.96 (d, J=7.5 Hz, 1H, ArH), 8.19 (s, 1H, ArH), 8.26 (s, 1H, ArH).

<Example 241> N-(1-Amino-4b-hydroxy-7-isopropyl-10-oxo-9b,10-dihydro-4bH-benzo[d]indeno[1,2-b]furan-9b-yl)acridine-9-carboxamide Fe (46 mg, 0.82 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)acridine-9-carboxamide (150 mg, 0.27 mmol) in an ethanol:water (20 ml:2 ml) solvent and heated for 2 hrs under reflux. After vacuum concentration, purification by column chromatography (ethylacetate:n-hexane=1:1) afforded the title compound as a yellow solid (90 mg, 65%).

$^1$H-NMR (500 MHz, CD$_3$OD) δ 1.14 (d, J=6.9 Hz, 6H, CH$_3$), 2.80 (sep, J=6.9 Hz, 1H, CH), 6.67 (s, 1H, ArH), 6.74 (d, J=7.4 Hz, 1H, ArH), 6.81 (d, J=7.5 Hz, 1H, ArH), 7.13 (d, J=6.8 Hz, 1H, ArH), 7.42 (d, J=7.0 Hz, 1H, ArH), 7.51 (t, J=7.5 Hz, 1H, ArH), 7.62 (t, J=7.1 Hz, 1H, ArH), 7.80 (t, J=7.0 Hz, 1H, ArH), 7.84 (t, J=6.8 Hz, 1H, ArH), 8.13~8.18 (m, 2H, ArH), 8.56 (d, J=7.5 Hz, 1H, ArH), 8.72 (d, J=7.5 Hz, 1H, ArH).

<Example 242> N-(1-Amino-4b-hydroxy-7-isopropyl-10-oxo-9b,10-dihydro-4bH-benzo[d]indeno[1,2-b]furan-9b-yl)-4-nitro-1H-pyrazole-3-carboxamide Fe (76 mg, 1.36 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-4-nitro-1H-pyrazole-3-carboxamide (217 mg, 0.45 mmol) in an ethanol:H$_2$O (20 ml:2 ml) solvent and heated for 2 hrs under reflux. After vacuum concentration, purification by column chromatography (methanol in methylene chloride 5%) afforded the title compound as a yellow solid (134 mg, 71%).

$^1$H-NMR (300 MHz, CD$_3$OD) δ 1.18 (d, J=6.8 Hz, 6H, CH$_3$), 2.84 (sep, J=6.8 Hz, 1H, CH), 6.66~6.68 (m, 2H, ArH), 6.87~6.89 (m, 1H, ArH), 7.01~7.03 (m, 1H, ArH), 7.44~7.48 (m, 2H, ArH), 8.48 (s, 1H, ArH).

<Example 243> N-(1-Amino-4b-hydroxy-7-isopropyl-10-oxo-9b,10-dihydro-4bH-benzo[d]indeno[1,2-b]furan-9b-yl)-4-methylpicolinamide Fe (109 mg, 1.96 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-4-methylpicolinamide (300 mg, 0.65 mmol) in an ethanol:H$_2$O (20 ml:2 ml) solvent and heated for 3 hrs under reflux. After vacuum concentration, purification by column chromatography (ethylacetate:n-hexane=1:3) afforded the title compound as a yellow solid (113 mg, 40%).

$^1$H-NMR (300 MHz, CD$_3$OD) δ 1.14 (d, J=6.7 Hz, 6H, CH$_3$), 2.35 (s, 3H, CH$_3$), 2.79 (sep, J=6.7 Hz, 1H, CH), 6.65~6.66 (m, 2H, ArH), 6.83 (d, J=5.9 Hz, 1H, ArH), 7.03 (d, J=6.2 Hz, 1H, ArH), 7.30 (d, J=4.1 Hz, 1H, ArH), 7.42~7.45 (m, 2H, ArH), 7.78 (d, 1H, ArH), 8.40 (d, J=4.6 Hz, 1H, ArH).

<Example 244> N-(1-Amino-4b-hydroxy-7-isopropyl-10-oxo-9b,10-dihydro-4bH-benzo[d]indeno[1,2-b]furan-9b-yl)-4-(trifluoromethyl)picolinamide Fe (104 mg, 1.87 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-4-(trifluoromethyl)picolinamide (320 mg, 0.62 mmol) in an ethanol:H$_2$O (20 ml:2 ml) solvent and heated for 4 hrs under reflux. After vacuum concentration, purification by column chromatography (ethylacetate:n-hexane=1:2) afforded the title compound as a yellow solid (127 mg, 42%).

$^1$H-NMR (300 MHz, CD$_3$OD) δ 1.15 (d, J=6.8 Hz, 6H, CH$_3$), 2.79 (sep, J=6.8 Hz, 1H, CH), 6.65~6.75 (m, 2H, ArH), 6.85 (d, J=6.7 Hz, 1H, ArH), 7.03 (d, J=6.7 Hz, 1H, ArH), 7.43~7.51 (m, 2H, ArH), 7.81 (d, J=4.6 Hz, 1H, ArH), 8.20 (s, 1H, ArH), 8.82 (d, J=4.6 Hz, 1H, ArH).

<Example 245> N-(1-Amino-4b-hydroxy-7-isopropyl-10-oxo-9b,10-dihydro-4bH-benzo[d]indeno[1,2-b]furan-9b-yl)-5-cyanopicolinamide Fe (107 mg, 1.91 mmol) and 2 drops of conc. HCl were sequentially added to a solution of 5-cyano-N-(4b-hydroxy-7-isopropyl-1-nitro-10-oxo-9b,10-dihydro-4bH-benzo[d]indeno[1,2-b]furan-9b-yl)picolinamide (300 mg, 0.64 mmol) in an ethanol:H$_2$O (20 ml:2 ml) solvent and heated for 4 hrs under reflux. After vacuum concentration, purification by column chromatography (ethylacetate:n-hexane=1:2) afforded the title compound as a yellow solid (40 mg, 14%).

$^1$H-NMR (300 MHz, CD$_3$OD) δ 1.17 (d, J=6.8 Hz, 6H, CH$_3$), 2.83 (sep, J=6.8 Hz, 1H, CH), 6.68~6.73 (m, 2H, ArH), 6.86 (d, J=7.3 Hz, 1H, ArH), 7.02 (d, J=6.8 Hz, 1H, ArH), 8.11 (d, J=8.1 Hz, 1H, ArH), 8.31 (d, J=8.1 Hz, 1H, ArH), 8.92 (s, 1H, ArH).

<Example 246> N-(1-Amino-4b-hydroxy-7-isopropyl-10-oxo-9b,10-dihydro-4bH-benzo[d]indeno[1,2-b]furan-9b-yl)-3-chloropicolinamide Fe (157 mg, 2.81 mmol) and 2 drops of conc. HCl were sequentially added to a solution of 3-chloro-N-(4b-hydroxy-7-isopropyl-1-nitro-10-oxo-9b,10-dihydro-4bH-benzo[d]indeno[1,2-b]furan-9b-yl)picolinamide (450 mg, 0.94 mmol) in an ethanol:H$_2$O (20 ml:2 ml) solvent and heated for 2.5 hrs under reflux. After vacuum concentration, purification by column chromatography (ethylacetate:n-hexane=1:2) afforded the title compound as a yellow solid (168 mg, 40%).

$^1$H-NMR (500 MHz, CD$_3$OD) δ 1.18 (dd, J=6.9 Hz, 2.2 Hz, 6H, CH$_3$), 2.83 (sep, J=6.9 Hz, 1H, CH), 6.67 (m, 2H, ArH), 6.85~6.86 (m, 1H, ArH), 7.02~7.03 (m, 1H, ArH), 7.44~7.51 (m, 3H, ArH), 7.93 (dd, J=8.1 Hz, 1.1 Hz, 1H, ArH), 8.51 (d, J=4.1 Hz, 1H, ArH).

<Example 247> N-(1-Amino-4b-hydroxy-7-isopropyl-10-oxo-9b,10-dihydro-4bH-benzo[d]indeno[1,2-b]furan-9b-yl)-4-methoxyquinoline-2-carboxamide Fe (140 mg, 2.51 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-4-methoxyquinoline-2-carboxamide (440 mg, 0.84 mmol) in an ethanol:H$_2$O (20 ml:2 ml) solvent and heated for 3 hrs under reflux. After vacuum concentration, purification by column chromatography (ethylacetate:n-hexane=1:3) afforded the title compound as a yellow solid (52 mg, 12%).

$^1$H-NMR (300 MHz, CD$_3$OD) δ 1.22 (d, J=6.9 Hz, 6H, CH$_3$), 2.87 (sep, J=6.9 Hz, 1H, CH), 4.11 (s, 3H, OCH$_3$), 6.72~6.74 (m, 2H, ArH), 6.90~6.93 (m, 1H, ArH), 7.03~7.06 (m, 1H, ArH), 7.45~7.55 (m, 3H, ArH), 7.61 (t, J=7.8 Hz, 1H, ArH), 7.77 (t, J=7.8 Hz, 1H, ArH), 8.05 (d, J=8.1 Hz, 1H, ArH), 8.24 (d, J=7.8 Hz, 1H, ArH).

<Example 248> N-(1-Amino-4b-hydroxy-7-isopropyl-10-oxo-9b,10-dihydro-4bH-indeno[1,2-b]benzofuran-9b-yl)isoquinoline-3-carboxamide Fe powder (0.16 g, 2.92 mmol), conc. HCl (0.04 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)isoquinoline-3-carboxamide (0.20 g, 0.40 mmol) in absolute ethanol (10 ml), and heated for 2 hrs under reflux. The reaction mixture was washed with ethylacetate, and filtered to remove Fe powder. The filtrate was alkalified with NaHCO$_3$, and washed many times with water. The organic layer was dried and filtered. This filtrate was purified for 30 min by column chromatography (ethylacetate:hexane=1:4) packed with Et$_3$N-treated silica gel to afford the title compound. 90 mg (50%).

$^1$H-NMR (300 MHz, CD$_3$OD) b 1.20 (d, J=6.9 Hz, 6H, CH$_3$) 2.81-2.88 (sept, 1H, CH) 6.70-6.80 (m, 2H, ArH) 6.85-6.90 (m, 1H, ArH) 7.07-7.10 (m, 1H, ArH) 7.45-7.52 (m, 2H, ArH) 7.77-7.87 (m, 2H, ArH) 8.05 (d, J=7.5 Hz, 1H, ArH) 8.17 (d, J=8.1 Hz, 1H, ArH) 8.43 (s, 1H, ArH) 9.27 (s, 1H, ArH).

<Example 249> N-(1-Amino-4b-hydroxy-7-isopropyl-10-oxo-9b,10-dihydro-4bH-indeno[1,2-b]benzofuran-9b-yl)-2-methylisonicotinamide Fe powder (0.17 g, 3.17 mmol), conc. HCl (0.04 ml) and water (1 ml) were added in that order to a solution of N-(4b-hydroxy-7-isopropyl-1-nitro-10-oxo-9b,10-dihydro-4bH-benzo[d]indeno[1,2-b]furan-9b-yl)-2-methylisonicotinamide (0.20 g, 0.43 mmol) in absolute ethanol (10 ml), and heated for 2 hrs under reflux. The reaction mixture was washed with ethylacetate, and filtered to remove Fe powder. The filtrate was alkalified with NaHCO$_3$, and washed many times with water. The organic layer was dried and filtered. The filtrate was purified for 30 min by column chromatography (ethylacetate:hexane=1:2) packed with Et$_3$N-treated silica gel to afford the title compound. 0.13 g (72%).

$^1$H-NMR (300 MHz, CD$_3$OD) b 1.17 (d, J=6.9 Hz, 6H, CH$_3$) 2.56 (s, 3H, CH$_3$) 6.67-6.70 (m, 2H, ArH) 6.87 (d, J=6.9 Hz, 1H, ArH) 7.01 (d, J=6.3 Hz, 1H, ArH) 7.42-7.44 (m, 2H, ArH) 7.58 (d, J=5.1 Hz, 1H, ArH) 7.67 (s, 1H, ArH) 8.49 (d, J=5.1 Hz, 1H, ArH).

<Example 250> N-(1-Amino-4b-hydroxy-7-isopropyl-10-oxo-9b,10-dihydro-4bH-indeno[1,2-b]benzofuran-9b-yl)-3-fluoroisonicotinamide Fe powder (0.26 g, 4.72 mmol), conc. HCl (0.04 ml), and water (1 ml) were added in that order to a solution of 3-fluoro-N-(4b-hydroxy-7-isopropyl-1-nitro-10-oxo-9b,10-dihydro-4bH-benzo[d]indeno[1,2-b]furan-9b-yl)isonicotinamide (0.30 g, 0.64 mmol) in absolute ethanol (10 ml), and heated for 2 hrs under reflux. The reaction mixture was washed with ethylacetate, and filtered to remove Fe powder. The filtrate was alkalified with NaHCO$_3$, and washed many times with water. The organic layer was dried and filtered, followed by purification for 30 min by column chromatography (ethylacetate:hexane=1:2) packed with Et$_3$N-treated silica gel to afford the title compound. 0.16 g (84%).

$^1$H-NMR (300 MHz, CD$_3$OD) δ 1.16 (d, J=6.9 Hz, 6H, CH$_3$) 2.80-2.84 (m, 1H, CH) 6.67-6.72 (m, 2H, ArH) 6.86 (d, J=5.7 Hz, 1H, ArH) 7.02 (d, J=6.3 Hz, 1H, ArH) 7.43-7.46 (m, 2H, ArH) 7.66 (t, J=5.1 Hz, 1H, ArH) 8.46 (d, J=4.5 Hz, 1H, ArH) 8.56 (s, 1H, ArH).

<Example 251> N-(1-Amino-4b-hydroxy-7-isopropyl-10-oxo-9b,10-dihydro-4bH-indeno[1,2-b]benzofuran-9b-yl)-3-chloroisonicotinamide Fe powder (0.16 g, 3.04 mmol), conc. HCl (0.04 ml), and water (1 ml) were added in that order to a solution of 3-chloro-N-(4b-hydroxy-7-isopropyl-1-nitro-10-oxo-9b,10-dihydro-4bH-benzo[d]indeno[1,2-b]furan-9b-yl)isonicotinamide (0.20 g, 0.41 mmol) in absolute ethanol (10 ml), and heated for 2 hrs under reflux. The reaction mixture was washed with ethylacetate, and filtered to remove Fe powder. The filtrate was alkalified with NaHCO₃, and washed many times with water. The organic layer was dried and filtered, followed by purification for 30 min by column chromatography (ethylacetate:hexane=1:2) packed with Et₃N-treated silica gel to afford the title compound. 0.15 g (83%).

$^1$H-NMR (300 MHz, CD₃OD) δ 1.16 (d, J=6.6 Hz, 6H, CH₃) 2.77-2.86 (m, 1H, CH) 6.66-6.71 (m, 2H, NH, ArH) 6.84 (d, J=7.5 Hz, 1H, ArH) 7.03 (d, J=6.9 Hz, 1H, ArH) 7.41-7.49 (m, 2H, ArH) 7.57 (d, J=4.8 Hz, 1H, ArH) 8.52 (d, J=4.8 Hz, 1H, ArH) 8.62 (s, 1H, ArH).

<Example 252> N-(1-Amino-4b-hydroxy-7-isopropyl-10-oxo-9b,10-dihydro-4bH-indeno[1,2-b]benzofuran-9b-yl)-1-methyl-1H-imidazole-2-carboxamide Fe powder (0.10 g, 1.95 mmol), conc. HCl (0.04 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)-1-methyl-1H-imidazole-2-carboxamide (0.12 g, 0.26 mmol) in absolute ethanol (10 ml), and heated for 2 hrs under reflux. The reaction mixture was washed with ethylacetate, and filtered to remove Fe powder. The filtrate was alkalified with NaHCO₃, and washed many times with water. The organic layer was dried and filtered, followed by purification for 30 min by column chromatography (ethylacetate:hexane=1:2) packed with Et₃N-treated silica gel to afford the title compound. 20 mg (18%).

$^1$H-NMR (300 MHz, CD₃OD) δ 1.18 (d, J=6.9 Hz, 6H, CH₃) 2.79-2.87 (m, 1H, CH) 3.89 (m, 3H, CH₃) 6.67 (s, 1H, ArH) 6.73 (d, J=6.3 Hz, 1H, ArH) 6.86 (d, J=7.1 Hz, 1H, ArH) 7.00-7.02 (m, 2H, ArH) 7.20 (s, 1H, ArH) 7.39-7.48 (m, 2H, ArH).

<Example 253> 2-((1-Amino-4b-hydroxy-7-isopropyl-10-oxo-9b,10-dihydro-4bH-indeno[1,2-b]benzofuran-9b-yl)carbamoyl)pyridine 1-oxide Fe (109 mg, 1.95 mmol) and 2 drops of conc. HCl were sequentially added to a solution of 2-((4b-hydroxy-7-isopropyl-1-nitro-10-oxo-9b,10-dihydro-4bH-indeno[1,2-b]benzofuran-9b-yl)carbamoyl)pyridine 1-oxide (300 mg, 0.65 mmol) in an ethanol:H₂O (20 ml:2 ml) solvent and heated for 2 hrs under reflux. After vacuum concentration, purification by column chromatography (EtOAc:hexane=2:1) afforded the title compound as a yellow solid (110 mg, 39%).

$^1$H-NMR (300 MHz, CD₃OD) δ 1.19 (d, J=6.9 Hz, 6H, CH₃), 2.84 (sep, J=6.9 Hz, 1H, CH), 6.68~6.76 (m, 2H, ArH), 6.87 (d, J=7.4 Hz, 1H, ArH), 7.02 (d, J=7.2 Hz, 1H, ArH), 7.39~7.50 (m, 2H, ArH), 7.62~7.64 (m, 2H, ArH), 8.20~8.23 (m, 1H, ArH), 8.39~8.40 (m, 1H, ArH).

<Example 254> N-(1-Amino-4b-hydroxy-7-isopropyl-10-oxo-9b,10-dihydro-4bH-indeno[1,2-b]benzofuran-9b-yl)-4-chloronicotinamide Fe (24 mg, 0.44 mmol) and 2 drops of conc. HCl were sequentially added to a solution of 4-chloro-N-(4b-hydroxy-7-isopropyl-1-nitro-10-oxo-9b,10-dihydro-4bH-indeno[1,2-b]benzofuran-9b-yl)nicotinamide (70 mg, 0.15 mmol) in an ethanol:H₂O (20 ml:2 ml) solvent and heated for 2 hrs under reflux. After vacuum concentration, purification by column chromatography (10% MeOH in CH₂Cl) afforded the title compound as a yellow solid (50 mg, 74%).

$^1$H-NMR (300 MHz, CD₃OD) δ 1.18 (d, J=6.8 Hz, 6H, CH₃), 2.83 (sep, J=6.8 Hz, 1H, CH), 6.56 (d, J=7.2 Hz, 1H, ArH), 6.66~6.68 (m, 2H, ArH), 6.86 (d, J=7.7 Hz, 1H, ArH), 7.00 (d, J=7.1 Hz, 1H, ArH), 7.40~7.46 (m, 2H, ArH), 7.77 (d, J=7.1 Hz, 1H, ArH), 8.40 (s, 1H, ArH).

<Example 255> N-(1-Amino-4b-hydroxy-7-isopropyl-10-oxo-9b,10-dihydro-4bH-indeno[1,2-b]benzofuran-9b-yl)-5-fluoronicotinamide Fe (72 mg, 1.29 mmol) and 2 drops of conc. HCl were sequentially added to a solution of 5-fluoro-N-(4b-hydroxy-7-isopropyl-1-nitro-10-oxo-9b,10-dihydro-4bH-indeno[1,2-b]benzofuran-9b-yl)nicotinamide (200 mg, 0.43 mmol) in an ethanol:H₂O (20 ml:2 ml) solvent, and heated for 4 hrs under reflux. After vacuum concentration, purification by column chromatography (EtOAc:hexane=2:1) afforded the title compound as a yellow solid (50 mg, 27%).

$^1$H-NMR (300 MHz, CD₃OD) δ 1.18 (d, J=6.8 Hz, 6H, CH₃), 2.84 (sep, J=6.8 Hz, 1H, CH), 6.67~6.71 (m, 2H, ArH), 6.88 (d, J=7.9 Hz, 1H, ArH), 7.01 (d, J=7.3 Hz, 1H, ArH), 7.42~7.45 (m, 2H, ArH), 8.03 (d, J=8.7 Hz, 1H, ArH), 8.60 (s, 1H, ArH), 8.86 (s, 1H, ArH).

<Example 256> N-(1-Amino-4b-hydroxy-7-isopropyl-10-oxo-9b,10-dihydro-4bH-indeno[1,2-b]benzofuran-9b-yl)-5-hydroxynicotinamide A solution of 5-hydroxy-N-(4b-hydroxy-7-isopropyl-1-nitro-10-oxo-9b,10-dihydro-4bH-indeno[1,2-b]benzofuran-9b-yl)nicotinamide (50 mg, 0.11 mmol) in methanol (5 ml) was mixed with 20 wt % ammonium sulfide (0.2 ml), and heated for 3.5 hrs under reflux. After removal of the solvent, the reaction mixture was extracted with CH₂Cl₂, dehydrated with Na₂SO₄, filtered, and concentrated. Purification by column chromatography (3% MeOH in CH₂Cl₂) afforded the title compound as a yellow solid (168 mg, 40%).

$^1$H-NMR (300 MHz, CD₃OD) δ 1.18 (d, J=6.8 Hz, 6H, CH₃), 2.84 (sep, J=6.8 Hz, 1H, CH), 6.66~6.71 (m, 2H, ArH), 6.88 (d, J=7.9 Hz, 1H, ArH), 7.00 (d, J=7.5 Hz, 1H, ArH), 8.05 (br, 1H, ArH), 8.24 (br, 1H, ArH).

<Example 257> N-(1-Amino-4b-hydroxy-7-isopropyl-10-oxo-9b,10-dihydro-4bH-indeno[1,2-b]benzofuran-9b-yl)-3-hydroxypicolinamide A solution of 3-hydroxy-N-(4b-hydroxy-7-isopropyl-1-nitro-10-oxo-9b,10-dihydro-4bH-indeno[1,2-b]benzofuran-9b-yl)picolinamide (190 mg, 0.41 mmol) in methanol (5 ml) was mixed with 20 wt % ammonium sulfide (0.2 ml), and heated for 2 hrs under reflux. After removal of the solvent, the reaction mixture was extracted with CH₂Cl₂, dehydrated with Na₂SO₄, filtered, and concentrated. Purification by column chromatography (EtOAc:hexane=1:1) afforded the title compound as a yellow solid (47 mg, 27%).

$^1$H-NMR (300 MHz, CD₃OD) δ 1.16 (d, J=6.9 Hz, 6H, CH₃), 2.79 (sep, J=6.9 Hz, 1H, CH), 6.50~6.74 (m, 2H, ArH), 6.80 (d, J=7.8 Hz, 1H, ArH), 7.00~7.02 (m, 1H, ArH), 7.33~7.55 (m, 2H, ArH).

<Example 258> N-(1-Amino-4b-hydroxy-7-isopropyl-10-oxo-9b,10-dihydro-4bH-indeno[1,2-b]benzofuran-9b-yl)-4-methylnicotinamide Fe powder (0.17 g, 3.17 mmol), conc. HCl (0.01 ml), and water (1 ml) were added in that order to a solution of N-(4b-hydroxy-7-isopropyl-1-nitro-10-oxo-9b,10-dihydro- 4bH-indeno[1,2-b]benzofuran-9b-yl)-4-methylnicotinamide (0.20 g, 0.43 mmol) in absolute ethanol (10 ml), and heated for 2 hrs under reflux. The reaction mixture was washed with ethylacetate, and filtered to remove Fe powder. The filtrate was alkalified with $NaHCO_3$, and washed many times with water. The organic layer was dried and filtered, followed by purification for 30 min by column chromatography (ethylacetate:hexane=1:4) packed with $Et_3N$-treated silica gel to afford the title compound. 0.11 g (53%).

$^1$H-NMR (300 MHz, $CD_3OD$) δ 1.17 (d, J=6.9 Hz, 6H, $CH_3$) 2.49 (s, 3H, $CH_3$) 2.77-2.87 (sept, 1H, CH) 6.66-6.80 (m, 2H, ArH) 6.85 (d, J=7.5 Hz, 1H, ArH) 7.04 (d, J=6.9 Hz, 1H, ArH) 7.32 (d, J=5.1 Hz, 1H, ArH) 7.44-7.49 (m, 2H, ArH) 8.41 (d, J=5.4 Hz, 1H, ArH) 8.63 (s, 1H, ArH).

<Example 259> N-(1-Amino-4b-hydroxy-7-isopropyl-10-oxo-9b,10-dihydro-4bH-indeno[1,2-b]benzofuran-9b-yl)-5-methylnicotinamide Fe powder (0.23 g, 4.28 mmol), conc. HCl (0.04 ml), and water (1 ml) were added in that order to a solution of N-(4b-hydroxy-7-isopropyl-1-nitro-10-oxo-9b,10-dihydro-4bH-indeno[1,2-b]benzofuran-9b-yl)-5-methylnicotinamide (0.27 g, 0.58 mmol) in absolute ethanol (10 ml), and heated for 2 hrs under reflux. The reaction mixture was washed with ethylacetate, and filtered to remove Fe powder. The filtrate was alkalified with $NaHCO_3$, and washed many times with water. The organic layer was dried and filtered, followed by purification for 30 min by column chromatography (ethylacetate:hexane=1:4) packed with $Et_3N$-treated silica gel to afford the title compound. 0.13 g (52%).

$^1$H-NMR (300 MHz, $CD_3OD$) δ 1.17 (d, J=6.9 Hz, 6H, $CH_3$) 2.37 (s, 3H, $CH_3$) 2.78-2.87 (sept, 1H, CH) 6.67-6.74 (m, 2H, ArH) 6.86 (d, J=7.8 Hz, 1H, ArH) 7.03 (d, J=7.2 Hz, 1H, ArH) 7.40-7.48 (m, 2H, ArH) 8.07 (s, 1H, ArH) 8.49 (s, 1H, ArH) 8.79 (s, 1H, ArH).

<Example 260> N-(1-Amino-4b-hydroxy-7,8-dimethyl-10-oxo-9b,10-dihydro-4bH-indeno[1,2-b]benzofuran-9b-yl)nicotinamide Fe powder (0.15 g, 2.70 mmol), conc. HCl (0.04 ml) and water (1 ml) were added in that order to a solution of N-(4b-hydroxy-7,8-dimethyl-1-nitro-10-oxo-9b,10-dihydro-4bH-indeno[1,2-b]benzofuran-9b-yl)nicotinamide (0.15 g, 0.34 mmol) in absolute ethanol (10 ml), and heated for 2 hrs under reflux.

The reaction mixture was washed with ethylacetate, and filtered to remove Fe powder. The filtrate was alkalified with $NaHCO_3$, and washed many times with water. The organic layer was dried and filtered, followed by purification for 30 min by column chromatography (ethylacetate:hexane=2:1) packed with $Et_3N$-treated silica gel to afford the title compound. 70 mg (50%).

$^1$H-NMR (300 MHz, $CD_3OD$) δ 1.17 (d, J=6.9 Hz, 6H, $CH_3$) 2.56 (s, 3H, $CH_3$) 6.67-6.70 (m, 2H, ArH) 6.87 (d, J=6.9 Hz, 1H, ArH) 7.01 (d, J=6.3 Hz, 1H, ArH) 7.42-7.44 (m, 2H, ArH) 7.58 (d, J=5.1 Hz, 1H, ArH) 7.67 (s, 1H, ArH) 8.49 (d, J=5.1 Hz, 1H, ArH).

<Example 261> N-(1-Amino-4b-hydroxy-7-isopropyl-10-oxo-9b,10-dihydro-4bH-indeno[1,2-b]benzofuran-9b-yl)-5-methoxynicotinamide Fe powder (0.12 g, 2.30 mmol), conc. HCl (0.03 ml), and water (1 ml) were added in that order to a solution of N-(4b-hydroxy-7-isopropyl-1-nitro-10-oxo-9b,10-dihydro-4bH-indeno[1,2-b]benzofuran-9b-yl)-5-methoxynicotinamide (0.15 g, 0.31 mmol) in absolute ethanol (10 ml), and heated for 2 hrs under reflux. The reaction mixture was washed with ethylacetate, and filtered to remove Fe powder. The filtrate was alkalified with $NaHCO_3$, and washed many times with water. The organic layer was dried and filtered, followed by purification for 30 min by column chromatography (ethylacetate:hexane=1:1) packed with $Et_3N$-treated silica gel to afford the title compound. 80 mg (57%).

$^1$H-NMR (300 MHz, $CD_3OD$) δ 1.18 (d, J=6.6 Hz, 6H, $CH_3$) 2.81-2.86 (sept, 1H, CH) 3.89 (s, 3H, OMe) 6.67-6.70 (m, 2H, ArH) 6.88 (d, J=7.2 Hz, 1H, ArH) 7.01 (d, J=6.6 Hz, 1H, ArH) 7.43-7.45 (m, 2H, ArH) 7.82 (s, 1H, ArH) 8.34 (s, 1H, ArH) 8.58 (s, 1H, ArH).

<Example 262> N-(1-Amino-4b-hydroxy-7,8-dimethyl-10-oxo-9b,10-dihydro-4bH-indeno[1,2-b]benzofuran-9b-yl)quinoline-6-carboxamide Fe powder (0.16 g, 3.03 mmol), conc. HCl (0.04 ml), and water (1 ml) were added in that order to a solution of N-(4b-hydroxy-7,8-dimethyl-1-nitro-10-oxo-9b,10-dihydro-4bH-indeno[1,2-b]benzofuran-9b-yl)quinoline-6-carboxamide (0.20 g, 0.41 mmol) in absolute ethanol (10 ml), and heated for 2 hrs under reflux. The reaction mixture was washed with ethylacetate, and filtered to remove Fe powder. The filtrate was alkalified with $NaHCO_3$, and washed many times with water. The organic layer was dried and filtered, followed by purification for 30 min by column chromatography (ethylacetate:hexane=2:1) packed with $Et_3N$-treated silica gel to afford the title compound. 0.16 g (86%).

$^1$H-NMR (300 MHz, $CD_3OD$) δ 2.22 (d, J=8.4 Hz, 6H, $CH_3$) 6.61 (s, 1H, ArH) 6.70 (d, J=8.1 Hz, 1H, ArH) 7.01 (d, J=6.6 Hz, 1H, ArH) 7.34 (s, 1H, ArH) 7.46-7.48 (m, 1H, ArH) 7.78-7.79 (m, 1H, ArH) 8.10-8.14 (m, 1H, ArH) 8.20-8.28 (m, 1H, ArH) 8.62 (s, 1H, ArH) 8.74 (d, J=6.9 Hz, 1H, ArH).

<Example 263> N-(1-Amino-4b-hydroxy-7-isopropyl-10-oxo-9b,10-dihydro-4bH-benzo[d]indeno[1,2-b]furan-9b-ylquinoline-2-carboxamide Fe (135 mg, 2.42 mmol and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-ylquinoline-2-carboxamide (400 mg, 0.81 mmol in an ethanol:$H_2O$ (20 ml:2 ml solvent and heated for 1.5 hrs under reflux. After vacuum concentration, purification by column chromatography (EtOAc:hexane=1:2) afforded the title compound as a yellow solid (132 mg, 35%).

$^1$H-NMR (300 MHz, $CD_3OD$) δ 1.21 (d, J=6.8 Hz, 6H, $CH_3$), 2.87 (sep, J=6.8 Hz, 1H, CH), 6.70~6.73 (m, 2H, ArH), 6.92 (d, J=7.9 Hz, 1H, ArH), 7.03 (d, J=7.3 Hz, 1H, ArH), 7.44~7.51 (m, 2H, ArH), 7.66 (t, J=7.6 Hz, 1H, ArH), 7.80 (t, J=7.3 Hz, 1H, ArH), 7.97 (d, J=8.1 Hz, 1H, ArH), 8.07~8.13 (m, 2H, ArH), 8.44 (d, J=8.4 Hz, 1H, ArH).

<Example 264> N-(1-Amino-4b-hydroxy-7-isopropyl-10-oxo-9b,10-dihydro-4bH-benzo[d]indeno[1,2-b]furan-9b-yl-3-bromobenzo[b]thiophene-2-carboxamide Fe (87 mg, 1.56 mmol and 2 drops of conc. HCl were sequentially added to a solution of 3-bromo-N-(4b-hydroxy-7-isopropyl-1-nitro-10-oxo-9b,10-dihydro-4bH-benzo[d]indeno[1,2-b]furan-9b-yl)benzo[b]thiophene-2-carboxamide (250 mg, 0.52 mmol in an ethanol:H₂O (20 ml:2 ml solvent and heated for 2 hrs under reflux. After vacuum concentration, purification by column chromatography (EtOAc:hexane=1:4) afforded the title compound as a yellow solid (130 mg, 46%).

$^1$H-NMR (300 MHz, CD$_3$OD) δ 1.19 (d, J=6.9 Hz, 6H, CH$_3$), 2.85 (sep, J=6.9 Hz, 1H, CH), 6.66~6.80 (m, 2H, ArH), 6.89~6.92 (m, 1H, ArH), 7.01~7.05 (m, 1H, ArH), 7.46~7.55 (m, 4H, ArH), 7.88~7.93 (m, 2H, ArH).

<Example 265> N-(1-Amino-4b-hydroxy-7-isopropyl-10-oxo-9b,10-dihydro-4bH-benzo[d]indeno[1,2-b]furan-9b-yl-1H-indole-2-carboxamide Fe (35 mg, 0.62 mmol and 2 drops of con. HCl were sequentially added to a solution of N-(4b-hydroxy-7-isopropyl-1-nitro-10-oxo-9b,10-dihydro-4bH-benzo[d]indeno[1,2-b]furan-9b-yl)-1H-indole-2-carboxamide (100 mg, 0.21 mmol) in an ethanol:H₂O (15 ml:1 ml) solvent and heated for 4 hrs under reflux. After vacuum concentration, purification by column chromatography (EtOAc:hexane=1:3) afforded the title compound as a yellow solid (80 mg, 84%).

$^1$H-NMR (300 MHz, CD$_3$OD) δ 1.19 (d, J=6.8 Hz, 6H, CH$_3$), 2.84 (sep, J=6.8 Hz, 1H, CH), 6.69~6.80 (m, 2H, ArH), 6.88 (d, J=8.1 Hz, 1H, ArH), 7.02~7.07 (m, 2H, ArH), 7.18~7.23 (m, 2H, ArH), 7.37~7.50 (m, 3H, ArH), 7.59 (d, J=8.0 Hz, 1H, ArH).

<Example 266> N-(1-Amino-4b-hydroxy-7-isopropyl-10-oxo-9b,10-dihydro-4bH-benzo[d]indeno[1,2-b]furan-9b-yl)isoquinoline-1-carboxamide Fe (68 mg, 1.21 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)isoquinoline-1-carboxamide (200 mg, 0.40 mmol) in an ethanol:H₂O (20 ml:2 ml) solvent and heated for 3.5 hrs under reflux. After vacuum concentration, purification by column chromatography (EtOAc:hexane=1:4) afforded the title compound as a yellow solid (155 mg, 81%).

$^1$H-NMR (300 MHz, CD$_3$OD) δ 1.14 (dd, J=6.9 Hz, 1.5 Hz, 6H, CH$_3$), 2.80 (sep, J=6.9 Hz, 1H, CH), 6.67 (s, 1H, ArH), 6.70 (d, J=8.3 Hz, 1H, ArH), 6.85 (dd, J=8.0 Hz, 1.0 Hz, 1H, ArH), 7.05 (d, J=7.1 Hz, 1H, ArH), 7.43~7.50 (m, 2H, ArH), 7.64 (t, J=7.5 Hz, 1H, ArH), 7.73 (t, J=8.0 Hz, 1H, ArH), 7.87~7.92 (m, 2H, ArH), 8.44 (d, J=5.6 Hz, 1H, ArH), 8.94 (d, J=8.4 Hz, 1H, ArH).

<Example 267> N-(1-Amino-4b-hydroxy-7-isopropyl-10-oxo-9b,10-dihydro-4bH-indeno[1,2-b]benzofuran-9b-yl)-6-fluoro-4-methoxyquinoline-3-carboxamide Fe powder (46.2 mg, 0.82 mmoles) and 5 drops of conc. HCl were sequentially added to a solution of 6-fluoro-N-(4b-hydroxy-7-isopropyl-1-nitro-10-oxo-9b,10-dihydro-4bH-benzo[d]indeno[1,2-b]furan-9b-yl)-4-methoxyquinoline-3-carboxamide (0.15 g, 0.28 mmoles) in an ethanol:water (10:1, 10 mL:1 mL) solvent, and heated for 3 hrs under reflux. The reaction mixture was washed with ethylacetate, and hot filtered to remove Fe powder. The filtrate was extracted ethylacetate and water, followed by separation and purification by column chromatography to afford the title compound. 15 mg (11%).

$^1$H-NMR (300 MHz, CD$_3$OD): δ 1.21 (d, J=6.9 Hz, 6H, CH$_3$) 2.87 (sept, J=6.9 Hz, 1H, CH) 3.85 (s, 3H, OCH$_3$) 6.69 (s, 2H, ArH) 6.82 (d, J=7.2 Hz, 1H, ArH) 6.90 (d, J=7.8 Hz, 1H, ArH) 7.44-7.46 (m, 2H, ArH) 7.56 (br, 1H, ArH) 7.66 (br, 1H, ArH) 8.0 (m, 1H, ArH) 8.67 (s, 1H, ArH).

<Example 268> N-(1-Amino-4b-hydroxy-7-isopropyl-10-oxo-9b,10-dihydro-4bH-indeno[1,2-b]benzofuran-9b-yl)-1-methyl-1H-indole-2-carboxamide Fe powder (0.12 g, 2.20 mmol), conc.HCl (0.03 ml), and water (1 ml) were added in that order to a solution of N-(4b-hydroxy-7-isopropyl-1-nitro-10-oxo-9b,10-dihydro-4bH-benzo[d]indeno[1,2-b]furan-9b-yl)-1-methyl-1H-indole-2-carboxamide (0.15 g, 0.31 mmol) in absolute ethanol (10 ml), and heated for 2 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (ethylacetate:hexane=1:2) packed with Et$_3$N-treated silica gel to afford the title compound. 50 mg (35%).

$^1$H-NMR (300 MHz, CD$_3$OD) δ 1.18 (d, J=6.9 Hz, 6H, CH$_3$) 2.82-2.86 (sept, 1H, CH) 3.89 (s, 3H, CH$_3$) 6.68 (s, 1H, ArH) 6.87-6.88 (m, 1H, ArH) 7.03-7.13 (m, 2H, ArH) 7.18 (s, 1H, ArH) 7.24-7.29 (m, 2H, ArH) 7.39-7.47 (m, 3H, ArH) 7.60 (d, J=7.8 Hz, 1H, ArH).

<Example 269> N-(1-Amino-4b-hydroxy-7-isopropyl-10-oxo-9b,10-dihydro-4bH-indeno[1,2-b]benzofuran-9b-yl)-3-chloro-6-fluorobenzo[b]thiophene-2-carboxamide Fe powder (0.05 g, 1.05 mmol), conc.HCl (0.02 ml), and water (0.5 ml) were added in that order to a solution of 3-chloro-6-fluoro-N-(4b-hydroxy-7-isopropyl-1-nitro-10-oxo-9b,10-dihydro-4bH-benzo[d]indeno[1,2-b]furan-9b-yl)benzo[b]thiophene-2-carboxamide (80 mg, 0.14 mmol) in an absolute ethanol (5 ml), and heated for 2 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (ethylacetate:hexane=1:4) packed with Et$_3$N-treated silica gel to afford the title compound. 50 mg (68%).

$^1$H-NMR (300 MHz, CD$_3$OD) δ 1.15 (d, J=6.6 Hz, 6H, CH$_3$) 2.76-2.85 (sept, 1H, CH) 6.69 (s, 1H, ArH) 6.75 (d, J=6.6 Hz, 1H, ArH) 6.84 (d, J=7.5 Hz, 1H, ArH) 7.03 (d, J=7.2 Hz, 1H, ArH) 7.28 (t, J=7.2 Hz, 1H, ArH) 7.43-7.48 (m, 2H, ArH) 7.66 (d, J=8.7 Hz, 1H, ArH) 7.83-7.88 (m, 1H, ArH).

<Example 270> N-(1-Amino-4b-hydroxy-7-isopropyl-10-oxo-9b,10-dihydro-4bH-indeno[1,2-b]benzofuran-9b-yl)-3-chloro-6-methylbenzo[b]thiophene-2-carboxamide Fe powder (0.11 g, 1.97 mmol), conc. HCl (0.05 ml), and water (1 ml) were added in that order to a solution of 3-chloro-N-(4b-hydroxy-7-isopropyl-1-nitro-10-oxo-9b,10-dihydro-4bH-benzo[d]indeno[1,2-b]furan-9b-yl)-6-methyl-benzo[b]thiophene-2-carboxamide (0.15 g, 0.27 mmol) in absolute ethanol (10 ml), and heated for 2 hrs under reflux. The reaction mixture was washed with ethylacetate, and filtered to remove Fe powder. The filtrate was alkalified with NaHCO$_3$, and washed many times with water. The organic layer was dried and filtered, followed by purification for 30 min by column chromatography (ethylacetate:hexane=1:4) packed with Et₃N-treated silica gel to afford the title compound. 21 mg (15%).

¹H-NMR (300 MHz, CD₃OD) δ 1.16-1.18 (m, 6H, CH₃) 2.45 (s, 3H, CH₃) 2.80-2.86 (sept, 1H, CH) 6.70 (s, 1H, ArH) 6.72-6.80 (m, 1H, ArH) 6.84-6.95 (m, 1H, ArH) 7.00-7.05 (m, 1H, ArH) 7.33 (d, J=8.1 Hz, 1H, ArH) 7.37-7.52 (m, 2H, ArH) 7.66 (s, 1H, ArH) 7.75 (d, J=8.1 Hz, 1H, ArH).

<Example 271> N-(1-Amino-4b-hydroxy-7-isopropyl-10-oxo-9b,10-dihydro-4bH-indeno[1,2-b]benzofuran-9b-yl)-1,3-dimethyl-1H-pyrazolo[3,4-b]pyridine-5-carboxamide Fe powder (137 mg, 2.45 mmol), conc. HCl (0.02 ml), and water (1 mL) were added in that order to a solution of N-(4b-hydroxy-7-isopropyl-1-nitro-10-oxo-9b,10-dihydro-4bH-indeno[1,2-b]benzofuran-9b-yl)-1,3-dimethyl-1H-pyrazolo[3,4-b]pyridine-5-carboxamide (180 mg, 0.35 mmol) in absolute ethanol (10 mL), and heated for 3 hrs under reflux. The reaction mixture was washed with ethylacetate, and hot filtered to remove Fe powder. The filtrate was alkalified with NaHCO₃, and washed many times with water. The organic layer was dried and filtered, followed by purification by column chromatography (ethylacetate:hexane=1:1) packed with Et₃N-treated silica gel to afford the title compound (25 mg, 16%).

¹H-NMR (300 MHz, CD₃OD) δ 1.15 (d, J=6.9 Hz, 6H), 2.54 (s, 3H), 2.80-2.89 (m, 1H), 4.03 (s, 3H), 6.68-6.71 (m, 2H), 6.88 (d, J=7.6 Hz, 1H), 7.02 (d, J=7.3 Hz, 1H), 7.42-7.50 (m, 2H), 8.71 (s, 1H), 8.94 (s, 1H).

<Example 272> N-(1-Amino-4b-hydroxy-7-isopropyl-10-oxo-9b,10-dihydro-4bH-indeno[1,2-b]benzofuran-9b-yl)imidazo[1,2-a]pyridine-6-carboxamide Fe (80 mg, 1.42 mmol) and 2 drops of conc. HCl were sequentially added to a solution of N-(4b-hydroxy-7-isopropyl-1-nitro-10-oxo-9b,10-dihydro-4bH-indeno[1,2-b]benzofuran-9b-yl)imidazo[1,2-a]pyridine-6-carboxamide (230 mg, 0.47 mmol) in an ethanol:H₂O (10 ml:1 ml) solvent, and heated for 4.5 hrs under reflux. After vacuum concentration, purification by column chromatography (5% methanol in methylene chloride) afforded the title compound as a brown solid (50 mg, 23%).

¹H-NMR (300 MHz, CD₃OD) δ 1.03-1.42 (m, 6H), 3.05-3.30 (m, 1H), 6.61-6.75 (m, 2H), 6.81-6.92 (m, 1H), 6.96-7.05 (m, 1H), 7.31-8.32 (m, 6H), 9.05-9.30 (m, 1H).

<Example 273> N-(1-Amino-4b-hydroxy-7-isopropyl-10-oxo-9b,10-dihydro-4bH-indeno[1,2-b]benzofuran-9b-yl)pyrazolo[1,5-a]pyrimidine-2-carboxamide Fe (97 mg, 1.73 mmol) and 2 drops of conc. HCl were sequentially added to a solution of N-(4b-hydroxy-7-isopropyl-1-nitro-10-oxo-9b,10-dihydro-4bH-indeno[1,2-b]benzofuran-9b-yl)pyrazolo[1,5-a]pyrimidine-2-carboxamide (280 mg, 0.58 mmol) in an ethanol:H₂O (20 ml:2 ml) solvent, and heated for 3.5 hrs under reflux. After vacuum concentration, purification by column chromatography (EtOAc:hexane=2:1) afforded the title compound as a yellow solid (80 mg, 30%).

¹H-NMR (300 MHz, CD₃OD) δ 1.17 (d, J=6.8 Hz, 6H, CH₃), 2.81 (sep, J=6.8 Hz, 1H, CH), 6.63~6.72 (m, 2H, ArH), 6.83~6.87 (m, 1H, ArH), 7.00~7.12 (m, 3H, ArH), 7.43~7.51 (m, 2H, ArH), 8.55~8.57 (m, 1H, ArH), 8.96 (d, J=7.3 Hz, 1H, ArH).

<Example 274> N-(1-Amino-4b-hydroxy-7-isopropyl-10-oxo-9b,10-dihydro-4bH-indeno[1,2-b]benzofuran-9b-yl)-3-methylbenzo[b]thiophene-2-carboxamide Fe powder (0.04 g, 0.85 mmol), conc. HCl (0.03 ml), and water (0.5 ml) were added in that order to a solution of N-(4b-hydroxy-7-isopropyl-1-nitro-10-oxo-9b,10-dihydro-4bH-indeno[1,2-b]benzofuran-9b-yl)-3-methylbenzo[b]thiophene-2-carboxamide (60 mg, 0.11 mmol) in absolute ethanol (5 ml), and heated for 2 hrs under reflux. The reaction mixture was washed with ethylacetate, and hot filtered to remove Fe powder. The filtrate was alkalified with NaHCO₃, and washed many times with water. The organic layer was dried and filtered, followed by purification for 30 min by column chromatography (ethylacetate:hexane=1:4) packed with Et₃N-treated silica gel to afford the title compound. 30 mg (53%).

¹H-NMR (300 MHz, CD₃OD) δ 1.00-1.27 (m, 6H), 2.53-2.64 (m, 3H), 2.70-2.84 (m, 1H), 6.54-6.87 (m, 3H), 6.96-7.10 (m, 1H), 7.25-7.52 (m, 4H), 7.69-7.86 (m, 2H).

<Example 275> N-(1-Amino-4b-hydroxy-7-isopropyl-10-oxo-9b,10-dihydro-4bH-indeno[1,2-b]benzofuran-9b-yl)quinoxaline-2-carboxamide Fe powder (0.16 g, 2.92 mmol), conc. HCl (0.03 ml) and water (1 ml) were added in that order to a solution of N-(4b-hydroxy-7-isopropyl-1-nitro-10-oxo-9b,10-dihydro-4bH-indeno[1,2-b]benzofuran-9b-yl)quinoxaline-2-carboxamide (0.20 g, 0.40 mmol) in absolute ethanol (10 ml), and heated for 2 hrs under reflux. The reaction mixture was washed with ethylacetate, and hot filtered to remove Fe powder. The filtrate was alkalified with NaHCO₃, and washed many times with water. The organic layer was dried and filtered, followed by purification for 30 min by column chromatography (ethylacetate:hexane=1:2) packed with Et₃N-treated silica gel to afford the title compound. 68 mg (37%).

¹H-NMR (300 MHz, CD₃OD) δ 1.21 (d, J=6.9 Hz, 6H, CH₃) 2.82-2.91 (sept, 1H, CH) 6.71 (s, 1H, ArH) 6.91 (d, J=7.5 Hz, 1H, ArH) 7.04 (d, J=7.2 Hz, 1H, ArH) 7.47-7.49 (m, 2H, ArH) 7.90-7.98 (m, 3H, ArH) 8.15-8.28 (m, 2H, ArH) 9.40 (s, 1H, ArH).

<Example 276> N-(1-Amino-4b-hydroxy-7-isopropyl-10-oxo-9b,10-dihydro-4bH-indeno[1,2-b]benzofuran-9b-yl)pyridazine-4-carboxamide Fe powder (0.03 g, 0.55 mmol), conc. HCl (0.01 ml), and water (0.5 ml) were added in that order to a solution of N-(4b-hydroxy-7-isopropyl-1-nitro-10-oxo-9b,10-dihydro-4bH-indeno[1,2-b]benzofuran-9b-yl)pyridazine-4-carboxamide (50 mg, 0.11 mmol) in absolute ethanol (5 ml), and heated for 2 hrs under reflux. The reaction mixture was washed with ethylacetate, and hot filtered to remove Fe powder. The filtrate was alkalified with NaHCO₃, and washed many times with water. The organic layer was dried and filtered, followed by purification for 30 min by column chromatography (ethylacetate:hexane=1:2) packed with Et₃N-treated silica gel to afford the title compound. 26 mg (56%).

¹H-NMR (300 MHz, CD₃OD) δ 1.17 (d, J=6.7 Hz, 6H, CH₃) 2.78-2.87 (sept, 1H, CH) 6.68-6.74 (m, 2H, ArH) 6.87 (d, J=7.5 Hz, 1H, ArH) 7.02 (d, J=7.2 Hz, 1H, ArH) 7.40-7.48 (m, 2H, ArH) 8.04 (s, 2H, ArH) 9.32 (d, J=5.0 Hz, 1H, ArH) 9.51 (s, 1H, ArH).

<Example 277> N-(1-Amino-4b-hydroxy-7-isopropyl-10-oxo-9b,10-dihydro-4bH-indeno[1,2-b]benzofuran-9b-yl)quinoxaline-6-carboxamide Fe powder (0.028 g, 0.50 mmol), conc. HCl (0.01 ml) and water (0.5 ml) were added in that order to a solution of N-(4b-hydroxy-7-isopropyl-1-nitro-10-oxo-9b,10-dihydro-4bH-indeno[1,2-b]benzofuran-9b-yl)quinoxaline-6-carboxamide (50 mg, 0.11 mmol) in absolute ethanol (5 ml), and heated for 2 hrs under reflux. The reaction mixture was washed with ethylacetate, and hot filtered to remove Fe powder. The filtrate was alkalified with NaHCO₃, and washed many times with water. The organic layer was dried and filtered, followed by purification for 30 min by column chromatography (ethylacetate 100%) packed with Et₃N-treated silica gel to afford the title compound. 38 mg (81%).

¹H-NMR (300 MHz, CD₃OD) δ 1.19 (d, J=6.8 Hz, 6H, CH₃) 2.83-2.89 (sept, 1H, CH) 6.75 (s, 1H, ArH) 6.96d, J=7.8 Hz, 1H, ArH) 7.47-7.54 (m, 3H, ArH) 8.08-8.24 (m, 3H, ArH) 8.63 (s, 1H, ArH) 8.93 (s, 1H, ArH).

<Example 278> N-(1-Amino-4b-hydroxy-7-isopropyl-10-oxo-9b,10-dihydro-4bH-indeno[1,2-b]benzofuran-9b-yl)tetrazolo[1,5-a]pyridine-6-carboxamide Fe (121 mg, 2.16 mmol) and 4 drops of conc. HCl were sequentially added to a solution of N-(4b-hydroxy-7-isopropyl-1-nitro-10-oxo-9b,10-dihydro-4bH-indeno[1,2-b]benzofuran-9b-yl)tetrazolo[1,5-a]pyridine-6-carboxamide (350 mg, 0.72 mmol) in an ethanol:H₂O (15 ml:1.5 ml) solvent, and heated for 2.5 hrs under reflux. After vacuum concentration, purification by column chromatography (EtOAc:hexane=2:1) afforded the title compound as a yellow solid (269 mg, 80%).

¹H-NMR (300 MHz, CD₃OD) δ 1.18 (d, J=6.9 Hz, 6H, CH₃), 2.85 (sep, J=6.9 Hz, 1H, CH), 6.69~6.71 (m, 2H, ArH), 6.90 (d, J=7.7 Hz, 1H, ArH), 7.02 (d, J=7.2 Hz, 1H, ArH), 7.43~7.46 (m, 2H, ArH), 8.07~8.18 (m, 2H, ArH), 9.65 (s, 1H, ArH).

<Example 279> N-(1-Amino-4b-hydroxy-7-isopropyl-10-oxo-9b,10-dihydro-4bH-indeno[1,2-b]benzofuran-9b-yl)tetrazolo[1,5-a]pyridine-8-carboxamide Fe (55 mg, 0.99 mmol) and 3 drops of conc. HCl were sequentially added to a solution of N-(4b-hydroxy-7-isopropyl-1-nitro-10-oxo-9b,10-dihydro-4bH-indeno[1,2-b]benzofuran-9b-yl)tetrazolo[1,5-a]pyridine-8-carboxamide (160 mg, 0.33 mmol) in an ethanol:H₂O (15 ml:1.5 ml), and heated for 2 hrs under reflux. After vacuum concentration, purification by column chromatography (EtOAc:hexane=2:1) afforded the title compound as a yellow solid (117 mg, 76%).

¹H-NMR (300 MHz, CD₃OD) δ 1.23 (d, J=6.9 Hz, 6H, CH₃), 2.89 (sep, J=6.9 Hz, 1H, CH), 6.70~6.74 (m, 2H, ArH), 6.95 (d, J=7.8 Hz, 1H, ArH), 7.02 (d, J=8.0 Hz, 1H, ArH), 7.44~7.55 (m, 3H, ArH), 8.41 (d, J=7.3 Hz, 1H, ArH), 9.29 (d, J=7.3 Hz, 1H, ArH).

<Example 280> N-(1-Amino-4b-hydroxy-7-isopropyl-10-oxo-9b,10-dihydro-4bH-indeno[1,2-b]benzofuran-9b-yl)-7-methylimidazo[1,2-a]pyridine-2-carboxamide Fe powder (0.27 g, 4.91 mmol), conc. HCl (0.04 ml) and water (1 ml) were added in that order to a solution of N-(4b-hydroxy-7-isopropyl-1-nitro-10-oxo-9b,10-dihydro-4bH-indeno[1,2-b]benzofuran-9b-yl)quinoxaline-6-carboxamide (0.49 g, 0.98 mmol) in absolute ethanol (10 ml). The reaction mixture was washed with ethylacetate, and hot filtered to remove Fe powder. The filtrate was alkalified with NaHCO₃, and washed many times with water. The organic layer was dried and filtered, followed by purification for 30 min by column chromatography (ethylacetate:hexane=1:1) packed with Et₃N-treated silica gel to afford the title compound. 80 mg (17%).

¹H-NMR (300 MHz, CDCl₃) δ 0.62-1.84 (m, 6H), 2.90-3.00 (m, 1H), 6.43-6.84 (m, 8H), 6.98-7.58 (m, 3H), 7.72-8.17 (m, 3H).

<Example 281> N-(1-Amino-4b-hydroxy-7-isopropyl-10-oxo-9b,10-dihydro-4bH-indeno[1,2-b]benzofuran-9b-yl)-7-methyl-[1,2,4]triazolo[1,5-a]pyrimidine-2-carboxamide Fe powder (0.23 g, 4.22 mmol), conc. HCl (0.04 ml), and water (1 ml) were added in that order to a solution of N-(4b-hydroxy-7-isopropyl-1-nitro-10-oxo-9b,10-dihydro-4bH-indeno[1,2-b]benzofuran-9b-yl)-7-methyl-[1,2,4]triazolo[1,5-a]pyrimidine-2-carboxamide (0.29 g, 0.57 mmol) in absolute ethanol (10 ml), and heated for 2 hrs under reflux. The reaction mixture was washed with ethylacetate, and hot filtered to remove Fe powder. The filtrate was alkalified with NaHCO₃, and washed many times with water. The organic layer was dried and filtered, followed by purification for 30 min by column chromatography (ethylacetate 100%) packed with Et₃N-treated silica gel to afford the title compound. 0.17 g (62%).

¹H-NMR (300 MHz, CD₃OD) δ 1.19 (d, J=6.9 Hz, 6H, CH₃) 2.82-2.85 (m, 4H, CH, CH₃) 6.67-6.74 (m, 2H, ArH) 6.87-6.94 (m, 1H, ArH) 7.00-7.04 (m, 1H, ArH) 7.30 (d, J=4.7 Hz, 1H, ArH) 7.44-7.51 (m, 2H, ArH) 8.81 (d, J=4.6 Hz, 1H, ArH).

<Example 282> N-(1-Amino-4b-hydroxy-7-isopropyl-10-oxo-9b,10-dihydro-4bH-indeno[1,2-b]benzofuran-9b-yl)-5,7-dimethylpyrazolo[1,5-a]pyrimidine-3-carboxamide Fe powder (0.06 g, 1.16 mmol), conc. HCl (0.04 ml), and water (0.5 ml) were added in that order to a solution of N-(4b-hydroxy-7-isopropyl-1-nitro-10-oxo-9b,10-dihydro-4bH-indeno[1,2-b]benzofuran-9b-yl)-5,7-dimethylpyrazolo[1,5-a]pyrimidine-3-carboxamide (0.12 g, 0.23 mmol) in absolute ethanol (5 ml), and heated for 2 hrs under reflux. The reaction mixture was washed with ethylacetate, and hot filtered to remove Fe powder. The filtrate was alkalified with NaHCO₃, and washed many times with water. The organic layer was dried and filtered, followed by purification for 30 min by column chromatography (ethylacetate 100%) packed with Et₃N-treated silica gel to afford the title compound. 60 mg (54%).

¹H-NMR (300 MHz, CD₃OD) δ 1.20 (dd, J=6.9, 2.3 Hz, 6H, CH₃) 2.53 (s, 3H, CH₃) 2.76 (s, 3H, CH₃) 2.84-2.88 (m, 1H, CH) 6.71-6.80 (m, 2H, ArH) 6.90 (d, J=7.8 Hz, 1H,

ArH) 6.99 (s, 1H, ArH) 7.04 (d, J=7.4 Hz, 1H, ArH) 7.42-7.51 (m, 2H, ArH) 8.39 (s, 1H, ArH).

<Example 283> N-(1-Amino-4b-hydroxy-7-isopropyl-10-oxo-9b,10-dihydro-4bH-indeno[1,2-b]benzofuran-9b-yl) indolizine-2-carboxamide Fe powder (76 mg, 1.37 mmol), conc. HCl (0.02 ml, and water (1.5 mL) were added in that order to a solution of N-(4b-hydroxy-7-isopropyl-4-nitro-10-oxo-9b,10-dihydro-4bH-indeno[1,2-b]benzofuran-9b-yl)indolizine-2-carboxamide (220 mg, 0.46 mmol) in absolute ethanol (15 mL), and heated for 3 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (ethylacetate:hexane=1:1) packed with Et$_3$N-treated silica gel to afford the title compound as a yellow solid (43 mg, 21%).

$^1$H-NMR (300 MHz, CD$_3$OD) δ 1.18 (d, J=6.8 Hz, 6H), 2.84 (sept, J=6.8 Hz, 1H), 6.50-6.56 (m, 2H), 6.65-6.72 (m, 3H), 6.79 (s, 1H), 6.88 (d, J=7.8 Hz, 1H), 7.01 (d, J=7.4 Hz, 1H), 7.33 (d, J=9.2 Hz, 1H), 7.44-7.48 (m, 1H), 7.87 (s, 1H), 8.02 (d, J=7.0 Hz, 1H).

<Example 284> N-(1-Amino-4b-hydroxy-7-isopropyl-10-oxo-9b,10-dihydro-4bH-indeno[1,2-b]benzofuran-9b-yl)-1,6-diisopropyl-1H-pyrazolo[3,4-b]pyridine-4-carboxamide Fe powder (78 mg, 1.39 mmol), conc. HCl (0.02 ml), and water (1.5 mL) were added in that order to a solution of N-(4b-hydroxy-7-isopropyl-4-nitro-10-oxo-9b,10-dihydro-4bH-indeno[1,2-b]benzofuran-9b-yl)-1,6-diisopropyl-1H-pyrazolo[3,4-b]pyridine-4-carboxamide (264 mg, 0.46 mmol) in absolute ethanol (15 mL), and heated for 3 hrs under reflux. The reaction mixture was washed with ethylacetate, and hot filtered to remove Fe powder. The filtrate was alkalified with NaHCO$_3$, and washed many times with water. The organic layer was dried and filtered, followed by purification by column chromatography (ethylacetate:hexane=1:1) packed with Et$_3$N-treated silica gel to afford the title compound as a white solid (79.5 mg, 32%).

$^1$H-NMR (300 MHz, CD$_3$OD) δ 1.19 (d, J=6.6 Hz, 6H), 1.37 (d, J=6.8 Hz, 6H), 1.54 (d, J=4.4 Hz, 6H), 2.75-2.90 (m, 1H), 3.17-3.30 (m, 1H), 5.23-5.35 (m, 1H), 6.60-6.75 (m, 2H), 6.85-6.93 (m, 1H), 6.97-7.10 (m, 1H), 7.40-7.53 (m, 1H), 7.57 (s, 1H), 8.23 (s, 1H).

<Example 285> N-(1-Amino-4b-hydroxy-7-isopropyl-10-oxo-9b,10-dihydro-4bH-indeno[1,2-b]benzofuran-9b-yl)imidazo[1,2-a]pyrimidine-2-carboxamide Fe powder (137 mg, 2.45 mmol), conc. HCl (0.02 ml), and water (1 mL) were added in that order to a solution of N-(4b-hydroxy-7-isopropyl-4-nitro-10-oxo-9b,10-dihydro-4bH-indeno[1,2-b]benzofuran-9b-yl)imidazo[1,2-a]pyrimidine-2-carboxamide (110 mg, 0.23 mmol) in absolute ethanol (10 mL), and heated for 3 hrs under reflux. The reaction mixture was washed with ethylacetate, and hot filtered to remove Fe powder.

The filtrate was alkalified with NaHCO$_3$, and washed many times with water. The organic layer was dried and filtered, followed by purification by column chromatography (DCM:MeO=10:1) packed with Et$_3$N-treated silica gel to afford the title compound as a yellow solid (31 mg, 30%).

$^1$H-NMR (300 MHz, CDCl$_3$) δ 1.03-1.10 (m, 6H), 2.67-2.76 (m, 1H), 5.57-5.62 (m, 1H), 6.40 (s, 1H), 6.63 (d, J=8.7 Hz, 1H), 6.74 (d, J=7.7 Hz, 1H), 6.91-6.67 (m, 2H), 7.20 (d, J=7.5 Hz, 1H), 7.46-7.52 (m, 1H), 7.56-7.64 (m, 1H), 7.95 (s, 1H), 8.34-8.39 (m, 1H), 8.63 (s, 1H).

<Example 286> N-(1-Amino-4b-hydroxy-7-isopropyl-10-oxo-9b,10-dihydro-4bH-indeno[1,2-b]benzofuran-9b-yl)-1-oxo-1,2-dihydroisoquinoline-3-carboxamide Fe powder (47 mg, 0.83 mmol), conc. HCl (0.02 ml), and water (0.9 mL) were added in that order to a solution of N-(4b-hydroxy-7-isopropyl-4-nitro-10-oxo-9b,10-dihydro-4bH-indeno[1,2-b]benzofuran-9b-yl)-1-oxo-1,2-dihydroisoquinoline-3-carboxamide (142 mg, 0.28 mmol) in absolute ethanol (9 mL), and heated for 3 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (EtOAc:hexane=2:1) packed with Et$_3$N-treated silica gel to afford the title compound as a yellow solid (58 mg, 43%).

$^1$H-NMR (300 MHz, CD$_3$OD) δ 1.19 (d, J=6.9 Hz, 6H), 2.84 (sept, J=6.9 Hz, 1H), 6.69-6.74 (m, 2H), 6.89 (d, J=7.4 Hz, 1H), 7.02 (d, J=7.5 Hz, 1H), 7.44-7.49 (m, 2H), 7.54 (s, 1H), 7.61-7.66 (m, 1H), 7.74-7.81 (m, 2H), 8.31 (d, J=7.9 Hz, 1H).

<Example 287> N-(1-Amino-4b-hydroxy-7-isopropyl-10-oxo-9b,10-dihydro-4bH-benzo[d]indeno[1,2-b]furan-9b-yl)-3-methylimidazo[1,5-a]pyridine-1-carboxamide Fe (77 mg, 1.38 mmol) and 4 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-3-methylimidazo[1,5-a]pyridine-1-carboxamide (230 mg, 0.46 mmol) in an ethanol:H$_2$O (20 ml:2 ml) solvent, and heated for 2 hrs under reflux. After vacuum concentration, purification by column chromatography (EtOAc:hexane=2:1) afforded N-(1-amino-4b-hydroxy-7-isopropyl-10-oxo-9b,10-dihydro-4bH-benzo[d]indeno[1,2-b]furan-9b-yl)-3-methylimidazo[1,5-a]pyridine-1-carboxamide as a yellow solid (90 mg, 42%).

$^1$H-NMR (300 MHz, CD$_3$OD) δ 1.19 (d, J=6.8 Hz, 6H, CH$_3$), 2.63 (s, 3H, CH$_3$), 2.85 (sep, J=6.8 Hz, 1H, CH), 6.67~6.74 (m, 2H, ArH), 6.81~6.89 (m, 2H, ArH), 7.00~7.09 (m, 2H, ArH), 7.42~7.49 (m, 2H, ArH), 7.93~7.96 (m, 1H, ArH), 8.09 (d, J=7.4 Hz, 1H, ArH).

<Example 288> N-(1-Amino-4b-hydroxy-7-isopropyl-10-oxo-9b,10-dihydro-4bH-benzo[d]indeno[1,2-b]furan-9b-yl)-2H-indazole-3-carboxamide Fe (35 mg, 0.62 mmol) and 3 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-2H-indazole-3-carboxamide (100 mg, 0.21 mmol) in an ethanol:H$_2$O (10 ml:1 ml) solvent, and heated for 3 hrs under reflux. After vacuum concentration, purification by column chromatography (EtOAc:hexane=1:1) afforded the title compound N-(1-amino-4b-hydroxy-7-isopropyl-10-oxo-9b,10-dihydro-4bH-benzo[d]indeno[1,2-b]furan-9b-yl)-2H-indazole-3-carboxamide as a yellow solid (63 mg, 66%).

$^1$H-NMR (300 MHz, CD$_3$OD) δ 1.15 (d, J=6.9 Hz, 6H, CH$_3$), 2.80 (sep, J=6.9 Hz, 1H, CH), 6.66~6.72 (m, 2H, ArH), 6.86 (d, J=7.9 Hz, 1H, ArH), 7.04 (d, J=7.3 Hz, 1H, ArH), 7.16~7.21 (m, 1H, ArH), 7.34~7.56 (m, 4H, ArH), 8.09 (d, J=8.1 Hz, 1H, ArH).

<Example 289> N-(1-Amino-4b-hydroxy-7-isopropyl-10-oxo-9b,10-dihydro-4bH-indeno[1,2-b]benzofuran-9b-yl)-7-methylpyrazolo[1,5-a]pyrimidine-6-carboxamide Fe powder (62 mg, 1.12 mmol), conc. HCl (0.02 ml) and water (1.2 mL) were added in that order to a solution of N-(4b-hydroxy-7-isopropyl-4-nitro-10-oxo-9b,10-dihydro-4bH-indeno[1,2-b]benzofuran-9b-yl)-7-methylpyrazolo[1,5-a]pyrimidine-6-carboxamide (186 mg, 0.37 mmol) in absolute ethanol (12 mL), and heated for 3 hrs under reflux. The reaction mixture was washed with ethylacetate, and hot filtered to remove Fe powder. The filtrate was alkalified with NaHCO$_3$, and washed many times with water. The organic layer was dried and filtered, followed by purification by column chromatography (EA:hexane=1:1) packed with Et$_3$N-treated silica gel to afford the title compound as a yellow solid (125 mg, 72%).

$^1$H-NMR (300 MHz, CD$_3$OD) δ 1.17 (d, J=6.9 Hz, 6H), 2.83 (sept, J=7.1 Hz, 1H), 2.97 (s, 3H), 6.68 (s, 1H), 6.70 (s, 1H), 6.71 (s, 1H), 6.87 (d, J=7.7 Hz, 1H), 7.06 (d, J=7.2 Hz, 1H), 7.34-7.51 (m, 2H), 8.25-8.26 (m, 1H), 8.63 (s, 1H).

<Example 290> N-(1-Amino-4b-hydroxy-7-isopropyl-10-oxo-9b,10-dihydro-4bH-indeno[1,2-b]benzofuran-9b-yl)-1H-benzo[d]imidazole-2-carboxamide Fe powder (54 mg, 0.96 mmol), conc. HCl (0.02 ml), and water (1.0 mL) were added in that order to a solution of N-(4b-hydroxy-7-isopropyl-4-nitro-10-oxo-9b,10-dihydro-4bH-indeno[1,2-b]benzofuran-9b-yl)-1H-benzo[d]imidazole-2-carboxamide (155 mg, 0.32 mmol) in absolute ethanol (10 mL) and heated for 3 hrs under reflux. The reaction mixture was washed with ethylacetate, and filtered to remove Fe powder. The filtrate was alkalified with NaHCO$_3$, and washed many times with water. The organic layer was dried and filtered, followed by purification by column chromatography (EA:hexane=1:1) packed with Et$_3$N-treated silica gel to afford the title compound as a yellow solid (67 mg, 46%).

$^1$H-NMR (300 MHz, CD$_3$OD) δ 1.19 (d, J=6.9 Hz, 6H), 2.84 (sept, J=6.7 Hz, 1H), 6.68 (s, 1H), 6.72 (s, 1H), 6.89 (d, J=7.4 Hz, 1H), 7.03 (d, J=7.3 Hz, 1H), 7.32 (s, 1H), 7.34 (s, 1H), 7.44-7.50 (m, 2H), 7.55 (s, 1H), 7.69 (s, 1H).

<Example 291> N-(1-Amino-4b-hydroxy-7-isopropyl-10-oxo-9b,10-dihydro-4bH-indeno[1,2-b]benzofuran-9b-yl)-5-fluoro-1H-benzo[d]imidazole-2-carboxamide Fe powder (76 mg, 1.36 mmol), conc. HCl (0.02 ml), and water (1.5 mL) were added in that order to a solution of 5-fluoro-N-(4b-hydroxy-7-isopropyl-4-nitro-10-oxo-9b,10-dihydro-4bH-indeno[1,2-b]benzofuran-9b-yl)-1H-benzo[d]imidazole-2-carboxamide (227 mg, 0.45 mmol) in absolute ethanol (15 mL), and heated for 3 hrs under reflux. The reaction mixture was washed with ethylacetate, and hot filtered to remove Fe powder. The filtrate was alkalified with NaHCO$_3$, and washed many times with water. The organic layer was dried and filtered, followed by purification by column chromatography (EA:hexane=1:1) packed with Et$_3$N-treated silica gel to afford the title compound as a yellow solid (144 mg, 68%).

$^1$H-NMR (300 MHz, CD$_3$OD) δ 1.19 (d, J=6.9 Hz, 6H), 2.85 (sept, J=6.6 Hz, 1H), 6.67 (s, 1H), 6.69 (d, J=7.4 Hz, 1H), 6.90 (d, J=7.3 Hz, 1H), 7.02 (d, J=7.4 Hz, 1H), 7.12 (s, 1H), 7.25 (s, 1H), 7.45-7.51 (m, 2H), 7.73 (s, 1H).

<Example 292> N-(1-Amino-4b-hydroxy-7-isopropyl-10-oxo-9b,10-dihydro-4bH-indeno[1,2-b]benzofuran-9b-yl)tetrazolo[1,5-a]pyridine-5-carboxamide Fe powder (0.17 g, 3.08 mmol), conc. HCl (0.03 ml), and water (1 ml) were added in that order to a solution of N-(4b-hydroxy-7-isopropyl-1-nitro-10-oxo-9b,10-dihydro-4bH-indeno[1,2-b]benzofuran-9b-yl)tetrazolo[1,5-a]pyridine-5-carboxamide (0.30 g, 0.61 mmol) in absolute ethanol (10 ml), and heated for 2 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (ethylacetate:hexane=1:1) packed with Et$_3$N-treated silica gel to afford the title compound. 0.11 g (40%).

$^1$H-NMR (300 MHz, CD$_3$OD) δ 1.18-1.23 (m, 6H, CH$_3$) 2.83-2.92 (sept, 1H, CH) 6.74 (m, 1H, ArH) 6.93 (d, J=7.5 Hz, 1H, ArH) 7.05 (d, J=6.9 Hz, 1H, ArH) 7.47-7.56 (m, 2H, ArH) 7.89 (s, 1H, ArH) 7.99 (t, J=7.2 Hz, 1H, ArH) 8.08 (d, J=7.2 Hz, 1H, ArH) 8.36 (d, J=7.8 Hz, 1H, ArH).

<Example 293> N-(1-Amino-4b-hydroxy-7-isopropyl-10-oxo-9b,10-dihydro-4bH-indeno[1,2-b]benzofuran-9b-yl)-1-methyl-1H-indazole-3-carboxamide Fe powder (0.16 g, 2.92 mmol), conc. HCl (0.03 ml), and water (1 ml) were added in that order to a solution of N-(4b-hydroxy-7-isopropyl-1-nitro-10-oxo-9b,10-dihydro-4bH-indeno[1,2-b]benzofuran-9b-yl)-1-methyl-3a,7a-dihydro-1H-indazole-3-carboxamide (0.27 g, 0.54 mmol) in absolute ethanol (10 ml), and heated for 3 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (ethylacetate:hexane=1:2) packed with Et$_3$N-treated silica gel to afford the title compound. 0.13 g (52%).

$^1$H-NMR (300 MHz, CD$_3$OD) δ 1.19 (d, J=6.9 Hz, 6H, CH$_3$) 2.80-2.88 (sept, 1H, CH) 4.12 (s, 1H, CH$_3$) 6.69-6.80 (m, 2H, ArH) 6.88 (d, J=6.9 Hz, 1H, ArH) 7.04 (d, J=6.6 Hz, 1H, ArH) 7.20-7.25 (m, 1H, ArH) 7.40-7.48 (m, 3H, ArH) 7.59 (d, J=8.7 Hz, 1H, ArH) 8.07 (d, J=8.4 Hz, 1H, ArH).

<Example 294> N-(1-Amino-4b-hydroxy-7-isopropyl-10-oxo-9b,10-dihydro-4bH-indeno[1,2-b]benzofuran-9b-yl)-1H-indole-5-carboxamide Fe powder (0.04 g, 0.82 mmol), conc. HCl (0.03 ml), and water (0.5 ml) were added in that order to a solution of N-(4b-hydroxy-7-isopropyl-1-nitro-10-oxo-9b,10-dihydro-4bH-indeno[1,2-b]benzofuran-9b-yl)-1H-indole-5-carboxamide (80 mg, 0.16 mmol) in absolute ethanol (5 ml) and heated for 3 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (ethylacetate:hexane=1:2) packed with Et$_3$N-treated silica gel to afford the title compound. 35 mg (47%).

$^1$H-NMR (300 MHz, CD$_3$OD) δ 1.19 (d, J=7.2 Hz, 6H, CH$_3$) 2.80-2.88 (sept, 1H, CH) 6.50-6.53 (m, 1H, ArH) 6.69-6.72 (m, 2H, ArH) 6.80-6.85 (m, 1H, ArH) 7.03-7.12 (m, 2H, ArH) 7.29-7.31 (m, 1H, ArH) 7.37-7.47 (m, 2H, ArH) 7.60-7.63 (m, 1H, ArH) 8.16 (s, 1H, ArH).

<Example 295> N-(1-Amino-4b-hydroxy-7-isopropyl-10-oxo-9b,10-dihydro-4bH-indeno[1,2-b]benzofuran-9b-yl)-1-methyl-3a,7a-dihydro-1H-indazole-3-carboxamide Fe powder (0.08 g, 1.46 mmol), conc. HCl (0.03 ml), and water (1 ml) were added in that order to a solution of N-(4b-hydroxy-7-isopropyl-1-nitro-10-oxo-9b,10-dihydro-4bH-indeno[1,2-b]benzofuran-9b-yl)-3-methyl-[1,2,4]triazolo[4,3-a]pyridine-8-carboxamide (0.13 g, 0.20 mmol) in absolute ethanol (10 ml), and heated for 23 hrs under reflux. The reaction mixture was washed with ethylacetate, and hot filtered to remove Fe powder. The filtrate was alkalified with NaHCO$_3$, and washed many times with water. The organic layer was dried and filtered, followed by purification for 30 min by column chromatography (ethylacetate 100%) packed with Et$_3$N-treated silica gel to afford the title compound. 44 mg (46%).

$^1$H-NMR (300 MHz, CD$_3$OD) δ 1.21 (d, J=6.9 Hz, 6H, CH$_3$) 2.77 (s, 3H, CH$_3$) 2.84-3.30 (sept, 1H, CH) 6.71-6.79 (m, 2H, ArH) 6.90 (d, J=8.7 Hz, 1H, ArH) 7.03 (d, J=5.7 Hz, 1H, ArH) 7.13 (t, J=7.2 Hz, 1H, ArH) 7.46-7.48 (m, 2H, ArH) 8.04 (d, J=6.3 Hz, 1H, ArH) 8.48 (d, J=7.2 Hz, 1H, ArH).

<Example 296> N-(1-Amino-4b-hydroxy-7-isopropyl-10-oxo-9b,10-dihydro-4bH-indeno[1,2-b]benzofuran-9b-yl)-1-methyl-1H-imidazole-4-carboxamide Fe powder (0.09 g, 1.62 mmol), conc. HCl (0.03 ml), and water (1 ml) were added in that order to a solution of N-(4b-hydroxy-7-isopropyl-1-nitro-10-oxo-9b,10-dihydro-4bH-indeno[1,2-b]benzofuran-9b-yl)-1-methyl-1H-imidazole-4-carboxamide (0.10 g, 0.22 mmol) in absolute ethanol (10 ml), and heated for 3 hrs under reflux. The reaction mixture was washed with ethylacetate, and filtered to remove Fe powder. The filtrate was alkalified with NaHCO$_3$, and washed many times with water. The organic layer was dried and filtered, followed by purification for 30 min by column chromatography (ethylacetate 100%) packed with Et$_3$N-treated silica gel to afford the title compound. 29 mg (31%).

$^1$H-NMR (300 MHz, CD$_3$OD) δ 1.18 (d, J=6.9 Hz, 6H, CH3) 2.80-2.86 (sept, 1H, CH) 6.66-6.69 (m, 2H, ArH) 6.87 (d, J=7.2 Hz, 1H, ArH) 6.99 (d, J=7.2 Hz, 1H, ArH) 7.41-7.45 (m, 2H, ArH) 7.57-7.61 (m, 2H, ArH).

<Example 297> N-(1-Amino-4b-hydroxy-7-isopropyl-10-oxo-9b,10-dihydro-4bH-indeno[1,2-b]benzofuran-9b-yl-1H-pyrrole-3-carboxamide Fe powder (31 mg, 0.55 mmoles) and 2 drops of conc. HCl were sequentially added to a solution of N-(4b-hydroxy-7-isopropyl-4-nitro-10-oxo-9b,10-dihydro-4bH-indeno[1,2-b]benzofuran-9b-yl)-1H-pyrrole-3-carboxamide (0.08 g, 0.18 mmoles) in an ethanol:water (10:1, 10 mL) solvent, and heated for 3 hrs under reflux. The reaction mixture was washed with ethylacetate, and hot filtered to remove Fe powder. The filtrate was concentrated in a vacuum and purified by silica gel column chromatography (30% ethylacetate mixed with 60% hexane) to afford the title compound. 35 mg (47%).

$^1$H-NMR (300 MHz, CD$_3$OD): δ 1.18 (d, J=6.9 Hz, 6H, CH$_3$) 2.84 (sept, 1H, CH) 6.53-6.58 (m, 1H, ArH) 6.64-6.76 (m, 3H, ArH) 6.86-6.90 (m, 1H, ArH) 6.98-7.01 (m, 1H, ArH) 7.36-7.46 (m, 3H, ArH).

<Example 298> tert-Butyl(tert-butoxycarbonylamino)(4b-hydroxy-7-isopropyl-10-oxo-9b,10-dihydro-4bH-benzo[d]indeno[1,2-b]furan-9b-ylamino)methylenecarbamate 4b,9b-dihydroxy-7-isopropyl-4bH-benzo[d]indeno[1,2-b]furan-10(9bH)-one (0.30 g, 1.02 mmol) was dissolved in 5 ml of THF, and stirred, together with DEAD (0.24 ml, 1.56 mmol and PPh$_3$ (0.41 g, 1.56 mmol), for 5 min, and then together with, Boc-guanidine (0.40 g, 1.56 mmol for 3 hrs at room temperature. Thereafter, vacuum concentration was performed, followed by purification by column chromatography (ethylacetate:hexane=1:2) to afford the title compound. 40 mg (7%).

$^1$H-NMR (300 MHz, CDCl$_3$) δ 1.15 (d, J=6.8 Hz, 6H), 1.30 (s, 9H), 1.50 (s, 9H), 2.81 (q, J=7.3 Hz, 1H), 6.69 (s, 1H), 6.81 (d, J=7.5 Hz, 1H), 7.30 (d, J=7.9 Hz, 1H), 7.51 (t, J=8.7 Hz, 1H), 7.67 (s, 1H), 7.73-7.82 (m, 2H), 8.00 (d, J=7.9 Hz, 1H), 9.36 (s, 1H), 11.17 (s, 1H).

<Example 299> N-(1-Amino-4b-hydroxy-7-isopropyl-10-oxo-9b,10-dihydro-4bH-indeno[1,2-b]benzofuran-9b-yl-1H-indazole-5-carboxamide Fe powder (104 mg, 1.86 mmol and 4 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl-1H-indazole-5-carboxamide (300 mg, 0.62 mmol in an ethanol:H$_2$O (20 ml:2 ml) solvent, and heated for 3 hrs under reflux. After vacuum concentration, purification by column chromatography (EtOAc:Hexane=2:1) afforded the title compound as a yellow solid. 90 mg (32%).

$^1$H-NMR (300 MHz, CD$_3$OD) δ 1.19 (d, J=6.8 Hz, 6H, CH$_3$), 2.85 (m, 1H, CH), 6.67-6.74 (m, 2H, ArH), 6.89 (d, J=8.0 Hz, 1H, ArH), 7.02 (d, J=7.4 Hz, 1H, ArH), 7.43-7.56 (m, 3H, ArH), 7.85-7.88 (m, 1H, ArH), 8.13 (s, 1H, ArH), 8.38 (s, 1H, ArH).

<Example 300> N-(1-Amino-4b-hydroxy-7-isopropyl-10-oxo-9b,10-dihydro-4bH-indeno[1,2-b]benzofuran-9b-yl)-3-methyl-1H-pyrazole-5-carboxamide Fe powder (36 mg, 0.65 mmol) and 2 drops of conc. HCl were sequentially added to a solution of N-(4b-hydroxy-7-isopropyl-1-nitro-10-oxo-9b,10-dihydro-4bH-benzo[d]indeno[1,2-b]furan-9b-yl)-3-methyl-1H-pyrazole-5-carboxamide (90 mg, 0.22 mmol) in an ethanol:H$_2$O (10 ml:1 ml) solvent, and heated for 3 hrs under reflux. After vacuum concentration, purification by column chromatography (EtOAc:Hexane=1:2) afforded the title compound as a yellow solid. 62 mg (74%).

$^1$H-NMR (300 MHz, CD$_3$OD) δ 1.18 (d, J=6.9 Hz, 1H, CH$_3$), 2.29 (s, 3H, CH$_3$), 2.84 (sep, J=6.9 Hz, 1H, CH), 6.42

(s, 1H, ArH), 6.66-6.70 (m, 2H, ArH), 6.87 (d, J=8.0 Hz, 1H, ArH), 6.99 (d, J=7.4 Hz, 1H, ArH), 7.41-7.47 (m, 2H, ArH).

<Example 301> 1-Amino-9b-(furane-2-carboxamido)-7-methoxy-10-oxo-9b,10-dihydro-4bH-indeno[1,2-b]benzofuran-4b-yl furane-2-carboxylate HATU (0.35 g, 3.52 mmol) was added at 0° C. to a solution of furane-2-carboxylic acid (0.20 g, 1.85 mmol) in anhydrous dimethylformamide (3 ml) which was then stirred, together with Et$_3$N (0.70 g, 1.85 mmol) and 9b-amino-4b-hydroxy-7-methoxy-4bH-indeno[1,2-b]benzofuran-10(9bH)-one (0.50 g, 1.76 mmol), at room temperature for 24 hrs. The reaction mixture was diluted in ethylacetate and washed many times with an aqueous K$_2$CO$_3$ solution and brine, and the organic layer was dried and filtered. Purification by column chromatography (ethylacetate:hexane=1:1) afforded the title compound. 13 mg (1.5%).
$^1$H-NMR (300 MHz, CDCl$_3$) δ 3.76 (m, 3H, OMe), 6.39-6.50 (m, 2H, ArH), 6.65 (m, 1H, ArH), 6.93-6.95 (m, 2H, ArH), 7.12 (d, J=3.9 Hz, 1H, ArH) 7.38 (s, 1H, ArH), 7.47 (s, 1H, ArH), 7.51-7.54 (m, 1H, ArH), 7.63 (t, J=7.5 Hz, 1H, ArH) 7.84 (t, J=7.2 Hz, 1H, ArH) 7.93 (d, J=7.5 Hz, 1H, ArH), 8.09 (t, J=7.8 Hz, 1H, ArH).

<Example 302> N-(4b-hydroxy-7,8-dimethyl-10-oxo-9b,10-dihydro-4bH-indeno[1,2-b]benzofuran-9b-yl)nicotinamide A solution of nicotinic acid (409 mg, 2.14 mmol in DCM was cooled to 0° C. It was stirred, together with EDCl (332 mg, 2.14 mmol, for 10 min, then together with DMF (3 mL) for an additional 10 min, and finally together with HOBt (289 mg, 2.14 mmol and 9b-amino-4b-hydroxy-7,8-dimethyl-4bH-indeno[1,2-b]benzofuran-10(9bH)-one (500 mg, 1.78 mmol for 15 hrs at room temperature. Subsequently, the reaction mixture was mixed with DCM, washed with water, and dehydrated with Na$_2$SO$_4$. After filtration and concentration, purification by column chromatography afforded the title compound as a solid. 178 mg (26%).
$^1$H-NMR (300 MHz, CD$_3$OD) δ 2.19 (s, 3H), 2.22 (s, 3H), 6.60 (s, 1H), 7.29 (s, 1H), 7.49-7.52 (m, 1H), 7.66-7.88 (m, 4H), 8.25 (d, J=2.1 Hz, 1H), 8.66 (d, J=3.4 Hz, 1H), 8.99 (s, 1H).

<Example 303> N-(4b-hydroxy-7,8-dimethyl-10-oxo-9b,10-dihydro-4bH-indeno[1,2-b]benzofuran-9b-yl-1H-pyrrole-2-carboxamide 9b-Amino-4b-hydroxy-7,8-dimethyl-4bH-indeno[1,2-b]benzofuran-10(9bH)-one (500 mg, 1.78 mmol and 1H-pyrrole-2-carboxylic acid (238 mg, 2.14 mmol were dissolved in DCM (17.8 mL, 0.1 M), mixed with DCC (442 mg, 2.14 mmol at room temperature while stirring. The reaction mixture was washed with water, dehydrated with Na$_2$SO$_4$, filtered, and concentrated, followed by purification by column chromatography to afford the title compound as a solid. 40 mg (6%).
$^1$H-NMR (300 MHz, CD$_3$OD) δ 2.17 (s, 3H), 2.19 (s, 3H), 6.3-6.15 (m, 1H), 6.58 (s, 1H), 6.88 (s, 1H), 6.92 (d, J=3.7 Hz, 1H), 7.28 (s, 1H), 7.54-7.59 (m, 1H), 7.75-7.82 (m, 1H), 7.91-7.93 (m, 1H).

<Example 304> N-(6-ethyl-4b-hydroxy-10-oxo-9b,10-dihydro-4bH-indeno[1,2-b]benzofuran-9b-yl-1H-pyrrole-2-carboxamide Pyrrole-2-carboxylic acid (133 mg, 1.96 mmol) and 9b-amino-6-ethyl-4b-hydroxy-4bH-benzo[d]indeno[1,2-b]furan-10(9bH)-one (500 g, 1.78 mmol were together dissolved in methylene chloride (10 ml), and mixed with DCC (367 mg, 1.78 mmol) at room temperature for 20 hrs while stirring. After extraction with CH$_2$Cl$_2$ and water, the organic layer was dried over MgSO$_4$ and concentrated in a vacuum. Purification by column chromatography (EA:Hex=1:1) afforded the title compound as a yellow solid. 151 mg (23%).
$^1$H-NMR (300 MHz, CDCl$_3$) δ 1.17 (t, J=7.5 Hz, 3H, CH$_3$), 2.64 (q, J=7.5 Hz, 2H, CH$_2$), 5.93 (s, 1H, OH), 6.26 (s, 1H, ArH), 6.79 (s, 1H, ArH), 6.85-6.98 (m, 3H, ArH), 7.21-7.26 (m, 1H, ArH), 7.56 (t, J=7.6 Hz, 1H, ArH), 7.80-7.85 (m, 2H, ArH), 8.04 (d, J=7.8 Hz, 1H, ArH).

<Example 305> N-(6-ethyl-4b-hydroxy-10-oxo-9b,10-dihydro-4bH-indeno[1,2-b]benzofuran-9b-yl)furane-2-carboxamide Furane-2-carboxylic acid (239 mg, 2.13 mmol) was dissolved in methylene chloride (10 ml), and mixed with EDCl (406 mg, 2.13 mmol) and HOBt (288 mg, 2.13 mmol) for 10 min, and then with 9b-amino-6-ethyl-4b-hydroxy-4bH-benzo[d]indeno[1,2-b]furan-10(9bH)-one (500 mg, 1.78 mmol) overnight at room temperature while stirring. After extraction with CH$_2$Cl$_2$ and water, the organic layer was dried over MgSO$_4$ and concentrated in a vacuum. Purification by column chromatography (EA:Hex=1:2) afforded the title compound as a yellow solid. 180 mg (27%).
$^1$H-NMR (300 MHz, CDCl$_3$) δ 1.17 (t, J=7.5 Hz, 3H, CH$_3$), 2.63 (q, J=7.5 Hz, 2H, CH$_2$), 5.63 (br, 1H, OH), 6.51 (q, 1.7 Hz, 1H, ArH), 6.89 (t, J=7.6 Hz, 1H, ArH), 7.09-7.14 (m, 2H, ArH), 7.23-7.26 (m, 1H, ArH), 7.46 (s, 1H, NH), 7.52 (s, 1H, ArH), 7.56 (t, J=7.5 Hz, 1H, ArH), 7.79-7.85 (m, 2H, ArH), 8.04 (d, J=7.8 Hz, 1H, ArH).

<Example 306> N-(8-chloro-4b-hydroxy-10-oxo-9b,10-dihydro-4bH-indeno[1,2-b]benzofuran-9b-yl)quinoline-4-carboxamide Quinoline-4-carboxylic acid (361 mg, 1.74 mmol) was dissolved in methylene chloride (10 ml), and mixed with EDCl (397 mg, 2.08 mmol) and HOBt (281 mg, 2.08 mmol) for 10 min and then with 9b-amino-6-ethyl-4b-hydroxy-4bH-benzo[d]indeno[1,2-b]furan-10(9bH)-one (500 mg, 1.74 mmol) overnight at room temperature while stirring. After extraction with CH$_2$Cl$_2$ and water, the organic layer was dried over MgSO$_4$ and concentrated in a vacuum. Purification by column chromatography (EA:Hex=1:1) afforded the title compound as a white solid. 112 mg (15%).
$^1$H-NMR (500 MHz, CDCl$_3$) δ 6.86 (d, J=8.6 Hz, 1H ArH), 7.19 (s, 1H, NH), 7.27~7.29 (m, 1H, ArH), 7.43 (d, J=2.1 Hz, 1H, ArH), 7.53 (d, J=4.2 Hz, 1H, ArH), 7.60-7.65 (m, 2H, ArH), 7.78 (t, J=7.9 Hz, 1H, ArH), 7.87-7.91 (m, 2H, ArH), 8.06-8.11 (m, 2H, ArH), 8.16 (d, J=8.1 Hz, 1H, ArH), 8.98 (d, J=4.2 Hz, 1H, ArH).

<Example 307> N-(8-Chloro-4b-hydroxy-10-oxo-9b,10-dihydro-4bH-indeno[1,2-b]benzofuran-9b-yl)tetrahydrofurane-2-carboxamide Tetrahydrofurane-2-carboxylic acid (242 mg, 2.08 mmol) was dissolved in methylene chloride (10 ml), and mixed with EDCl (397 mg, 2.08 mmol) and HOBt (281 mg, 2.08 mmol) for 10 min and then with 9b-amino-6-ethyl-4b-hydroxy-4bH-benzo[d]indeno[1,2-b]furan-10(9bH)-one (500 mg, 1.74 mmol) overnight at room temperature while stirring. After extraction with CH$_2$Cl$_2$ and water, the organic layer was dried over MgSO$_4$ and concentrated in a vacuum. Purification by column chromatography (EA:Hex=1:1) afforded the title compound as a yellow solid. 183 mg (27%).

$^1$H-NMR (300 MHz, CDCl$_3$) δ 1.88-1.95 (m, 3H, CH$_2$), 2.17-2.30 (m, 1H, CH$_2$), 3.88-3.95 (m, 1H, OCH$_2$), 3.98-4.09 (m, 1H, OCH$_2$), 4.29-4.40 (m, 1H, OCH), 6.75-6.77 (m, 1H, ArH), 7.19-7.21 (m, 1H, ARH), 7.30-7.34 (m, 1H, ArH), 7.57 (t, J=7.3 Hz, 1H, ArH), 7.79-7.84 (m, 2H, ArH), 7.97-7.99 (m, 1H, ArH).

In Table 1, chemical formulas of compounds of Examples 1 to 307 are shown.

TABLE 1

| Ex. | Chemical Structure |
|---|---|
| 1 | 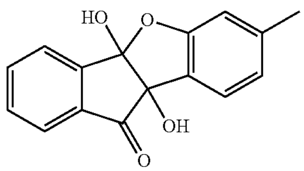 [SMILES: Cc1ccc2c(c1)OC1(O)c3ccccc3C(=O)C21O] |
| 2 | 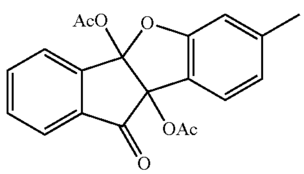 [SMILES: CC(=O)OC12Oc3cc(C)ccc3C1(OC(C)=O)C(=O)c1ccccc12] |
| 3 | 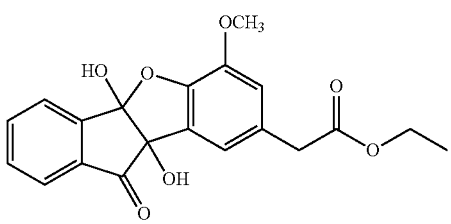 [SMILES: CCOC(=O)Cc1cc(OC)c2c(c1)C1(O)C(=O)c3ccccc3C1(O)O2] |
| 4 | 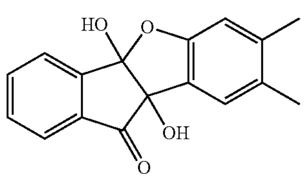 [SMILES: Cc1cc2c(cc1C)C1(O)C(=O)c3ccccc3C1(O)O2] |
| 5 | 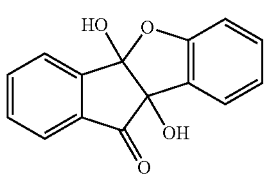 [SMILES: O=C1c2ccccc2C2(O)Oc3ccccc3C12O] |
| 6 | 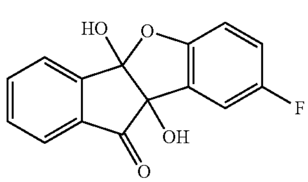 [SMILES: O=C1c2ccccc2C2(O)Oc3ccc(F)cc3C12O] |
| 7 | 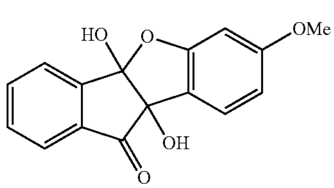 [SMILES: COc1ccc2c(c1)OC1(O)c3ccccc3C(=O)C21O] |
| 8 | |
| 9 | |
| 10 | |
| 11 | |
| 12 | |
| 13 | |
| 14 | |

TABLE 1-continued

| Ex. | Chemical Structure |
|---|---|
| 15 | 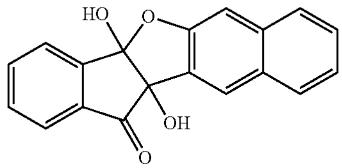 [SMILES: O=C1c2ccccc2C2(O)Oc3cc4ccccc4cc3C12O] |
| 16 | 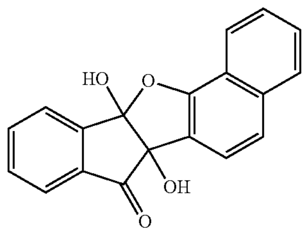 [SMILES: O=C1c2ccccc2C2(O)Oc3c(ccc4ccccc34)C12O] |
| 17 | 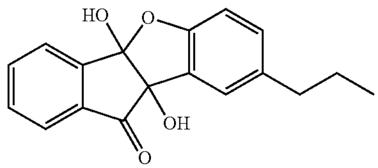 [SMILES: CCCc1ccc2c(c1)C1(O)C(=O)c3ccccc3C1(O)O2] |
| 18 | 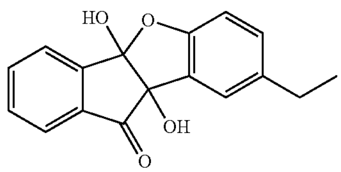 [SMILES: CCc1ccc2c(c1)C1(O)C(=O)c3ccccc3C1(O)O2] |
| 19 | 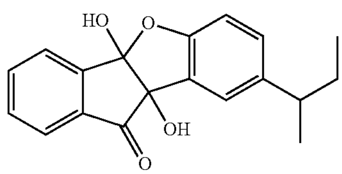 [SMILES: CCC(C)c1ccc2c(c1)C1(O)C(=O)c3ccccc3C1(O)O2] |
| 20 | 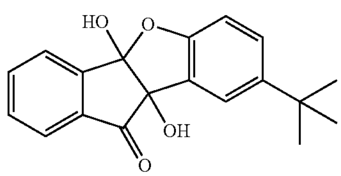 [SMILES: CC(C)(C)c1ccc2c(c1)C1(O)C(=O)c3ccccc3C1(O)O2] |
| 21 | 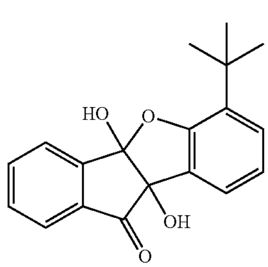 [SMILES: CC(C)(C)c1cccc2c1OC1(O)c3ccccc3C(=O)C21O] |
| 22 | 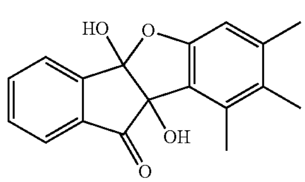 [SMILES: Cc1cc2c(c(C)c1C)C1(O)C(=O)c3ccccc3C1(O)O2] |
| 23 | |
| 24 | |
| 25 | |
| 26 | |
| 27 | |
| 28 | |
| 29 | |

TABLE 1-continued
Ex. Chemical Structure
30
31
32
33
34
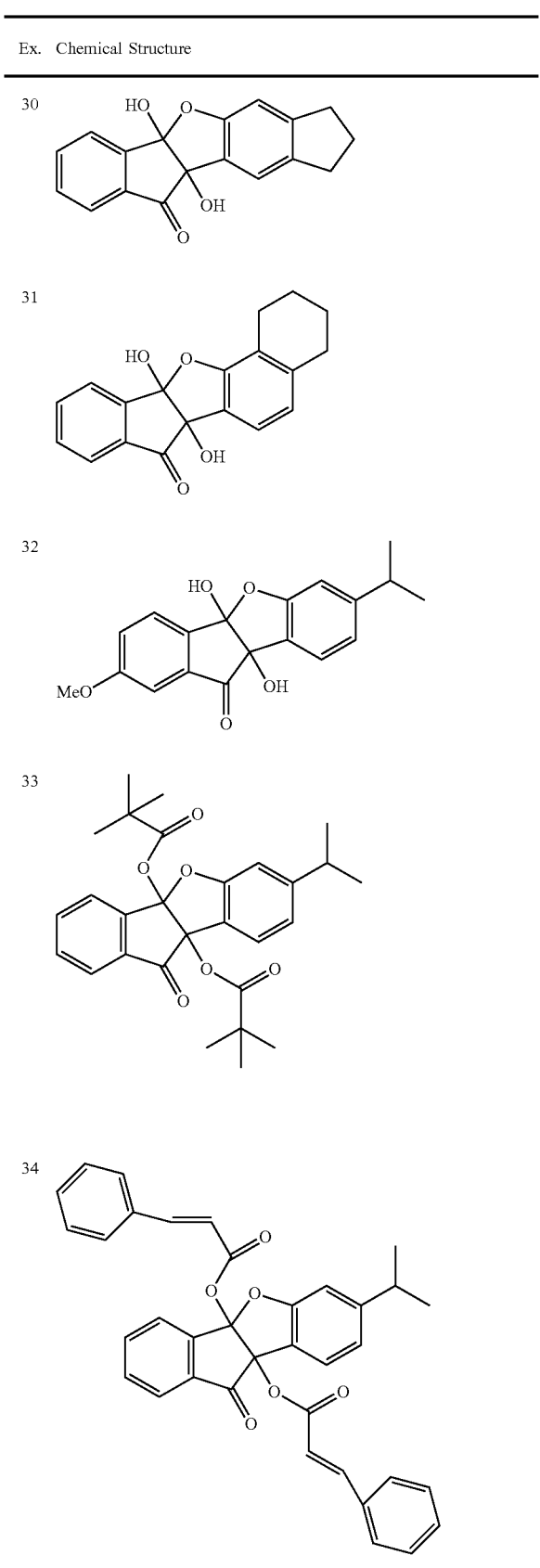
TABLE 1-continued
Ex. Chemical Structure
35
36
37
38
39
40
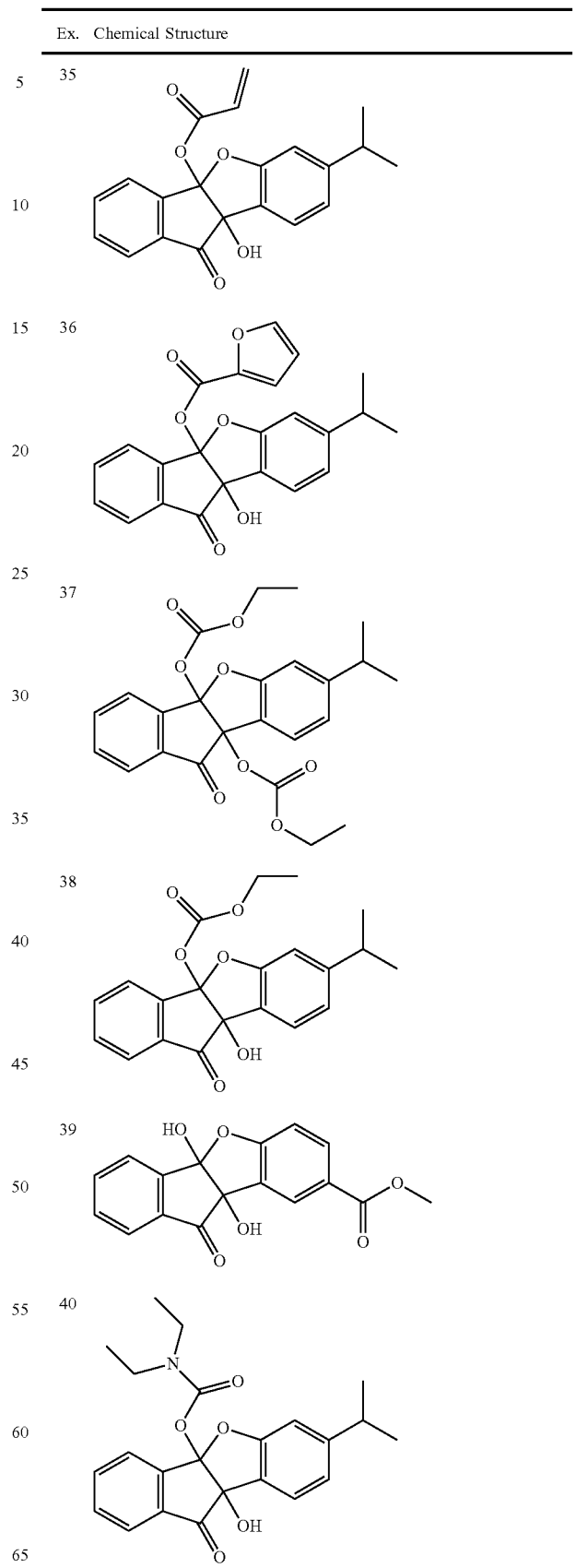

TABLE 1-continued
| Ex. | Chemical Structure |
|---|---|
| 41 | 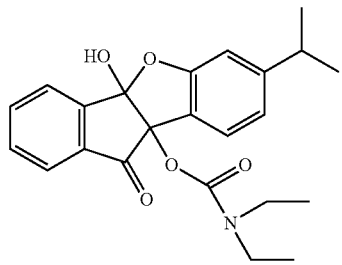 [SMILES: CCN(CC)C(=O)OC12C(=O)c3ccccc3C1(O)Oc1cc(C(C)C)ccc12] |
| 42 | 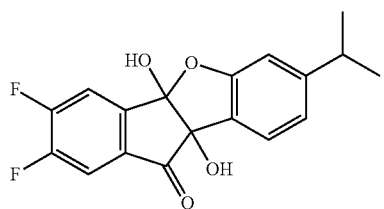 [SMILES: CC(C)c1ccc2c(c1)OC1(O)c3cc(F)c(F)cc3C(=O)C21O] |
| 43 | 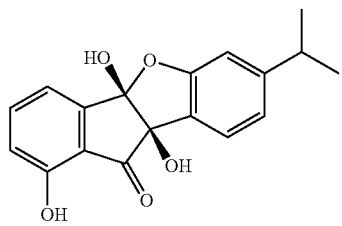 [SMILES: CC(C)c1ccc2c(c1)O[C@@]1(O)c3cccc(O)c3C(=O)[C@@]21O] |
| 44 | 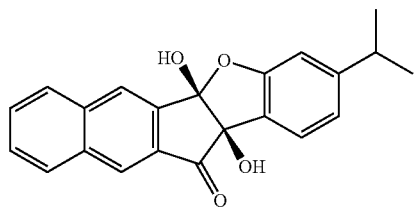 [SMILES: CC(C)c1ccc2c(c1)O[C@@]1(O)c3cc4ccccc4cc3C(=O)[C@@]21O] |
| 45 | 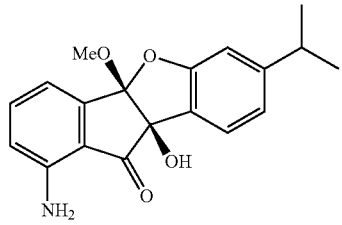 [SMILES: CO[C@@]12Oc3cc(C(C)C)ccc3[C@]1(O)C(=O)c1c(N)cccc12] |
| 46 | 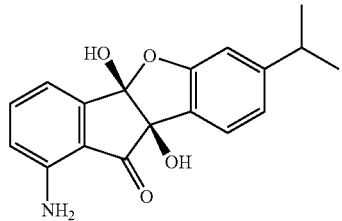 |
TABLE 1-continued
| Ex. | Chemical Structure |
|---|---|
| 47 | 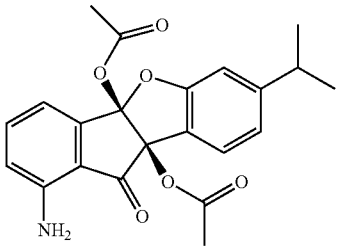 [SMILES: CC(=O)O[C@@]12Oc3cc(C(C)C)ccc3[C@]1(OC(C)=O)C(=O)c1c(N)cccc12] |
| 48 | 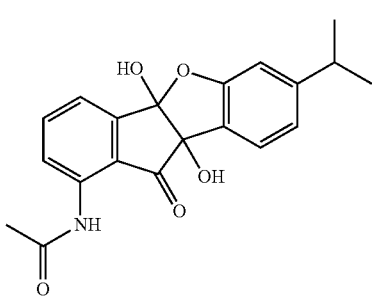 [SMILES: CC(=O)Nc1cccc2c1C(=O)C1(O)c3ccc(C(C)C)cc3OC21O] |
| 49 | 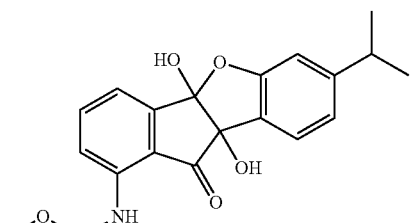 |
| 50 | 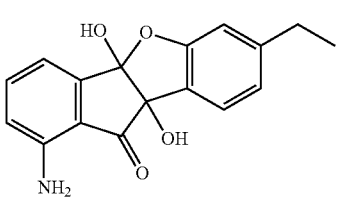 [SMILES: CCc1ccc2c(c1)OC1(O)c3cccc(N)c3C(=O)C21O] |
| 51 | 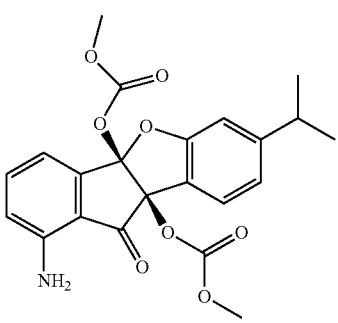 [SMILES: COC(=O)O[C@@]12Oc3cc(C(C)C)ccc3[C@]1(OC(=O)OC)C(=O)c1c(N)cccc12] |
| 52 | 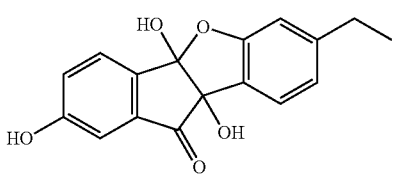 [SMILES: CCc1ccc2c(c1)OC1(O)c3ccc(O)cc3C(=O)C21O] |

TABLE 1-continued
| Ex. | Chemical Structure |
|---|---|
| 53 | 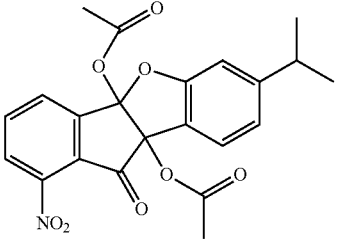 [SMILES: CC(=O)OC12Oc3cc(C(C)C)ccc3C1(OC(C)=O)C(=O)c1c([N+](=O)[O-])cccc12] |
| 54 | 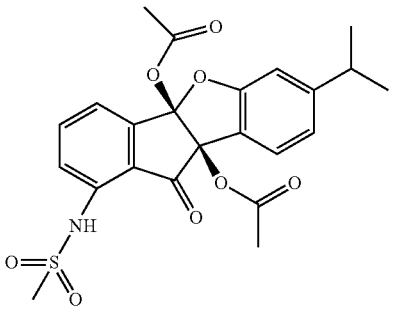 [SMILES: CC(=O)O[C@@]12Oc3cc(C(C)C)ccc3[C@]1(OC(C)=O)C(=O)c1c(NS(C)(=O)=O)cccc12] |
| 55 | 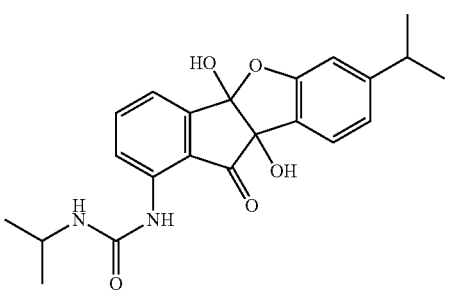 [SMILES: CC(C)NC(=O)Nc1cccc2c1C(=O)C1(O)c3ccc(C(C)C)cc3OC21O] |
| 56 | 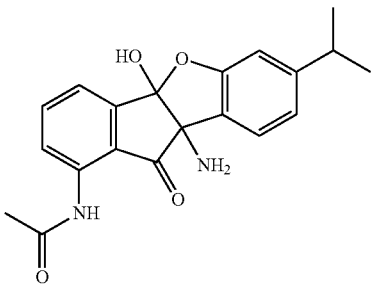 |
| 57 | 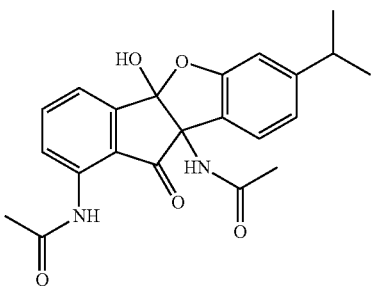 [SMILES: CC(=O)Nc1cccc2c1C(=O)C1(NC(C)=O)c3ccc(C(C)C)cc3OC21O] |
| 58 | 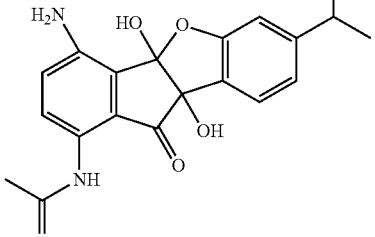 |
| 59 | 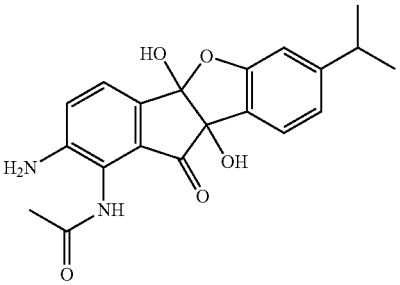 [SMILES: CC(=O)Nc1c(N)ccc2c1C(=O)C1(O)c3ccc(C(C)C)cc3OC21O] |
| 60 | 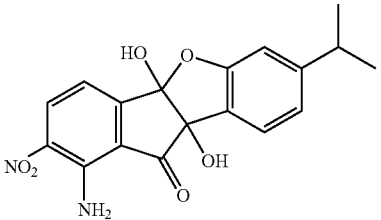 [SMILES: CC(C)c1ccc2c(c1)OC1(O)c3ccc([N+](=O)[O-])c(N)c3C(=O)C21O] |
| 61 | 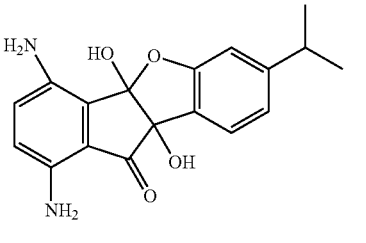 [SMILES: CC(C)c1ccc2c(c1)OC1(O)c3c(N)ccc(N)c3C(=O)C21O] |
| 62 | 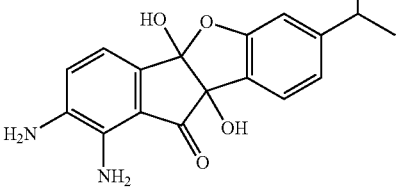 |
| 63 | 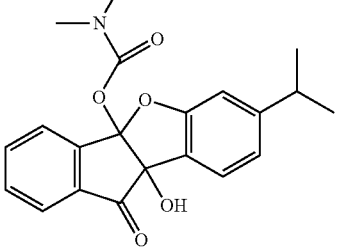 |

TABLE 1-continued
| Ex. | Chemical Structure |
|---|---|
| 64 | 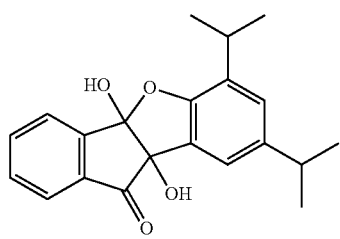 [SMILES: CC(C)c1cc(C(C)C)c2c(c1)C1(O)C(=O)c3ccccc3C1(O)O2] |
| 65 | 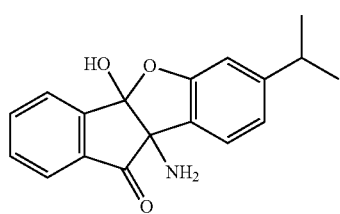 [SMILES: CC(C)c1ccc2c(c1)OC1(O)c3ccccc3C(=O)C21N] |
| 66 | 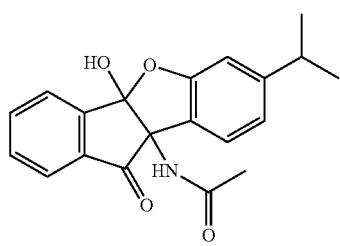 [SMILES: CC(=O)NC12C(=O)c3ccccc3C1(O)Oc1cc(C(C)C)ccc12] |
| 67 | 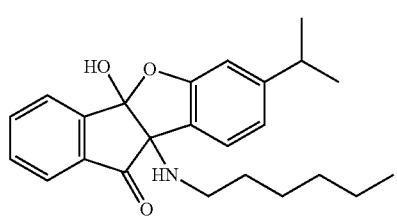 [SMILES: CCCCCCNC12C(=O)c3ccccc3C1(O)Oc1cc(C(C)C)ccc12] |
| 68 | 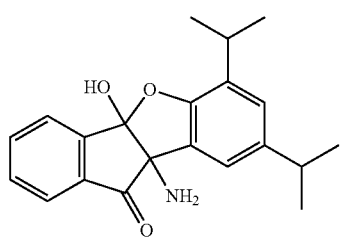 [SMILES: CC(C)c1cc(C(C)C)c2c(c1)C1(N)C(=O)c3ccccc3C1(O)O2] |
| 69 | 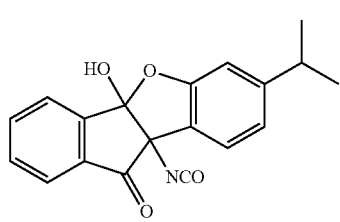 |
TABLE 1-continued
| Ex. | Chemical Structure |
|---|---|
| 70 | 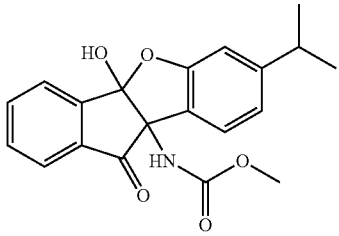 [SMILES: COC(=O)NC12C(=O)c3ccccc3C1(O)Oc1cc(C(C)C)ccc12] |
| 71 | 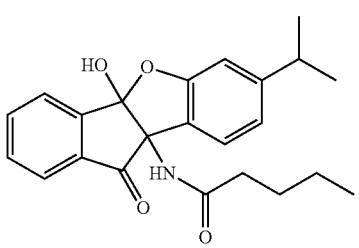 [SMILES: CCCCC(=O)NC12C(=O)c3ccccc3C1(O)Oc1cc(C(C)C)ccc12] |
| 72 | 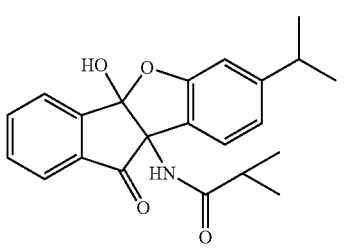 [SMILES: CC(C)C(=O)NC12C(=O)c3ccccc3C1(O)Oc1cc(C(C)C)ccc12] |
| 73 | 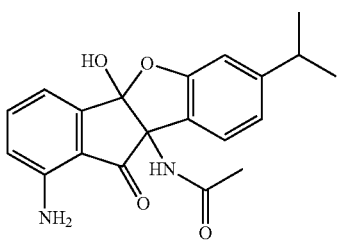 [SMILES: CC(=O)NC12C(=O)c3c(N)cccc3C1(O)Oc1cc(C(C)C)ccc12] |
| 74 | 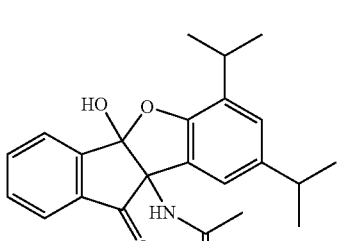 |
| 75 | 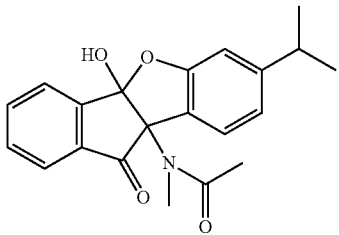 [SMILES: CC(=O)N(C)C12C(=O)c3ccccc3C1(O)Oc1cc(C(C)C)ccc12] |

TABLE 1-continued

| Ex. | Chemical Structure |
|---|---|
| 76 | (structure) |
| 77 | (structure) |
| 78 | (structure) |
| 79 | (structure) |
| 80 | (structure) |
| 81 | (structure) |
| 82 | (structure) |
| 83 | (structure) |
| 84 | (structure) |
| 85 | (structure) |
| 86 | (structure) |
| 87 | (structure) |
| 88 | (structure) |

TABLE 1-continued

| Ex. | Chemical Structure |
|---|---|
| 89 | (structure) |
| 90 | (structure) |
| 91 | (structure) |
| 92 | (structure) |
| 93 | (structure) |
| 94 | (structure) |
| 95 | (structure) |
| 96 | (structure) |
| 97 | (structure) |
| 98 | (structure) |
| 99 | (structure) |

TABLE 1-continued
| Ex. | Chemical Structure |
|---|---|
| 100 | 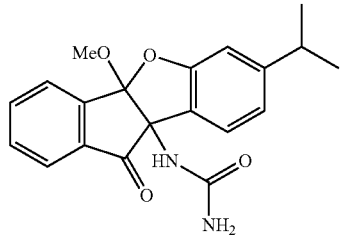 [SMILES: COC12Oc3cc(C(C)C)ccc3C1(NC(N)=O)C(=O)c1ccccc12] |
| 101 | 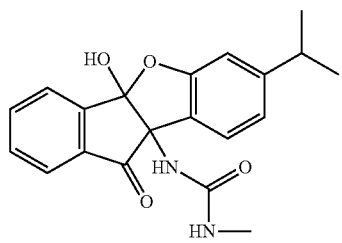 [SMILES: CNC(=O)NC12C(=O)c3ccccc3C1(O)Oc1cc(C(C)C)ccc12] |
| 102 | 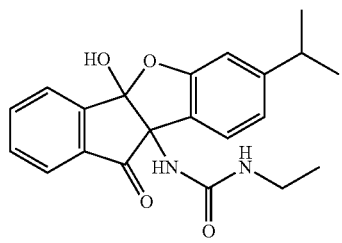 [SMILES: CCNC(=O)NC12C(=O)c3ccccc3C1(O)Oc1cc(C(C)C)ccc12] |
| 103 | 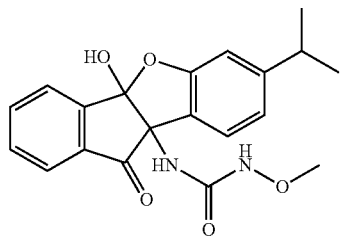 |
| 104 | 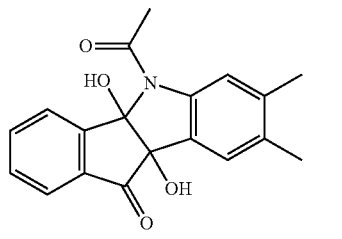 [SMILES: CC(=O)N1c2cc(C)c(C)cc2C2(O)C(=O)c3ccccc3C12O] |
| 105 | 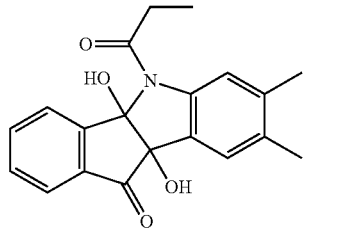 [SMILES: CCC(=O)N1c2cc(C)c(C)cc2C2(O)C(=O)c3ccccc3C12O] |
TABLE 1-continued
| Ex. | Chemical Structure |
|---|---|
| 106 | 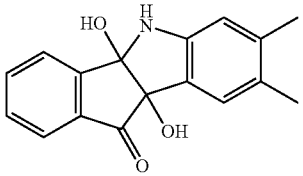 [SMILES: Cc1cc2c(cc1C)C1(O)C(=O)c3ccccc3C1(O)N2] |
| 107 | 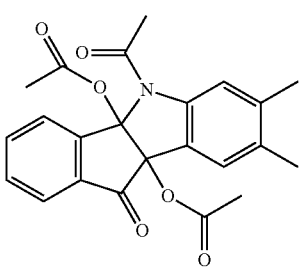 [SMILES: CC(=O)OC12C(=O)c3ccccc3C1(OC(C)=O)N(C(C)=O)c1cc(C)c(C)cc12] |
| 108 | 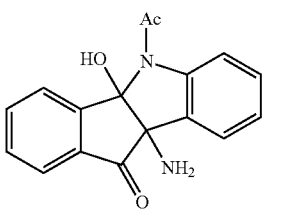 [SMILES: CC(=O)N1c2ccccc2C2(N)C(=O)c3ccccc3C12O] |
| 109 | 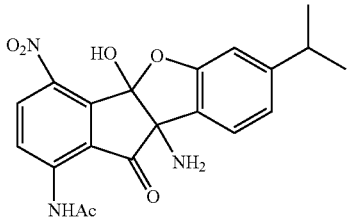 [SMILES: CC(=O)Nc1ccc([N+](=O)[O-])c2c1C(=O)C1(NC(C)=O)c3ccc(C(C)C)cc3OC21OC(C)=O] |
| 110 | 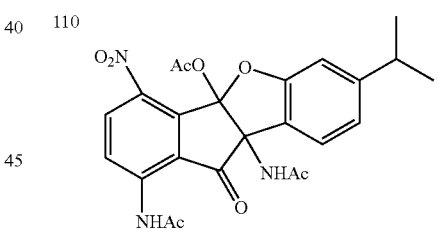 |
| 111 | 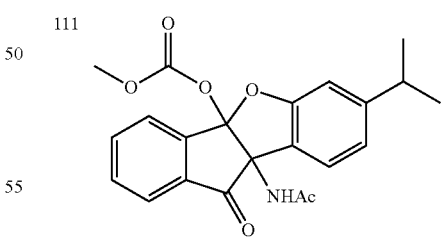 |
| 112 | 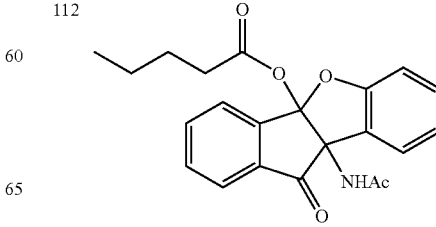 |

TABLE 1-continued
| Ex. | Chemical Structure |
|---|---|
| 113 | 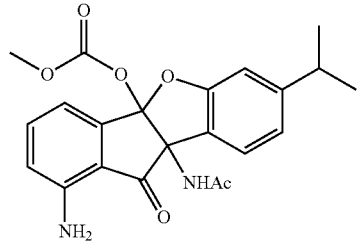 [SMILES: COC(=O)OC12Oc3cc(C(C)C)ccc3C1(NC(C)=O)C(=O)c1c(N)cccc12] |
| 114 | 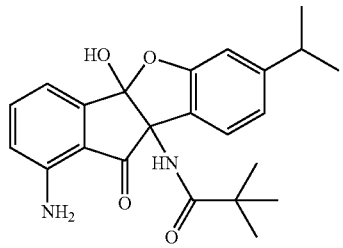 [SMILES: CC(C)c1ccc2c(c1)OC1(O)c3cccc(N)c3C(=O)C21NC(=O)C(C)(C)C] |
| 115 | 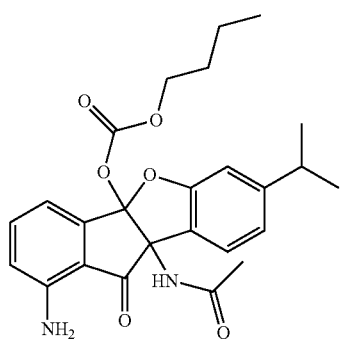 [SMILES: CCCCOC(=O)OC12Oc3cc(C(C)C)ccc3C1(NC(C)=O)C(=O)c1c(N)cccc12] |
| 116 | 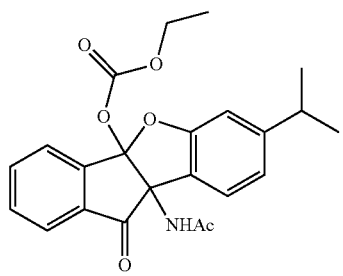 [SMILES: CCOC(=O)OC12Oc3cc(C(C)C)ccc3C1(NC(C)=O)C(=O)c1ccccc12] |
| 117 | 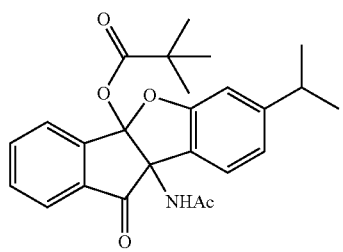 [SMILES: CC(=O)NC12C(=O)c3ccccc3C1(OC(=O)C(C)(C)C)Oc1cc(C(C)C)ccc12] |
| 118 | 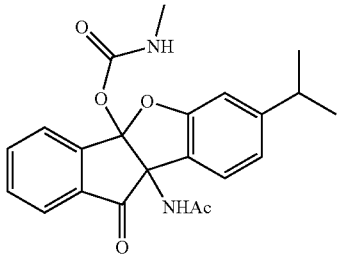 [SMILES: CNC(=O)OC12Oc3cc(C(C)C)ccc3C1(NC(C)=O)C(=O)c1ccccc12] |
| 119 | 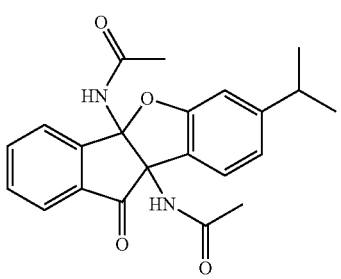 [SMILES: CC(=O)NC12Oc3cc(C(C)C)ccc3C1(NC(C)=O)C(=O)c1ccccc12] |
| 120 | 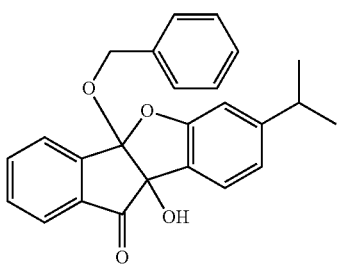 [SMILES: CC(C)c1ccc2c(c1)OC1(OCc3ccccc3)c3ccccc3C(=O)C21O] |
| 121 | 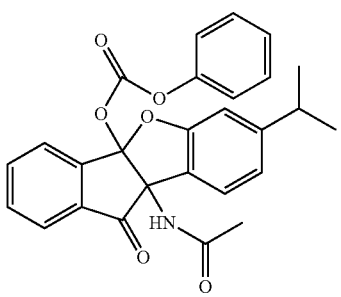 [SMILES: CC(=O)NC12C(=O)c3ccccc3C1(OC(=O)Oc1ccccc1)Oc1cc(C(C)C)ccc12] |
| 122 | 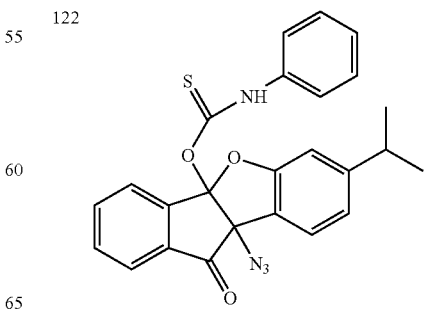 |

TABLE 1-continued
| Ex. | Chemical Structure |
|---|---|
| 123 | 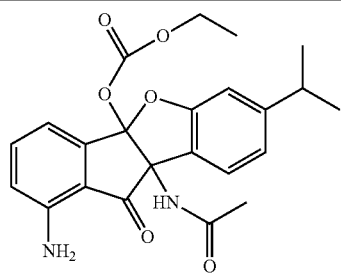 |
| 124 | 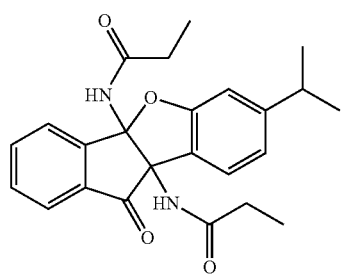 [SMILES: CCC(=O)NC12Oc3cc(C(C)C)ccc3C1(NC(=O)CC)C(=O)c1ccccc12] |
| 125 | 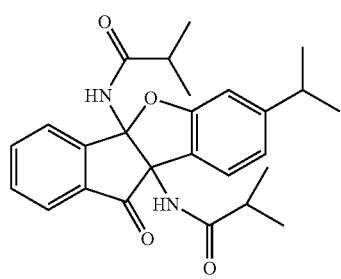 [SMILES: CC(C)C(=O)NC12Oc3cc(C(C)C)ccc3C1(NC(=O)C(C)C)C(=O)c1ccccc12] |
| 126 | 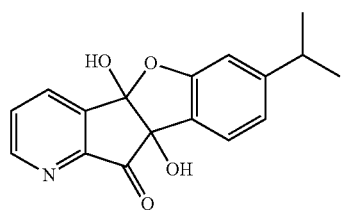 [SMILES: CC(C)c1ccc2c(c1)OC1(O)c3cccnc3C(=O)C21O] |
| 127 | 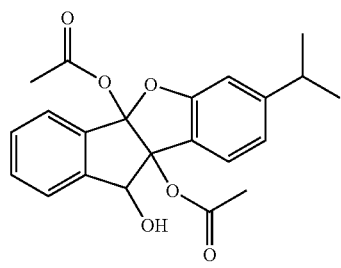 [SMILES: CC(=O)OC12Oc3cc(C(C)C)ccc3C1(OC(C)=O)C(O)c1ccccc12] |
| 128 | 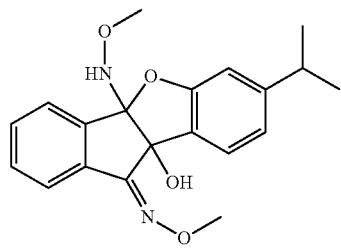 [SMILES: CO/N=C1/c2ccccc2C2(NOC)Oc3cc(C(C)C)ccc3C12O] |
TABLE 1-continued
| Ex. | Chemical Structure |
|---|---|
| 129 | 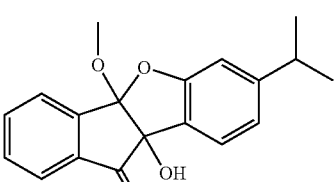 |
| 130 | 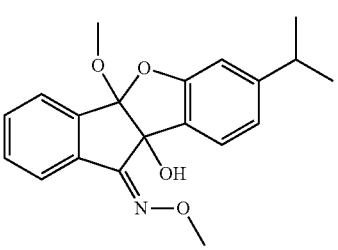 [SMILES: CO/N=C1/c2ccccc2C2(OC)Oc3cc(C(C)C)ccc3C12O] |
| 131 | 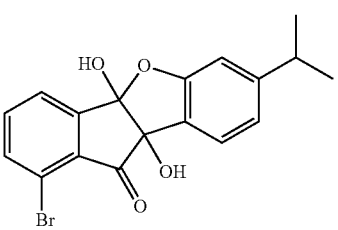 [SMILES: CC(C)c1ccc2c(c1)OC1(O)c3cccc(Br)c3C(=O)C21O] |
| 132 | 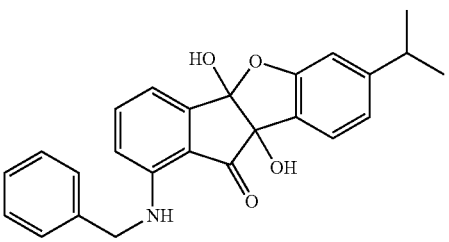 [SMILES: CC(C)c1ccc2c(c1)OC1(O)c3cccc(NCc4ccccc4)c3C(=O)C21O] |
| 133 | 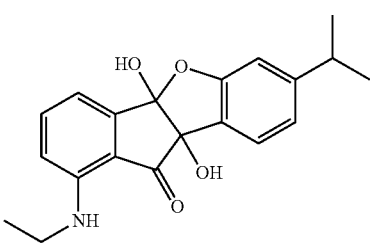 [SMILES: CCNc1cccc2c1C(=O)C1(O)c3ccc(C(C)C)cc3OC21O] |
| 134 | 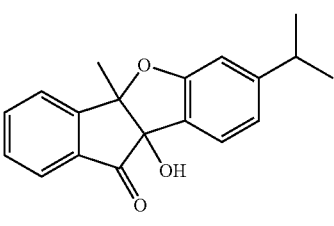 [SMILES: CC(C)c1ccc2c(c1)OC1(C)c3ccccc3C(=O)C21O] |

TABLE 1-continued
| Ex. | Chemical Structure |
|---|---|
| 135 | 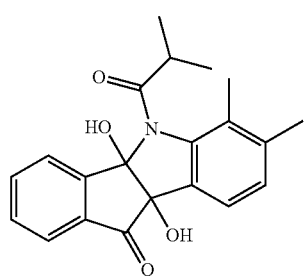 [SMILES: Cc1ccc2c(c1C)N(C(=O)C(C)C)C1(O)c3ccccc3C(=O)C21O] |
| 136 | 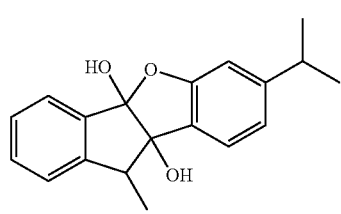 [SMILES: CC(C)c1ccc2c(c1)OC1(O)c3ccccc3C(C)C21O] |
| 137 | 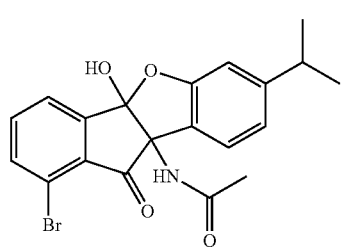 [SMILES: CC(=O)NC12C(=O)c3c(Br)cccc3C1(O)Oc1cc(C(C)C)ccc12] |
| 138 | 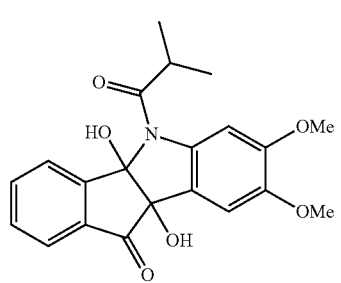 [SMILES: COc1cc2c(cc1OC)C1(O)C(=O)c3ccccc3C1(O)N2C(=O)C(C)C] |
| 139 | 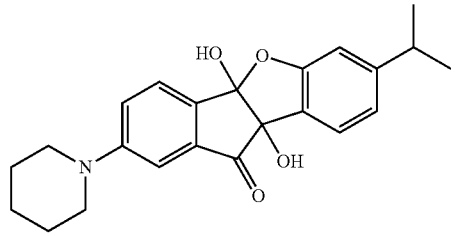 [SMILES: CC(C)c1ccc2c(c1)OC1(O)c3ccc(N4CCCCC4)cc3C(=O)C21O] |
| 140 | 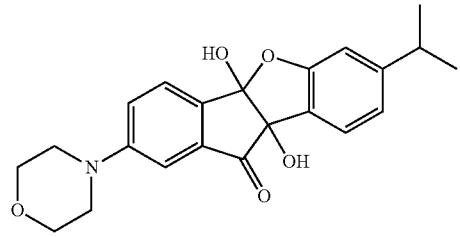 [SMILES: CC(C)c1ccc2c(c1)OC1(O)c3ccc(N4CCOCC4)cc3C(=O)C21O] |
TABLE 1-continued
| Ex. | Chemical Structure |
|---|---|
| 141 | 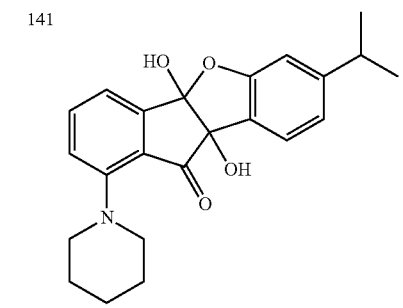 |
| 142 | 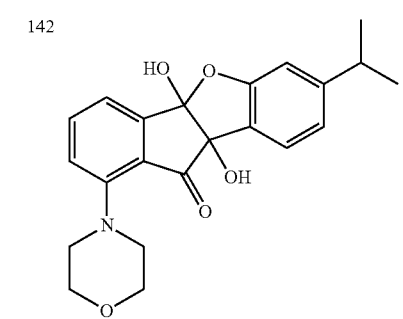 |
| 143 | 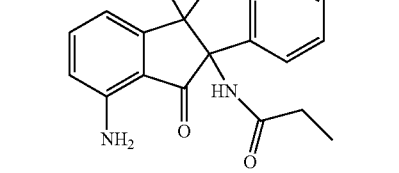 |
| 144 | 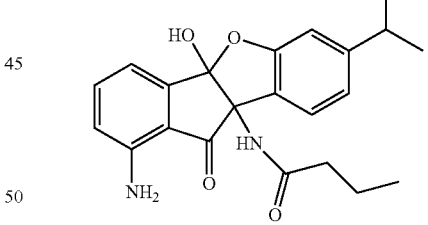 |
| 145 | 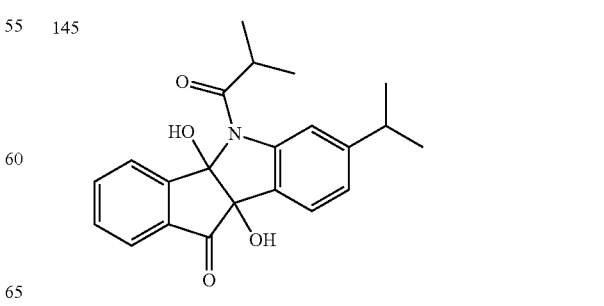 |

TABLE 1-continued
| Ex. | Chemical Structure |
|---|---|
| 146 | 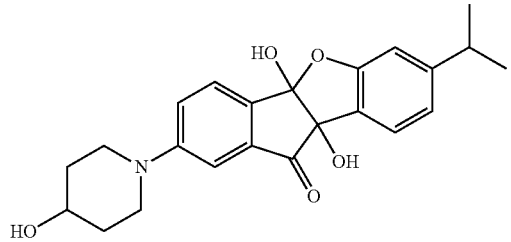 [SMILES: CC(C)c1ccc2c(c1)OC1(O)c3ccc(N4CCC(O)CC4)cc3C(=O)C21O] |
| 147 | 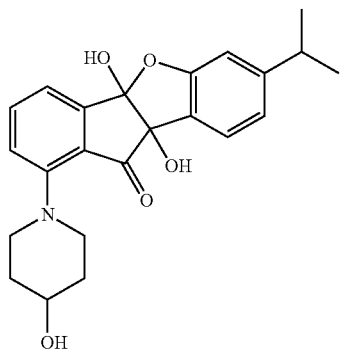 [SMILES: CC(C)c1ccc2c(c1)OC1(O)c3cccc(N4CCC(O)CC4)c3C(=O)C21O] |
| 148 | 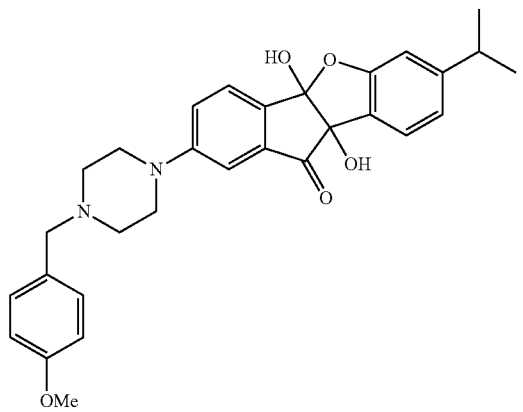 [SMILES: COc1ccc(CN2CCN(c3ccc4c(c3)C(=O)C3(O)c5ccc(C(C)C)cc5OC43O)CC2)cc1] |
| 149 | 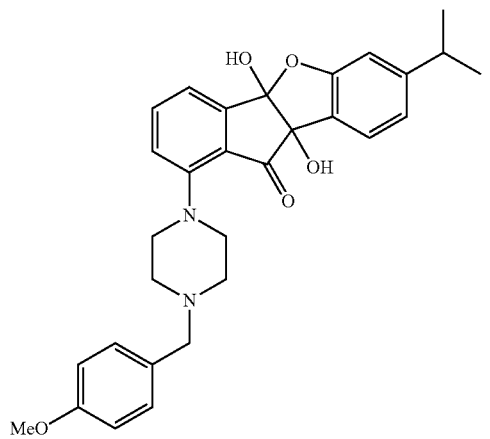 [SMILES: COc1ccc(CN2CCN(c3cccc4c3C(=O)C3(O)c5ccc(C(C)C)cc5OC43O)CC2)cc1] |
TABLE 1-continued
| Ex. | Chemical Structure |
|---|---|
| 150 | 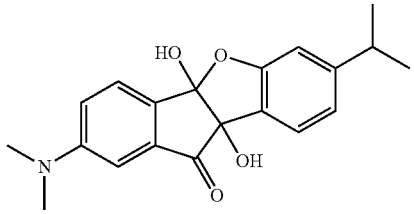 [SMILES: CC(C)c1ccc2c(c1)OC1(O)c3ccc(N(C)C)cc3C(=O)C21O] |
| 151 | 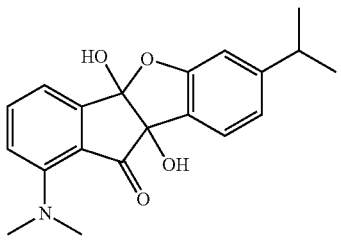 [SMILES: CC(C)c1ccc2c(c1)OC1(O)c3cccc(N(C)C)c3C(=O)C21O] |
| 152 | 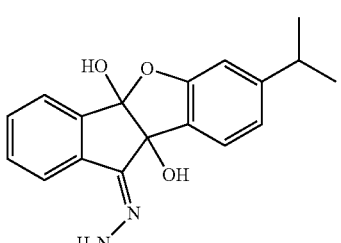 |
| 153 | 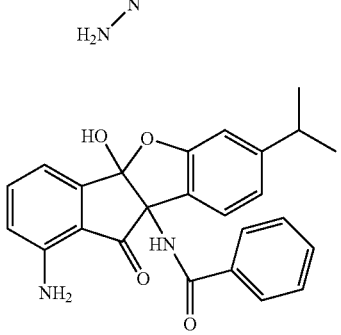 |
| 154 | 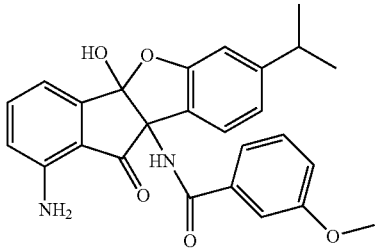 [SMILES: COc1cccc(C(=O)NC23C(=O)c4c(N)cccc4C2(O)Oc2cc(C(C)C)ccc23)c1] |
| 155 | 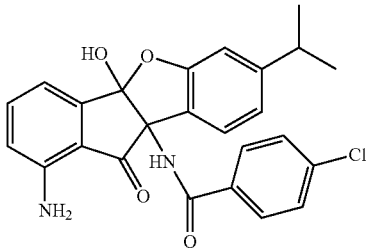 [SMILES: CC(C)c1ccc2c(c1)OC1(O)c3cccc(N)c3C(=O)C21NC(=O)c1ccc(Cl)cc1] |

TABLE 1-continued
| Ex. | Chemical Structure |
|---|---|
| 156 | 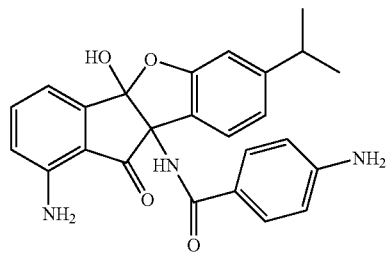 [SMILES: CC(C)c1ccc2c(c1)OC1(O)c3cccc(N)c3C(=O)C21NC(=O)c1ccc(N)cc1] |
| 157 | 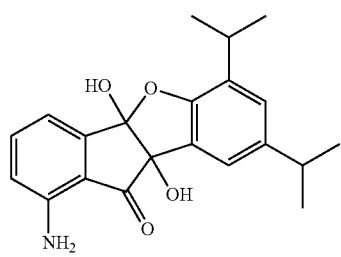 [SMILES: CC(C)c1cc(C(C)C)c2c(c1)C1(O)C(=O)c3c(N)cccc3C1(O)O2] |
| 158 | 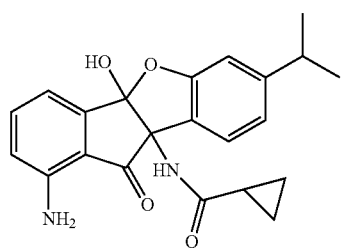 [SMILES: CC(C)c1ccc2c(c1)OC1(O)c3cccc(N)c3C(=O)C21NC(=O)C1CC1] |
| 159 | 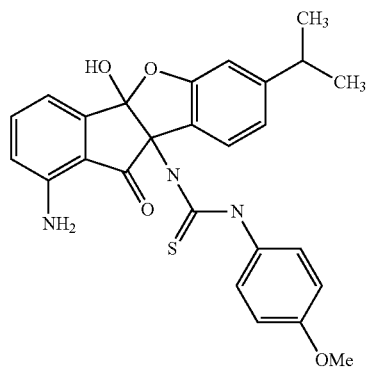 [SMILES: COc1ccc(NC(=S)NC23C(=O)c4c(N)cccc4C2(O)Oc2cc(C(C)C)ccc23)cc1] |
| 160 | 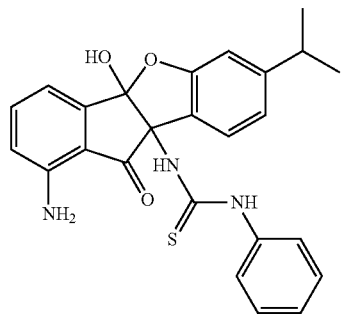 [SMILES: CC(C)c1ccc2c(c1)OC1(O)c3cccc(N)c3C(=O)C21NC(=S)Nc1ccccc1] |
TABLE 1-continued
| Ex. | Chemical Structure |
|---|---|
| 161 | 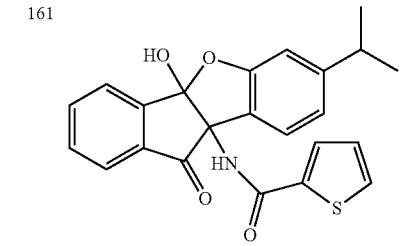 |
| 162 | 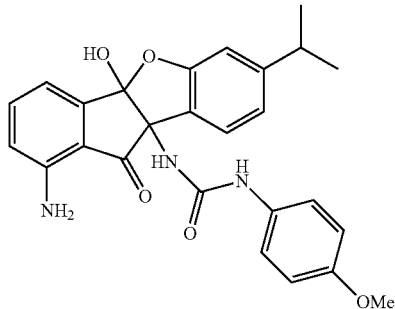 [SMILES: COc1ccc(NC(=O)NC23C(=O)c4c(N)cccc4C2(O)Oc2cc(C(C)C)ccc23)cc1] |
| 163 | 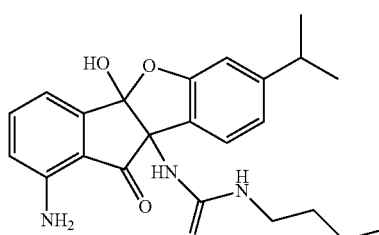 |
| 164 | 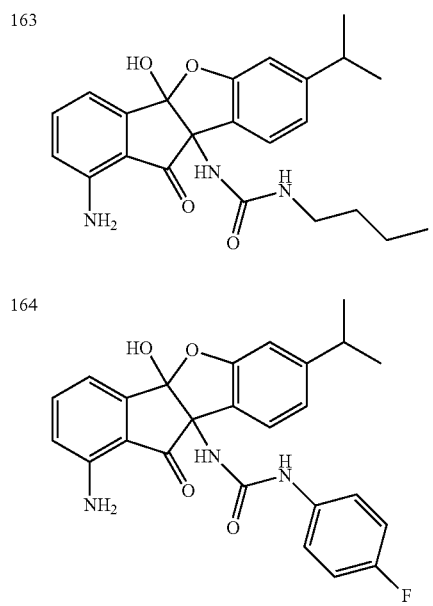 |
| 165 | 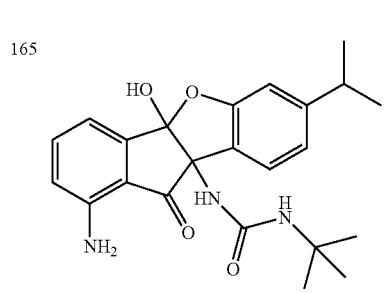 |

TABLE 1-continued
| Ex. | Chemical Structure |
|---|---|
| 166 | 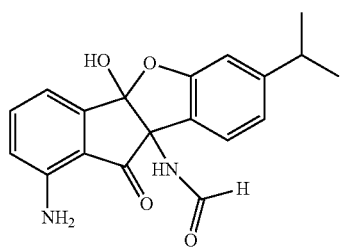 [SMILES: CC(C)c1ccc2c(c1)OC1(O)c3cccc(N)c3C(=O)C21NC=O] |
| 167 | 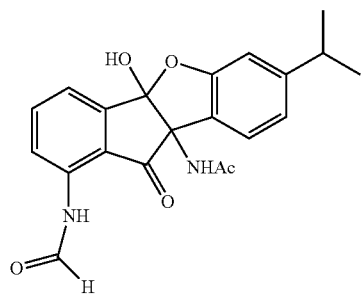 [SMILES: CC(=O)NC12C(=O)c3c(NC=O)cccc3C1(O)Oc1cc(C(C)C)ccc12] |
| 168 | 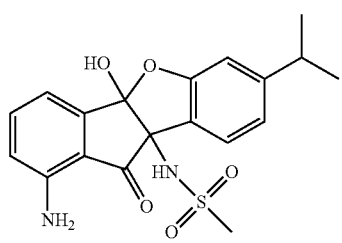 [SMILES: CC(C)c1ccc2c(c1)OC1(O)c3cccc(N)c3C(=O)C21NS(C)(=O)=O] |
| 169 | 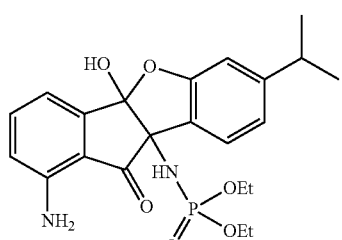 |
| 170 | 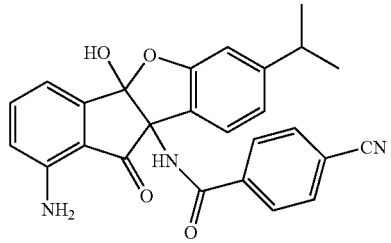 [SMILES: CC(C)c1ccc2c(c1)OC1(O)c3cccc(N)c3C(=O)C21NC(=O)c1ccc(C#N)cc1] |
| 171 | 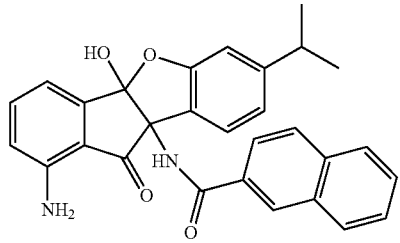 [SMILES: CC(C)c1ccc2c(c1)OC1(O)c3cccc(N)c3C(=O)C21NC(=O)c1ccc2ccccc2c1] |
| 172 | 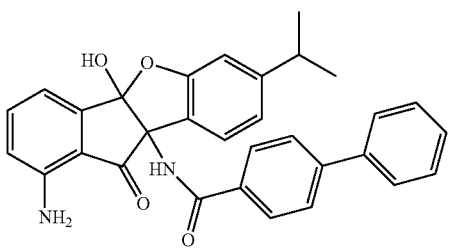 [SMILES: CC(C)c1ccc2c(c1)OC1(O)c3cccc(N)c3C(=O)C21NC(=O)c1ccc(-c2ccccc2)cc1] |
| 173 | 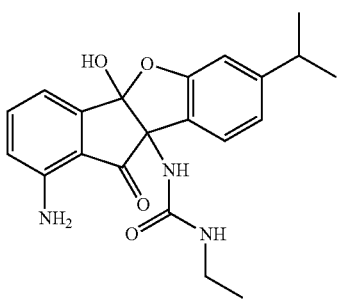 [SMILES: CCNC(=O)NC12C(=O)c3c(N)cccc3C1(O)Oc1cc(C(C)C)ccc12] |
| 174 | 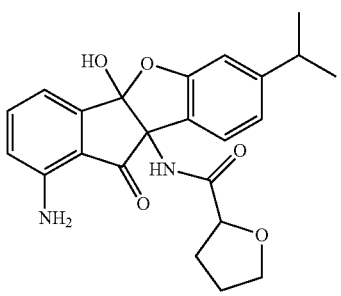 [SMILES: CC(C)c1ccc2c(c1)OC1(O)c3cccc(N)c3C(=O)C21NC(=O)C1CCCO1] |
| 175 | 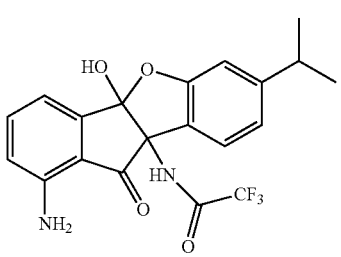 [SMILES: CC(C)c1ccc2c(c1)OC1(O)c3cccc(N)c3C(=O)C21NC(=O)C(F)(F)F] |
| 176 | 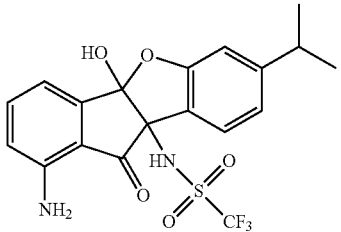 [SMILES: CC(C)c1ccc2c(c1)OC1(O)c3cccc(N)c3C(=O)C21NS(=O)(=O)C(F)(F)F] |
| 177 | 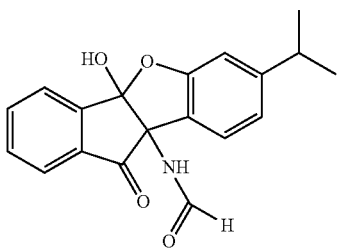 [SMILES: CC(C)c1ccc2c(c1)OC1(O)c3ccccc3C(=O)C21NC=O] |

TABLE 1-continued
| Ex. | Chemical Structure |
|---|---|
| 178 | 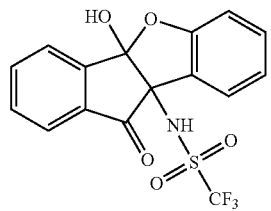 [SMILES: O=C1c2ccccc2C2(O)Oc3ccccc3C12NS(=O)(=O)C(F)(F)F] |
| 179 | 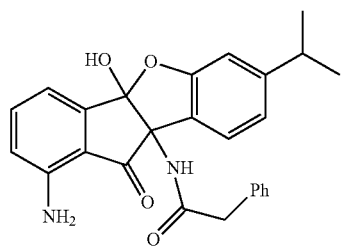 [SMILES: CC(C)c1ccc2c(c1)OC1(O)c3cccc(N)c3C(=O)C21NC(=O)Cc1ccccc1] |
| 180 | 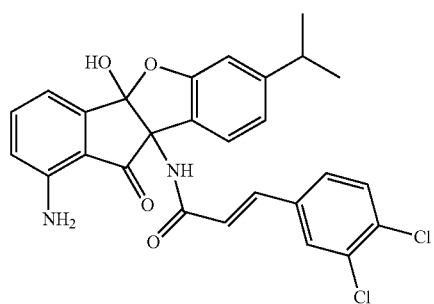 [SMILES: CC(C)c1ccc2c(c1)OC1(O)c3cccc(N)c3C(=O)C21NC(=O)/C=C/c1ccc(Cl)c(Cl)c1] |
| 181 | 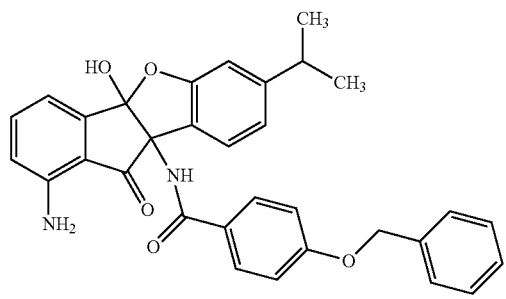 [SMILES: CC(C)c1ccc2c(c1)OC1(O)c3cccc(N)c3C(=O)C21NC(=O)c1ccc(OCc2ccccc2)cc1] |
| 182 | 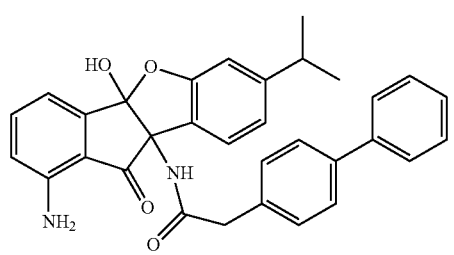 [SMILES: CC(C)c1ccc2c(c1)OC1(O)c3cccc(N)c3C(=O)C21NC(=O)Cc1ccc(-c2ccccc2)cc1] |
TABLE 1-continued
| Ex. | Chemical Structure |
|---|---|
| 183 | 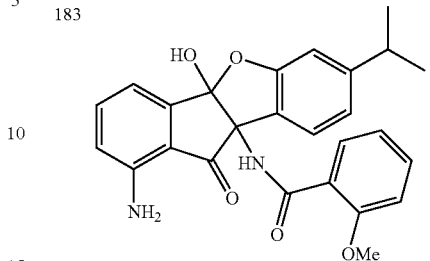 |
| 184 | 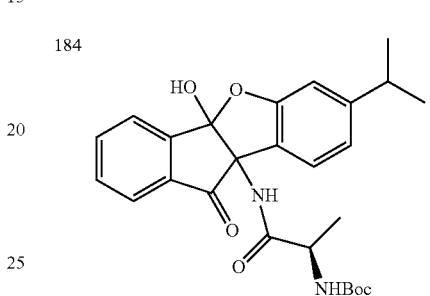 |
| 185 | 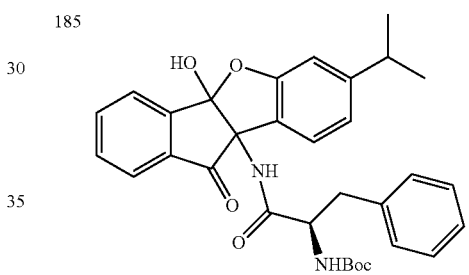 |
| 186 | 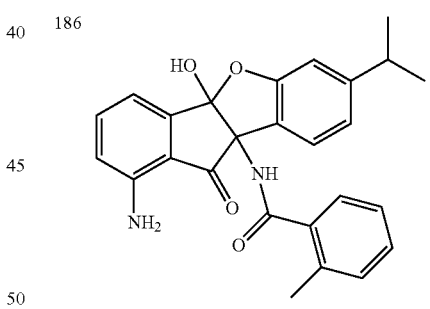 |
| 187 | 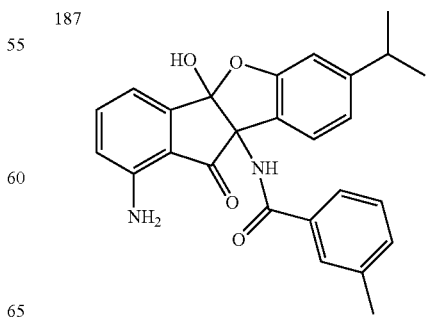 |

TABLE 1-continued
Ex. Chemical Structure
188
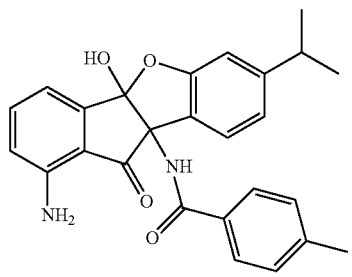 [SMILES: Cc1ccc(C(=O)NC23C(=O)c4c(N)cccc4C2(O)Oc2cc(C(C)C)ccc23)cc1]
189
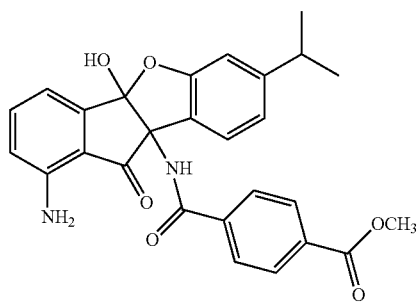 [SMILES: COC(=O)c1ccc(C(=O)NC23C(=O)c4c(N)cccc4C2(O)Oc2cc(C(C)C)ccc23)cc1]
190
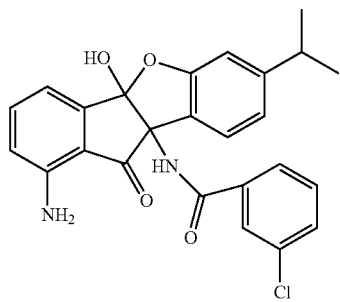 [SMILES: CC(C)c1ccc2c(c1)OC1(O)c3cccc(N)c3C(=O)C21NC(=O)c1cccc(Cl)c1]
191
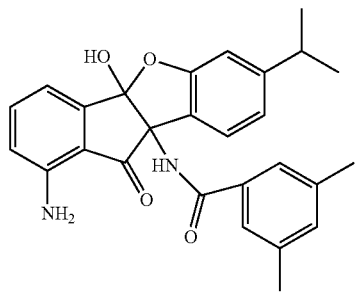 [SMILES: Cc1cc(C)cc(C(=O)NC23C(=O)c4c(N)cccc4C2(O)Oc2cc(C(C)C)ccc23)c1]
192
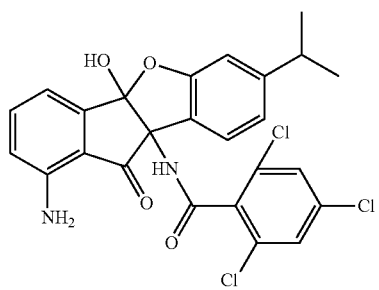 [SMILES: CC(C)c1ccc2c(c1)OC1(O)c3cccc(N)c3C(=O)C21NC(=O)c1c(Cl)cc(Cl)cc1Cl]
TABLE 1-continued
Ex. Chemical Structure
193
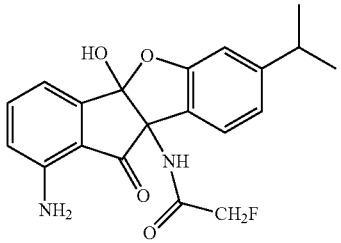
194
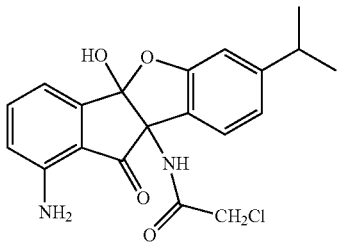
195
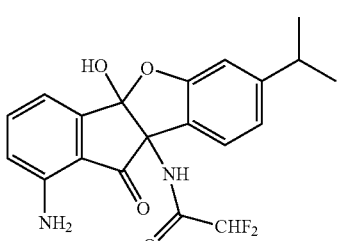
196
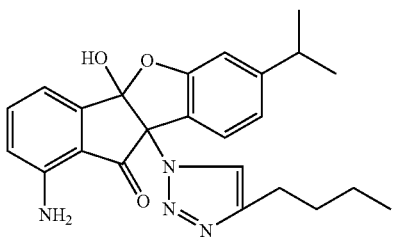 [SMILES: CCCCc1cn(C23C(=O)c4c(N)cccc4C2(O)Oc2cc(C(C)C)ccc23)nn1]
197
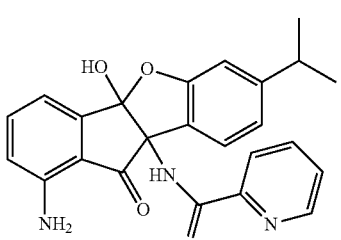
198
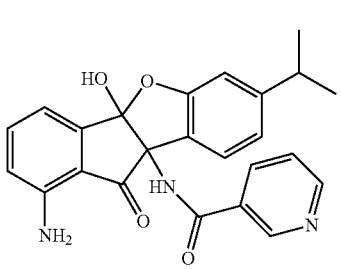 [SMILES: CC(C)c1ccc2c(c1)OC1(O)c3cccc(N)c3C(=O)C21NC(=O)c1cccnc1]

TABLE 1-continued
| Ex. | Chemical Structure |
|---|---|
| 199 | 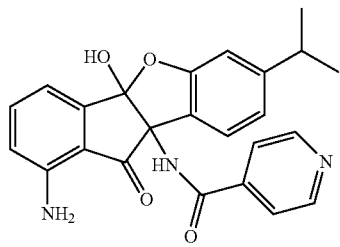 [SMILES: CC(C)c1ccc2c(c1)OC1(O)c3cccc(N)c3C(=O)C21NC(=O)c1ccncc1] |
| 200 | 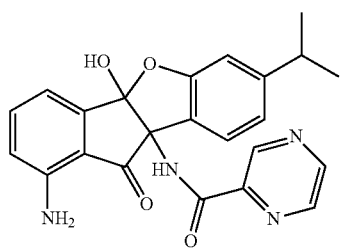 [SMILES: CC(C)c1ccc2c(c1)OC1(O)c3cccc(N)c3C(=O)C21NC(=O)c1cnccn1] |
| 201 | 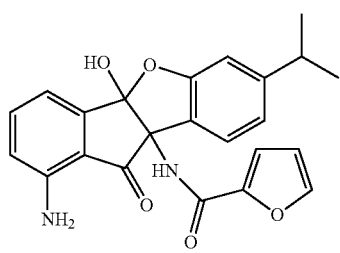 [SMILES: CC(C)c1ccc2c(c1)OC1(O)c3cccc(N)c3C(=O)C21NC(=O)c1ccco1] |
| 202 | 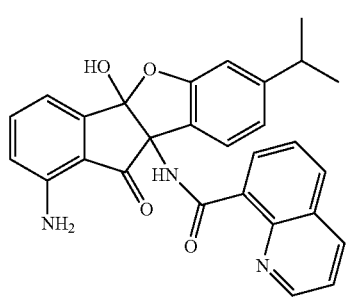 [SMILES: CC(C)c1ccc2c(c1)OC1(O)c3cccc(N)c3C(=O)C21NC(=O)c1cccc2cccnc12] |
| 203 | 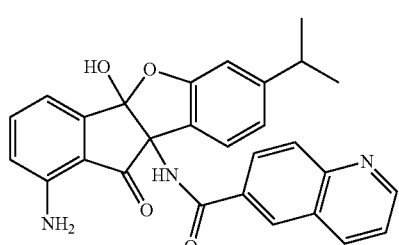 |
| 204 | 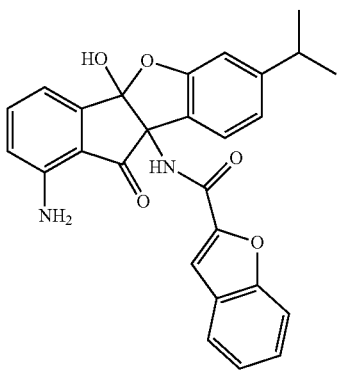 [SMILES: CC(C)c1ccc2c(c1)OC1(O)c3cccc(N)c3C(=O)C21NC(=O)c1cc2ccccc2o1] |
| 205 | 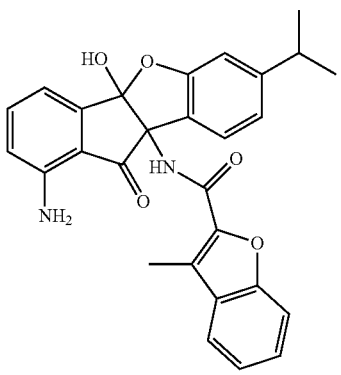 [SMILES: Cc1c(C(=O)NC23C(=O)c4c(N)cccc4C2(O)Oc2cc(C(C)C)ccc23)oc2ccccc12] |
| 206 | 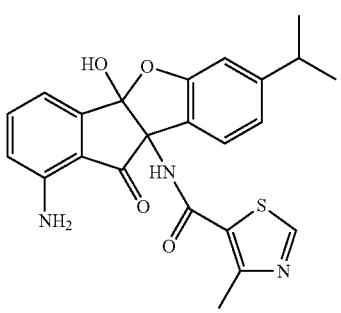 [SMILES: Cc1ncsc1C(=O)NC12C(=O)c3c(N)cccc3C1(O)Oc1cc(C(C)C)ccc12] |
| 207 | 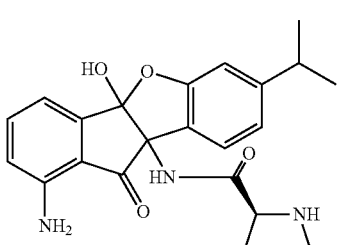 |
| 208 | 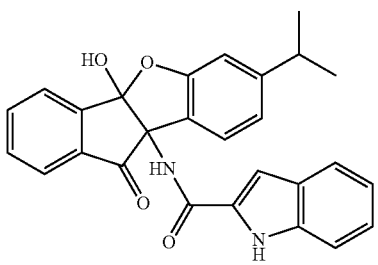 [SMILES: CC(C)c1ccc2c(c1)OC1(O)c3ccccc3C(=O)C21NC(=O)c1cc2ccccc2[nH]1] |

TABLE 1-continued
| Ex. | Chemical Structure |
|---|---|
| 209 | 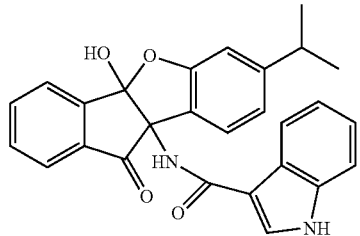 [SMILES: CC(C)c1ccc2c(c1)OC1(O)c3ccccc3C(=O)C21NC(=O)c1c[nH]c2ccccc12] |
| 210 | 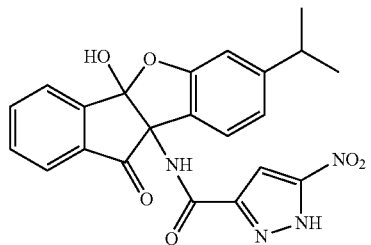 [SMILES: CC(C)c1ccc2c(c1)OC1(O)c3ccccc3C(=O)C21NC(=O)c1cc([N+](=O)[O-])[nH]n1] |
| 211 | 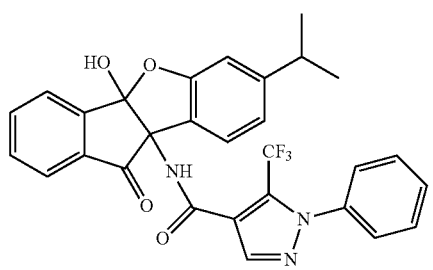 [SMILES: CC(C)c1ccc2c(c1)OC1(O)c3ccccc3C(=O)C21NC(=O)c1cnn(-c2ccccc2)c1C(F)(F)F] |
| 212 | 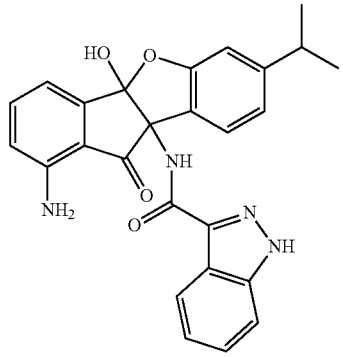 [SMILES: CC(C)c1ccc2c(c1)OC1(O)c3cccc(N)c3C(=O)C21NC(=O)c1n[nH]c2ccccc12] |
| 213 | 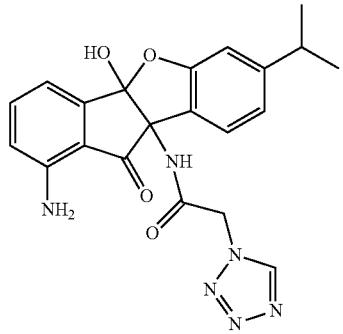 [SMILES: CC(C)c1ccc2c(c1)OC1(O)c3cccc(N)c3C(=O)C21NC(=O)Cn1cnnn1] |
TABLE 1-continued
| Ex. | Chemical Structure |
|---|---|
| 214 | 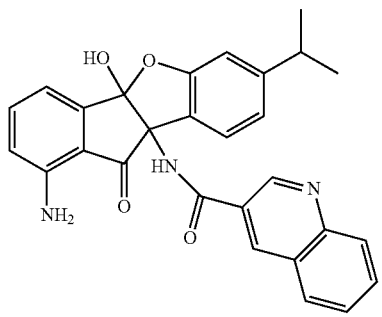 [SMILES: CC(C)c1ccc2c(c1)OC1(O)c3cccc(N)c3C(=O)C21NC(=O)c1cnc2ccccc2c1] |
| 215 | 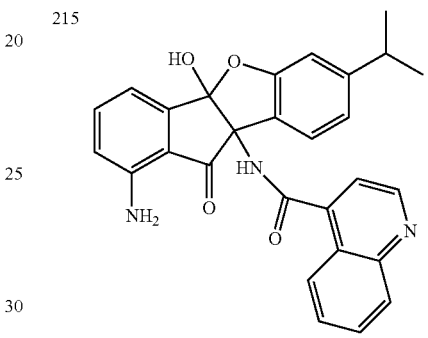 |
| 216 | 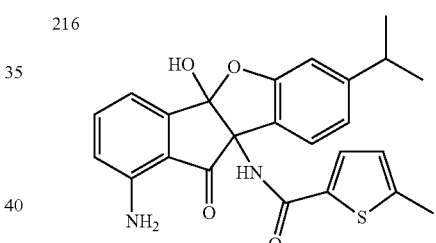 |
| 217 | 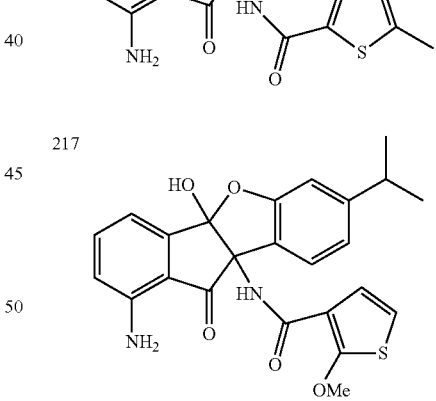 |
| 218 | 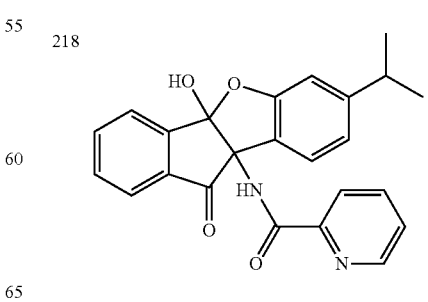 |

TABLE 1-continued
| Ex. | Chemical Structure |
|---|---|
| 219 | 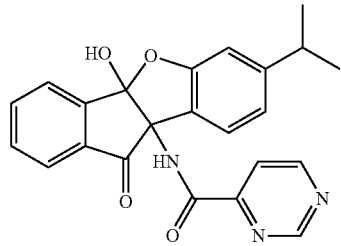 [SMILES: CC(C)c1ccc2c(c1)OC1(O)c3ccccc3C(=O)C21NC(=O)c1ccncn1] |
| 220 | 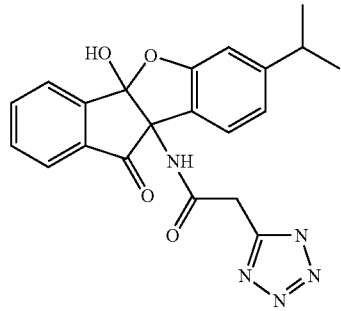 [SMILES: CC(C)c1ccc2c(c1)OC1(O)c3ccccc3C(=O)C21NC(=O)Cc1nnn[nH]1] |
| 221 | 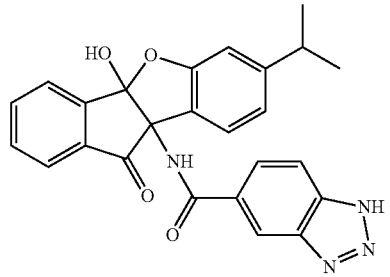 [SMILES: CC(C)c1ccc2c(c1)OC1(O)c3ccccc3C(=O)C21NC(=O)c1ccc2[nH]nnc2c1] |
| 222 | 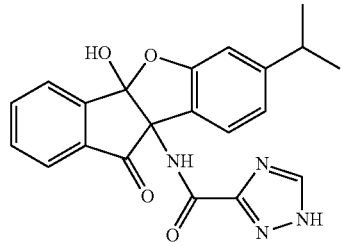 [SMILES: CC(C)c1ccc2c(c1)OC1(O)c3ccccc3C(=O)C21NC(=O)c1nc[nH]n1] |
| 223 | 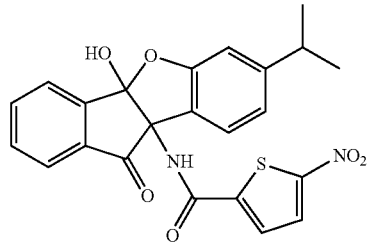 [SMILES: CC(C)c1ccc2c(c1)OC1(O)c3ccccc3C(=O)C21NC(=O)c1ccc([N+](=O)[O-])s1] |
| 224 | 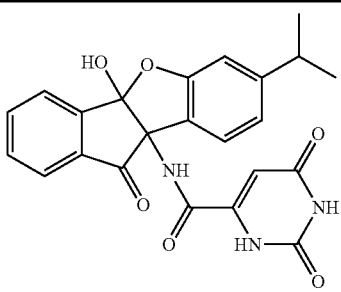 |
| 225 | 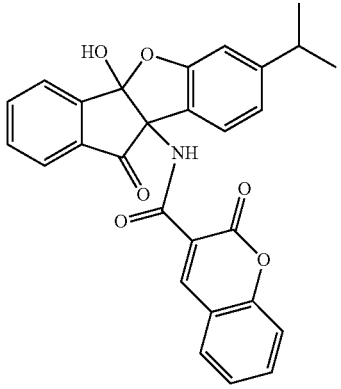 [SMILES: CC(C)c1ccc2c(c1)OC1(O)c3ccccc3C(=O)C21NC(=O)c1cc2ccccc2oc1=O] |
| 226 | 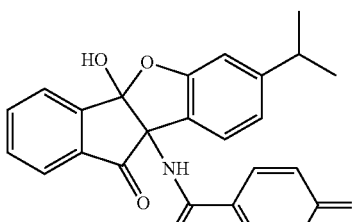 |
| 227 | 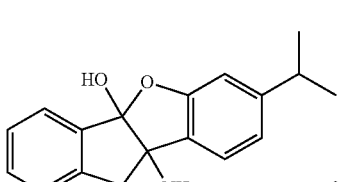 |
| 228 | 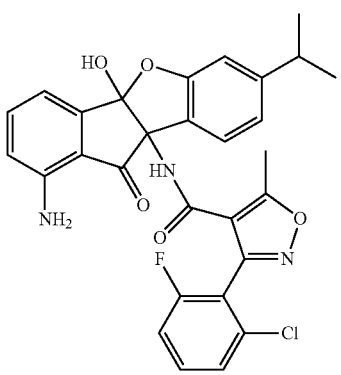 [SMILES: Cc1onc(-c2c(F)cccc2Cl)c1C(=O)NC12C(=O)c3c(N)cccc3C1(O)Oc1cc(C(C)C)ccc12] |

TABLE 1-continued
| Ex. | Chemical Structure |
|---|---|
| 229 | 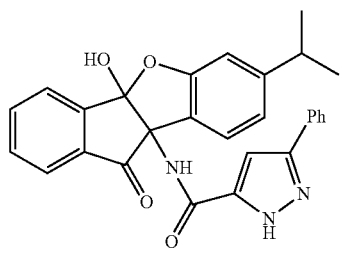 [SMILES: CC(C)c1ccc2c(c1)OC1(O)c3ccccc3C(=O)C21NC(=O)c1cc(-c2ccccc2)n[nH]1] |
| 230 | 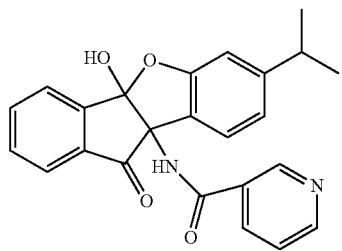 [SMILES: CC(C)c1ccc2c(c1)OC1(O)c3ccccc3C(=O)C21NC(=O)c1cccnc1] |
| 231 | 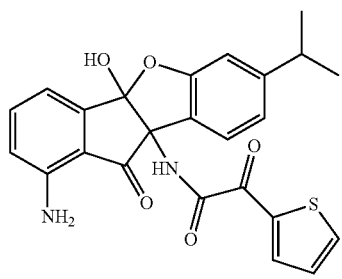 [SMILES: CC(C)c1ccc2c(c1)OC1(O)c3cccc(N)c3C(=O)C21NC(=O)C(=O)c1cccs1] |
| 232 | 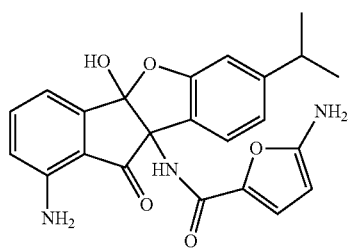 [SMILES: CC(C)c1ccc2c(c1)OC1(O)c3cccc(N)c3C(=O)C21NC(=O)c1ccc(N)o1] |
| 233 | 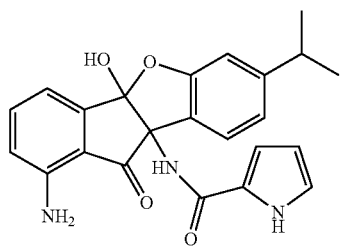 |
| 234 | 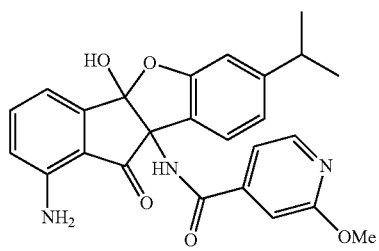 [SMILES: COc1cc(C(=O)NC23C(=O)c4c(N)cccc4C2(O)Oc2cc(C(C)C)ccc23)ccn1] |
TABLE 1-continued
| Ex. | Chemical Structure |
|---|---|
| 235 | 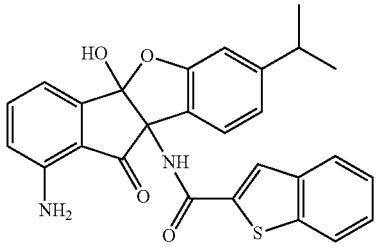 [SMILES: CC(C)c1ccc2c(c1)OC1(O)c3cccc(N)c3C(=O)C21NC(=O)c1cc2ccccc2s1] |
| 236 | 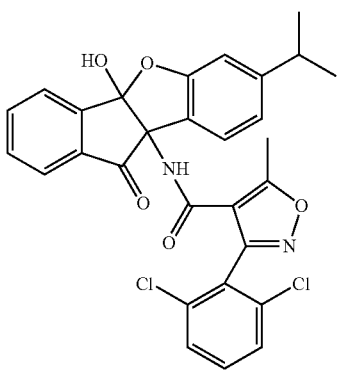 [SMILES: Cc1onc(-c2c(Cl)cccc2Cl)c1C(=O)NC12C(=O)c3ccccc3C1(O)Oc1cc(C(C)C)ccc12] |
| 237 | 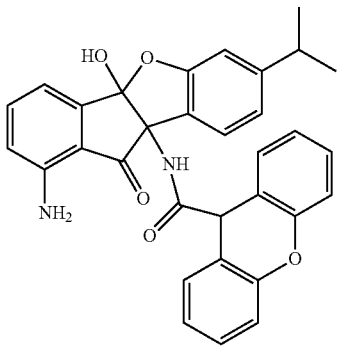 [SMILES: CC(C)c1ccc2c(c1)OC1(O)c3cccc(N)c3C(=O)C21NC(=O)C1c2ccccc2Oc2ccccc21] |
| 238 | 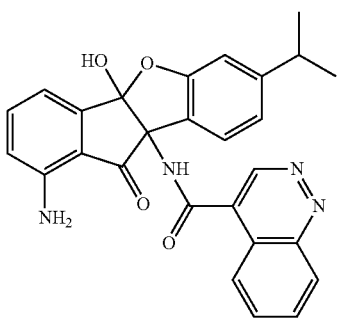 [SMILES: CC(C)c1ccc2c(c1)OC1(O)c3cccc(N)c3C(=O)C21NC(=O)c1cnnc2ccccc12] |

TABLE 1-continued
| Ex. | Chemical Structure |
|---|---|
| 239 | 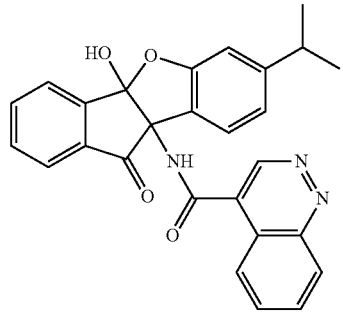 [SMILES: CC(C)c1ccc2c(c1)OC1(O)c3ccccc3C(=O)C21NC(=O)c1cnnc2ccccc12] |
| 240 | 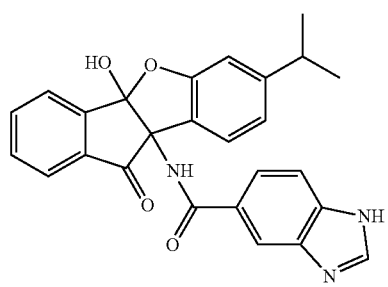 [SMILES: CC(C)c1ccc2c(c1)OC1(O)c3ccccc3C(=O)C21NC(=O)c1ccc2[nH]cnc2c1] |
| 241 | 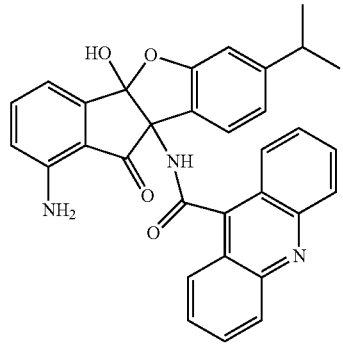 [SMILES: CC(C)c1ccc2c(c1)OC1(O)c3cccc(N)c3C(=O)C21NC(=O)c1c2ccccc2nc2ccccc12] |
| 242 | 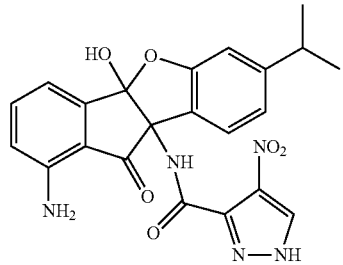 [SMILES: CC(C)c1ccc2c(c1)OC1(O)c3cccc(N)c3C(=O)C21NC(=O)c1n[nH]cc1[N+](=O)[O-]] |
| 243 | 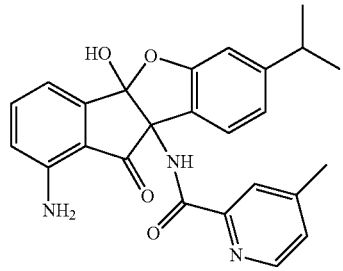 [SMILES: Cc1ccnc(C(=O)NC23C(=O)c4c(N)cccc4C2(O)Oc2cc(C(C)C)ccc23)c1] |
TABLE 1-continued
| Ex. | Chemical Structure |
|---|---|
| 244 | 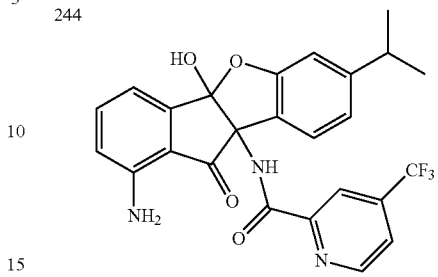 |
| 245 | 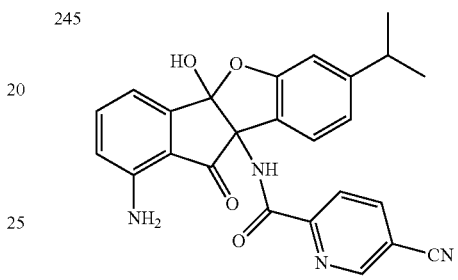 |
| 246 | 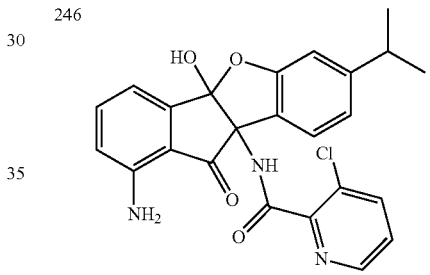 |
| 247 | 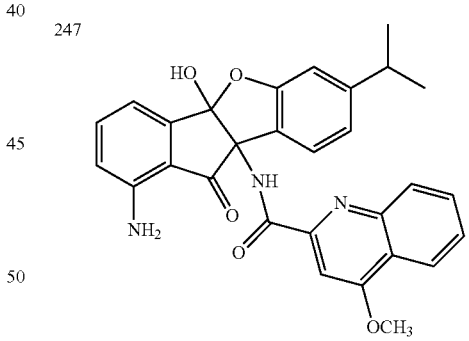 |
| 248 | 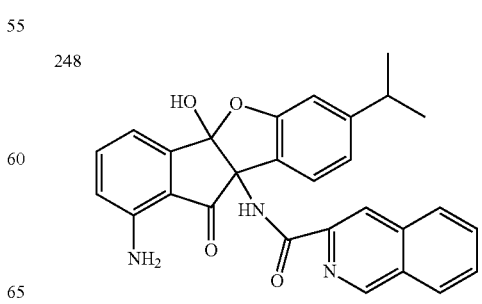 |

TABLE 1-continued
| Ex. | Chemical Structure |
|---|---|
| 249 | 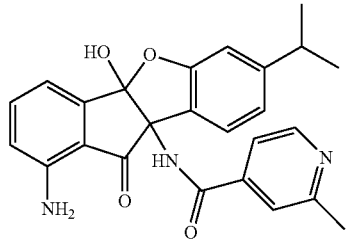 [SMILES: Cc1cc(C(=O)NC23C(=O)c4c(N)cccc4C2(O)Oc2cc(C(C)C)ccc23)ccn1] |
| 250 | 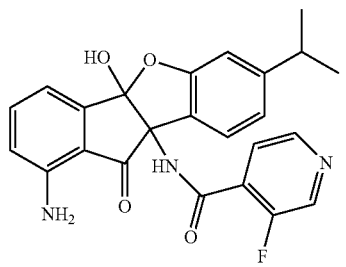 |
| 251 | 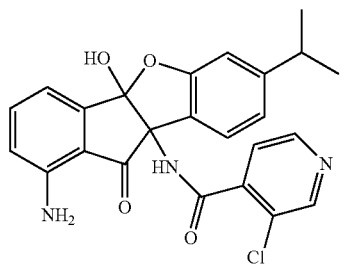 [SMILES: CC(C)c1ccc2c(c1)OC1(O)c3cccc(N)c3C(=O)C21NC(=O)c1ccncc1Cl] |
| 252 | 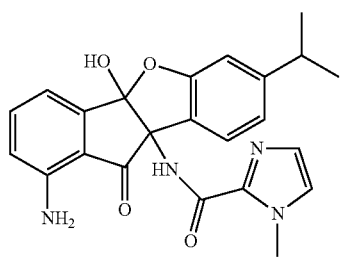 [SMILES: CC(C)c1ccc2c(c1)OC1(O)c3cccc(N)c3C(=O)C21NC(=O)c1nccn1C] |
| 253 | 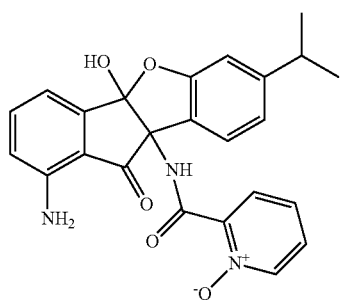 |
| 254 | 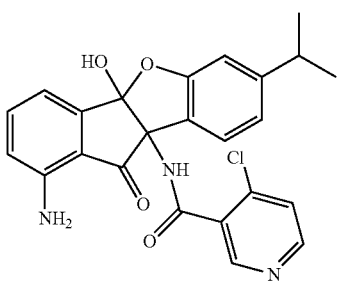 [SMILES: CC(C)c1ccc2c(c1)OC1(O)c3cccc(N)c3C(=O)C21NC(=O)c1cnccc1Cl] |
| 255 | 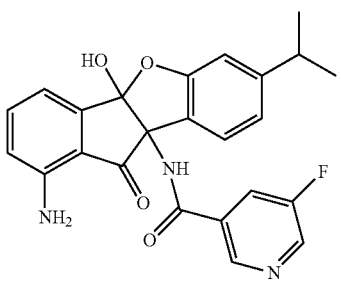 [SMILES: CC(C)c1ccc2c(c1)OC1(O)c3cccc(N)c3C(=O)C21NC(=O)c1cncc(F)c1] |
| 256 | 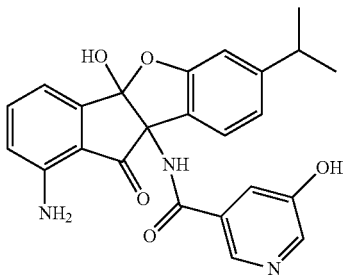 [SMILES: CC(C)c1ccc2c(c1)OC1(O)c3cccc(N)c3C(=O)C21NC(=O)c1cncc(O)c1] |
| 257 | 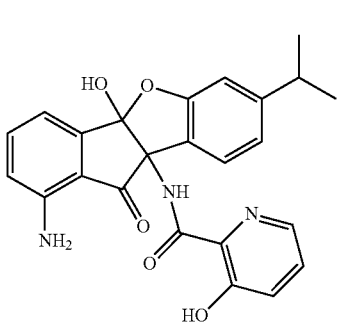 [SMILES: CC(C)c1ccc2c(c1)OC1(O)c3cccc(N)c3C(=O)C21NC(=O)c1ncccc1O] |
| 258 | 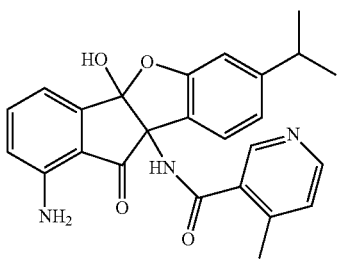 [SMILES: Cc1ccncc1C(=O)NC12C(=O)c3c(N)cccc3C1(O)Oc1cc(C(C)C)ccc12] |

TABLE 1-continued
| Ex. | Chemical Structure |
|---|---|
| 259 | 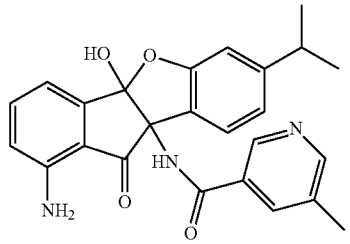 |
| 260 | 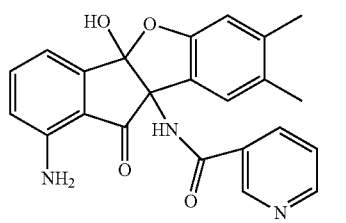 [SMILES: Cc1cc2c(cc1C)C1(NC(=O)c3cccnc3)C(=O)c3c(N)cccc3C1(O)O2] |
| 261 | 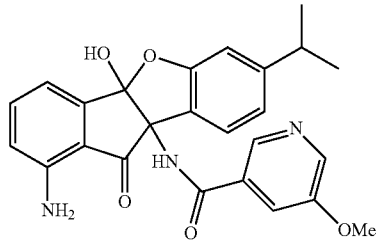 [SMILES: COc1cncc(C(=O)NC23C(=O)c4c(N)cccc4C2(O)Oc2cc(C(C)C)ccc23)c1] |
| 262 | 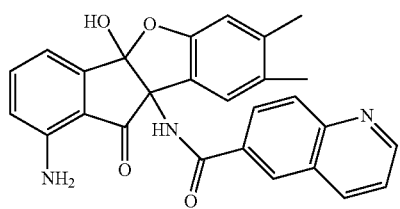 [SMILES: Cc1cc2c(cc1C)C1(NC(=O)c3ccc4ncccc4c3)C(=O)c3c(N)cccc3C1(O)O2] |
| 263 | 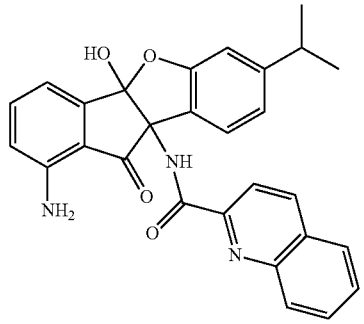 [SMILES: CC(C)c1ccc2c(c1)OC1(O)c3cccc(N)c3C(=O)C21NC(=O)c1ccc2ccccc2n1] |
| 264 | 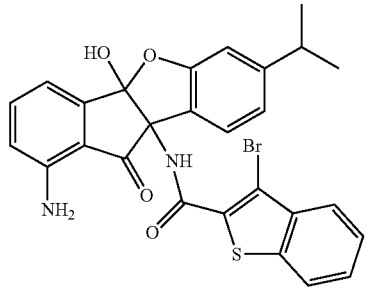 [SMILES: CC(C)c1ccc2c(c1)OC1(O)c3cccc(N)c3C(=O)C21NC(=O)c1sc2ccccc2c1Br] |
TABLE 1-continued
| Ex. | Chemical Structure |
|---|---|
| 265 | 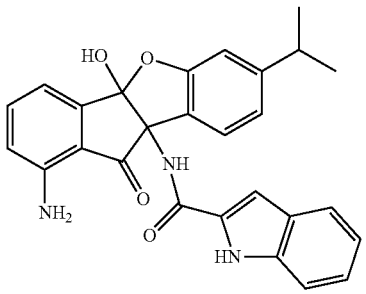 [SMILES: CC(C)c1ccc2c(c1)OC1(O)c3cccc(N)c3C(=O)C21NC(=O)c1cc2ccccc2[nH]1] |
| 266 | 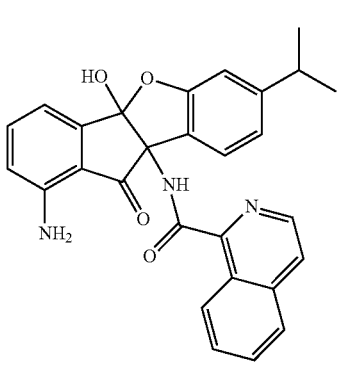 [SMILES: CC(C)c1ccc2c(c1)OC1(O)c3cccc(N)c3C(=O)C21NC(=O)c1nccc2ccccc12] |
| 267 | 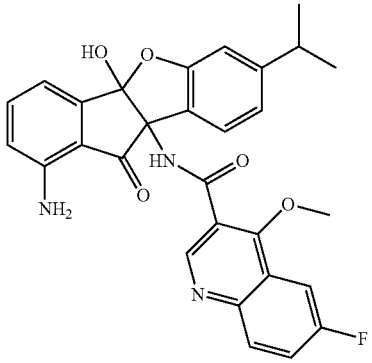 [SMILES: COc1c(C(=O)NC23C(=O)c4c(N)cccc4C2(O)Oc2cc(C(C)C)ccc23)cnc2ccc(F)cc12] |
| 268 | 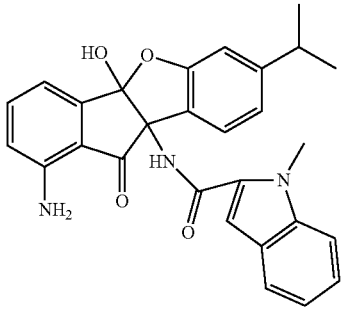 [SMILES: CC(C)c1ccc2c(c1)OC1(O)c3cccc(N)c3C(=O)C21NC(=O)c1cc2ccccc2n1C] |
| 269 | 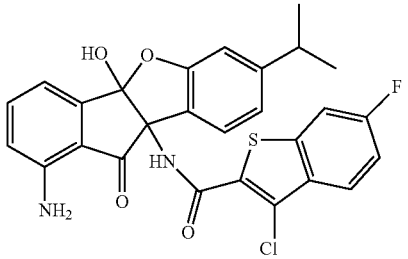 [SMILES: CC(C)c1ccc2c(c1)OC1(O)c3cccc(N)c3C(=O)C21NC(=O)c1sc2cc(F)ccc2c1Cl] |

TABLE 1-continued
| Ex. | Chemical Structure |
|---|---|
| 270 | 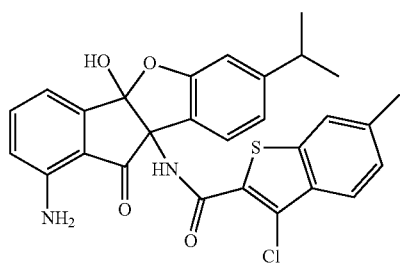 [SMILES: Cc1ccc2c(Cl)c(C(=O)NC34C(=O)c5c(N)cccc5C3(O)Oc3cc(C(C)C)ccc34)sc2c1] |
| 271 | 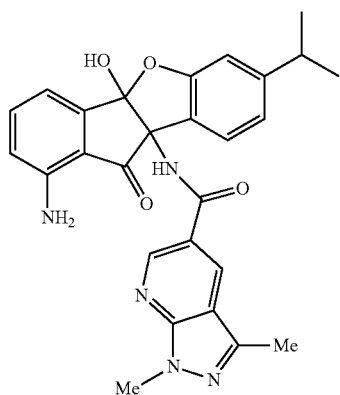 [SMILES: Cc1nn(C)c2ncc(C(=O)NC34C(=O)c5c(N)cccc5C3(O)Oc3cc(C(C)C)ccc34)cc12] |
| 272 | 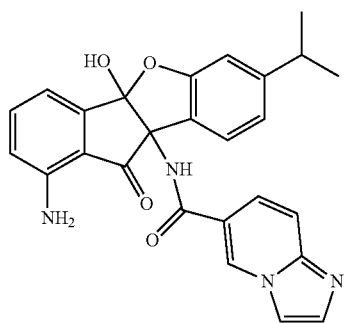 [SMILES: CC(C)c1ccc2c(c1)OC1(O)c3cccc(N)c3C(=O)C21NC(=O)c1ccc2nccn2c1] |
| 273 | 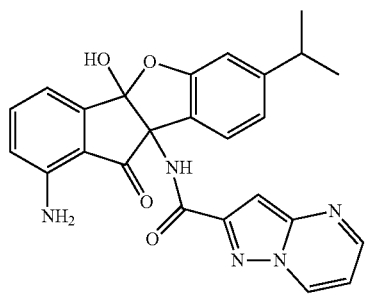 [SMILES: CC(C)c1ccc2c(c1)OC1(O)c3cccc(N)c3C(=O)C21NC(=O)c1cc2ncccn2n1] |
| 274 | 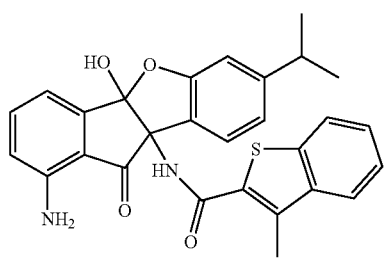 [SMILES: Cc1c(C(=O)NC23C(=O)c4c(N)cccc4C2(O)Oc2cc(C(C)C)ccc23)sc2ccccc12] |
TABLE 1-continued
| Ex. | Chemical Structure |
|---|---|
| 275 | 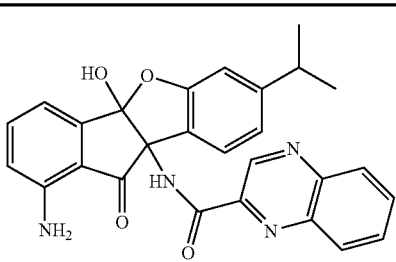 |
| 276 | 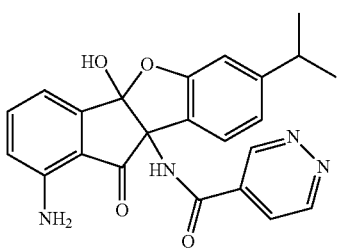 [SMILES: CC(C)c1ccc2c(c1)OC1(O)c3cccc(N)c3C(=O)C21NC(=O)c1ccnnc1] |
| 277 | 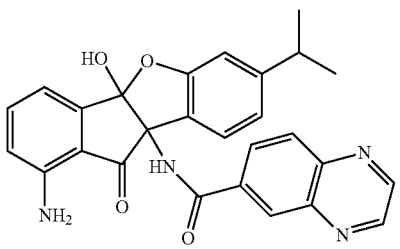 [SMILES: CC(C)c1ccc2c(c1)OC1(O)c3cccc(N)c3C(=O)C21NC(=O)c1ccc2nccnc2c1] |
| 278 | 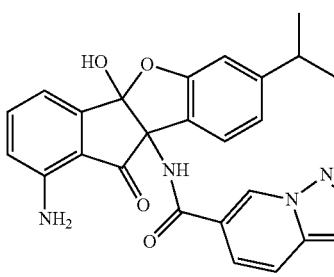 |
| 279 | 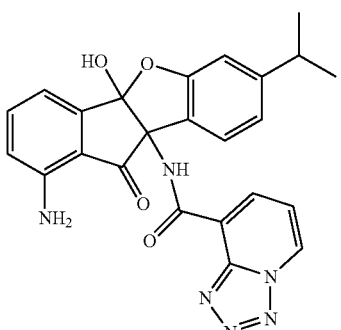 |

TABLE 1-continued
| Ex. | Chemical Structure |
|---|---|
| 280 | 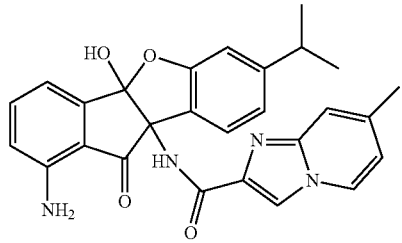 [SMILES: Cc1ccn2cc(C(=O)NC34C(=O)c5c(N)cccc5C3(O)Oc3cc(C(C)C)ccc34)nc2c1] |
| 281 | 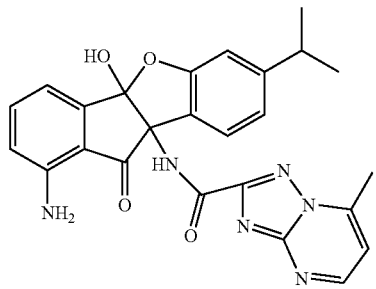 [SMILES: Cc1ccnc2nc(C(=O)NC34C(=O)c5c(N)cccc5C3(O)Oc3cc(C(C)C)ccc34)nn12] |
| 282 | 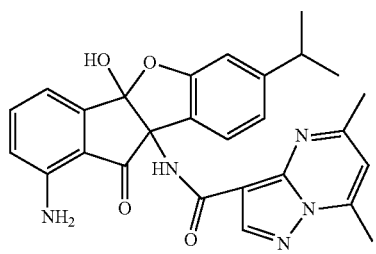 [SMILES: Cc1cc(C)n2ncc(C(=O)NC34C(=O)c5c(N)cccc5C3(O)Oc3cc(C(C)C)ccc34)c2n1] |
| 283 | 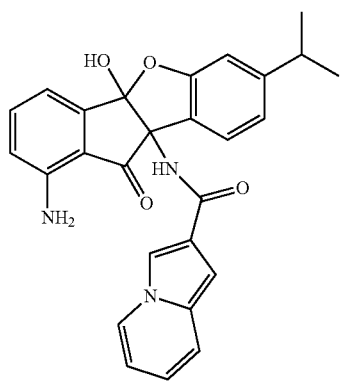 [SMILES: CC(C)c1ccc2c(c1)OC1(O)c3cccc(N)c3C(=O)C21NC(=O)c1cc2ccccn2c1] |
| 284 | 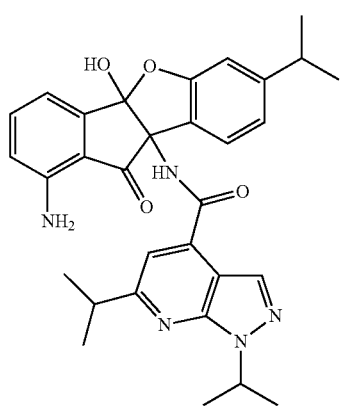 [SMILES: CC(C)c1ccc2c(c1)OC1(O)c3cccc(N)c3C(=O)C21NC(=O)c1cc(C(C)C)nc2c1cnn2C(C)C] |
TABLE 1-continued
| Ex. | Chemical Structure |
|---|---|
| 285 | 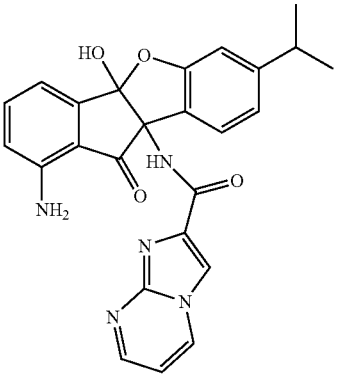 [SMILES: CC(C)c1ccc2c(c1)OC1(O)c3cccc(N)c3C(=O)C21NC(=O)c1cn2cccnc2n1]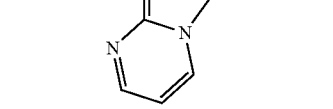 |
| 286 | 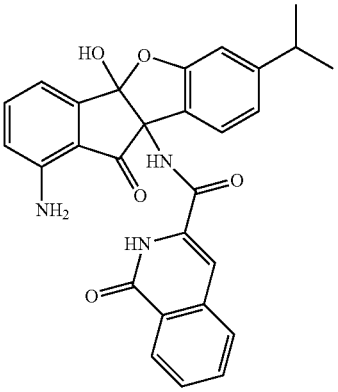 [SMILES: CC(C)c1ccc2c(c1)OC1(O)c3cccc(N)c3C(=O)C21NC(=O)c1cc2ccccc2c(=O)[nH]1]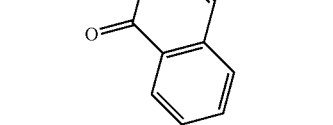 |
| 287 | 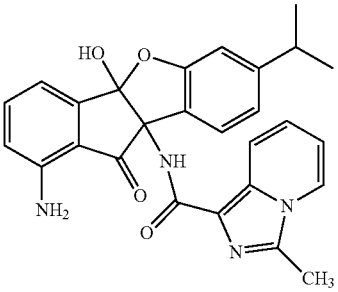 [SMILES: Cc1nc(C(=O)NC23C(=O)c4c(N)cccc4C2(O)Oc2cc(C(C)C)ccc23)c2ccccn12]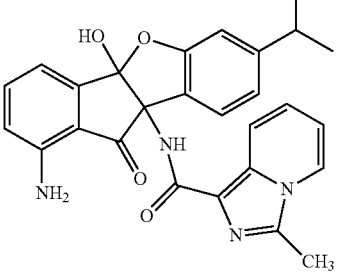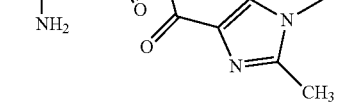 |
| 288 | 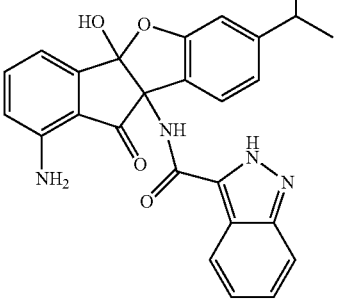 |

TABLE 1-continued
| Ex. | Chemical Structure |
|---|---|
| 289 | 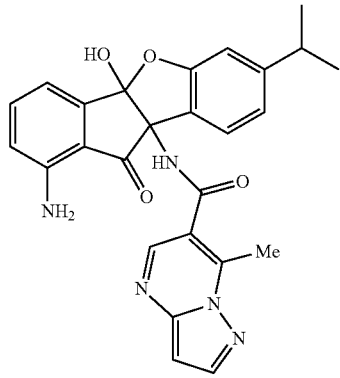 [SMILES: Cc1c(C(=O)NC23C(=O)c4c(N)cccc4C2(O)Oc2cc(C(C)C)ccc23)cnc2ccnn12] |
| 290 | 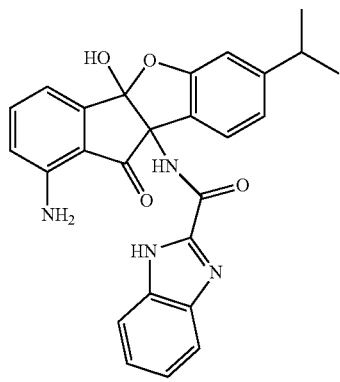 [SMILES: CC(C)c1ccc2c(c1)OC1(O)c3cccc(N)c3C(=O)C21NC(=O)c1nc2ccccc2[nH]1] |
| 291 | 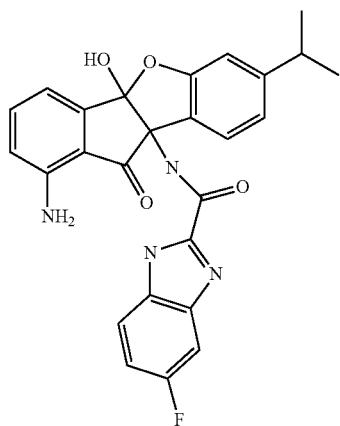 [SMILES: CC(C)c1ccc2c(c1)OC1(O)c3cccc(N)c3C(=O)C21NC(=O)c1nc2cc(F)ccc2[nH]1] |
| 292 | 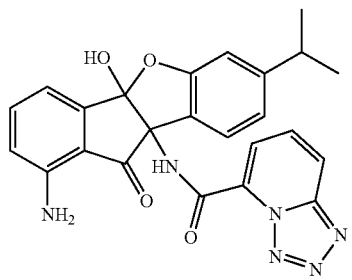 [SMILES: CC(C)c1ccc2c(c1)OC1(O)c3cccc(N)c3C(=O)C21NC(=O)c1cccc2nnnn12] |
| 293 | 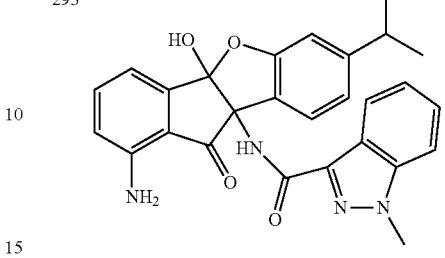 |
| 294 | 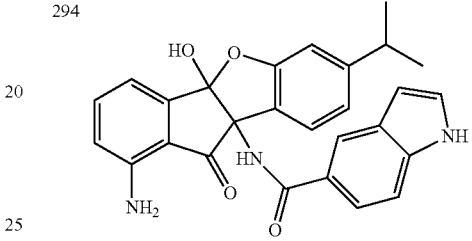 |
| 295 | 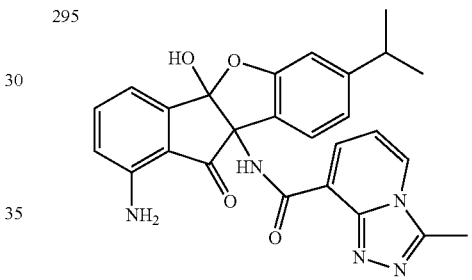 |
| 296 | 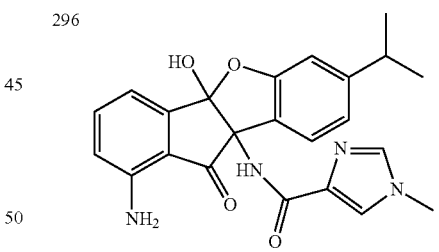 |
| 297 | 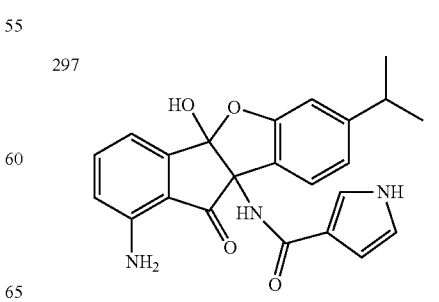 |

TABLE 1-continued
| Ex. | Chemical Structure |
|---|---|
| 298 | 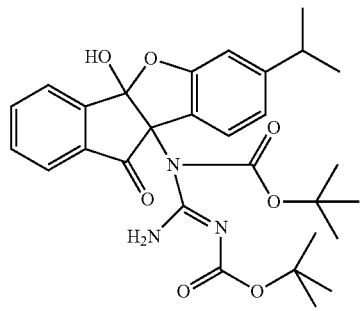 [SMILES: CC(C)c1ccc2c(c1)OC1(O)c3ccccc3C(=O)C21N(C(=O)OC(C)(C)C)/C(N)=N/C(=O)OC(C)(C)C] |
| 299 | 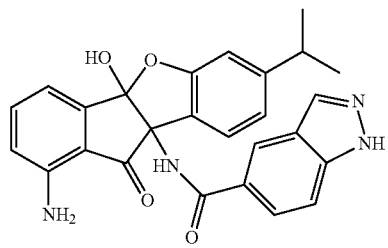 [SMILES: CC(C)c1ccc2c(c1)OC1(O)c3cccc(N)c3C(=O)C21NC(=O)c1ccc2[nH]ncc2c1] |
| 300 | 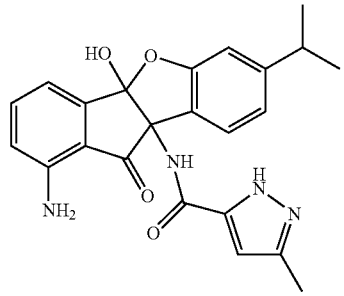 [SMILES: Cc1cc(C(=O)NC23C(=O)c4c(N)cccc4C2(O)Oc2cc(C(C)C)ccc23)[nH]n1] |
| 301 | 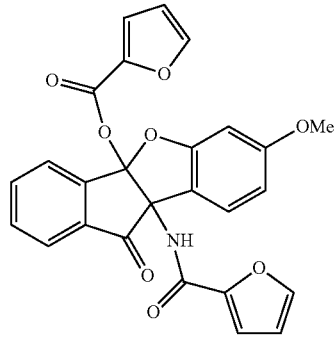 [SMILES: COc1ccc2c(c1)OC1(OC(=O)c3ccco3)c3ccccc3C(=O)C21NC(=O)c1ccco1] |
| 302 | 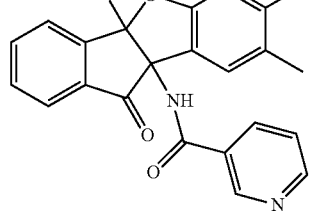 |
TABLE 1-continued
| Ex. | Chemical Structure |
|---|---|
| 303 | 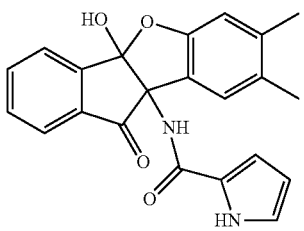 [SMILES: Cc1cc2c(cc1C)C1(NC(=O)c3ccc[nH]3)C(=O)c3ccccc3C1(O)O2] |
| 304 | 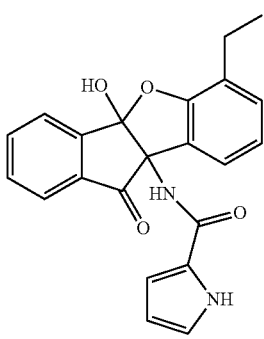 [SMILES: CCc1cccc2c1OC1(O)c3ccccc3C(=O)C21NC(=O)c1ccc[nH]1] |
| 305 | 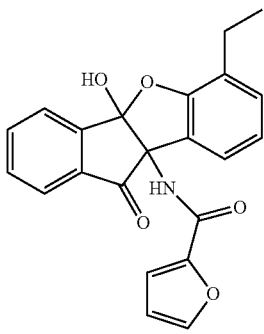 [SMILES: CCc1cccc2c1OC1(O)c3ccccc3C(=O)C21NC(=O)c1ccco1] |
| 306 | 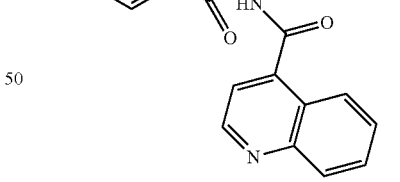 |
| 307 | 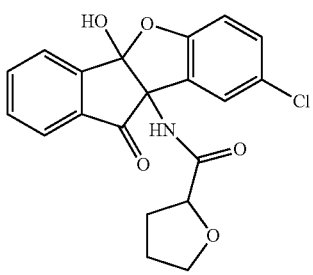 [SMILES: O=C(NC12C(=O)c3ccccc3C1(O)Oc1ccc(Cl)cc12)C1CCCO1] |

<Experimental Example 1> Cytopathic Effect (CPE) Inhibition Assay for Antiviral Activity Against Picornaviruses In the assay, HeLa (human cervical cancer cells), MRC-5 (human fetal lung fibroblast cells), and RD cells (derived from human rhabdomyosarcoma) were employed. For comparison, ribavirin (Riv), pleconaril (pleco), and BTA-798 (BTA) were used as controls. Reagents were dissolved at a concentration of 10~40 mg/ml in 100% dimethylsulfoxide (DMSO). Water-soluble reagents were dissolved in PBS (−) solution and stored at −20° C. On the day of the experiment, they were used in 3× to 5× concentrations in such a manner that the concentration of dimethylsulfoxide in each well was between 0.5% and 1%.

Pharmaceutical effects were determined using a virus-induced cytopathic effect (CPE) inhibition assay. In this regard, after cells suitable for viruses were grown in 96-well plates, dilutions of viruses in DME supplemented with 2% FBS (DME/2% FBS) or MEM supplemented with 2% FBS (MEM/2% FBS) were inoculated in an amount of 100 μl with a concentration corresponding to 100 CCID$_{50}$ (50% cell culture infective dose) into each well of the plates, and incubated for 30 min~1 hrs at 33° C. or 37° C. to allow the viruses to adosrb to the cells. The culture medium was removed before aliquots of drug dilutions with various concentrations were added in an amount of 100 μl to each well. While HRV was grown at 33° C., the other viruses were incubated in a 37° C. CO$_2$ incubator for 2~3 days. Alternatively, the cells were cultured for 2~3 days without removal of the medium after they were added with 50 μl of each drug dilution having a 2-fold higher concentration and then with 50 μl of the virus dilution.

Test conditions for each virus are summarized in Table 2, below.

TABLE 2

| Virus | Note | Host cell | Incubation Temp. | Incubation Term | Medium |
|---|---|---|---|---|---|
| Coxsackie A9 | — | RD | 37° C. | 2 days | MEM/2% FBS |
| Coxsackie A24 | — | MRC-5 | 37° C. | 2 days | MEM/2% FBS |
| Coxsackie A24 | Isolated from patients | MRC-5 | 37° C. | 2 days | MEM/2% FBS |
| Coxsackie B1 | — | HeLa | 37° C. | 2 days | DME/2% FBS |
| Coxsackie B3 | — | HeLa | 37° C. | 2 days | DME/2% FBS |
| Coxsackie B4 | — | HeLa | 37° C. | 2 days | DME/2% FBS |
| Entero 70 | — | MRC-5 | 37° C. | 2 days | MEM/2% FBS |
| Poliovirus3 | — | HeLa | 37° C. | 2 days | DME/2% FBS |
| Rhinovirus | — | HeLa | 33° C. | 3 days | MEM/2% FBS |

For HeLa cells, the drugs were measured for EC$_{50}$ (50% maximal effective concentration), which is the concentration of a drug inducing a response halfway between the baseline and maximum, using an MTT assay. With regard to RD and MRC-5 cells, CPE was determined using FDA (Fluorescein diacetate). In order for the evaluation results of drug potency to reflect the toxic effect of the drug, mock-infected cells which were prepared by adding a virus-free medium to a cell culture were treated in the same manner. That is, the medium was removed after one hour of incubation, and dilutions of drugs in the medium were added once more. Following incubation for 2~3 days, the cells were observed under a microscope and the drugs were determined for CC$_{50}$ (50% cytotoxic concentration), using an MTT assay in which counts of viable cells in mock-infected wells containing drugs were compared to those of viable cells in control wells containing no drugs. In an FDA hydrolysis assay, FDA was added to each well after removal of the medium, and incubated for 20~30 min before fluorescence intensity was measured using a spectrofluorimeter to determine CPE in the same manner as in MTT.

Survival rate (% survival) of mock-infected cells was calculated using the following Mathematic Formula 1:

$$\text{Cell Survival by Drug} = \frac{A(\text{Drug}) - A(\text{Background } Sol'n)}{A(\text{Cell Control}) - A(Bakground\ Sol'n)} \times 100\%$$ [Mathmatic Formula 1]

While 100% cell survival means no cytotoxicity of the drug, the highest cytotoxicity is reflected by 0% cell survival. The 50% cytotoxic concentration (CC$_{50}$) was defined as the concentration required to reduce the cell number by 50% compared to that for the untreated controls. Higher CC$_{50}$ values mean lower cytotoxicity.

In addition, antiviral effects can be calculated using the following Mathematic Formula 2:

$$\text{Antiviral Effect} = \frac{A(\text{Drug/Virus}) - A(\text{Virus Control})}{A(\text{Cell Control}) - A(\text{Virus Control})} \times 100\%$$ [Mathmatic Formula 2]

A survival rate of 100% means a perfect antiviral effect (100%) whereas the drugs are regarded to be devoid of antiviral effects at a survival rate of 0%. The viral cytopathic effect (CPE) was recorded, and the 50% effective concentration (EC$_{50}$) was defined as the compound concentration required to reduce the viral CPE by 50% compared to that for the untreated control. Lower EC$_{50}$ values mean higher antiviral activities.

CC$_{50}$ and EC$_{50}$ values of the compounds which account cytotoxicity and antiviral activity against picornaviruses, respectively, are given in Tables 3 and 4.

TABLE 3

| Ex. No. | CC$_{50}$ (μg/mL) | Coxsackie B1 EC$_{50}$ (μg/mL) | Coxsackie B3 EC$_{50}$ (μg/mL) | Coxsackie B4 EC$_{50}$ (μg/mL) | Coxsackie A24(DN) EC$_{50}$ (μg/mL) | Coxsackie A24(HG) EC$_{50}$ (μg/mL) | Poliovirus 3 EC$_{50}$ (μg/mL) | Poliovirus 2 EC$_{50}$ (μg/mL) |
|---|---|---|---|---|---|---|---|---|
| 43 | 33.17 | <0.01 | — | <0.01 | — | — | — | — |
| 47 | 15.38 | <0.01 | <0.01 | — | 0.055 | <0.01 | <0.1 | — |
| 50 | 49.89 | <0.01 | <0.01 | — | — | — | <0.1 | — |
| 71 | 38.85 | <0.01 | <0.01 | <0.01 | 0.1 | 0.056 | <0.1 | <0.1 |
| 74 | 9.26 | <0.01 | <0.01 | — | 0.36 | 0.34 | — | — |

TABLE 4

| Ex. No. | Picorana CC$_{50}$ (μg/mL) | Coxsackie B1 EC$_{50}$ (μg/mL) | Coxsackie B3 EC$_{50}$ (μg/mL) | Poliovirus3 EC$_{50}$ (μg/mL) | Rhino CC$_{50}$ (μg/mL) | Rhino HRV14 EC$_{50}$ (μg/mL) | Rhino HRV21 EC$_{50}$ (μg/mL) | Rhino HRV71 EC$_{50}$ (μg/mL) |
|---|---|---|---|---|---|---|---|---|
| 1 | >50 | 0.026 | — | — | — | — | — | — |
| 2 | >50 | — | 0.02 | — | — | — | — | — |
| 3 | >50 | — | — | — | — | — | — | — |
| 4 | >50 | — | 0.019 | — | — | — | — | — |
| 5 | >50 | — | — | — | — | — | — | — |
| 6 | 47.51 | — | — | — | — | — | — | — |
| 7 | >50 | — | — | — | — | — | — | — |
| 8 | 44.1 | — | — | — | — | — | — | — |
| 9 | 18 | <0.01 | 0.027 | — | — | — | — | — |
| 10 | 14.2 | <0.01 | <0.01 | — | 18.43 | — | — | <1.0 |
| 11 | 16.2 | <0.01 | <0.01 | — | — | — | — | — |
| 12 | >50 | — | — | — | — | — | — | — |
| 13 | 8.08 | — | — | — | — | — | — | — |
| 14 | >50 | — | — | — | — | — | — | — |
| 15 | 8.57 | — | — | — | — | — | — | — |
| 16 | 7.82 | — | — | — | — | — | — | — |
| 17 | 7.85 | — | — | — | — | — | — | — |
| 18 | 37.48 | — | — | — | — | — | — | — |
| 19 | 8.34 | — | — | — | — | — | — | — |
| 20 | 7.93 | — | — | — | — | — | — | — |
| 21 | 32.1 | — | — | — | — | — | — | — |
| 22 | 8.01 | — | — | — | — | — | — | — |
| 23 | 9.3 | — | — | — | — | — | — | — |
| 24 | 8.8 | 0.013 | — | — | — | — | — | — |
| 25 | >50 | — | — | — | — | — | — | — |
| 26 | <4 | — | — | — | — | — | — | — |
| 27 | 43.9 | — | — | — | — | — | — | — |
| 28 | 9.2 | — | — | — | — | — | — | — |
| 29 | 7.49 | 0.355 | — | — | — | — | — | — |
| 30 | 45.5 | 0.014 | — | — | — | — | — | — |
| 31 | 8.9 | — | — | — | — | — | — | — |
| 32 | 8.1 | — | — | — | — | — | — | — |
| 33 | >50 | — | — | — | — | — | — | — |
| 34 | >50 | — | — | — | — | — | — | — |
| 35 | 46.69 | <0.01 | — | — | — | — | — | — |
| 36 | 9.34 | <0.01 | — | — | — | — | — | — |
| 37 | 9.68 | <0.01 | — | — | — | — | — | — |
| 38 | 9.5 | <0.01 | — | — | — | — | — | — |
| 39 | 45.12 | — | — | — | — | — | — | — |
| 40 | 43.96 | <0.01 | — | — | — | — | — | — |
| 41 | 27.14 | <0.01 | — | — | — | — | — | — |
| 42 | 8.94 | — | — | — | — | — | — | — |
| 43 | 33.17 | <0.01 | — | — | — | — | — | — |
| 44 | 6.25 | — | — | — | — | — | — | — |
| 45 | 12.23 | <0.01 | — | — | — | — | — | — |
| 46 | 9.42 | <0.01 | — | <0.01 | 18.33 | <0.01 | — | — |
| 47 | 15.38 | <0.01 | <0.01 | <0.1 | — | — | — | — |
| 48 | 35.01 | — | — | — | — | — | — | — |
| 49 | 9.18 | 0.373 | — | — | — | — | — | — |
| 50 | 49.89 | <0.01 | <0.01 | <0.1 | — | — | — | — |
| 51 | 17.47 | <0.01 | <0.01 | — | — | — | — | — |
| 52 | >50 | — | — | — | — | — | — | — |
| 53 | 45.65 | 0.04 | — | — | — | — | — | — |
| 54 | >50 | 0.014 | 0.0147 | — | — | — | — | — |
| 55 | 7.49 | 0.084 | — | — | — | — | — | — |
| 56 | 42.16 | 0.0784 | — | — | — | — | — | — |
| 57 | 46.66 | 0.35 | — | — | — | — | — | — |
| 58 | >50 | — | — | — | — | — | — | — |
| 59 | >50 | — | — | — | — | — | — | — |
| 60 | 10.56 | <0.01 | <0.01 | — | — | — | — | — |
| 61 | >50 | <0.01 | <0.01 | — | — | — | — | — |
| 62 | >50 | <0.01 | <0.01 | — | — | — | — | — |
| 63 | >50 | <0.01 | — | — | — | — | — | — |
| 64 | 8.13 | <0.01 | <0.01 | — | — | — | — | — |
| 65 | 18.19 | <0.01 | 0.015 | — | — | — | — | — |
| 66 | 44.72 | <0.01 | <0.01 | — | — | — | — | — |
| 67 | 9.42 | 0.596 | — | — | — | — | — | — |
| 68 | 8.94 | <0.01 | <0.01 | — | — | — | — | — |
| 69 | 70 | 0.43 | — | — | — | — | — | — |
| 70 | 47.08 | <0.01 | <0.01 | — | — | — | — | — |
| 71 | 38.85 | <0.01 | <0.01 | <0.1 | — | — | — | — |
| 72 | 43.91 | <0.01 | <0.01 | — | — | — | — | — |
| 73 | 47.08 | <0.01 | <0.01 | <0.01 | 56.4 | <0.01 | <1.0 | <1.0 |
| 74 | 9.26 | <0.01 | <0.01 | — | — | — | — | — |
| 75 | 46.66 | <0.01 | <0.01 | — | — | — | — | — |

TABLE 4-continued

| Ex. No. | Picorana CC$_{50}$ (μg/mL) | Coxsackie B1 EC$_{50}$ (μg/mL) | Coxsackie B3 EC$_{50}$ (μg/mL) | Poliovirus3 EC$_{50}$ (μg/mL) | Rhino CC$_{50}$ (μg/mL) | Rhino HRV14 EC$_{50}$ (μg/mL) | Rhino HRV21 EC$_{50}$ (μg/mL) | Rhino HRV71 EC$_{50}$ (μg/mL) |
|---|---|---|---|---|---|---|---|---|
| 76 | >50 | — | — | — | — | — | — | — |
| 77 | >50 | <0.01 | <0.01 | — | 53.86 | <0.01 | — | — |
| 78 | 47.74 | 0.025 | — | — | 20.65 | <0.01 | — | — |
| 79 | 10.43 | — | — | — | — | — | — | — |
| 80 | 47.51 | 0.0139 | — | — | — | — | — | — |
| 81 | 8.61 | — | — | — | — | — | — | — |
| 82 | 1.9 | — | — | — | — | — | — | — |
| 83 | 46.25 | — | — | — | — | — | — | — |
| 84 | >50 | — | — | — | — | — | — | — |
| 85 | 19.25 | — | — | — | — | — | — | — |
| 86 | | — | — | — | — | — | — | — |
| 87 | 36.77 | <0.01 | <0.01 | — | — | — | — | — |
| 88 | 8.16 | 0.017 | — | — | — | — | — | — |
| 89 | >50 | <0.01 | <0.01 | — | — | — | — | — |
| 90 | 33.95 | <0.01 | <0.01 | — | — | — | — | — |
| 91 | >50 | — | — | — | — | — | — | — |
| 92 | >50 | — | — | — | — | — | — | — |
| 93 | 8.49 | <0.01 | <0.01 | — | 6.23 | <0.01 | — | — |
| 94 | 42.39 | <0.01 | <0.01 | — | 58.06 | <0.01 | — | — |
| 95 | 38.07 | <0.01 | <0.01 | — | 25.99 | <0.01 | — | — |
| 96 | >50 | <0.01 | <0.01 | 0.016 | 23.97 | <0.01 | — | — |
| 97 | >50 | <0.01 | <0.01 | — | 8.8 | <0.01 | — | — |
| 98 | 7.8 | <0.01 | 0.022 | — | — | — | — | — |
| 99 | >50 | <0.01 | <0.01 | — | 7.7 | 0.0101 | — | — |
| 100 | 40.64 | — | — | — | — | — | — | — |
| 101 | >50 | — | — | — | — | — | — | — |
| 102 | >50 | — | — | — | — | — | — | — |
| 103 | >50 | — | — | — | — | — | — | — |
| 104 | >50 | 0.015 | — | — | — | — | — | — |
| 105 | >50 | 0.018 | 0.016 | — | — | — | — | — |
| 106 | 3.53 | — | — | — | — | — | — | — |
| 107 | >50 | — | — | — | — | — | — | — |
| 108 | 1.81 | — | — | — | — | — | — | — |
| 109 | >50 | — | — | — | — | — | — | — |
| 110 | 14.41 | — | — | — | — | — | — | — |
| 111 | 43.58 | <0.01 | <0.01 | — | — | — | — | — |
| 112 | 41.98 | <0.01 | <0.01 | — | — | — | — | — |
| 113 | 45.46 | <0.01 | <0.01 | <0.01 | 48.78 | <0.01 | <1.0 | — |
| 114 | 45.85 | <0.01 | <0.01 | 0.034 | 43.12 | <0.01 | — | — |
| 115 | 42.79 | <0.01 | <0.01 | <0.01 | 23.11 | <0.01 | — | — |
| 116 | 41.72 | <0.01 | <0.01 | — | — | — | — | — |
| 117 | >50 | 0.012 | — | — | — | — | — | — |
| 118 | >50 | <0.01 | <0.01 | — | — | — | — | — |
| 119 | 38.22 | 0.027 | — | — | — | — | — | — |
| 120 | 8.16 | — | — | — | — | — | — | — |
| 121 | >50 | 0.02 | — | — | — | — | — | — |
| 122 | 11.96 | — | — | — | — | — | — | — |
| 123 | 37.54 | <0.01 | <0.01 | <0.01 | 43.35 | <0.01 | <1.0 | — |
| 124 | >50 | — | — | — | — | — | — | — |
| 125 | 45.46 | — | — | — | — | — | — | — |
| 126 | 47.06 | — | — | — | — | — | — | — |
| 127 | 37.61 | — | — | — | — | — | — | — |
| 128 | 37.31 | — | — | — | — | — | — | — |
| 129 | 6.79 | — | — | — | — | — | — | — |
| 130 | >50 | — | — | — | — | — | — | — |
| 131 | 2.05 | <0.01 | <0.01 | — | — | — | — | — |
| 132 | 0.72 | 0.03 | — | — | — | — | — | — |
| 133 | 1.58 | <0.01 | — | — | — | — | — | — |
| 134 | 6.69 | — | — | — | — | — | — | — |
| 135 | 10.94 | — | — | — | — | — | — | — |
| 136 | 7.8 | — | — | — | — | — | — | — |
| 137 | 39.97 | <0.01 | <0.01 | — | — | — | — | — |
| 138 | 38.8 | — | — | — | — | — | — | — |
| 139 | 0.45 | — | — | — | — | — | — | — |
| 140 | 2.08 | — | — | — | — | — | — | — |
| 141 | 3.47 | — | — | — | — | — | — | — |
| 142 | 18.68 | — | — | — | — | — | — | — |
| 143 | >50 | <0.01 | <0.01 | <0.01 | 58.06 | <0.01 | <1.0 | — |
| 144 | 35.48 | <0.01 | <0.01 | <0.01 | 21.71 | <0.01 | <1.0 | — |
| 145 | 18.33 | 0.026 | — | — | — | — | — | — |
| 146 | 1.53 | — | — | — | — | — | — | — |
| 147 | 32.88 | — | — | — | — | — | — | — |
| 148 | 1.72 | — | — | — | — | — | — | — |
| 149 | 8.48 | — | — | — | — | — | — | — |
| 150 | 1.32 | — | — | — | — | — | — | — |

TABLE 4-continued

| Ex. No. | Picorana CC$_{50}$ (μg/mL) | Coxsackie B1 EC$_{50}$ (μg/mL) | Coxsackie B3 EC$_{50}$ (μg/mL) | Poliovirus3 EC$_{50}$ (μg/mL) | Rhino CC$_{50}$ (μg/mL) | Rhino HRV14 EC$_{50}$ (μg/mL) | Rhino HRV21 EC$_{50}$ (μg/mL) | Rhino HRV71 EC$_{50}$ (μg/mL) |
|---|---|---|---|---|---|---|---|---|
| 151 | 1.52 | 0.04 | — | — | — | — | — | — |
| 152 | 0.9 | — | — | — | 10.52 | — | — | — |
| 153 | 9.02 | <0.01 | <0.01 | <0.01 | 16.03 | <0.01 | <1.0 | <1.0 |
| 154 | 46.23 | <0.01 | <0.01 | <0.01 | 22.71 | <0.01 | <1.0 | <1.0 |
| 155 | 9.02 | <0.01 | <0.01 | <0.01 | 7.81 | <0.01 | <1.0 | <1.0 |
| 156 | 36.38 | <0.01 | <0.01 | <0.01 | >10 | <0.01 | <1.0 | <1.0 |
| 157 | >100 | <0.01 | <0.01 | — | 28.49 | — | — | — |
| 158 | 44.72 | <0.01 | <0.01 | <0.01 | 39.42 | <0.01 | <1.0 | — |
| 159 | 44.72 | 0.021 | — | — | 42.39 | — | — | — |
| 160 | 47.19 | <0.01 | <0.01 | — | 18.52 | — | — | — |
| 161 | 40.73 | <0.01 | <0.01 | <0.01 | 17.89 | <0.01 | <1.0 | — |
| 162 | >10 | — | — | — | >10 | — | — | — |
| 163 | >10 | — | — | — | >10 | — | — | — |
| 164 | >10 | 0.04 | 0.04 | — | >10 | — | — | — |
| 165 | >10 | <0.01 | <0.01 | — | >10 | <0.01 | — | — |
| 166 | >10 | <0.01 | <0.01 | <0.01 | >10 | <0.01 | <1.0 | <1.0 |
| 167 | >10 | <0.01 | 0.034 | — | >10 | 0.038 | — | — |
| 168 | >10 | 0.04 | — | — | >10 | — | — | — |
| 169 | >10 | — | — | — | >10 | — | — | — |
| 170 | >10 | <0.01 | <0.01 | <0.01 | >10 | <0.01 | <1.0 | <1.0 |
| 171 | >10 | <0.01 | <0.01 | 0.03 | >10 | — | <1.0 | <1.0 |
| 172 | >10 | <0.01 | 0.027 | — | >10 | 0.0125 | — | — |
| 173 | >10 | 0.036 | — | — | >10 | — | — | — |
| 174 | >10 | <0.01 | <0.01 | 0.019 | >10 | <0.01 | — | — |
| 175 | >11 | <0.01 | <0.01 | <0.01 | >10 | <0.01 | — | — |
| 176 | >10 | 0.037 | 0.037 | — | >10 | — | — | — |
| 177 | >10 | <0.01 | <0.01 | — | >10 | <0.01 | — | — |
| 178 | >10 | <0.01 | 0.035 | — | >10 | — | — | — |
| 179 | >10 | <0.01 | <0.01 | <0.01 | >10 | <0.01 | <1.0 | — |
| 180 | 4.32 | <0.01 | <0.01 | 0.033 | >10 | 0.0114 | — | — |
| 181 | >10 | <0.01 | <0.01 | 0.036 | >10 | 0.0124 | — | — |
| 182 | 6.42 | <0.01 | 0.022 | — | 5.85 | 0.035 | — | — |
| 183 | 8.54 | <0.01 | <0.01 | 0.014 | >10 | <0.01 | — | — |
| 184 | 36.38 | <0.01 | 0.025 | — | >10 | — | — | — |
| 185 | 7.18 | 0.028 | — | — | >10 | — | — | — |
| 186 | 8.31 | <0.01 | <0.01 | 0.026 | >10 | <0.01 | — | — |
| 187 | 7.43 | <0.01 | <0.01 | <0.01 | >10 | <0.01 | <1.0 | <1.0 |
| 188 | 8.38 | <0.01 | <0.01 | <0.01 | >10 | <0.01 | <1.0 | <1.0 |
| 189 | 8.56 | <0.01 | <0.01 | <0.01 | >10 | <0.01 | <1.0 | <1.0 |
| 190 | >10 | <0.01 | <0.01 | <0.01 | 5.52 | <0.01 | <1.0 | <1.0 |
| 191 | 4.12 | <0.01 | <0.01 | <0.01 | >10 | <0.01 | — | <1.0 |
| 192 | >10 | <0.01 | <0.01 | — | >10 | — | — | — |
| 193 | >10 | <0.01 | <0.01 | 0.011 | >10 | <0.01 | <1.0 | — |
| 194 | >10 | <0.01 | <0.01 | — | >10 | <0.01 | — | — |
| 195 | — | — | — | — | — | — | — | — |
| 196 | 48.47 | <0.01 | <0.01 | — | 16.18 | — | — | — |
| 197 | 34.45 | <0.01 | <0.01 | <0.01 | 16.03 | <0.01 | — | — |
| 198 | >50 | <0.01 | <0.01 | <0.01 | 27.94 | <0.01 | <1.0 | <1.0 |
| 199 | 48.28 | <0.01 | <0.01 | <0.01 | 42.95 | <0.01 | <1.0 | <1.0 |
| 200 | >10 | <0.01 | <0.01 | <0.01 | >10 | <0.01 | <1.0 | <1.0 |
| 201 | >10 | <0.01 | <0.01 | <0.01 | >10 | <0.01 | <1.0 | <1.0 |
| 202 | 9.6 | <0.01 | <0.01 | — | 3.24 | <0.01 | — | — |
| 203 | >10 | <0.01 | <0.01 | <0.01 | >10 | <0.01 | <1.0 | <1.0 |
| 204 | >4.51 | <0.01 | <0.01 | 0.011 | >10 | <0.01 | — | <1.0 |
| 205 | >10 | <0.01 | <0.01 | 0.036 | >10 | <0.01 | — | — |
| 206 | >10 | <0.01 | <0.01 | <0.01 | >10 | <0.01 | <1.0 | <1.0 |
| 207 | >10 | <0.01 | <0.01 | <0.01 | >10 | <0.01 | <1.0 | — |
| 208 | >10 | <0.01 | <0.01 | — | >10 | <0.01 | — | — |
| 209 | >10 | <0.01 | <0.01 | 0.036 | 8.43 | <0.01 | — | — |
| 210 | >10 | <0.01 | <0.01 | — | >10 | — | — | — |
| 211 | >10 | <0.01 | <0.01 | — | >10 | 0.039 | — | — |
| 212 | >10 | <0.01 | <0.01 | <0.01 | >10 | <0.01 | — | <1.0 |
| 213 | >10 | <0.01 | <0.01 | <0.01 | >10 | <0.01 | <1.0 | <1.0 |
| 214 | >10 | <0.01 | <0.01 | <0.01 | >10 | <0.01 | <1.0 | <1.0 |
| 215 | >10 | <0.01 | <0.01 | <0.01 | >10 | <0.01 | <1.0 | — |
| 216 | 4.75 | 0.036 | 0.037 | — | 9.69 | — | — | — |
| 217 | 4.24 | <0.01 | <0.01 | 0.038 | >10 | <0.01 | — | — |
| 218 | 8.49 | <0.01 | <0.01 | — | >10 | <0.01 | — | — |
| 219 | 45.12 | <0.01 | <0.01 | — | >10 | <0.01 | — | — |
| 220 | >50 | — | — | — | >10 | — | — | — |
| 221 | 14.5 | <0.01 | <0.01 | 0.016 | 6.53 | <0.01 | — | — |
| 222 | 39.43 | <0.01 | <0.01 | — | >10 | 0.037 | — | — |
| 223 | 7.46 | <0.01 | <0.01 | <0.01 | 4.36 | — | — | — |
| 224 | >50 | <0.01 | 0.013 | — | >10 | — | — | — |
| 225 | 22.87 | <0.01 | <0.01 | — | >10 | — | — | — |

TABLE 4-continued

| Ex. No. | Picorana CC$_{50}$ (μg/mL) | Coxsackie B1 EC$_{50}$ (μg/mL) | Coxsackie B3 EC$_{50}$ (μg/mL) | Poliovirus3 EC$_{50}$ (μg/mL) | Rhino CC$_{50}$ (μg/mL) | Rhino HRV14 EC$_{50}$ (μg/mL) | Rhino HRV21 EC$_{50}$ (μg/mL) | Rhino HRV71 EC$_{50}$ (μg/mL) |
|---|---|---|---|---|---|---|---|---|
| 226 | 28.18 | <0.01 | <0.01 | — | >10 | — | — | — |
| 227 | 9.62 | <0.01 | <0.01 | — | >10 | — | — | — |
| 228 | 24.08 | <0.01 | <0.01 | — | >10 | 0.029 | — | — |
| 229 | 8.63 | <0.01 | <0.01 | — | 4.51 | 0.036 | — | — |
| 230 | 42.83 | <0.01 | <0.01 | — | >10 | <0.01 | <1.0 | — |
| 231 | 8.64 | <0.01 | <0.01 | <0.01 | >10 | <0.01 | — | — |
| 232 | >50 | 0.012 | 0.024 | — | >10 | — | — | — |
| 233 | 31.89 | <0.01 | <0.01 | <0.01 | >10 | <0.01 | <1.0 | <1.0 |
| 234 | 9.1 | <0.01 | <0.01 | <0.01 | >10 | <0.01 | <1.0 | <1.0 |
| 235 | 7.97 | <0.01 | <0.01 | <0.01 | 8.88 | <0.01 | <1.0 | <1.0 |
| 236 | 21.36 | — | — | — | >10 | — | — | — |
| 237 | 6.27 | — | — | — | >10 | — | — | — |
| 238 | 8.33 | <0.01 | <0.01 | <0.01 | >10 | <0.01 | <1.0 | — |
| 239 | >50 | <0.01 | <0.01 | — | >10 | — | — | — |
| 240 | 8.25 | <0.01 | <0.01 | <0.01 | >10 | <0.01 | — | — |
| 241 | 7.86 | <0.01 | <0.01 | — | >10 | — | — | — |
| 242 | 8.55 | <0.01 | <0.01 | <0.01 | >10 | <0.01 | <1.0 | <1.0 |
| 243 | 7.36 | <0.01 | <0.01 | <0.01 | >10 | <0.01 | — | — |
| 244 | 15.71 | <0.01 | <0.01 | <0.01 | >10 | <0.01 | — | <1.0 |
| 245 | 8.47 | <0.01 | <0.01 | <0.01 | >10 | <0.01 | <1.0 | <1.0 |
| 246 | 9.84 | <0.01 | <0.01 | <0.01 | >10 | <0.01 | — | — |
| 247 | 20 | <0.01 | 0.013 | — | >10 | 0.036 | — | — |
| 248 | 4.99 | <0.01 | <0.01 | 0.027 | >10 | <0.01 | — | — |
| 249 | >10 | <0.01 | <0.01 | <0.01 | >10 | <0.01 | <1.0 | <1.0 |
| 250 | >10 | <0.01 | <0.01 | <0.01 | >10 | <0.01 | <1.0 | <1.0 |
| 251 | >10 | <0.01 | <0.01 | <0.01 | >10 | <0.01 | <1.0 | — |
| 252 | 3.64 | <0.01 | <0.01 | <0.01 | 3.53 | <0.01 | — | — |
| 253 | >10 | <0.01 | <0.01 | <0.01 | >10 | <0.01 | — | — |
| 254 | >10 | <0.01 | <0.01 | — | >10 | <0.01 | — | — |
| 255 | >10 | <0.01 | <0.01 | <0.01 | >10 | <0.01 | <1.0 | <1.0 |
| 256 | >10 | <0.01 | <0.01 | <0.01 | >10 | <0.01 | <1.0 | <1.0 |
| 257 | >10 | <0.01 | <0.01 | 0.031 | >10 | <0.01 | — | — |
| 258 | >10 | <0.01 | <0.01 | 0.04 | >10 | <0.01 | <1.0 | — |
| 259 | >10 | <0.01 | <0.01 | <0.01 | >10 | <0.01 | <1.0 | <1.0 |
| 260 | >10 | <0.01 | <0.01 | 0.04 | >10 | <0.01 | — | — |
| 261 | >10 | <0.01 | <0.01 | <0.01 | >10 | <0.01 | <1.0 | <1.0 |
| 262 | >10 | <0.01 | <0.01 | 0.0124 | >10 | <0.01 | — | — |
| 263 | 7.65 | <0.01 | <0.01 | 0.039 | 5.4 | <0.01 | — | — |
| 264 | >10 | 0.011 | 0.035 | — | >10 | 0.034 | — | — |
| 265 | 4.75 | <0.01 | <0.01 | <0.01 | 4.4 | <0.01 | <1.0 | <1.0 |
| 266 | 6.41 | <0.01 | <0.01 | <0.01 | >10 | <0.01 | — | — |
| 267 | 0.87 | <0.01 | <0.01 | — | 0.86 | 0.012 | <1.0 | <1.1 |
| 268 | 9.28 | <0.01 | <0.01 | 0.036 | >10 | <0.01 | — | <1.0 |
| 269 | >10 | 0.018 | 0.035 | — | >10 | 0.036 | — | — |
| 270 | 6.57 | 0.03 | 0.036 | — | 5.93 | 0.039 | — | — |
| 271 | >10 | <0.01 | <0.01 | <0.01 | >10 | <0.01 | <1.0 | <1.0 |
| 272 | >10 | <0.01 | <0.01 | <0.01 | >10 | <0.01 | <1.0 | <1.0 |
| 273 | >10 | <0.01 | <0.01 | <0.01 | >10 | <0.01 | <1.0 | <1.0 |
| 274 | >10 | <0.01 | 0.027 | 0.036 | >10 | <0.01 | — | <1.0 |
| 275 | 4.78 | <0.01 | <0.01 | 0.035 | 4.55 | <0.01 | — | — |
| 276 | >10 | <0.01 | <0.01 | <0.01 | >10 | <0.01 | <1.0 | <1.0 |
| 277 | >10 | <0.01 | <0.01 | — | >10 | 0.026 | — | — |
| 278 | >10 | <0.01 | <0.01 | <0.01 | >10 | <0.01 | <1.0 | <1.0 |
| 279 | 7.88 | <0.01 | <0.01 | 0.035 | 4.94 | <0.01 | <1.0 | <1.0 |
| 280 | >10 | <0.01 | <0.01 | — | >10 | <0.01 | — | — |
| 281 | >10 | <0.01 | <0.01 | 0.025 | >10 | <0.01 | — | — |
| 282 | 6.78 | <0.01 | 0.011 | — | >10 | 0.011 | — | — |
| 283 | 5.47 | 0.024 | — | — | >10 | 0.024 | — | — |
| 284 | 4.56 | <0.01 | 0.016 | — | 3.71 | 0.028 | — | — |
| 285 | >10 | <0.01 | <0.01 | <0.01 | >10 | <0.01 | <1.0 | — |
| 286 | 4.28 | <0.01 | <0.01 | <0.01 | 4.04 | <0.01 | <1.0 | <1.0 |
| 287 | 7.01 | <0.01 | <0.01 | 0.036 | >10 | <0.01 | — | — |
| 288 | >10 | <0.01 | <0.01 | 0.029 | >10 | <0.01 | — | <1.0 |
| 289 | >10 | <0.01 | <0.01 | — | >10 | <0.01 | <1.0 | <1.0 |
| 290 | 4.32 | <0.01 | <0.01 | 0.032 | 4.51 | <0.01 | <1.0 | <1.0 |
| 291 | 4.43 | <0.01 | <0.01 | 0.036 | 4.51 | <0.01 | <1.0 | <1.0 |
| 298 | >100 | — | — | — | — | — | — | — |

As is understood from data of Tables 3 and 4, most of the indanone derivatives of the present invention exhibited low cytotoxicity because they had high $CC_{50}$ values. In addition, most of the indanone derivatives of the present invention were found to be highly inhibitory of coxsackie-, polio- and rhinoviruses because their $EC_{50}$ values were 0.01 μg/mL or less.

Accordingly, the indanone derivatives represented by Chemical Formula 1 in accordance with the present invention exhibit low cytotoxicity and high inhibitory activity against a broad spectrum of picornaviruses, and thus may be usefully applied to a pharmaceutical composition for preventing or treating picornavirus-caused diseases.

<Experimental Example 2> Multicycle Cytopathic Effect (CPE) Reduction Assay for Antiviral Effect Against Picornaviruses The test compounds were evaluated for anti-picornavirus activity by a multicycle cytopathic effect (CPE) reduction assay. The antiviral activity was initially determined using an MTS [3-(4,5-dimethylthiazol-2-yl)-5-(3-carboxymethoxyphenyl)-2-(4-sulfophenyl-2H-tetrazolium]-based CPE reduction assay.

In this regard, cells grown to confluence in 96-well plates were infected with 100 50% cell culture infective doses ($CCID_{50}$) of virus. After an adsorption period of 2 hrs at 37° C., virus was removed and serial dilutions of the compounds were added. The cultures were further incubated at 37° C. for 3 days, until complete CPE was observed in the infected and untreated virus control (VC). After removal of the medium, 90 μl of a culture medium and 10 μl of MTS-phenazine methosulfate (Promega, Leiden, The Netherlands) were added to each well. After an incubation period of 2 hrs at 37° C., the optical density (OD) of each well was read at 498 nm in a microplate reader.

CPE values for evaluating antiviral activity were calculated using the following Mathematic Formula 3:

$$\% \ CPE = 100 \times \frac{OD_{CC} - OD_{virus+compound}}{OD_{CC} - OD_{VC}} \quad \text{[Mathmatic Formula 3]}$$

CPE values for evaluating cytotoxicity were calculated using the following Mathematic Formula 4:

$$\% \ CPE = 100 \times \frac{OD_{CC} - OD_{compound}}{OD_{CC} - OD_{Blank}} \quad \text{[Mathmatic Formula 4]}$$

In Formulas 3 and 4, $OD_{CC}$ corresponds to the OD of the uninfected and untreated, background cell cultures, $OD_{VC}$ represents the OD of the infected and untreated control cell cultures, $OD_{virus+Compound}$ represents the OD of the virus-infected cell cultures treated with a given concentration of compound, and ODBlank represents the OD of the well added with the cell culture medium alone.

The 50% effective concentration ($EC_{50}$) and the 50% cytotoxic concentration ($CC_{50}$) were defined as the concentrations of compound that offered 50% protection against virus-induced CPE and that killed cells by 50%, respectively, and were calculated using logarithmic interpolation.

$CC_{50}$ and $EC_{50}$ against various viruses of some compounds are given in Table 3, below.

TABLE 5

| | Ex. 10 | Ex. 46 | Ex. 66 |
|---|---|---|---|
| $CC_{50}$ [μM] | >100 | >100 | >100 |
| Coxsackie B3[c] $EC_{50}$ [μM] | 0.021 ± 0.0072 | 0.0026 ± 0.0012 | 0.0033 ± 0.0013 |
| Coxsackie A16[d] $EC_{50}$ [μM] | 0.090 ± 0.035 | — | — |
| Coxsackie A9[f] $EC_{50}$ [μM] | — | 0.0017 ± 0.000037 | 0.0083 ± 0.00043 |
| Coxsackie A21[d] $EC_{50}$ [μM] | 1.1 ± 0.58 | — | — |
| Entero 71[e] $EC_{50}$ [μM] | 0.012 ± 0.0020 | 0.0031 ± 0.00034 | 0.025 ± 0.00092 |
| Echo 9[d] $EC_{50}$ [μM] | 0.025 ± 0.0057 | 0.0035 ± 0.00057 | — |
| Echo 11[f] $EC_{50}$ [μM] | 0.021 ± 0.083 | 0.0023 ± 0.00088 | 0.0072 ± 0.00018 |
| Polio 1[f] $EC_{50}$ [μM] | 0.75 ± 0.37 | 0.068 ± 0.0072 | 0.69 ± 0.17 |
| Polio 2[f] $EC_{50}$ [μM] | 0.36 ± 0.15 | 0.018 ± 0.0019 | 0.23 ± 0.020 |
| Polio 3[f] $EC_{50}$ [μM] | 1.0 ± 0.57 | 0.043 ± 0.017 | 0.58 ± 0.0069 |
| Rhino 2[g] $EC_{50}$ [μM] | >50 | >10 | 5.9 ± 0.25 |
| Rhino 9[g] $EC_{50}$ [μM] | >50 | 3.5 ± 0.15 | 2.3 ± 0.70 |
| Rhino 15[g] $EC_{50}$ [μM] | >50 | 2.8 ± 0.26 | 4.6 ± 1.3 |
| Rhino 29[g] $EC_{50}$ [μM] | >50 | 4.6 ± 0.72 | 6.4 ± 0.83 |
| Rhino 39[g] $EC_{50}$ [μM] | >50 | 3.0 ± 0.17 | 1.8 ± 0.37 |
| Rhino 41[g] $EC_{50}$ [μM] | 8.8 ± 0.12 | 0.47 ± 0.036 | 0.60 ± 0.026 |
| Rhino 45[g] $EC_{50}$ [μM] | 3.4 ± 1.5 | <0.078 | 1.7 ± 0.46 |
| Rhino 59[g] $EC_{50}$ [μM] | — | — | >10 |
| Rhino 63[g] $EC_{50}$ [μM] | >50 | 8.5 ± 0.13 | >10 |
| Rhino 85[g] $EC_{50}$ [μM] | >50 | 6.2 ± 0.70 | >5.8 |
| Rhino 89[g] $EC_{50}$ [μM] | >50 | 0.34 ± 0.86 | 0.63 ± 0.023 |
| Rhino 14[g] $EC_{50}$ [μM] | — | <0.01 | — |
| Rhino 42[g] $EC_{50}$ [μM] | >50 | — | 0.15 ± 0.023 |
| Rhino 70[g] $EC_{50}$ [μM] | 2.4 ± 0.36 | >0.078 | 0.057 ± 0.017 |
| Rhino 72[g] $EC_{50}$ [μM] | 5.3 ± 1.2 | — | 0.13 ± 0.069 |
| Rhino 86[g] $EC_{50}$ [μM] | 8 ± 2.9 | — | 0.070 ± 0.0066 |

In Table 5, the superscript c represents incubation at 37° C. in Vero cells, the superscript d represents incubation at 37° C. in MRC-5 cells, the superscript e represents incubation at 37° C. in RD cells, the superscript f represents incubation at 37° C. in BGM cells, the superscript g represents incubation at 37° C. in HeLa cells, and the superscript i represents 100% inhibition of viral replication with compounds of 0.078 μM or higher.

As can be seen in Table 5, the indanone derivatives according to the present invention are low in cytotoxicity because their $CC_{50}$ was measured at 100 μM or higher. In addition, the indanone derivatives were observed to have an $EC_{50}$ of 1.1 μM or less against coxsackieviruses B3, A16, A9, and $A^{21}$. Particularly high antiviral activity was detected in the compound of Example 46 with an $EC_{50}$ of as low as 0.0017 μM.

With regard to enterovirus 71, the indanone derivatives according to the present invention showed an $EC_{50}$ of 0.025 μM or less. Particularly high antiviral activity was detected in the compound of Example 46 with an $EC_{50}$ of as low as 0.0031 μM.

The indanone derivatives according to the invention showed an $EC_{50}$ of 0.025 μM or less against echovirus 9 and echovirus 11, while the highest antiviral activity was detected in the compound of Example 46 as demonstrated by the $EC_{50}$ of 0.0035 μM.

In the case of polioviruses 1, 2 and 3, $EC_{50}$ values of the indanone derivatives according to present invention were measured to be 1.0 μM or less. Particularly high antiviral activity was detected in the compound of Example 46 with an $EC_{50}$ of as low as 0.068 μM.

Also, the indanone derivatives according to the invention were highly inhibitory of rhinoviruses. For example, the compound of Example 46 had an $EC_{50}$ of 0.078 μM or less against rhinoviruses 45 and 70.

Consequently, the indanone derivatives of the present invention are of low cytotoxicity and exhibit excellent antiviral activity against picornaviruses including coxsackie-, entero-, echo-, polio- and rhinoviruses, so that they can be usefully applied to the prevention or treatment of picornavirus-caused respiratory, cardiocirculatory, and nervous system diseases, including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis and otitis media.

<Formulation Example 1> Preparation of Pharmaceutical Formulations

<1-1> Preparation of Powder
Indanone derivative of Chemical Formula 1:2 g
Lactose: 1 g
The above ingredients were mixed and loaded into an airtight sac to produce a powder agent.

<1-2> Preparation of Tablet
Indanone derivative of Chemical Formula 1:100 mg
Corn starch: 100 mg
Lactose: 100 mg
Mg stearate: 2 mg
These ingredients were mixed and prepared into tablets using a typical tabletting method.

<1-3> Preparation of Capsule
Indanone derivative of Chemical Formula 1:100 mg
Corn starch: 100 mg
Lactose: 100 mg
Mg stearate: 2 mg
These ingredients were mixed and loaded into gelatin capsules according to a typical method to produce capsules.

<1-4> Preparation of Injection
Indanone derivative of Chemical Formula 1: 10 μg/ml
Diluted Hydrochloric acid BP: to be pH 3.5
Sodium chloride BP for injection: maximum 1 ml The indanone derivative of the present invention was dissolved in a appropriate volume of sodium chloride BP for injection. The pH of the resultant solution was regulated to be pH 3.5 with dil.HCl BP, and then its volume was regulated with sodium chloride BP for Injection and the solution was mixed completely. The solution was then filled in 5-ml type 1 ample that is made of transparent glass. The air was sealed in upper lattice by melting the glass. The solution contained in ample was autoclaved at 120° C. for 15 min or more to be sterilized and thereby to obtain an injection.

INDUSTRIAL APPLICABILITY

Having excellent inhibitory activity against picornaviruses including coxsackie-, entero-, echo-, Polio-, and rhinoviruses, as well as exhibiting low cytotoxicity, as described hitherto, the indanone derivative of Chemical Formula 1 can be useful as an active ingredient of a pharmaceutical composition for the prevention or treatment of viral diseases including poliomyelitis, paralysis, acute hemorrhagic conjunctivitis, viral meningitis, hand-foot-and-mouth disease, vesicular disease, hepatitis A, myositis, myocarditis, pancreatitis, diabetes, epidemic myalgia, encephalitis, cold, herpangina, foot-and-mouth disease, asthma, chronic obstructive pulmonary disease, pneumonia, sinusitis or otitis media.

The invention claimed is:

1. A compound represented by the following Chemical Formula 1, a pharmaceutically acceptable salt thereof, or an enantiomer thereof:

[Chemical Formula 1]

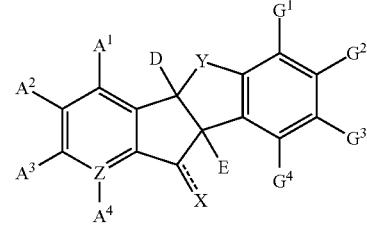

wherein,
$A^1$, $A^2$, and $A^3$ are, independently or optionally, selected from the group consisting of —H, halogen, —OH, —CN, —N$_3$, $C_1$-$C_{10}$ alkoxy, linear or branched $C_1$-$C_{10}$ alkyl, 5-7-membered heterocycloalkyl unsubstituted or substituted with —OH or methoxyphenylalkyl, $C_6$-$C_{12}$ aryl, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$, —NR$^1$(SO$_2$)R$^2$, and —NR$^1$(C=S)—NR$^2$R$^3$, with a proviso that at least two of $A^1$, $A^2$, and $A^3$ may form a ring together if they are adjacent to each other;
$A^4$ is —NR$^1$R$^2$;
D is —OH, halogen, linear or branched $C_1$-$C_{10}$ alkyl, $C_1$-$C_{10}$ alkoxy unsubstituted or substituted with phenyl, —O(CH$_2$)$_n$OH, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(O)R$^2$, —NR$^1$(C=O)R$^2$, —NR$^1$(C=S)R$^2$, —NR$^1$(C=O)OR$^2$, —NR$^1$(C=O)—NR$^1$R$^2$, or —NR$^1$(C=S)—NR$^1$R$^2$;
E is halogen, —OH, —CN, —N=C=O, —N$_3$, $C_1$-$C_{10}$ alkoxy, —O(C=O)R$^1$, —(C=O)R$^1$, —(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^1$R$^2$, —NR$^1$(C=O)NR$^2$OR$^3$, —NR$^1$(SO$_2$)R$^2$, —NR$^1$(C=S)—NR$^1$R$^2$, —NR$^1$(P=O)(OR$^2$)$_2$, or

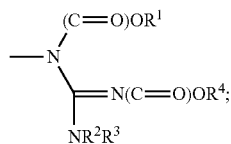

G$^1$, G$^3$, and G$^4$ are independently or optionally selected from the group consisting of —H, halogen, —OH, CN, C$_1$-C$_{10}$ alkoxy, linear or branched C$_1$-C$_{20}$ alkyl, C$_6$-C$_{12}$ aryl, —O(C=O)R$^1$, —(C=O)R$^1$, —(C=O)OR$^1$, —(CH$_2$)$_n$—(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$, and —NR$^1$(C=S)—NR$^2$R$^3$;

G$^2$ is selected from the group consisting of halogen, —OH, CN, C$_1$-C$_{10}$ alkoxy, branched C$_3$-C$_{20}$ alkyl, C$_6$-C$_{12}$ aryl, —O(C=O)R$^1$, —(C=O)R$^1$, —(C=O)OR$^1$, —(CH$_2$)$_n$—(C=O)OR$^1$, —O(C=O)OR$^1$, —O(C=O)NR$^1$R$^2$, —NO$_2$, —NR$^1$R$^2$, —NR$^1$(C=O)R$^2$, —NR$^1$(C=S)R$^2$, —NR$^1$(C=O)OR$^2$, —NR$^1$(C=O)—NR$^2$R$^3$, and —NR$^1$(C=S)—NR$^2$R$^3$;

X is hydrogen, oxygen, sulfur, hydroxy, linear or branched C$_1$-C$_{10}$ alkyl, linear or branched C$_1$-C$_{10}$ alkylene, =N—NR$^1$R$^2$, —NR$^1$—OR$^2$, or =N—OR$^1$;

Y is —O—;

R$^5$ is —(C=O)H, —(C=O)OH, —(C=O)R$^1$, —(C=S)R$^1$, or —(C=O)OR$^1$;

Z is C or N;

R$^1$, R$^2$, R$^3$, and R$^4$ are independently hydrogen, linear or branched C$_1$-C$_{10}$ alkyl, linear or branched C$_1$-C$_{10}$ alkylene unsubstituted or substituted with phenyl, C$_3$-C$_7$ cycloalkyl, C$_3$-C$_7$ heterocycloalkyl, C$_6$-C$_{12}$ aryl, or 5-14-membered heteroaryl;

wherein the heterocycloalkyl may be substituted with at least one oxygen atom via a double bond, the aryl is mono- or bicyclic and may have at least one substituent selected from the group consisting of halogen, —CN, phenyl, linear or branched C$_1$-C$_6$ alkyl, R$^5$, and C$_1$-C$_6$ alkoxy, the heteroaryl is mono-, bi- or tricyclic, and may have at least one substituent selected from the group consisting of halogen, —OH, —NO$_2$, —NH$_2$, —CN, =O or —O$^-$, linear or branched C$_1$-C$_{10}$ alkyl, linear or branched C$_1$-C$_{10}$ alkoxy, and phenyl, the linear or branched alkyl may be unsubstituted or substituted with at least one substituent selected from the group consisting of phenyl, halogen, 5-7-membered heteroaryl, and —NHBoc, the phenyl may be substituted with at least one substituent selected from the group consisting of halogen, phenyl, or phenyl-substituted C$_1$-C$_6$ alkoxy, the heterocycloalkyl or heteroaryl contains at least one heteroatom selected from the group consisting of N, O, and S, the halogen is F, Cl, Br, or I, n is an integer of 1-10, and '⸺' represents a single or double bond;

wherein when Z is N, A$^4$ is not present.

2. The compound, pharmaceutically acceptable salt, or enantiomer of claim 1, wherein A$^1$, A$^2$, and A$^3$ are, independently or optionally, selected from the group consisting of —H, C$_1$-C$_5$ alkoxy, linear or branched C$_1$-C$_5$ alkyl, 5-7-membered heterocycloalkyl unsubstituted or substituted with —OH or methoxyphenylalkyl, C$_6$-C$_{12}$ aryl, —NO$_2$, and —NR$^1$R$^2$;

D is —OH, halogen, linear or branched C$_1$-C$_5$ alkyl, or C$_1$-C$_5$ alkoxy unsubstituted or substituted with phenyl;

E is halogen, —OH, C$_1$-C$_5$ alkoxy, —NR$^1$(C=O)R$^2$, —NR$^1$(C=O)OR$^2$, or —NR$^1$(C=O)—NR$^1$R$^2$;

G$^1$, G$^3$, and G$^4$ are, independently or optionally, selected from the group consisting of —H, C$_1$-C$_5$ alkoxy, and linear or branched C$_1$-C$_{16}$ alkyl;

G$^2$ is C$_1$-C$_5$ alkoxy or isopropyl;

X is oxygen, hydroxyl, or linear or branched C$_1$-C$_5$ alkyl;

Z is C or N;

R$^1$, R$^2$, R$^3$, and R$^4$ are independently hydrogen, linear or branched C$_1$-C$_7$ alkyl, C$_3$-C$_7$ heterocycloalkyl, C$_6$-C$_{12}$ aryl, or 5-14-membered heteroaryl;

wherein the heterocycloalkyl may be substituted with at least one oxygen atom via a double bond, the aryl is mono- or bicyclic and may have at least one substituent selected from the group consisting of halogen, phenyl, linear or branched C$_1$-C$_3$ alkyl, and C$_1$-C$_3$ alkoxy, the heteroaryl is mono-, bi- or tricyclic, and may have at least one substituent selected from the group consisting of halogen, —OH, —NO$_2$, —NH$_2$, —CN, =O or —O$^-$, linear or branched C$_1$-C$_{10}$ alkyl, linear or branched C$_1$-C$_{10}$ alkoxy, and phenyl, the linear or branched alkyl may be unsubstituted or substituted with at least one substituent selected from the group consisting of phenyl, halogen, and 5-7-membered heteroaryl, the phenyl may be substituted with at least one substituent selected from the group consisting of halogen, and phenyl, the heterocycloalkyl or heteroaryl contains at least one heteroatom selected from the group consisting of N, O, and S, the halogen is F, or Cl, and '⸺' represents a single or double bond.

3. The compound, pharmaceutically acceptable salt, or enantiomer of claim 1, wherein A$^1$, A$^2$, and A$^3$ are, independently or optionally, selected from the group consisting of —H and —NR$^1$R$^2$;

D is —OH;

E is —OH or —NR$^1$(C=O)R$^2$;

G$^1$, G$^3$, and G$^4$ are, independently or optionally, linear or branched C$_1$-C$_{15}$ alkyl;

G$^2$ is isopropyl;

X is oxygen;

Z is C;

R$^1$, R$^2$, R$^3$, and R$^4$ are, independently, hydrogen or 5-14-membered heteroaryl;

wherein, the 5-14-membered heteroaryl is monocyclic, bicyclic, or tricyclic, and may be substituted with a substituent selected from the group consisting of halogen, —OH, —NO$_2$, —NH$_2$, —CN, =O or —O$^-$, linear or branched C$_1$-C$_{10}$ alkyl, linear or branched C$_1$-C$_{10}$ alkoxy, and phenyl, the phenyl may be substituted with at least one substituent selected form the group consisting of halogen and phenyl, the heteroaryl contains a heteroatom selected from the group consisting of N, O, and S, and
the halogen is F or Cl, and
'` - - - `' represents a single or double bond.

4. The compound, pharmaceutically acceptable salt, or enantiomer of claim 1, wherein
$A^1$, $A^2$, and $A^3$ are —H, and $A^4$ is —NH$_2$;
D is —OH;
E is —NR$^1$(C=O)R$^2$;
$G^1$, $G^3$ and $G^4$ are —H, and $G^2$ is isopropyl;
X is oxygen;
Z is C;
$R^1$ is hydrogen and $R^2$ is 5-14-membered heteroaryl;
wherein the heteroaryl is furane, benzofurane, pyridine, pyrazolopyridine, pyrimidine, pyrazolopyrimidine, pyrazine, thiopene, quinoline, isoquinoline, triazole, thiazole, indole, pyrazole, indazole, tetrazole, benzotriazole, chromene, pyrane, pyrrole, benzopyrazole, isoxazole, xanthene, cinnoline, imidazole, benzoimidazole, acridine, imidazopyridine, imidazopyrimidine, quinoxaline, pyridazine, tetrazolopyridine, triazolopyridine, triazolopyrimidine or indolizine, and may be substituted with at least one substituent selected from the group consisting of halogen, —OH, —NO$_2$, —NH$_2$, —CN, =O or —O$^-$, linear or branched $C_3$-$C_{10}$ alkyl, linear or branched $C_1$-$C_{10}$ alkoxy, and phenyl, and
the halogen is F or Cl, and
'` - - - `' represents a double bond.

5. The compound, pharmaceutically acceptable salt, or enantiomer of claim 1, wherein the compound is selected from the group consisting of:
9b-hydroxy-7-isopropyl-4b-methoxy-1-nitro-4bH-benzo[d]indeno[1,2-b]furan-10(9bH)-one;
1-amino-4b,9b-dihydroxy-7-isopropyl-4bH-benzo[d]indeno[1,2-b]furan-10(9bH)-one;
1-amino-7-isopropyl-10-oxo-9b,10-dihydro-4bH-benzo[d]indeno[1,2-b]furane-4b,9b-diyl diacetate;
7-ethyl-4b,9b-dihydroxy-1-nitro-4b,9b-dihydro-5-oxa-indeno[2,1-a]inden-10-one;
1-amino-4b,9b-dihydroxy-7-isopropyl-2-nitro-4bH-indeno[1,2-b]benzofuran-10(9bH)-one;
1,4-diamino-4b,9b-dihydroxy-7-isopropyl-4bH-benzo[d]indeno[1,2-b]furan-10(9bH)-one;
1,2-diamino-4b,9b-dihydroxy-7-isopropyl-4bH-indeno[1,2-b]benzofuran-10(9bH)-one;
N-(1-amino-9b-hydroxy-7-isopropyl-10-oxo-9b,10-dihydro-5-oxa-indeno[2,1-a]inden-4b-yl)-acetamide;
N-(1-amino-4b-hydroxy-7-isopropyl-10-oxo-4b,10-dihydro-5-oxa-indeno[2,1-a]inden-9b-yl)-isobutylamide;
pentanoic acid (1-amino-4b-hydroxy-7-isopropyl-10-oxo-4b,10-dihydro-5-oxa-indeno[2,1-a]inden-9b-yl)-amide;
1-amino-7-isopropyl-10-oxo-9b-pentanamido-9b,10-dihydro-4bH-benzo[d]indeno[1,2-b]furan-4b-yl pentanoate;
1-amino-9b-hexanamido-7-isopropyl-10-oxo-9b,10-dihydro-4bH-benzo[d]indeno[1,2-b]furan-4b-yl hexanoate;
1-amino-9b-heptanamido-7-isopropyl-10-oxo-9b,10-dihydro-4bH-benzo[d]indeno[1,2-b]furan-4b-yl heptanoate;
9b-acetamido-1-amino-7-isopropyl-10-oxo-9b,10-dihydro-4bH-indeno[1,2-b]benzofuran-4b-yl methyl carbonate;
N-(1-amino-4b-hydroxy-7-isopropyl-10-oxo-9b,10-dihydro-4bH-benzo[d]indeno[1,2-b]furan-9b-yl)pivalamide;
9b-acetamido-1-amino-7-isopropyl-10-oxo-9b,10-dihydro-4bH-benzo[d]indeno[1,2-b]furan-4b-yl butyl carbonate;
9b-acetamido-1-amino-7-isopropyl-10-oxo-9b,10-dihydro-4bH-benzo[d]indeno[1,2-b]furan-4b-yl ethyl carbonate;
4b,9b-dihydroxy-7-isopropyl-4bH-benzofuro[2',3':3,4]cyclopenta[1,2-b]pyridin-10(9bH)-one;
1-(ethylamino)-4b,9b-dihydroxy-7-isopropyl-4bH-indeno[1,2-b]benzofuran-10(9bH)-one;
N-(1-amino-4b-hydroxy-7-isopropyl-10-oxo-9b,10-dihydro-4bH-indeno[1,2-b]benzofuran-9b-yl)propionamide;
N-(1-amino-4b-hydroxy-7-isopropyl-10-oxo-9b,10-dihydro-4bH-indeno[1,2-b]benzofuran-9b-yl)butyramide;
1-(dimethylamino)-4b,9b-dihydroxy-7-isopropyl-4bH-benzo[d]indeno[1,2-b]-furan-10(9bH)-one;
N-(1-amino-4b-hydroxy-7-isopropyl-10-oxo-9b,10-dihydro-4bH-indeno[1,2-b]benzofuran-9b-yl)benzamide;
N-(1-amino-4b-hydroxy-7-isopropyl-10-oxo-9b,10-dihydro-4bH-indeno[1,2-b]benzofuran-9b-yl)-3-methoxybenzamide;
N-(1-amino-4b-hydroxy-7-isopropyl-10-oxo-9b,10-dihydro-4bH-indeno[1,2-b]benzofuran-9b-yl)-4-chlorobenzamide;
N-(1-amino-4b-hydroxy-7-isopropyl-10-oxo-9b,10-dihydro-4bH-indeno[1,2-b]benzofuran-9b-yl)cyclopropanecarboxamide;
1-(4b-hydroxy-6,8-diisopropyl-1-amino-10-oxo-9b,10-dihydro-4bH-benzo[d]-indeno[1,2-b]furan-9b-yl)-3-(4-methoxyphenyl)thiourea;
1-(4b-hydroxy-6,8-diisopropyl-1-amino-10-oxo-9b,10-dihydro-4bH-benzo[d]indeno[1,2-b]furan-9b-yl)-3-(phenyl)thiourea;
1-(1-amino-4b-hydroxy-7-isopropyl-10-oxo-9b,10-dihydro-4bH-indeno[1,2-b]benzofuran-9b-yl)-3-(4-methoxyphenyl)urea;
1-(1-amino-4b-hydroxy-7-isopropyl-10-oxo-9b,10-dihydro-4bH-indeno[1,2-b]benzofuran-9b-yl)-3-butylurea;
1-(1-amino-4b-hydroxy-7-isopropyl-10-oxo-9b,10-dihydro-4bH-indeno[1,2-b]benzofuran-9b-yl)-3-(4-fluorophenyl)urea;
1-(1-amino-4b-hydroxy-7-isopropyl-10-oxo-9b,10-dihydro-4bH-indeno[1,2-b]benzofuran-9b-yl)-3-(tert-butyl)urea;
N-(1-amino-4b-hydroxy-7-isopropyl-10-oxo-9b,10-dihydro-4bH-indeno[1,2-b]benzofuran-9b-yl)formamide;
N-(1-amino-4b-hydroxy-7-isopropyl-10-oxo-9b,10-dihydro-4bH-benzo[d]indeno[1,2-b]furan-9b-yl)methanesulfonamide;
diethyl (1-amino-4b-hydroxy-7-isopropyl-10-oxo-9b,10-dihydro-4bH-indeno[1,2-b]benzofuran-9b-yl)phosphoamidate;
N-(1-amino-4b-hydroxy-7-isopropyl-10-oxo-9b,10-dihydro-4bH-indeno[1,2-b]benzofuran-9b-yl)-4-cyanobenzamide;
N-(1-amino-4b-hydroxy-7-isopropyl-10-oxo-9b,10-dihydro-4bH-indeno[1,2-b]benzofuran-9b-yl)-2-naphthamide;

N-(1-amino-4b-hydroxy-7-isopropyl-10-oxo-9b,10-dihydro-4bH-indeno[1,2-b]benzofuran-9b-yl)-[1,1'-biphenyl]-4-carboxamide;
1-(1-amino-4b-hydroxy-7-isopropyl-10-oxo-9b,10-dihydro-4bH-benzo[d]indeno[1,2-b]furan-9b-yl)-3-ethylurea;
N-(1-amino-4b-hydroxy-7-isopropyl-10-oxo-9b,10-dihydro-4bH-benzo[d]indeno[1,2-b]furan-9b-yl)tetrahydrofurane-2-carboxamide;
N-(1-amino-4b-hydroxy-7-isopropyl-10-oxo-9b,10-dihydro-4bH-indeno[1,2-b]benzofuran-9b-yl)-2,2,2-trifluoroacetamide;
N-(1-amino-4b-hydroxy-7-isopropyl-10-oxo-9b,10-dihydro-4bH-benzo[d]indeno[1,2-b]furan-9b-yl)-1,1,1-trifluoromethanesulfonamide;
N-(1-amino-4b-hydroxy-7-isopropyl-10-oxo-9b,10-dihydro-4bH-indeno[1,2-b]benzofuran-9b-yl)-2-phenylacetamide;
(E)-N-(1-amino-4b-hydroxy-7-isopropyl-10-oxo-9b,10-dihydro-4bH-indeno[1,2-b]benzofuran-9b-yl)-3-(3,4-dichlorophenyl)acrylamide;
2-([1,1'-biphenyl]-4-yl)-N-(1-amino-4b-hydroxy-7-isopropyl-10-oxo-9b,10-dihydro-4bH-indeno[1,2-b]benzofuran-9b-yl)acetamide;
N-(1-amino-4b-hydroxy-7-isopropyl-10-oxo-9b,10-dihydro-4bH-indeno[1,2-b]benzofuran-9b-yl)-2-methoxybenzamide;
N-(1-amino-4b-hydroxy-7-isopropyl-10-oxo-9b,10-dihydro-4bH-benzo[d]indeno[1,2-b]furan-9b-yl)-2-methylbenzamide;
N-(1-amino-4b-hydroxy-7-isopropyl-10-oxo-9b,10-dihydro-4bH-benzo[d]indeno[1,2-b]furan-9b-yl)-3-methylbenzamide;
N-(1-amino-4b-hydroxy-7-isopropyl-10-oxo-9b,10-dihydro-4bH-benzo[d]indeno[1,2-b]furan-9b-yl)-4-methylbenzamide;
methyl-4-(1-amino-4b-hydroxy-7-isopropyl-10-oxo-9b,10-dihydro-4bH-benzo[d]indeno[1,2-b]furan-9b-ylcarbamoyl)benzoate;
N-(1-amino-4b-hydroxy-7-isopropyl-10-oxo-9b,10-dihydro-4bH-indeno[1,2-b]benzofuran-9b-yl)-3-chlorobenzamide;
N-(1-amino-4b-hydroxy-7-isopropyl-10-oxo-9b,10-dihydro-4bH-indeno[1,2-b]benzofuran-9b-yl)-3,5-dimethylbenzamide;
N-(1-amino-4b-hydroxy-7-isopropyl-10-oxo-9b,10-dihydro-4bH-indeno[1,2-b]benzofuran-9b-yl)-2,4,6-trichlorobenzamide;
N-(1-amino-4b-hydroxy-7-isopropyl-10-oxo-9b,10-dihydro-4bH-benzo[d]indeno[1,2-b]furan-9b-yl)-2-fluoroacetamide;
N-(1-amino-4b-hydroxy-7-isopropyl-10-oxo-9b,10-dihydro-4bH-benzo[d]indeno[1,2-b]furan-9b-yl)-2-chloroacetamide;
N-(1-amino-4b-hydroxy-7-isopropyl-10-oxo-9b,10-dihydro-4bH-indeno[1,2-b]benzofuran-9b-yl)picolinamide;
N-(1-amino-4b-hydroxy-7-isopropyl-10-oxo-9b,10-dihydro-4bH-indeno[1,2-b]benzofuran-9b-yl)nicotinamide;
N-(1-amino-4b-hydroxy-7-isopropyl-10-oxo-9b,10-dihydro-4bH-indeno[1,2-b]benzofuran-9b-yl)isonicotinamide;
N-(1-amino-4b-hydroxy-7-isopropyl-10-oxo-9b,10-dihydro-4bH-indeno[1,2-b]benzofuran-9b-yl)pyrazine-2-carboxamide;
N-(1-amino-4b-hydroxy-7-isopropyl-10-oxo-9b,10-dihydro-4bH-indeno[1,2-b]benzofuran-9b-yl)furane-2-carboxamide;
N-(1-amino-4b-hydroxy-7-isopropyl-10-oxo-9b,10-dihydro-4bH-indeno[1,2-b]benzofuran-9b-yl)quinoline-8-carboxamide;
N-(1-amino-4b-hydroxy-7-isopropyl-10-oxo-9b,10-dihydro-4bH-indeno[1,2-b]benzofuran-9b-yl)quinoline-6-carboxamide;
N-(1-amino-4b-hydroxy-7-isopropyl-10-oxo-9b,10-dihydro-4bH-benzo[d]indeno[1,2-b]furan-9b-yl)benzofurane-2-carboxamide;
N-(1-amino-4b-hydroxy-7-isopropyl-10-oxo-9b,10-dihydro-4bH-benzo[d]indeno[1,2-b]furan-9b-yl)-3-methylbenzofurane-2-carboxamide;
N-(1-amino-4b-hydroxy-7-isopropyl-10-oxo-9b,10-dihydro-4bH-indeno[1,2-b]benzofuran-9b-yl)-4-methylthiazole-5-carboxamide;
(4R)—N-(1-amino-4b-hydroxy-7-isopropyl-10-oxo-9b,10-dihydro-4bH-indeno[1,2-b]benzofuran-9b-yl)-2-oxothiazolidine-4-carboxamide;
N-(1-amino-4b-hydroxy-7-isopropyl-10-oxo-9b,10-dihydro-4bH-benzo[d]indeno[1,2-b]furan-9b-yl)-1H-indazole-3-carboxamide;
N-(1-amino-4b-hydroxy-7-isopropyl-10-oxo-9b,10-dihydro-4bH-benzo[d]indeno[1,2-b]furan-9b-yl)-2-(1H-tetrazol-1-yl)acetamide;
N-(1-amino-4b-hydroxy-7-isopropyl-10-oxo-9b,10-dihydro-4bH-indeno[1,2-b]benzofuran-9b-yl)quinoline-3-carboxamide;
N-(1-amino-4b-hydroxy-7-isopropyl-10-oxo-9b,10-dihydro-4bH-indeno[1,2-b]benzofuran-9b-yl)quinoline-4-carboxamide;
N-(1-amino-4b-hydroxy-7-isopropyl-10-oxo-9b,10-dihydro-4bH-indeno[1,2-b]benzofuran-9b-yl)-5-methylthiophene-2-carboxamide;
N-(1-amino-4b-hydroxy-7-isopropyl-10-oxo-9b,10-dihydro-4bH-indeno[1,2-b]benzofuran-9b-yl)-2-methoxythiophene-3-carboxamide;
N-(1-amino-4b-hydroxy-7-isopropyl-10-oxo-9b,10-dihydro-4bH-indeno[1,2-b]benzofuran-9b-yl)-3-(2-chloro-6-fluorophenyl)-5-methylisooxazole-4-carboxamide;
5-amino-N-(1-amino-4b-hydroxy-7-isopropyl-10-oxo-9b,10-dihydro-4bH-indeno[1,2-b]benzofuran-9b-yl)furane-2-carboxamide;
N-(1-amino-4b-hydroxy-7-isopropyl-10-oxo-9b,10-dihydro-4bH-indeno[1,2-b]benzofuran-9b-yl)-1H-pyrrole-2-carboxamide;
N-(1-amino-4b-hydroxy-7-isopropyl-10-oxo-9b,10-dihydro-4bH-indeno[1,2-b]benzofuran-9b-yl)-2-methoxyisonicotinamide;
N-(1-amino-4b-hydroxy-7-isopropyl-10-oxo-9b,10-dihydro-4bH-benzo[d]indeno[1,2-b]furan-9b-yl)benzo[b]thiophene-2-carboxamide;
N-(1-amino-4b-hydroxy-7-isopropyl-10-oxo-9b,10-dihydro-4bH-benzo[d]indeno[1,2-b]furan-9b-yl)-9H-xanthene-9-carboxamide;
N-(1-amino-4b-hydroxy-7-isopropyl-10-oxo-9b,10-dihydro-4bH-benzo[d]indeno[1,2-b]furan-9b-yl)cinnoline-4-carboxamide;
N-(1-amino-4b-hydroxy-7-isopropyl-10-oxo-9b,10-dihydro-4bH-benzo[d]indeno[1,2-b]furan-9b-yl)acridine-9-carboxamide;
N-(1-amino-4b-hydroxy-7-isopropyl-10-oxo-9b,10-dihydro-4bH-benzo[d]indeno[1,2-b]furan-9b-yl)-4-nitro-1H-pyrazole-3-carboxamide;

N-(1-amino-4b-hydroxy-7-isopropyl-10-oxo-9b,10-dihydro-4bH-benzo[d]indeno[1,2-b]furan-9b-yl)-4-methylpicolinamide;
N-(1-amino-4b-hydroxy-7-isopropyl-10-oxo-9b,10-dihydro-4bH-benzo[d]indeno[1,2-b]furan-9b-yl)-4-(trifluoromethyl)picolinamide;
N-(1-amino-4b-hydroxy-7-isopropyl-10-oxo-9b,10-dihydro-4bH-benzo[d]indeno[1,2-b]furan-9b-yl)-5-cyanopicolinamide;
N-(1-amino-4b-hydroxy-7-isopropyl-10-oxo-9b,10-dihydro-4bH-benzo[d]indeno[1,2-b]furan-9b-yl)-3-chloropicolinamide;
N-(1-amino-4b-hydroxy-7-isopropyl-10-oxo-9b,10-dihydro-4bH-benzo[d]indeno[1,2-b]furan-9b-yl)-4-methoxyquinoline-2-carboxamide;
N-(1-amino-4b-hydroxy-7-isopropyl-10-oxo-9b,10-dihydro-4bH-indeno[1,2-b]benzofuran-9b-yl)isoquinoline-3-carboxamide;
N-(1-amino-4b-hydroxy-7-isopropyl-10-oxo-9b,10-dihydro-4bH-indeno[1,2-b]benzofuran-9b-yl)-2-methylisonicotinamide;
N-(1-amino-4b-hydroxy-7-isopropyl-10-oxo-9b,10-dihydro-4bH-indeno[1,2-b]benzofuran-9b-yl)-3-fluoroisonicotinamide;
N-(1-amino-4b-hydroxy-7-isopropyl-10-oxo-9b,10-dihydro-4bH-indeno[1,2-b]benzofuran-9b-yl)-3-chloroisonicotinamide;
N-(1-amino-4b-hydroxy-7-isopropyl-10-oxo-9b,10-dihydro-4bH-indeno[1,2-b]benzofuran-9b-yl)-1-methyl-1H-imidazole-2-carboxamide;
2-((1-amino-4b-hydroxy-7-isopropyl-10-oxo-9b,10-dihydro-4bH-indeno[1,2-b]benzofuran-9b-yl)carbamoyl)pyridine 1-oxide;
N-(1-amino-4b-hydroxy-7-isopropyl-10-oxo-9b,10-dihydro-4bH-indeno[1,2-b]benzofuran-9b-yl)-4-chloronicotinamide;
N-(1-amino-4b-hydroxy-7-isopropyl-10-oxo-9b,10-dihydro-4bH-indeno[1,2-b]benzofuran-9b-yl)-5-fluoronicotinamide;
N-(1-amino-4b-hydroxy-7-isopropyl-10-oxo-9b,10-dihydro-4bH-indeno[1,2-b]benzofuran-9b-yl)-5-hydroxynicotinamide;
N-(1-amino-4b-hydroxy-7-isopropyl-10-oxo-9b,10-dihydro-4bH-indeno[1,2-b]benzofuran-9b-yl)-3-hydroxypicolinamide;
N-(1-amino-4b-hydroxy-7-isopropyl-10-oxo-9b,10-dihydro-4bH-indeno[1,2-b]benzofuran-9b-yl)-4-methylnicotinamide;
N-(1-amino-4b-hydroxy-7-isopropyl-10-oxo-9b,10-dihydro-4bH-indeno[1,2-b]benzofuran-9b-yl)-5-methylnicotinamide;
N-(1-amino-4b-hydroxy-7-isopropyl-10-oxo-9b,10-dihydro-4bH-indeno[1,2-b]benzofuran-9b-yl)-5-methoxynicotinamide;
N-(1-amino-4b-hydroxy-7-isopropyl-10-oxo-9b,10-dihydro-4bH-benzo[d]indeno[1,2-b]furan-9b-yl)quinoline-2-carboxamide;
N-(1-amino-4b-hydroxy-7-isopropyl-10-oxo-9b,10-dihydro-4bH-benzo[d]indeno[1,2-b]furan-9b-yl)-3-bromobenzo[b]thiophene-2-carboxamide;
N-(1-amino-4b-hydroxy-7-isopropyl-10-oxo-9b,10-dihydro-4bH-benzo[d]indeno[1,2-b]furan-9b-yl)-1H-indole-2-carboxamide;
N-(1-amino-4b-hydroxy-7-isopropyl-10-oxo-9b,10-dihydro-4bH-benzo[d]indeno[1,2-b]furan-9b-yl)isoquinoline-1-carboxamide;
N-(1-amino-4b-hydroxy-7-isopropyl-10-oxo-9b,10-dihydro-4bH-indeno[1,2-b]benzofuran-9b-yl)-6-fluoro-4-methoxyquinoline-3-carboxamide;
N-(1-amino-4b-hydroxy-7-isopropyl-10-oxo-9b,10-dihydro-4bH-indeno[1,2-b]benzofuran-9b-yl)-1-methyl-1H-indole-2-carboxamide;
N-(1-amino-4b-hydroxy-7-isopropyl-10-oxo-9b,10-dihydro-4bH-indeno[1,2-b]benzofuran-9b-yl)-3-chloro-6-fluorobenzo[b]thiophene-2-carboxamide;
N-(1-amino-4b-hydroxy-7-isopropyl-10-oxo-9b,10-dihydro-4bH-indeno[1,2-b]benzofuran-9b-yl)-3-chloro-6-methylbenzo[b]thiophene-2-carboxamide;
N-(1-amino-4b-hydroxy-7-isopropyl-10-oxo-9b,10-dihydro-4bH-indeno[1,2-b]benzofuran-9b-yl)-1,3-dimethyl-1H-pyrazolo[3,4-b]pyridine-5-carboxamide;
N-(1-amino-4b-hydroxy-7-isopropyl-10-oxo-9b,10-dihydro-4bH-indeno[1,2-b]benzofuran-9b-yl)imidazo[1,2-a]pyridine-6-carboxamide;
N-(1-amino-4b-hydroxy-7-isopropyl-10-oxo-9b,10-dihydro-4bH-indeno[1,2-b]benzofuran-9b-yl)pyrazolo[1,5-a]pyrimidine-2-carboxamide;
N-(1-amino-4b-hydroxy-7-isopropyl-10-oxo-9b,10-dihydro-4bH-indeno[1,2-b]benzofuran-9b-yl)-3-methylbenzo[b]thiophene-2-carboxamide;
N-(1-amino-4b-hydroxy-7-isopropyl-10-oxo-9b,10-dihydro-4bH-indeno[1,2-b]benzofuran-9b-yl)quinoxaline-2-carboxamide;
N-(1-amino-4b-hydroxy-7-isopropyl-10-oxo-9b,10-dihydro-4bH-indeno[1,2-b]benzofuran-9b-yl)pyridazine-4-carboxamide;
N-(1-amino-4b-hydroxy-7-isopropyl-10-oxo-9b,10-dihydro-4bH-indeno[1,2-b]benzofuran-9b-yl)quinoxaline-6-carboxamide;
N-(1-amino-4b-hydroxy-7-isopropyl-10-oxo-9b,10-dihydro-4bH-indeno[1,2-b]benzofuran-9b-yl)tetrazolo[1,5-a]pyridine-6-carboxamide;
N-(1-amino-4b-hydroxy-7-isopropyl-10-oxo-9b,10-dihydro-4bH-indeno[1,2-b]benzofuran-9b-yl)tetrazolo[1,5-a]pyridine-8-carboxamide;
N-(1-amino-4b-hydroxy-7-isopropyl-10-oxo-9b,10-dihydro-4bH-indeno[1,2-b]benzofuran-9b-yl)-7-methylimidazo[1,2-a]pyridine-2-carboxamide;
N-(1-amino-4b-hydroxy-7-isopropyl-10-oxo-9b,10-dihydro-4bH-indeno[1,2-b]benzofuran-9b-yl)-7-methyl-[1,2,4]triazolo[1,5-a]pyrimidine-2-carboxamide;
N-(1-amino-4b-hydroxy-7-isopropyl-10-oxo-9b,10-dihydro-4bH-indeno[1,2-b]benzofuran-9b-yl)-5,7-dimethylpyrazolo[1,5-a]pyrimidine-3-carboxamide;
N-(1-amino-4b-hydroxy-7-isopropyl-10-oxo-9b,10-dihydro-4bH-indeno[1,2-b]benzofuran-9b-yl)indolizine-2-carboxamide;
N-(1-amino-4b-hydroxy-7-isopropyl-10-oxo-9b,10-dihydro-4bH-indeno[1,2-b]benzofuran-9b-yl)-1,6-diisopropyl-1H-pyrazolo[3,4-b]pyridine-4-carboxamide;
N-(1-amino-4b-hydroxy-7-isopropyl-10-oxo-9b,10-dihydro-4bH-indeno[1,2-b]benzofuran-9b-yl)imidazo[1,2-a]pyrimidine-2-carboxamide;
N-(1-amino-4b-hydroxy-7-isopropyl-10-oxo-9b,10-dihydro-4bH-indeno[1,2-b]benzofuran-9b-yl)-1-oxo-1,2-dihydroisoquinoline-3-carboxamide;
N-(1-amino-4b-hydroxy-7-isopropyl-10-oxo-9b,10-dihydro-4bH-benzo[d]indeno[1,2-b]furan-9b-yl)-3-methylimidazo[1,5-a]pyridine-1-carboxamide;
N-(1-amino-4b-hydroxy-7-isopropyl-10-oxo-9b,10-dihydro-4bH-benzo[d]indeno[1,2-b]furan-9b-yl)-2H-indazole-3-carboxamide;

N-(1-amino-4b-hydroxy-7-isopropyl-10-oxo-9b,10-di-hydro-4bH-indeno[1,2-b]benzofuran-9b-yl)-7-methyl-pyrazolo[1,5-a]pyrimidine-6-carboxamide;
N-(1-amino-4b-hydroxy-7-isopropyl-10-oxo-9b,10-di-hydro-4bH-indeno[1,2-b]benzofuran-9b-yl)-1H-benzo[d]imidazole-2-carboxamide;
N-(1-amino-4b-hydroxy-7-isopropyl-10-oxo-9b,10-di-hydro-4bH-indeno[1,2-b]benzofuran-9b-yl)-5-fluoro-1H-benzo[d]imidazole-2-carboxamide;
N-(1-amino-4b-hydroxy-7-isopropyl-10-oxo-9b,10-di-hydro-4bH-indeno[1,2-b]benzofuran-9b-yl)tetrazolo[1,5-a]pyridine-5-carboxamide;
N-(1-amino-4b-hydroxy-7-isopropyl-10-oxo-9b,10-di-hydro-4bH-indeno[1,2-b]benzofuran-9b-yl)-1-methyl-1H-indazole-3-carboxamide;
N-(1-amino-4b-hydroxy-7-isopropyl-10-oxo-9b,10-di-hydro-4bH-indeno[1,2-b]benzofuran-9b-yl)-1H-indole-5-carboxamide;
N-(1-amino-4b-hydroxy-7-isopropyl-10-oxo-9b,10-di-hydro-4bH-indeno[1,2-b]benzofuran-9b-yl)-1-methyl-3a,7a-dihydro-1H-indazole-3-carboxamide;
N-(1-amino-4b-hydroxy-7-isopropyl-10-oxo-9b,10-di-hydro-4bH-indeno[1,2-b]benzofuran-9b-yl)-1-methyl-1H-imidazole-4-carboxamide;
N-(1-amino-4b-hydroxy-7-isopropyl-10-oxo-9b,10-di-hydro-4bH-indeno[1,2-b]benzofuran-9b-yl)-1H-pyrrole-3-carboxamide;
N-(1-amino-4b-hydroxy-7-isopropyl-10-oxo-9b,10-di-hydro-4bH-indeno[1,2-b]benzofuran-9b-yl)-1H-indazole-5-caboxamide; and
N-(1-amino-4b-hydroxy-7-isopropyl-10-oxo-9b,10-di-hydro-4bH-indeno[1,2-b]benzofuran-9b-yl)-3-methyl-1H-pyrazole-5-carboxamide.

6. The compound, pharmaceutically acceptable salt, or enantiomer of claim 1, wherein the compound is selected from the group consisting of:
9b-hydroxy-7-isopropyl-4b-methoxy-1-nitro-4bH-benzo[d]indeno[1,2-b]furan-10(9bH)-one;
1-amino-4b,9b-dihydroxy-7-isopropyl-4bH-benzo[d]indeno[1,2-b]furan-10(9bH)-one;
1-amino-7-isopropyl-10-oxo-9b,10-dihydro-4bH-benzo[d]indeno[1,2-b]furane-4b,9b-diyl diacetate;
7-ethyl-4b,9b-dihydroxy-1-nitro-4b,9b-dihydro-5-oxa-indeno[2,1-a]inden-10-one;
1-amino-4b,9b-dihydroxy-7-isopropyl-2-nitro-4bH-indeno[1,2-b]benzofuran-10(9bH)-one;
1,4-diamino-4b,9b-dihydroxy-7-isopropyl-4bH-benzo[d]indeno[1,2-b]furan-10(9bH)-one;
1,2-diamino-4b,9b-dihydroxy-7-isopropyl-4bH-indeno[1,2-b]benzofuran-10(9bH)-one;
N-(1-amino-9b-hydroxy-7-isopropyl-10-oxo-9b,10-di-hydro-5-oxa-indeno[2,1-a]inden-4b-yl)-acetamide;
N-(1-amino-4b-hydroxy-7-isopropyl-10-oxo-4b,10-di-hydro-5-oxa-indeno[2,1-a]inden-9b-yl)-isobutylamide;
pentanoic acid (1-amino-4b-hydroxy-7-isopropyl-10-oxo-4b,10-dihydro-5-oxa-indeno[2,1-a]inden-9b-yl)-amide;
1-amino-7-isopropyl-10-oxo-9b-pentanamido-9b,10-di-hydro-4bH-benzo[d]indeno[1,2-b]furan-4b-yl pentanoate;
1-amino-9b-hexanamido-7-isopropyl-10-oxo-9b,10-di-hydro-4bH-benzo[d]indeno[1,2-b]furan-4b-yl hexanoate;
1-amino-9b-heptanamido-7-isopropyl-10-oxo-9b,10-di-hydro-4bH-benzo[d]indeno[1,2-b]furan-4b-yl heptanoate;
9b-acetamido-1-amino-7-isopropyl-10-oxo-9b,10-di-hydro-4bH-indeno[1,2-b]benzofuran-4b-yl methyl carbonate;
N-(1-amino-4b-hydroxy-7-isopropyl-10-oxo-9b,10-di-hydro-4bH-benzo[d]indeno[1,2-b]furan-9b-yl)pivalamide;
9b-acetamido-1-amino-7-isopropyl-10-oxo-9b,10-di-hydro-4bH-benzo[d]indeno[1,2-b]furan-4b-yl butyl carbonate;
9b-acetamido-1-amino-7-isopropyl-10-oxo-9b,10-di-hydro-4bH-benzo[d]indeno[1,2-b]furan-4b-yl ethyl carbonate;
4b,9b-dihydroxy-7-isopropyl-4bH-benzofuro[2',3':3,4]cyclopenta[1,2-b]pyridin-10(9bH)-one;
1-(ethylamino)-4b,9b-dihydroxy-7-isopropyl-4bH-indeno[1,2-b]benzofuran-10(9bH)-one;
N-(1-amino-4b-hydroxy-7-isopropyl-10-oxo-9b,10-di-hydro-4bH-indeno[1,2-b]benzofuran-9b-yl)propionamide;
N-(1-amino-4b-hydroxy-7-isopropyl-10-oxo-9b,10-di-hydro-4bH-indeno[1,2-b]benzofuran-9b-yl)butyramide;
1-(dimethylamino)-4b,9b-dihydroxy-7-isopropyl-4bH-benzo[d]indeno[1,2-b]-furan-10(9bH)-one;
N-(1-amino-4b-hydroxy-7-isopropyl-10-oxo-9b,10-di-hydro-4bH-indeno[1,2-b]benzofuran-9b-yl)benzamide;
N-(1-amino-4b-hydroxy-7-isopropyl-10-oxo-9b,10-di-hydro-4bH-indeno[1,2-b]benzofuran-9b-yl)-3-methoxybenzamide;
N-(1-amino-4b-hydroxy-7-isopropyl-10-oxo-9b,10-di-hydro-4bH-indeno[1,2-b]benzofuran-9b-yl)-4-chlorobenzamide;
N-(1-amino-4b-hydroxy-7-isopropyl-10-oxo-9b,10-di-hydro-4bH-indeno[1,2-b]benzofuran-9b-yl)cyclopropanecarboxamide;
1-(4b-hydroxy-6,8-diisopropyl-1-amino-10-oxo-9b,10-dihydro-4bH-benzo[d]-indeno[1,2-b]furan-9b-yl)-3-(4-methoxyphenyl)thiourea;
1-(4b-hydroxy-6,8-diisopropyl-1-amino-10-oxo-9b,10-dihydro-4bH-benzo[d]-indeno[1,2-b]furan-9b-yl)-3-(phenyl)thiourea;
1-(1-amino-4b-hydroxy-7-isopropyl-10-oxo-9b,10-di-hydro-4bH-indeno[1,2-b]benzofuran-9b-yl)-3-(4-methoxyphenyl)urea;
1-(1-amino-4b-hydroxy-7-isopropyl-10-oxo-9b,10-di-hydro-4bH-indeno[1,2-b]benzofuran-9b-yl)-3-butylurea;
1-(1-amino-4b-hydroxy-7-isopropyl-10-oxo-9b,10-di-hydro-4bH-indeno[1,2-b]benzofuran-9b-yl)-3-(4-fluorophenyl)urea;
1-(1-amino-4b-hydroxy-7-isopropyl-10-oxo-9b,10-di-hydro-4bH-indeno[1,2-b]benzofuran-9b-yl)-3-(tert-butyl)urea;
1-(1-amino-4b-hydroxy-7-isopropyl-10-oxo-9b,10-di-hydro-4bH-indeno[1,2-b]benzofuran-9b-yl)formamide;
N-(1-amino-4b-hydroxy-7-isopropyl-10-oxo-9b,10-di-hydro-4bH-indeno[1,2-b]benzofuran-9b-yl)formamide;
N-(1-amino-4b-hydroxy-7-isopropyl-10-oxo-9b,10-di-hydro-4bH-benzo[d]indeno[1,2-b]furan-9b-yl)methanesulfonamide;
diethyl (1-amino-4b-hydroxy-7-isopropyl-10-oxo-9b,10-dihydro-4bH-indeno[1,2-b]benzofuran-9b-yl)phosphoamidate;

N-(1-amino-4b-hydroxy-7-isopropyl-10-oxo-9b,10-dihydro-4bH-indeno[1,2-b]benzofuran-9b-yl)-4-cyanobenzamide;
N-(1-amino-4b-hydroxy-7-isopropyl-10-oxo-9b,10-dihydro-4bH-indeno[1,2-b]benzofuran-9b-yl)-2-naphthamide;
N-(1-amino-4b-hydroxy-7-isopropyl-10-oxo-9b,10-dihydro-4bH-indeno[1,2-b]benzofuran-9b-yl)-[1,1'-biphenyl]-4-carboxamide;
1-(1-amino-4b-hydroxy-7-isopropyl-10-oxo-9b,10-dihydro-4bH-benzo[d]indeno[1,2-b]furan-9b-yl)-3-ethylurea;
N-(1-amino-4b-hydroxy-7-isopropyl-10-oxo-9b,10-dihydro-4bH-benzo[d]indeno[1,2-b]furan-9b-yl)tetrahydrofurane-2-carboxamide;
N-(1-amino-4b-hydroxy-7-isopropyl-10-oxo-9b,10-dihydro-4bH-indeno[1,2-b]benzofuran-9b-yl)-2,2,2-trifluoroacetamide;
N-(1-amino-4b-hydroxy-7-isopropyl-10-oxo-9b,10-dihydro-4bH-benzo[d]indeno[1,2-b]furan-9b-yl)-1,1,1-trifluoromethanesulfonamide;
N-(1-amino-4b-hydroxy-7-isopropyl-10-oxo-9b,10-dihydro-4bH-indeno[1,2-b]benzofuran-9b-yl)-2-phenylacetamide;
(E)-N-(1-amino-4b-hydroxy-7-isopropyl-10-oxo-9b,10-dihydro-4bH-indeno[1,2-b]benzofuran-9b-yl)-3-(3,4-dichlorophenyl)acrylamide;
2-([1,1'-biphenyl]-4-yl)-N-(1-amino-4b-hydroxy-7-isopropyl-10-oxo-9b,10-dihydro-4bH-indeno[1,2-b]benzofuran-9b-yl)acetamide;
N-(1-amino-4b-hydroxy-7-isopropyl-10-oxo-9b,10-dihydro-4bH-indeno[1,2-b]benzofuran-9b-yl)-2-methoxybenzamide;
N-(1-amino-4b-hydroxy-7-isopropyl-10-oxo-9b,10-dihydro-4bH-benzo[d]indeno[1,2-b]furan-9b-yl)-2-methylbenzamide;
N-(1-amino-4b-hydroxy-7-isopropyl-10-oxo-9b,10-dihydro-4bH-benzo[d]indeno[1,2-b]furan-9b-yl)-3-methylbenzamide;
N-(1-amino-4b-hydroxy-7-isopropyl-10-oxo-9b,10-dihydro-4bH-benzo[d]indeno[1,2-b]furan-9b-yl)-4-methylbenzamide;
methyl-4-(1-amino-4b-hydroxy-7-isopropyl-10-oxo-9b,10-dihydro-4bH-benzo[d]indeno[1,2-b]furan-9b-ylcarbamoyl)benzoate;
N-(1-amino-4b-hydroxy-7-isopropyl-10-oxo-9b,10-dihydro-4bH-indeno[1,2-b]benzofuran-9b-yl)-3-chlorobenzamide;
N-(1-amino-4b-hydroxy-7-isopropyl-10-oxo-9b,10-dihydro-4bH-indeno[1,2-b]benzofuran-9b-yl)-3,5-dimethylbenzamide;
N-(1-amino-4b-hydroxy-7-isopropyl-10-oxo-9b,10-dihydro-4bH-indeno[1,2-b]benzofuran-9b-yl)-2,4,6-trichlorobenzamide;
N-(1-amino-4b-hydroxy-7-isopropyl-10-oxo-9b,10-dihydro-4bH-benzo[d]indeno[1,2-b]furan-9b-yl)-2-fluoroacetamide;
N-(1-amino-4b-hydroxy-7-isopropyl-10-oxo-9b,10-dihydro-4bH-benzo[d]indeno[1,2-b]furan-9b-yl)-2-chloroacetamide;
N-(1-amino-4b-hydroxy-7-isopropyl-10-oxo-9b,10-dihydro-4bH-indeno[1,2-b]benzofuran-9b-yl)picolinamide;
N-(1-amino-4b-hydroxy-7-isopropyl-10-oxo-9b,10-dihydro-4bH-indeno[1,2-b]benzofuran-9b-yl)nicotinamide;
N-(1-amino-4b-hydroxy-7-isopropyl-10-oxo-9b,10-dihydro-4bH-indeno[1,2-b]benzofuran-9b-yl)isonicotinamide;
N-(1-amino-4b-hydroxy-7-isopropyl-10-oxo-9b,10-dihydro-4bH-indeno[1,2-b]benzofuran-9b-yl)pirazine-2-carboxamide;
N-(1-amino-4b-hydroxy-7-isopropyl-10-oxo-9b,10-dihydro-4bH-indeno[1,2-b]benzofuran-9b-yl)furane-2-carboxamide;
N-(1-amino-4b-hydroxy-7-isopropyl-10-oxo-9b,10-dihydro-4bH-indeno[1,2-b]benzofuran-9b-yl)quinoline-8-carboxamide;
N-(1-amino-4b-hydroxy-7-isopropyl-10-oxo-9b,10-dihydro-4bH-indeno[1,2-b]benzofuran-9b-yl)quinoline-6-carboxamide;
N-(1-amino-4b-hydroxy-7-isopropyl-10-oxo-9b,10-dihydro-4bH-benzo[d]indeno[1,2-b]furan-9b-yl)benzofurane-2-carboxamide;
N-(1-amino-4b-hydroxy-7-isopropyl-10-oxo-9b,10-dihydro-4bH-benzo[d]indeno[1,2-b]furan-9b-yl)-3-methylbenzofurane-2-carboxamide;
N-(1-amino-4b-hydroxy-7-isopropyl-10-oxo-9b,10-dihydro-4bH-indeno[1,2-b]benzofuran-9b-yl)-4-methylthiazole-5-carboxamide;
(4R)—N-(1-amino-4b-hydroxy-7-isopropyl-10-oxo-9b,10-dihydro-4bH-indeno[1,2-b]benzofuran-9b-yl)-2-oxothiazolidine-4-carboxamide;
N-(1-amino-4b-hydroxy-7-isopropyl-10-oxo-9b,10-dihydro-4bH-benzo[d]indeno[1,2-b]furan-9b-yl)-1H-indazole-3-carboxamide;
N-(1-amino-4b-hydroxy-7-isopropyl-10-oxo-9b,10-dihydro-4bH-benzo[d]indeno[1,2-b]furan-9b-yl)-2-(1H-tetrazol-1-yl)acetamide;
N-(1-amino-4b-hydroxy-7-isopropyl-10-oxo-9b,10-dihydro-4bH-indeno[1,2-b]benzofuran-9b-yl)quinoline-3-carboxamide;
N-(1-amino-4b-hydroxy-7-isopropyl-10-oxo-9b,10-dihydro-4bH-indeno[1,2-b]benzofuran-9b-yl)quinoline-4-carboxamide;
N-(1-amino-4b-hydroxy-7-isopropyl-10-oxo-9b,10-dihydro-4bH-indeno[1,2-b]benzofuran-9b-yl)-5-methylthiophene-2-carboxamide;
N-(1-amino-4b-hydroxy-7-isopropyl-10-oxo-9b,10-dihydro-4bH-indeno[1,2-b]benzofuran-9b-yl)-2-methoxythiophene-3-carboxamide;
N-(1-amino-4b-hydroxy-7-isopropyl-10-oxo-9b,10-dihydro-4bH-indeno[1,2-b]benzofuran-9b-yl)-3-(2-chloro-6-fluorophenyl)-5-methylisooxazole-4-carboxamide;
5-amino-N-(1-amino-4b-hydroxy-7-isopropyl-10-oxo-9b,10-dihydro-4bH-indeno[1,2-b]benzofuran-9b-yl)furane-2-carboxamide;
N-(1-amino-4b-hydroxy-7-isopropyl-10-oxo-9b,10-dihydro-4bH-indeno[1,2-b]benzofuran-9b-yl)-1H-pyrrole-2-carboxamide;
N-(1-amino-4b-hydroxy-7-isopropyl-10-oxo-9b,10-dihydro-4bH-indeno[1,2-b]benzofuran-9b-yl)-2-methoxyisonicotinamide;
N-(1-amino-4b-hydroxy-7-isopropyl-10-oxo-9b,10-dihydro-4bH-benzo[d]indeno[1,2-b]furan-9b-yl)benzo[b]thiophene-2-carboxamide;
N-(1-amino-4b-hydroxy-7-isopropyl-10-oxo-9b,10-dihydro-4bH-benzo[d]indeno[1,2-b]furan-9b-yl)-9H-xanthene-9-carboxamide;
N-(1-amino-4b-hydroxy-7-isopropyl-10-oxo-9b,10-dihydro-4bH-benzo[d]indeno[1,2-b]furan-9b-yl)cinnoline-4-carboxamide;

N-(1-amino-4b-hydroxy-7-isopropyl-10-oxo-9b,10-dihydro-4bH-benzo[d]indeno[1,2-b]furan-9b-yl)acridine-9-carboxamide;
N-(1-amino-4b-hydroxy-7-isopropyl-10-oxo-9b,10-dihydro-4bH-benzo[d]indeno[1,2-b]furan-9b-yl)-4-nitro-1H-pyrazole-3-carboxamide;
N-(1-amino-4b-hydroxy-7-isopropyl-10-oxo-9b,10-dihydro-4bH-benzo[d]indeno[1,2-b]furan-9b-yl)-4-methylpicolinamide;
N-(1-amino-4b-hydroxy-7-isopropyl-10-oxo-9b,10-dihydro-4bH-benzo[d]indeno[1,2-b]furan-9b-yl)-4-(trifluoromethyl)picolinamide;
N-(1-amino-4b-hydroxy-7-isopropyl-10-oxo-9b,10-dihydro-4bH-benzo[d]indeno[1,2-b]furan-9b-yl)-5-cyanopicolinamide;
N-(1-amino-4b-hydroxy-7-isopropyl-10-oxo-9b,10-dihydro-4bH-benzo[d]indeno[1,2-b]furan-9b-yl)-3-chloropicolinamide;
N-(1-amino-4b-hydroxy-7-isopropyl-10-oxo-9b,10-dihydro-4bH-benzo[d]indeno[1,2-b]furan-9b-yl)-4-methoxyquinoline-2-carboxamide;
N-(1-amino-4b-hydroxy-7-isopropyl-10-oxo-9b,10-dihydro-4bH-indeno[1,2-b]benzofuran-9b-yl)isoquinoline-3-carboxamide;
N-(1-amino-4b-hydroxy-7-isopropyl-10-oxo-9b,10-dihydro-4bH-indeno[1,2-b]benzofuran-9b-yl)-2-methylisonicotinamide;
N-(1-amino-4b-hydroxy-7-isopropyl-10-oxo-9b,10-dihydro-4bH-indeno[1,2-b]benzofuran-9b-yl)-3-fluoroisonicotinamide;
N-(1-amino-4b-hydroxy-7-isopropyl-10-oxo-9b,10-dihydro-4bH-indeno[1,2-b]benzofuran-9b-yl)-3-chloroisonicotinamide;
N-(1-amino-4b-hydroxy-7-isopropyl-10-oxo-9b,10-dihydro-4bH-indeno[1,2-b]benzofuran-9b-yl)-1-methyl-1H-imidazole-2-carboxamide;
2-((1-amino-4b-hydroxy-7-isopropyl-10-oxo-9b,10-dihydro-4bH-indeno[1,2-b]benzofuran-9b-yl)carbamoyl)pyridine 1-oxide;
N-(1-amino-4b-hydroxy-7-isopropyl-10-oxo-9b,10-dihydro-4bH-indeno[1,2-b]benzofuran-9b-yl)-4-chloronicotinamide;
N-(1-amino-4b-hydroxy-7-isopropyl-10-oxo-9b,10-dihydro-4bH-indeno[1,2-b]benzofuran-9b-yl)-5-fluoronicotinamide;
N-(1-amino-4b-hydroxy-7-isopropyl-10-oxo-9b,10-dihydro-4bH-indeno[1,2-b]benzofuran-9b-yl)-5-hydroxynicotinamide;
N-(1-amino-4b-hydroxy-7-isopropyl-10-oxo-9b,10-dihydro-4bH-indeno[1,2-b]benzofuran-9b-yl)-3-hydroxypicolinamide;
N-(1-amino-4b-hydroxy-7-isopropyl-10-oxo-9b,10-dihydro-4bH-indeno[1,2-b]benzofuran-9b-yl)-4-methylnicotinamide;
N-(1-amino-4b-hydroxy-7-isopropyl-10-oxo-9b,10-dihydro-4bH-indeno[1,2-b]benzofuran-9b-yl)-5-methylnicotinamide;
N-(1-amino-4b-hydroxy-7-isopropyl-10-oxo-9b,10-dihydro-4bH-indeno[1,2-b]benzofuran-9b-yl)-5-methoxynicotinamide;
N-(1-amino-4b-hydroxy-7-isopropyl-10-oxo-9b,10-dihydro-4bH-benzo[d]indeno[1,2-b]furan-9b-yl)quinoline-2-carboxamide;
N-(1-amino-4b-hydroxy-7-isopropyl-10-oxo-9b,10-dihydro-4bH-benzo[d]indeno[1,2-b]furan-9b-yl)-3-bromobenzo[b]thiophene-2-carboxamide;
N-(1-amino-4b-hydroxy-7-isopropyl-10-oxo-9b,10-dihydro-4bH-benzo[d]indeno[1,2-b]furan-9b-yl)-1H-indole-2-carboxamide;
N-(1-amino-4b-hydroxy-7-isopropyl-10-oxo-9b,10-dihydro-4bH-benzo[d]indeno[1,2-b]furan-9b-yl)isoquinoline-1-carboxamide;
N-(1-amino-4b-hydroxy-7-isopropyl-10-oxo-9b,10-dihydro-4bH-indeno[1,2-b]benzofuran-9b-yl)-6-fluoro-4-methoxyquinoline-3-carboxamide;
N-(1-amino-4b-hydroxy-7-isopropyl-10-oxo-9b,10-dihydro-4bH-indeno[1,2-b]benzofuran-9b-yl)-1-methyl-1H-indole-2-carboxamide;
N-(1-amino-4b-hydroxy-7-isopropyl-10-oxo-9b,10-dihydro-4bH-indeno[1,2-b]benzofuran-9b-yl)-3-chloro-6-fluorobenzo[b]thiophene-2-carboxamide;
N-(1-amino-4b-hydroxy-7-isopropyl-10-oxo-9b,10-dihydro-4bH-indeno[1,2-b]benzofuran-9b-yl)-3-chloro-6-methylbenzo[b]thiophene-2-carboxamide;
N-(1-amino-4b-hydroxy-7-isopropyl-10-oxo-9b,10-dihydro-4bH-indeno[1,2-b]benzofuran-9b-yl)-1,3-dimethyl-1H-pyrazolo[3,4-b]pyridine-5-carboxamide;
N-(1-amino-4b-hydroxy-7-isopropyl-10-oxo-9b,10-dihydro-4bH-indeno[1,2-b]benzofuran-9b-yl)imidazo[1,2-a]pyridine-6-carboxamide;
N-(1-amino-4b-hydroxy-7-isopropyl-10-oxo-9b,10-dihydro-4bH-indeno[1,2-b]benzofuran-9b-yl)pyrazolo[1,5-a]pyrimidine-2-carboxamide;
N-(1-amino-4b-hydroxy-7-isopropyl-10-oxo-9b,10-dihydro-4bH-indeno[1,2-b]benzofuran-9b-yl)-3-methylbenzo[b]thiophene-2-carboxamide;
N-(1-amino-4b-hydroxy-7-isopropyl-10-oxo-9b,10-dihydro-4bH-indeno[1,2-b]benzofuran-9b-yl)quinoxaline-2-carboxamide;
N-(1-amino-4b-hydroxy-7-isopropyl-10-oxo-9b,10-dihydro-4bH-indeno[1,2-b]benzofuran-9b-yl)pyridazine-4-carboxamide;
N-(1-amino-4b-hydroxy-7-isopropyl-10-oxo-9b,10-dihydro-4bH-indeno[1,2-b]benzofuran-9b-yl)quinoxaline-6-carboxamide;
N-(1-amino-4b-hydroxy-7-isopropyl-10-oxo-9b,10-dihydro-4bH-indeno[1,2-b]benzofuran-9b-yl)tetrazolo[1,5-a]pyridine-6-carboxamide;
N-(1-amino-4b-hydroxy-7-isopropyl-10-oxo-9b,10-dihydro-4bH-indeno[1,2-b]benzofuran-9b-yl)tetrazolo[1,5-a]pyridine-8-carboxamide;
N-(1-amino-4b-hydroxy-7-isopropyl-10-oxo-9b,10-dihydro-4bH-indeno[1,2-b]benzofuran-9b-yl)-7-methylimidazo[1,2-a]pyridine-2-carboxamide;
N-(1-amino-4b-hydroxy-7-isopropyl-10-oxo-9b,10-dihydro-4bH-indeno[1,2-b]benzofuran-9b-yl)-7-methyl-[1,2,4]triazolo[1,5-a]pyrimidine-2-carboxamide;
N-(1-amino-4b-hydroxy-7-isopropyl-10-oxo-9b,10-dihydro-4bH-indeno[1,2-b]benzofuran-9b-yl)-5,7-dimethylpyrazolo[1,5-a]pyrimidine-3-carboxamide;
N-(1-amino-4b-hydroxy-7-isopropyl-10-oxo-9b,10-dihydro-4bH-indeno[1,2-b]benzofuran-9b-yl)indolizine-2-carboxamide;
N-(1-amino-4b-hydroxy-7-isopropyl-10-oxo-9b,10-dihydro-4bH-indeno[1,2-b]benzofuran-9b-yl)-1,6-diisopropyl-1H-pyrazolo[3,4-b]pyridine-4-carboxamide;
N-(1-amino-4b-hydroxy-7-isopropyl-10-oxo-9b,10-dihydro-4bH-indeno[1,2-b]benzofuran-9b-yl)imidazo[1,2-a]pyrimidine-2-carboxamide;
N-(1-amino-4b-hydroxy-7-isopropyl-10-oxo-9b,10-dihydro-4bH-indeno[1,2-b]benzofuran-9b-yl)-1-oxo-1,2-dihydroisoquinoline-3-carboxamide;

N-(1-amino-4b-hydroxy-7-isopropyl-10-oxo-9b,10-dihydro-4bH-benzo[d]indeno[1,2-b]furan-9b-yl)-3-methylimidazo[1,5-a]pyridine-1-carboxamide;

N-(1-amino-4b-hydroxy-7-isopropyl-10-oxo-9b,10-dihydro-4bH-benzo[d]indeno[1,2-b]furan-9b-yl)-2H-indazole-3-carboxamide;

N-(1-amino-4b-hydroxy-7-isopropyl-10-oxo-9b,10-dihydro-4bH-indeno[1,2-b]benzofuran-9b-yl)-7-methylpyrazolo[1,5-a]pyrimidine-6-carboxamide;

N-(1-amino-4b-hydroxy-7-isopropyl-10-oxo-9b,10-dihydro-4bH-indeno[1,2-b]benzofuran-9b-yl)-1H-benzo[d]imidazole-2-carboxamide;

N-(1-amino-4b-hydroxy-7-isopropyl-10-oxo-9b,10-dihydro-4bH-indeno[1,2-b]benzofuran-9b-yl)-5-fluoro-1H-benzo[d]imidazole-2-carboxamide;

N-(1-amino-4b-hydroxy-7-isopropyl-10-oxo-9b,10-dihydro-4bH-indeno[1,2-b]benzofuran-9b-yl)tetrazolo[1,5-a]pyridine-5-carboxamide;

N-(1-amino-4b-hydroxy-7-isopropyl-10-oxo-9b,10-dihydro-4bH-indeno[1,2-b]benzofuran-9b-yl)-1-methyl-1H-indazole-3-carboxamide;

N-(1-amino-4b-hydroxy-7-isopropyl-10-oxo-9b,10-dihydro-4bH-indeno[1,2-b]benzofuran-9b-yl)-1H-indole-5-carboxamide;

N-(1-amino-4b-hydroxy-7-isopropyl-10-oxo-9b,10-dihydro-4bH-indeno[1,2-b]benzofuran-9b-yl)-1-methyl-3a,7a-dihydro-1H-indazole-3-carboxamide;

N-(1-amino-4b-hydroxy-7-isopropyl-10-oxo-9b,10-dihydro-4bH-indeno[1,2-b]benzofuran-9b-yl)-1-methyl-1H-imidazole-4-carboxamide;

N-(1-amino-4b-hydroxy-7-isopropyl-10-oxo-9b,10-dihydro-4bH-indeno[1,2-b]benzofuran-9b-yl)-1H-pyrrole-3-carboxamide;

N-(1-amino-4b-hydroxy-7-isopropyl-10-oxo-9b,10-dihydro-4bH-indeno[1,2-b]benzofuran-9b-yl)-1H-indazole-5-caboxamide; and N-(1-amino-4b-hydroxy-7-isopropyl-10-oxo-9b,10-dihydro-4bH-indeno[1,2-b]benzofuran-9b-yl)-3-methyl-1H-pyrazole-5-carboxamide.

7. The compound, pharmaceutically acceptable salt, or enantiomer of claim 1, wherein the compound is selected from the group consisting of:

N-(1-amino-4b-hydroxy-7-isopropyl-10-oxo-9b,10-dihydro-4bH-indeno[1,2-b]benzofuran-9b-yl)picolinamide;

N-(1-amino-4b-hydroxy-7-isopropyl-10-oxo-9b,10-dihydro-4bH-indeno[1,2-b]benzofuran-9b-yl)nicotinamide;

N-(1-amino-4b-hydroxy-7-isopropyl-10-oxo-9b,10-dihydro-4bH-indeno[1,2-b]benzofuran-9b-yl)isonicotinamide;

N-(1-amino-4b-hydroxy-7-isopropyl-10-oxo-9b,10-dihydro-4bH-indeno[1,2-b]benzofuran-9b-yl)pirazine-2-carboxamide;

N-(1-amino-4b-hydroxy-7-isopropyl-10-oxo-9b,10-dihydro-4bH-indeno[1,2-b]benzofuran-9b-yl)furane-2-carboxamide;

N-(1-amino-4b-hydroxy-7-isopropyl-10-oxo-9b,10-dihydro-4bH-indeno[1,2-b]benzofuran-9b-yl)quinoline-8-carboxamide;

N-(1-amino-4b-hydroxy-7-isopropyl-10-oxo-9b,10-dihydro-4bH-indeno[1,2-b]benzofuran-9b-yl)quinoline-6-carboxamide;

N-(1-amino-4b-hydroxy-7-isopropyl-10-oxo-9b,10-dihydro-4bH-benzo[d]indeno[1,2-b]furan-9b-yl)benzofurane-2-carboxamide;

N-(1-amino-4b-hydroxy-7-isopropyl-10-oxo-9b,10-dihydro-4bH-benzo[d]indeno[1,2-b]furan-9b-yl)-3-methylbenzofurane-2-carboxamide;

N-(1-amino-4b-hydroxy-7-isopropyl-10-oxo-9b,10-dihydro-4bH-indeno[1,2-b]benzofuran-9b-yl)-4-methylthiazole-5-carboxamide;

(4R)—N-(1-amino-4b-hydroxy-7-isopropyl-10-oxo-9b,10-dihydro-4bH-indeno[1,2-b]benzofuran-9b-yl)-2-oxothiazolidine-4-carboxamide;

N-(1-amino-4b-hydroxy-7-isopropyl-10-oxo-9b,10-dihydro-4bH-benzo[d]indeno[1,2-b]furan-9b-yl)-1H-indazole-3-carboxamide;

N-(1-amino-4b-hydroxy-7-isopropyl-10-oxo-9b,10-dihydro-4bH-benzo[d]indeno[1,2-b]furan-9b-yl)-2-(1H-tetrazol-1-yl)acetamide;

N-(1-amino-4b-hydroxy-7-isopropyl-10-oxo-9b,10-dihydro-4bH-indeno[1,2-b]benzofuran-9b-yl)quinoline-3-carboxamide;

N-(1-amino-4b-hydroxy-7-isopropyl-10-oxo-9b,10-dihydro-4bH-indeno[1,2-b]benzofuran-9b-yl)quinoline-4-carboxamide;

N-(1-amino-4b-hydroxy-7-isopropyl-10-oxo-9b,10-dihydro-4bH-indeno[1,2-b]benzofuran-9b-yl)-5-methylthiophene-2-carboxamide;

N-(1-amino-4b-hydroxy-7-isopropyl-10-oxo-9b,10-dihydro-4bH-indeno[1,2-b]benzofuran-9b-yl)-2-methoxythiophene-3-carboxamide;

N-(1-amino-4b-hydroxy-7-isopropyl-10-oxo-9b,10-dihydro-4bH-indeno[1,2-b]benzofuran-9b-yl)-3-(2-chloro-6-fluorophenyl)-5-methylisooxazole-4-carboxamide;

5-amino-N-(1-amino-4b-hydroxy-7-isopropyl-10-oxo-9b,10-dihydro-4bH-indeno[1,2-b]benzofuran-9b-yl)furane-2-carboxamide;

N-(1-amino-4b-hydroxy-7-isopropyl-10-oxo-9b,10-dihydro-4bH-indeno[1,2-b]benzofuran-9b-yl)-1H-pyrrole-2-carboxamide;

N-(1-amino-4b-hydroxy-7-isopropyl-10-oxo-9b,10-dihydro-4bH-indeno[1,2-b]benzofuran-9b-yl)-2-methoxyisonicotinamide;

N-(1-amino-4b-hydroxy-7-isopropyl-10-oxo-9b,10-dihydro-4bH-benzo[d]indeno[1,2-b]furan-9b-yl)benzo[b]thiophene-2-carboxamide;

N-(1-amino-4b-hydroxy-7-isopropyl-10-oxo-9b,10-dihydro-4bH-benzo[d]indeno[1,2-b]furan-9b-yl)-9H-xanthene-9-carboxamide;

N-(1-amino-4b-hydroxy-7-isopropyl-10-oxo-9b,10-dihydro-4bH-benzo[d]indeno[1,2-b]furan-9b-yl)cinnoline-4-carboxamide;

N-(1-amino-4b-hydroxy-7-isopropyl-10-oxo-9b,10-dihydro-4bH-benzo[d]indeno[1,2-b]furan-9b-yl)acridine-9-carboxamide;

N-(1-amino-4b-hydroxy-7-isopropyl-10-oxo-9b,10-dihydro-4bH-benzo[d]indeno[1,2-b]furan-9b-yl)-4-nitro-1H-pyrazole-3-carboxamide;

N-(1-amino-4b-hydroxy-7-isopropyl-10-oxo-9b,10-dihydro-4bH-benzo[d]indeno[1,2-b]furan-9b-yl)-4-methylpicolinamide;

N-(1-amino-4b-hydroxy-7-isopropyl-10-oxo-9b,10-dihydro-4bH-benzo[d]indeno[1,2-b]furan-9b-yl)-4-(trifluoromethyl)picolinamide;

N-(1-amino-4b-hydroxy-7-isopropyl-10-oxo-9b,10-dihydro-4bH-benzo[d]indeno[1,2-b]furan-9b-yl)-5-cyanopicolinamide;

N-(1-amino-4b-hydroxy-7-isopropyl-10-oxo-9b,10-dihydro-4bH-benzo[d]indeno[1,2-b]furan-9b-yl)-3-chloropicolinamide;

N-(1-amino-4b-hydroxy-7-isopropyl-10-oxo-9b,10-dihydro-4bH-benzo[d]indeno[1,2-b]furan-9b-yl)-4-methoxyquinoline-2-carboxamide;
N-(1-amino-4b-hydroxy-7-isopropyl-10-oxo-9b,10-dihydro-4bH-indeno[1,2-b]benzofuran-9b-yl)isoquinoline-3-carboxamide;
N-(1-amino-4b-hydroxy-7-isopropyl-10-oxo-9b,10-dihydro-4bH-indeno[1,2-b]benzofuran-9b-yl)-2-methylisonicotinamide;
N-(1-amino-4b-hydroxy-7-isopropyl-10-oxo-9b,10-dihydro-4bH-indeno[1,2-b]benzofuran-9b-yl)-3-fluoroisonicotinamide;
N-(1-amino-4b-hydroxy-7-isopropyl-10-oxo-9b,10-dihydro-4bH-indeno[1,2-b]benzofuran-9b-yl)-3-chloroisonicotinamide;
N-(1-amino-4b-hydroxy-7-isopropyl-10-oxo-9b,10-dihydro-4bH-indeno[1,2-b]benzofuran-9b-yl)-1-methyl-1H-imidazole-2-carboxamide;
2-((1-amino-4b-hydroxy-7-isopropyl-10-oxo-9b,10-dihydro-4bH-indeno[1,2-b]benzofuran-9b-yl)carbamoyl)pyridine 1-oxide;
N-(1-amino-4b-hydroxy-7-isopropyl-10-oxo-9b,10-dihydro-4bH-indeno[1,2-b]benzofuran-9b-yl)-4-chloronicotinamide;
N-(1-amino-4b-hydroxy-7-isopropyl-10-oxo-9b,10-dihydro-4bH-indeno[1,2-b]benzofuran-9b-yl)-5-fluoronicotinamide;
N-(1-amino-4b-hydroxy-7-isopropyl-10-oxo-9b,10-dihydro-4bH-indeno[1,2-b]benzofuran-9b-yl)-5-hydroxynicotinamide;
N-(1-amino-4b-hydroxy-7-isopropyl-10-oxo-9b,10-dihydro-4bH-indeno[1,2-b]benzofuran-9b-yl)-3-hydroxypicolinamide;
N-(1-amino-4b-hydroxy-7-isopropyl-10-oxo-9b,10-dihydro-4bH-indeno[1,2-b]benzofuran-9b-yl)-4-methylnicotinamide;
N-(1-amino-4b-hydroxy-7-isopropyl-10-oxo-9b,10-dihydro-4bH-indeno[1,2-b]benzofuran-9b-yl)-5-methylnicotinamide;
N-(1-amino-4b-hydroxy-7-isopropyl-10-oxo-9b,10-dihydro-4bH-indeno[1,2-b]benzofuran-9b-yl)-5-methoxynicotinamide;
N-(1-amino-4b-hydroxy-7-isopropyl-10-oxo-9b,10-dihydro-4bH-benzo[d]indeno[1,2-b]furan-9b-yl)quinoline-2-carboxamide;
N-(1-amino-4b-hydroxy-7-isopropyl-10-oxo-9b,10-dihydro-4bH-benzo[d]indeno[1,2-b]furan-9b-yl)-3-bromobenzo[b]thiophene-2-carboxamide;
N-(1-amino-4b-hydroxy-7-isopropyl-10-oxo-9b,10-dihydro-4bH-benzo[d]indeno[1,2-b]furan-9b-yl)-1H-indole-2-carboxamide;
N-(1-amino-4b-hydroxy-7-isopropyl-10-oxo-9b,10-dihydro-4bH-benzo[d]indeno[1,2-b]furan-9b-yl)isoquinoline-1-carboxamide;
N-(1-amino-4b-hydroxy-7-isopropyl-10-oxo-9b,10-dihydro-4bH-indeno[1,2-b]benzofuran-9b-yl)-6-fluoro-4-methoxyquinoline-3-carboxamide;
N-(1-amino-4b-hydroxy-7-isopropyl-10-oxo-9b,10-dihydro-4bH-indeno[1,2-b]benzofuran-9b-yl)-1-methyl-1H-indole-2-carboxamide;
N-(1-amino-4b-hydroxy-7-isopropyl-10-oxo-9b,10-dihydro-4bH-indeno[1,2-b]benzofuran-9b-yl)-3-chloro-6-fluorobenzo[b]thiophene-2-carboxamide;
N-(1-amino-4b-hydroxy-7-isopropyl-10-oxo-9b,10-dihydro-4bH-indeno[1,2-b]benzofuran-9b-yl)-3-chloro-6-methylbenzo[b]thiophene-2-carboxamide;
N-(1-amino-4b-hydroxy-7-isopropyl-10-oxo-9b,10-dihydro-4bH-indeno[1,2-b]benzofuran-9b-yl)-1,3-dimethyl-1H-pyrazolo[3,4-b]pyridine-5-carboxamide;
N-(1-amino-4b-hydroxy-7-isopropyl-10-oxo-9b,10-dihydro-4bH-indeno[1,2-b]benzofuran-9b-yl)imidazo[1,2-a]pyridine-6-carboxamide;
N-(1-amino-4b-hydroxy-7-isopropyl-10-oxo-9b,10-dihydro-4bH-indeno[1,2-b]benzofuran-9b-yl)pyrazolo[1,5-a]pyrimidine-2-carboxamide;
N-(1-amino-4b-hydroxy-7-isopropyl-10-oxo-9b,10-dihydro-4bH-indeno[1,2-b]benzofuran-9b-yl)-3-methylbenzo[b]thiophene-2-carboxamide;
N-(1-amino-4b-hydroxy-7-isopropyl-10-oxo-9b,10-dihydro-4bH-indeno[1,2-b]benzofuran-9b-yl)quinoxaline-2-carboxamide;
N-(1-amino-4b-hydroxy-7-isopropyl-10-oxo-9b,10-dihydro-4bH-indeno[1,2-b]benzofuran-9b-yl)pyridazine-4-carboxamide;
N-(1-amino-4b-hydroxy-7-isopropyl-10-oxo-9b,10-dihydro-4bH-indeno[1,2-b]benzofuran-9b-yl)quinoxaline-6-carboxamide;
N-(1-amino-4b-hydroxy-7-isopropyl-10-oxo-9b,10-dihydro-4bH-indeno[1,2-b]benzofuran-9b-yl)tetrazolo[1,5-a]pyridine-6-carboxamide;
N-(1-amino-4b-hydroxy-7-isopropyl-10-oxo-9b,10-dihydro-4bH-indeno[1,2-b]benzofuran-9b-yl)tetrazolo[1,5-a]pyridine-8-carboxamide;
N-(1-amino-4b-hydroxy-7-isopropyl-10-oxo-9b,10-dihydro-4bH-indeno[1,2-b]benzofuran-9b-yl)-7-methylimidazo[1,2-a]pyridine-2-carboxamide;
N-(1-amino-4b-hydroxy-7-isopropyl-10-oxo-9b,10-dihydro-4bH-indeno[1,2-b]benzofuran-9b-yl)-7-methyl-[1,2,4]triazolo[1,5-a]pyrimidine-2-carboxamide;
N-(1-amino-4b-hydroxy-7-isopropyl-10-oxo-9b,10-dihydro-4bH-indeno[1,2-b]benzofuran-9b-yl)-5,7-dimethylpyrazolo[1,5-a]pyrimidine-3-carboxamide;
N-(1-amino-4b-hydroxy-7-isopropyl-10-oxo-9b,10-dihydro-4bH-indeno[1,2-b]benzofuran-9b-yl)indolizine-2-carboxamide;
N-(1-amino-4b-hydroxy-7-isopropyl-10-oxo-9b,10-dihydro-4bH-indeno[1,2-b]benzofuran-9b-yl)-1,6-diisopropyl-1H-pyrazolo[3,4-b]pyridine-4-carboxamide;
N-(1-amino-4b-hydroxy-7-isopropyl-10-oxo-9b,10-dihydro-4bH-indeno[1,2-b]benzofuran-9b-yl)imidazo[1,2-a]pyrimidine-2-carboxamide;
N-(1-amino-4b-hydroxy-7-isopropyl-10-oxo-9b,10-dihydro-4bH-indeno[1,2-b]benzofuran-9b-yl)-1-oxo-1,2-dihydroisoquinoline-3-carboxamide;
N-(1-amino-4b-hydroxy-7-isopropyl-10-oxo-9b,10-dihydro-4bH-benzo[d]indeno[1,2-b]furan-9b-yl)-3-methylimidazo[1,5-a]pyridine-1-carboxamide;
N-(1-amino-4b-hydroxy-7-isopropyl-10-oxo-9b,10-dihydro-4bH-benzo[d]indeno[1,2-b]furan-9b-yl)-2H-indazole-3-carboxamide;
N-(1-amino-4b-hydroxy-7-isopropyl-10-oxo-9b,10-dihydro-4bH-indeno[1,2-b]benzofuran-9b-yl)-7-methylpyrazolo[1,5-a]pyrimidine-6-carboxamide;
N-(1-amino-4b-hydroxy-7-isopropyl-10-oxo-9b,10-dihydro-4bH-indeno[1,2-b]benzofuran-9b-yl)-1H-benzo[d]imidazole-2-carboxamide;
N-(1-amino-4b-hydroxy-7-isopropyl-10-oxo-9b,10-dihydro-4bH-indeno[1,2-b]benzofuran-9b-yl)-5-fluoro-1H-benzo[d]imidazole-2-carboxamide;
N-(1-amino-4b-hydroxy-7-isopropyl-10-oxo-9b,10-dihydro-4bH-indeno[1,2-b]benzofuran-9b-yl)tetrazolo[1,5-a]pyridine-5-carboxamide;

N-(1-amino-4b-hydroxy-7-isopropyl-10-oxo-9b,10-dihydro-4bH-indeno[1,2-b]benzofuran-9b-yl)-1-methyl-1H-indazole-3-carboxamide;

N-(1-amino-4b-hydroxy-7-isopropyl-10-oxo-9b,10-dihydro-4bH-indeno[1,2-b]benzofuran-9b-yl)-1H-indole-5-carboxamide;

N-(1-amino-4b-hydroxy-7-isopropyl-10-oxo-9b,10-dihydro-4bH-indeno[1,2-b]benzofuran-9b-yl)-1-methyl-3a,7a-dihydro-1H-indazole-3-carboxamide;

N-(1-amino-4b-hydroxy-7-isopropyl-10-oxo-9b,10-dihydro-4bH-indeno[1,2-b]benzofuran-9b-yl)-1-methyl-1H-imidazole-4-carboxamide;

N-(1-amino-4b-hydroxy-7-isopropyl-10-oxo-9b,10-dihydro-4bH-indeno[1,2-b]benzofuran-9b-yl)-1H-pyrrole-3-carboxamide;

N-(1-amino-4b-hydroxy-7-isopropyl-10-oxo-9b,10-dihydro-4bH-indeno[1,2-b]benzofuran-9b-yl)-1H-indazole-5-caboxamide; and N-(1-amino-4b-hydroxy-7-isopropyl-10-oxo-9b,10-dihydro-4bH-indeno[1,2-b]benzofuran-9b-yl)-3-methyl-1H-pyrazole-5-carboxamide.

8. A method of treating a viral disease in a patient, comprising administering a therapeutically effective amount of the compound, pharmaceutically acceptable salt, or enantiomer of claim 1 to the patient.

9. The method of claim 8, wherein the viral disease is caused by coxsackieviruses.

10. The method of claim 8, wherein the viral disease is caused by polioviruses.

11. The method of claim 8, wherein the viral disease is caused by echoroviruses.

12. The method of claim 8, wherein the viral disease is caused by enteroviruses.

13. The method of claim 8, wherein the viral disease is caused by rhinoviruses.

14. The method of claim 8, wherein the viral disease is caused by picornaviruses.

15. The method of claim 8, wherein the viral disease is poliomyelitis, paralysis, acute hemorrhagic conjunctivitis, viral meningitis, hand-foot-and-mouth disease, vesicular disease, hepatitis A, myositis, myocarditis, pancreatitis, epidemic myalgia, encephalitis, cold, herpangina, foot-and-mouth disease, asthma, chronic obstructive pulmonary disease, pneumonia, sinusitis or otitis media.

16. The compound, pharmaceutically acceptable salt, or enantiomer of claim 1, wherein
D is —OH;
E is —OH or —NR$^1$(C=O)R$^2$;
G$^2$ is isopropyl; and
Z is C.

17. The compound, pharmaceutically acceptable salt, or enantiomer of claim 1, wherein
E is —OH; and
G$^2$ is isopropyl.

18. A pharmaceutical composition comprising a therapeutically effective amount of the compound of claim 1, a pharmaceutically acceptable salt thereof, or an enantiomer thereof, and a diluent or excipient.

* * * * *

UNITED STATES PATENT AND TRADEMARK OFFICE
CERTIFICATE OF CORRECTION

PATENT NO. : 9,890,133 B2
APPLICATION NO. : 15/189771
DATED : February 13, 2018
INVENTOR(S) : Young Sik Jung et al.

It is certified that error appears in the above-identified patent and that said Letters Patent is hereby corrected as shown below:

In the Claims

In Claim 11, Column 206, Line 2 "echoroviruses" should read --echoviruses--

Signed and Sealed this
Twenty-ninth Day of May, 2018

Andrei Iancu
*Director of the United States Patent and Trademark Office*